(12) United States Patent
Aktoudianakis et al.

(10) Patent No.: US 12,037,342 B2
(45) Date of Patent: *Jul. 16, 2024

(54) SUBSTITUTED ENEOXINDOLES AND USES THEREOF

(71) Applicant: Gilead Sciences, Inc., Foster City, CA (US)

(72) Inventors: Evangelos Aktoudianakis, Redwood City, CA (US); Jayaraman Chandrasekhar, Redmond, WA (US); Julian A. Codelli, Mountlake Terrace, WA (US); John H. Conway, Somerville, MA (US); Kristyna M. Elbel, San Francisco, CA (US); Rao V. Kalla, Foster City, CA (US); Samuel E. Metobo, Newark, CA (US); Scott A. Mitchell, Kenmore, WA (US); Thao D. Perry, San Jose, CA (US); Scott P. Simonovich, Oakland, CA (US); Christopher A. Ziebenhaus, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,374

(22) Filed: Aug. 17, 2022

(65) Prior Publication Data

US 2023/0183262 A1    Jun. 15, 2023

Related U.S. Application Data

(63) Continuation of application No. 16/880,134, filed on May 21, 2020, now Pat. No. 11,453,681.

(60) Provisional application No. 62/851,875, filed on May 23, 2019.

(51) Int. Cl.
| C07D 498/04 | (2006.01) |
| C07D 413/14 | (2006.01) |
| C07D 471/04 | (2006.01) |
| C07D 519/00 | (2006.01) |

(52) U.S. Cl.
CPC ......... *C07D 498/04* (2013.01); *C07D 413/14* (2013.01); *C07D 471/04* (2013.01); *C07D 519/00* (2013.01)

(58) Field of Classification Search
CPC .. C07D 498/04; C07D 413/14; C07D 471/04; C07D 519/00
See application file for complete search history.

(56) References Cited

U.S. PATENT DOCUMENTS

| 7,713,973 | B2 | 5/2010 | Dong et al. |
| 8,288,536 | B2 | 10/2012 | Dong et al. |
| 9,725,769 | B1 | 8/2017 | Knudsen |
| 10,722,495 | B2 | 7/2020 | Vechorkin et al. |
| 10,745,388 | B2 | 8/2020 | Vechorkin et al. |
| 11,034,694 | B2 | 6/2021 | Kaila et al. |
| 11,071,730 | B2 | 7/2021 | Balan et al. |
| 11,203,591 | B2 | 12/2021 | Balan et al. |
| 11,453,681 | B2 * | 9/2022 | Aktoudianakis ..... C07D 413/14 |
| 2014/0275033 | A1 | 9/2014 | Li et al. |
| 2017/0298443 | A1 | 10/2017 | Dai |
| 2017/0306303 | A1 | 10/2017 | Taunton et al. |
| 2018/0072720 | A1 | 3/2018 | Vechorkin et al. |
| 2018/0280394 | A1 | 10/2018 | Bates et al. |
| 2019/0315717 | A1 | 10/2019 | Hummel et al. |
| 2020/0048241 | A1 | 2/2020 | Hummel et al. |
| 2020/0087301 | A1 | 3/2020 | Vechorkin et al. |
| 2020/0140456 | A1 | 5/2020 | Phillips et al. |
| 2020/0291076 | A1 | 9/2020 | Dalton et al. |
| 2020/0299279 | A1 | 9/2020 | Burkart et al. |
| 2021/0078996 | A1 | 3/2021 | Kaila et al. |
| 2021/0078997 | A1 | 3/2021 | Kaila et al. |
| 2021/0078998 | A1 | 3/2021 | Kaila et al. |
| 2021/0139484 | A1 | 5/2021 | Aicher et al. |
| 2021/0163417 | A1 | 6/2021 | Chan et al. |
| 2021/0171518 | A1 | 6/2021 | Hummel et al. |

FOREIGN PATENT DOCUMENTS

| CL | 2019002734 A1 | 1/2020 |
| CL | 2020002146 A1 | 1/2021 |
| CN | 103110932 A | 5/2013 |
| CN | 103114087 B | 5/2015 |
| CN | 105555780 A | 5/2016 |
| CN | 104878084 B | 1/2018 |
| CN | 109721620 A | 5/2019 |
| CN | 108823307 B | 10/2020 |
| CN | 112239473 A | 1/2021 |

(Continued)

OTHER PUBLICATIONS

Barrientos; Blood 2013, 122, 4176. http://doi.org/10.1182/blood.V122.21.4176.4176 (Year: 2013).*

Schmidt; Semin Immunopathol 2019, 41, 21-30. https://doi.org/10.1007/s00281-018-0714-9 (Year: 2019).*

Alzabin, S. (2007) "Hematopoietic Progenitor Kinase is a negative regulator of the immune system" Dissertation, NYU, 278 pages.

Alzabin, S. et al. (2009) "Hematopoietic Progenitor Kinase 1 Is a Negative Regulator of Dendritic Cell Activation" The Journal of Immunology, 6187-6194.

Alzabin, S. et al. (2010) "Hematopoietic progenitor kinase 1 is a critical component of prostaglandin E2-mediated suppression of the anti-tumor immune response" Cancer Immunol Immunother, 59:419-429.

(Continued)

*Primary Examiner* — Daniel R Carcanague

(57) ABSTRACT

The present disclosure relates generally to certain eneoxindole compounds, pharmaceutical compositions comprising thereof. Also disclosed are methods of making and using said compounds and pharmaceutical compositions. The compounds and compositions disclosed herein may be used for the treatment or prevention of diseases, disorders, or infections modifiable by hematopoietic progenitor kinase 1 (HPK1) inhibitors, such as HBV, HIV, cancer, and/or a hyper-proliferative disease.

54 Claims, No Drawings

(56) References Cited

FOREIGN PATENT DOCUMENTS

| | | |
|---|---|---|
| CN | 113336747 A | 9/2021 |
| CN | 113845531 A | 12/2021 |
| CN | 113861188 A | 12/2021 |
| CN | 114315796 A | 4/2022 |
| CN | 114437074 A | 5/2022 |
| CN | 114516857 A | 5/2022 |
| CN | 114685489 A | 7/2022 |
| CN | 114685490 A | 7/2022 |
| CN | 114767676 A | 7/2022 |
| CN | 114805330 A | 7/2022 |
| CN | 114853730 A | 8/2022 |
| CN | 114907374 A | 8/2022 |
| CN | 114907375 A | 8/2022 |
| CN | 114907377 A | 8/2022 |
| CN | 114940683 A | 8/2022 |
| DK | 3322711 T3 | 4/2021 |
| EP | 3042903 A1 | 7/2016 |
| EP | 3257847 A1 | 12/2017 |
| EP | 3873608 A1 | 9/2021 |
| EP | 3873903 A1 | 9/2021 |
| JP | 2016529244 A | 9/2016 |
| JP | 2018522858 A | 8/2018 |
| JP | 2022509533 A | 1/2022 |
| WO | WO-0035909 A1 | 6/2000 |
| WO | WO-200055153 A1 | 9/2000 |
| WO | WO-200183485 A1 | 11/2001 |
| WO | WO-2005035520 A1 | 4/2005 |
| WO | WO-2005063766 A2 | 7/2005 |
| WO | WO-2005120510 A1 | 12/2005 |
| WO | WO-2006004702 A1 | 1/2006 |
| WO | WO-2007032371 A1 | 3/2007 |
| WO | WO-2007041511 A2 | 4/2007 |
| WO | WO-2007058850 A2 | 5/2007 |
| WO | WO-2008025539 A1 | 3/2008 |
| WO | WO-2008046083 A2 | 4/2008 |
| WO | WO-2008077550 A1 | 7/2008 |
| WO | WO-2008077552 A1 | 7/2008 |
| WO | WO-2008078091 A1 | 7/2008 |
| WO | WO-2008113469 A2 | 9/2008 |
| WO | WO-2008124323 A1 | 10/2008 |
| WO | WO-2008131859 A2 | 11/2008 |
| WO | WO-2009010299 A1 | 1/2009 |
| WO | WO-2009015867 A1 | 2/2009 |
| WO | WO-2009099801 A1 | 8/2009 |
| WO | WO-2010020675 A1 | 2/2010 |
| WO | WO-2010059393 A1 | 5/2010 |
| WO | WO-2011014795 A2 | 2/2011 |
| WO | WO-2011090738 A2 | 7/2011 |
| WO | WO-2011119777 A2 | 9/2011 |
| WO | WO-2011130146 A1 | 10/2011 |
| WO | WO-2011134971 A1 | 11/2011 |
| WO | WO-2012020813 A1 | 2/2012 |
| WO | WO-2012097479 A1 | 7/2012 |
| WO | WO-2012101064 A1 | 8/2012 |
| WO | WO-2012123312 A1 | 9/2012 |
| WO | WO-2013020062 A1 | 2/2013 |
| WO | WO-2013055645 A1 | 4/2013 |
| WO | WO-2013117285 A1 | 8/2013 |
| WO | WO-2013130660 A1 | 9/2013 |
| WO | WO-2014100065 A1 | 6/2014 |
| WO | WO-2014202493 A1 | 12/2014 |
| WO | WO-2015017610 A1 | 2/2015 |
| WO | WO-2015082887 A2 | 6/2015 |
| WO | WO-2015089479 A1 | 6/2015 |
| WO | WO-2015089481 A2 | 6/2015 |
| WO | WO-2015140051 A1 | 9/2015 |
| WO | WO-2015140054 A1 | 9/2015 |
| WO | WO-2015140055 A1 | 9/2015 |
| WO | WO-2015144001 A1 | 10/2015 |
| WO | WO-2016004272 A1 | 1/2016 |
| WO | WO-2016/057624 A1 | 4/2016 |
| WO | WO-2016067112 A1 | 5/2016 |
| WO | WO-2016073378 A1 | 5/2016 |
| WO | WO-2016073738 A2 | 5/2016 |
| WO | WO-2016/100285 A1 | 6/2016 |
| WO | WO-2016/100608 A1 | 6/2016 |
| WO | WO-2016090300 A1 | 6/2016 |
| WO | WO-2016097863 A1 | 6/2016 |
| WO | WO-2016097870 A1 | 6/2016 |
| WO | WO-2016100975 A1 | 6/2016 |
| WO | WO-2016106623 A1 | 7/2016 |
| WO | WO-2016106624 A1 | 7/2016 |
| WO | WO-2016106625 A1 | 7/2016 |
| WO | WO-2016106626 A1 | 7/2016 |
| WO | WO-2016106652 A1 | 7/2016 |
| WO | WO-2016108707 A1 | 7/2016 |
| WO | WO-2016109219 A1 | 7/2016 |
| WO | WO-2016109220 A1 | 7/2016 |
| WO | WO-2016109221 A1 | 7/2016 |
| WO | WO-2016109222 A1 | 7/2016 |
| WO | WO-2016109223 A1 | 7/2016 |
| WO | WO-2016109480 A1 | 7/2016 |
| WO | WO-2016120196 A1 | 8/2016 |
| WO | WO-2016/149351 A1 | 9/2016 |
| WO | WO-2016145252 A1 | 9/2016 |
| WO | WO-2016146985 A1 | 9/2016 |
| WO | WO-2016149668 A1 | 9/2016 |
| WO | WO-2016161145 A1 | 10/2016 |
| WO | WO-2016161196 A1 | 10/2016 |
| WO | WO-2016161960 A1 | 10/2016 |
| WO | WO-2016162867 A1 | 10/2016 |
| WO | WO-2016164428 A1 | 10/2016 |
| WO | WO-2016164641 A1 | 10/2016 |
| WO | WO-2016172010 A1 | 10/2016 |
| WO | WO-2016176726 A1 | 11/2016 |
| WO | WO-2016/201370 A1 | 12/2016 |
| WO | WO-2016205942 A1 | 12/2016 |
| WO | WO-2017002078 A1 | 1/2017 |
| WO | WO-2017021501 A1 | 2/2017 |
| WO | WO-2017055530 A1 | 4/2017 |
| WO | WO-2017055533 A1 | 4/2017 |
| WO | WO-2017087723 A1 | 5/2017 |
| WO | WO-2017103205 A1 | 6/2017 |
| WO | WO-2017151732 A1 | 9/2017 |
| WO | WO-2017181177 A1 | 10/2017 |
| WO | WO-2017222285 A1 | 12/2017 |
| WO | WO-2017222287 A1 | 12/2017 |
| WO | WO-2018004213 A1 | 1/2018 |
| WO | WO-2018049152 A1 | 3/2018 |
| WO | WO-2018049191 A1 | 3/2018 |
| WO | WO-2018049200 A1 | 3/2018 |
| WO | WO-2018049214 A1 | 3/2018 |
| WO | WO-2018081531 A2 | 5/2018 |
| WO | WO-2018089212 A1 | 5/2018 |
| WO | WO-2018102366 A1 | 6/2018 |
| WO | WO-2018148745 A1 | 8/2018 |
| WO | WO-2018152220 A1 | 8/2018 |
| WO | WO-2018167147 A1 | 9/2018 |
| WO | WO-2018183956 A1 | 10/2018 |
| WO | WO-2018183964 A1 | 10/2018 |
| WO | WO-2018215668 A1 | 11/2018 |
| WO | WO-2018228920 A1 | 12/2018 |
| WO | WO-2018228923 A1 | 12/2018 |
| WO | WO-2018228925 A1 | 12/2018 |
| WO | WO-2019057102 A1 | 3/2019 |
| WO | WO-2019089641 A1 | 5/2019 |
| WO | WO-2019090198 A1 | 5/2019 |
| WO | WO-2019141250 A1 | 7/2019 |
| WO | WO-2019164846 A1 | 8/2019 |
| WO | WO-2019164847 A1 | 8/2019 |
| WO | WO-2019200120 A1 | 10/2019 |
| WO | WO-2019206049 A1 | 10/2019 |
| WO | WO-2019238067 A1 | 12/2019 |
| WO | WO-2020023551 A1 | 1/2020 |
| WO | WO-2020023560 A1 | 1/2020 |
| WO | WO-2020061377 A1 | 3/2020 |
| WO | WO-2020069402 A1 | 4/2020 |
| WO | WO-2020070331 A1 | 4/2020 |
| WO | WO-2020070332 A1 | 4/2020 |
| WO | WO-2020072627 A1 | 4/2020 |
| WO | WO-2020072695 A1 | 4/2020 |
| WO | WO-2020089892 A1 | 5/2020 |
| WO | WO-2020092528 A1 | 5/2020 |

(56) References Cited

FOREIGN PATENT DOCUMENTS

| | | |
|---|---|---|
| WO | WO-2020100027 A1 | 5/2020 |
| WO | WO-2020103896 A1 | 5/2020 |
| WO | WO-2020113233 A1 | 6/2020 |
| WO | WO-2020120257 A1 | 6/2020 |
| WO | WO-2020163248 A1 | 8/2020 |
| WO | WO-2020163382 A1 | 8/2020 |
| WO | WO-2020163401 A1 | 8/2020 |
| WO | WO-2020163405 A1 | 8/2020 |
| WO | WO-2020163409 A1 | 8/2020 |
| WO | WO-2020163544 A1 | 8/2020 |
| WO | WO-2020188467 A1 | 9/2020 |
| WO | WO-2020193511 A1 | 10/2020 |
| WO | WO-2020193512 A1 | 10/2020 |
| WO | WO-2020210537 A1 | 10/2020 |
| WO | WO-2020219934 A1 | 10/2020 |
| WO | WO-2020227325 A1 | 11/2020 |
| WO | WO-2020235902 A1 | 11/2020 |
| WO | WO-2020237025 A1 | 11/2020 |
| WO | WO-2020255022 A1 | 12/2020 |
| WO | WO-2021000925 A1 | 1/2021 |
| WO | WO-2021000935 A1 | 1/2021 |
| WO | WO-2021004535 A1 | 1/2021 |
| WO | WO-2021004547 A1 | 1/2021 |
| WO | WO-2021013083 A1 | 1/2021 |
| WO | WO-2021026180 A1 | 2/2021 |
| WO | WO-2021029896 A1 | 2/2021 |
| WO | WO-2021030627 A1 | 2/2021 |
| WO | WO-2021032148 A1 | 2/2021 |
| WO | WO-2021046254 A1 | 3/2021 |
| WO | WO-2021050964 A1 | 3/2021 |
| WO | WO-2021057872 A1 | 4/2021 |
| WO | WO-2021074279 A1 | 4/2021 |
| WO | WO-2021146370 A1 | 7/2021 |
| WO | WO-2021213317 A1 | 10/2021 |
| WO | WO-2021220185 A1 | 11/2021 |
| WO | WO-2021224818 A1 | 11/2021 |
| WO | WO-2021226262 A1 | 11/2021 |
| WO | WO-2021226707 A1 | 11/2021 |
| WO | WO-2021249913 A1 | 12/2021 |
| WO | WO-2021254118 A1 | 12/2021 |
| WO | WO-2022002237 A1 | 1/2022 |
| WO | WO-2022089225 A1 | 5/2022 |
| WO | WO-2022089398 A1 | 5/2022 |
| WO | WO-2022095904 A1 | 5/2022 |
| WO | WO-2022098806 A1 | 5/2022 |
| WO | WO-2022098807 A1 | 5/2022 |
| WO | WO-2022098809 A1 | 5/2022 |
| WO | WO-2022100688 A1 | 5/2022 |
| WO | WO-2022107919 A1 | 5/2022 |
| WO | WO-2022111517 A1 | 6/2022 |
| WO | WO-2022131741 A1 | 6/2022 |
| WO | WO-2022166920 A1 | 8/2022 |
| WO | WO-2022167627 A1 | 8/2022 |
| WO | WO-2022171034 A1 | 8/2022 |
| WO | WO-2022174253 A1 | 8/2022 |
| WO | WO-2022184152 A1 | 9/2022 |
| WO | WO-2022187856 A1 | 9/2022 |
| WO | WO-2022188735 A1 | 9/2022 |
| WO | WO-2022188823 A1 | 9/2022 |
| WO | WO-2022192145 A1 | 9/2022 |
| WO | WO-2022197641 A1 | 9/2022 |

OTHER PUBLICATIONS

Arnold, R. et al. (2001) "Caspase-mediated Cleavage of Hematopoietic Progenitor Kinase 1 (HPK1) Converts an Activator of NFkB into an Inhibitor of NFkB" The Journal of Biological Chemistry, 276(18):14675-14684.

Arnold, R. et al. (2005) "Activation of Hematopoietic Progenitor Kinase 1 Involves Relocation, Autophosphorylation, and Transphosphorylation by Protein Kinase D1" Molecular and Cellular Biology, 25(6):2364-2383.

Arnold, S. et al. (2007) "Sustained JNK signaling by proteolytically processed HPK1 mediates IL-3 independent survival during monocytic differentiation" Cell Death and Differentiation, 14:568-575.

Bader, A. et al. (2022) "Decoding the signaling profile of hematopoietic progenitor kinase 1 (HPK1) in innate immunity: A proteomic approach" Eur. J. Immunol. 0: 1-10.

Batcha, M. et al. (2019) "Identification of a new type of haematopoietic progenitor kinase-interacting protein (HIP-55) in Aedes aegypti mosquito haemocytes and its involvement in immunity-like functions in mosquito: a molecular study" Parasitology Research, 118:2509-2521.

Bhattarai, D. et al. (2017) "Design, synthesis, and biological evaluation of structurally modified isoindolinone and quinazolinone derivatives as hedgehog pathway inhibitors" European Journal of Medicinal Chemistry, 125:1036-1050.

Boomer, J. et al. (2005) "Functional Interactions of HPK1 With Adaptor Proteins" Journal of Cellular Biochemistry, 95:34-44.

Borgogno, A. et al. (2013) "The impact of either 4-R-hydroxyproline or 4-R-fluoroproline on the conformation and SH3m-cort binding of HPK1 proline-rich peptide" Amino Acids, 44:607,614.

Bos, P. et al. (2019) "Development of MAP4 Kinase Inhibitors as Motor Neuron-Protecting Agents" Cell Chemical Biology, 26:1703-1715.e37.

Brenner, D. et al. (2007) "Caspase-cleaved HPK1 induces CD95L-independent activation-induced cell death in T and B lymphocytes" Blood, 110(12):3968-3977.

Brenner, D. et al. (2009) "Phosphorylation of CARMA1 by HPK1 is critical for NF-B activation in T cells" PNAS, 106(34):14508-14513.

Burns, J. et al. (2011) "The SLP-76 Src Homology 2 Domain Is Required for T Cell Development and Activation" The Journal of Immunology, 187:4459-4466.

Chan, B. et al. (2021) "Discovery of Spiro-azaindoline Inhibitors of Hematopoietic Progenitor Kinase 1 (HPK1)" ACS Med. Chem. Lett., 8 pages.

Chatrikhi, R. et al. (2021) "A synthetic small molecule stalls pre-mRNA splicing by promoting an early-stage U2AF2-RNA complex" Cell Chemical Biology, 20 pages.

Chen, N. (2021) "Impact of posttranslational modifications in pancreatic carcinogenesis and treatments" Cancer and Metastasis Reviews, 21 pages.

Chen, N. et al. (2021) "Impact of posttranslational modifications in pancreatic carcinogenesis and treatments" Cancer and Metastasis Reviews, 21 pages.

Chen, Y. et al. (2020) "Abstract 4513: The role of HPK1 in the regulation of T cell function and anti-tumor immune activity" Cancer Research [downloaded from https://cancerres.aacrjournals.org/content/80/16_Supplement/4513] 4 pages.

Chen-Deutsch, X. et al. (2012) "Dual role of hematopoietic progenitor kinase 1 (HPK1) as a positive regulator of 1?,25-dihydroxyvitamin D-induced differentiation and cell cycle arrest of AML cells and as a mediator of vitamin D resistance" Cell Cycle, 11(7):1364-1373.

Chen-Deutsch, X. et al. (2012) "The pan-caspase inhibitor Q-VD-OPh has anti-leukemia effects and can interact with vitamin D analogs to increase HPK1 signaling in AML cells" Leukemia Research, 36:884-888.

Chmielewski, S. et al.(2020) "Abstract 1947: Development and characterization of small molecule HPK1 inhibitors" Cancer Research [downloaded from https://cancerres.aacrjournals.org/content/80/16_Supplement/1947] 5 pages.

Chuang, H. et al. (2016) "MAP4K Family Kinases in Immunity and Inflammation" Advances in Immunology, 129:277-314.

Chuang, H. et al. (2019) "MAP4K Family Kinases and DUSP Family Phosphatases in T-Cell Signaling and Systemic Lupus Erythematosus" Cells, 8:1-13.

Chuang, H. et al. (2019) "MAP4K3/GLK in autoimmune disease, cancer and aging" Journal of Biomedical Science, 26(82):1-8.

Ciccone, D. et al. (2020) "A Highly Selective and Potent HPK1 Inhibitor Enhances Immune Cell Activation and Induces Robust Tumor Growth Inhibition in a Syngeneic Tumor Model" SITC 2020 Poster, Nimbus Therapeutics.

Ciccone, D. et al. (2020) "Abstract 942: HPK1, hematopoietic progenitor kinase 1, is a promising therapeutic target for cancer

(56) References Cited

OTHER PUBLICATIONS immunotherapy" Cancer Research [downloaded from https://cancerres.aacrjournals.org/content/80/16_Supplement/942] 4 pages.

Ciccone, D. et al. (2020) Abstract for "A Highly Selective and Potent HPK1 Inhibitor Enhances Immune Cell Activation and Induces Robust Tumor Growth Inhibition in a Murine Syngeneic Tumor Model" Journal for ImmoTherapy of Cancer preprint, A724.

Ciccone, D. et al. (2021) "A Highly Selective and Potent HPK1 Inhibitor Induces Robust Tumor Growth Inhibition as a Single Agent and in Combination with anti-PD1 in Multiple Syngeneic Tumor Models" AACR 2021 Poster, Nimbus Therapeutics.

Cossa, G. et al. (2020) "Localized Inhibition of Protein Phosphatase 1 by NUAK1 Promotes Spliceosome Activity and Reveals a MYC-Sensitive Feedback Control of Transcription" Molecular Cell 77:1322-1339.

Das, S. et al. (2021) "Novel Small Molecule HPK1 Inhibitor PCC-1 Induces Strong Anti-Tumor Activity" J Immunother Cancer, A889.

Deford-Watts, L. et al. (2007) "The Membrane-proximal Portion of CD3 Associates with the Serine/Threonine Kinase GRK2" The Journal of Biological Chemistry, 282(22):16126-16134.

Degnan, A. et al. (2021) "Discovery of Orally Active Isofuranones as Potent, Selective Inhibitors of Hematopoetic Progenitor Kinase 1 Discovery of Orally Active Isofuranones as Potent, Selective Inhibitors of Hematopoetic Progenitor Kinase 1" ACS Medicinal Chemistry Letters, 12 (3), 443-450.

Deng, X. et al. (2010) "Broad spectrum alkynyl inhibitors of T315I Bcr-Abl" Bioorganic & Medicinal Chemistry Letters, 20:4196-4200.

Di Bartolo, V. et al. (2007) "A novel pathway down-modulating T cell activation involves HPK-1-dependent recruitment of 14-3-3 proteins on SLP-76" JEM, 204(3):681-691.

Doering, K. et al. (2021) "Nuclear Hormone Receptor NHR-49 controls a HIF-1-independent hypoxia adaptation pathway in *Caenorhabditis elegans*" bioRxiv, 71 pages.

Ensenat, D. et al. (1999) "A Novel Src Homology 3 Domain-containing Adaptor Protein, HIP-55, That Interacts with Hematopoietic Progenitor Kinase 1" The Journal of Biological Chemistry, 274(48):33945-33950.

Escobar-Hoyos, L. et al. (2020) "Altered RNA Splicing by Mutant p53 Activates Oncogenic RAS Signaling in Pancreatic Cancer" Cancer Cell, 38:198-211.e8.

Eymin, B. (2020) "Targeting the spliceosome machinery: A new therapeutic axis in cancer?" Biochemical Pharmacology, 1-11.

Faia, K. et al. (2021) "MAP4K1 inhibition enhances immune cell activation and anti-tumor immunity in preclinical tumor models" AACR, Poster #1717.

Fornvik, K. et al. (2016) "ITPP Treatment of RG2 Glioblastoma in a Rat Model" Anticancer Research, 36:5751-5756.

Fukuda, T. et al. (2020) "BMP signaling is a therapeutic target in ovarian cancer" Cell Death Discovery, 6(139):1-15.

Geisberger, R. et al. (2002) "Phage Display Based Cloning of Proteins Interacting with the Cytoplasmic Tail of Membrane Immunoglobulins" Developmental Immunology, 9(3):127-134.

Ghosh, A. et al. (2021) "Design and synthesis of herboxidiene derivatives that potently inhibit in vitro splicing" Org. Biomol. Chem. 19:1365-1377.

Ghosh, A. et al. (2021) "Spliceostatins and Derivatives: Chemical Syntheses and Biological Properties of Potent Splicing Inhibitors" J. Nat. Prod. 84:1681-1706.

Gilardi, D. et al. (2020) "PK, PD, and interactions: the new scenario with JAK inhibitors and S1P receptor modulators, two classes of small molecule drugs, in IBD" Expert Review of Gastroenterology & Hepatology, 1-10.

Hamid, O. et al. (2021) "TWT-101: A Phase 1 Study of the Novel HPK1 Inhibitor CFI-402411 in Patients With Advanced Cancer" J Immunother Cancer, A519.

Han, A. et al. (2003) "Bam32 Links the B Cell Receptor to ERK and JNK and Mediates B Cell Proliferation but Not Survival" Immunity, 19:621-632.

Han, J. et al. (2003) "The SH3 Domain-containing Adaptor HIP-55 Mediates c-Jun N-terminal Kinase Activation in T Cell Receptor Signaling" The Journal of Biological Chemistry, 278(52):52195-52202.

Han, J. et al. (2005) "HIP-55 Is Important for T-Cell Proliferation, Cytokine Production, and Immune Responses" Molecular and Cellular Biology, 25(16):6869-6878.

Hansen, S. (2016) "Tumor cell checkpoints" BioCentury on BioBusiness, 1-3.

He, T. et al. (2021) "The Kinase MAP4K1 Inhibits Cytosolic RNA-Induced Antiviral Signaling by Promoting Proteasomal Degradation of TBK1/IKK" ASM Journals, Microbiology Spectrum 9(3):1-17.

Hehner, S. et al. (2000) "Tyrosine-phosphorylated Vav1 as a Point of Integration for T-cell Receptor- and CD28-mediated Activation of JNK, p38, and Interleukin-2 Transcription" The Journal of Biological Chemistry, 275(24):18160-18171.

Hellwig, S. et al. (2012) "Small-Molecule Inhibitors of the c-Fes Protein-Tyrosine Kinase" Chemistry & Biology, 19:529-540.

Hernandez, S. et al. (2018) "The Kinase Activity of Hematopoietic Progenitor Kinase 1 Is Essential for the Regulation of T Cell Function" Cell Reports 25:80-94.

Hsieh, W. et al. (2009) "Pharmacodynamic Effects of Seliciclib, an OrallyAdministered Cell CycleModulator, in Undifferentiated Nasopharyngeal Cancer" Clin Cancer Res, 15(4):1435-1442.

Hu, M. et al. (1996) "Human HPK1, a novel human hematopoietic progenitor kinase that activates the JNK/SAPK kinase cascade" Genes & Development, 10:2251-2264.

Intl. Search Report and Written Opinion dated Jul. 13, 2020 for Intl. Appl. No. PCT/US2020/033955.

Iribarren, K. et al. (2016) "Trial Watch: Immunostimulation with Toll-like receptor agonists in cancer therapy" OncoImmunology, 5(3):1-11.

Ishak, C. et al. (2021) "Spliceosome-Targeted Therapies Induce dsRNA Responses" Immunity, 54:11-13.

Ito, Y. et al. (2001) "Interaction of Hematopoietic Progenitor Kinase 1 and c-Abl Tyrosine Kinase in Response to Genotoxic Stress" The Journal of Biological Chemistry, 276(21):18130-18138.

Jagtap, P. et al. (2020) "Identification of phenothiazine derivatives as UHMbinding inhibitors of early spliceosome assembly" Nature Communications, 1-11.

Jakob, S. et al. (2013) "Hematopoietic progenitor kinase 1 (HPK1) is required for LFA-1-mediated neutrophil recruitment during the acute inflammatory response" Blood, 121(20):4184-4194.

Jiang, Y. et al. (2020) "Multi-omic analysis reveals HIP-55-dependent regulation of cytokines release" Bioscience Reports, 40(3):1-22.

Karaosmanoglu, O. (2020) "P38-b/SAPK-inhibiting and apoptosisinducing activities of (E)-4-chloro-2-((3-ethoxy-2-hydroxybenzylidene)amino)phenol" Human and Experimental Toxicology, 1-16.

Kaur, H. et al. (2021) "Network Theory Reveals Principles of Spliceosome Structure and Dynamics" bioRxiv, 1-39.

Keilhack, H. et al. (2001) "Negative Regulation of Ros Receptor Tyrosine Kinase Signaling: An Epithelial Function of the SH2 Domain Protein Tyrosine Phosphatase SHP-1" The Journal of Cell Biology, 152(2):325-334.

Kiefer, F. et al. (1996) "HPK1, a hematopoietic protein kinase activating the SAPK/JNK pathway" The EMBO Journal, 15(24):7013-7025.

Kiefer, F. et al. (2002) "Signal transduction and co-stimulatory pathways" Transplant Immunology, 9:69-82.

Knight, T. et al. (2021) "MAP4K1 expression is a novel resistance mechanism and independent prognostic marker in AML-but can be overcome via targeted inhibition" EBioMedicine, 2 pages.

Konigsberger, S. et al. (2010) "HPK1 Associates with SKAP-HOM to Negatively Regulate Rap1-Mediated B-Lymphocyte Adhesion" Plos One, 5(9):1-9.

Krammer, P. et al. (2007) "Life and death in peripheral T cells" Nature, 7:532-542.

Kumar, S. et al. (2020) "Mitogen-Activated Protein Kinase Inhibitors and T-Cell-Dependent Immunotherapy in Cancer" Pharmaceuticals, 13(9):1-11.

(56) References Cited

OTHER PUBLICATIONS

Kwon, S. et al. (2020) "Global spliceosome activity regulates entry into cellular senescence" The Faseb Journal, 35:1-13.
Lacey, B. et al. (2020) "Development of High-Throughput Assays for Evaluation of Hematopoietic Progenitor Kinase 1 Inhibitors" SLAS Discovery, 1-12.
Lacey, B. et al. (2021) "Development of High-Throughput Assays for Evaluation of Hematopoietic Progenitor Kinase 1 Inhibitors" SLAS Discovery, 26(1):88-99.
Lai, B. et al. (2020) "Activation of c-Jun N-Terminal Kinase, a Potential Therapeutic Target in Autoimmune Arthritis" Cells, 9:1-17.
Larsen, N. (2020) "The SF3b Complex is an Integral Component of the Spliceosome and Targeted by Natural Product-Based Inhibitors" Macromolecular Protein Complexes III: Structure and Function, 409-432.
Lasserre, R. et al. (2011) "Release of serine/threonine-phosphorylated adaptors from signaling microclusters down-regulates T cell activation" JCB, 195(5):839-853.s6.
Lau, W. et al. (2021) "Using yeast surface display to engineer a soluble and crystallizable construct of hematopoietic progenitor kinase 1 (HPK1)" Acta Cryst, F77:22-28.
Le Bras, S. et al. (2004) "Recruitment of the Actin-binding Protein HIP-55 to the Immunological Synapse Regulates T Cell Receptor Signaling and Endocytosis" The Journal of Biological Chemistry, 279(15):15550-15560.
Lee, J. et al. (2009) "Recruitment of Sprouty1 to Immune Synapse Regulates T Cell Receptor Signaling1" The Journal of Immunology, 183:7178-7186.
Lee, Y. et al. (2020) Abstract for "Inhibition of the Kinase Activity of Hematopoietic Progenitor Kinase 1 Enhances Anti-PD-1-Induced Reinvigoration of Human Tumor-Infiltrating CD8+ T Cells" Journal of ImmunoTherapy of Cancer preprint, A912.
Leung, I. et al. (2001) "The Kinase Activation Loop Is the Key to Mixed Lineage Kinase-3 Activation via Both Autophosphorylation and Hematopoetic Progenitor Kinase 1 Phosphorylation" The Journal of Biological Chemistry, 276(3):1961-1967.
Lewitzky, M. et al. (2004) "Mona/Gads SH3C Binding to Hematopoietic Progenitor Kinase 1 (HPK1) Combines an Atypical SH3 Binding Motif, R/KXXK, with a Classical P XXP Motif Embedded in a Polyproline Type II (PPII) Helix" The Journal of Biological Chemistry, 279(27):28724-28732.
Lin, J. et al. (2008) "Critical role for Rsk2 in T-lymphocyte activation" Blood, 111(2):525-533.
Ling, P. et al. (1999) "Interaction of Hematopoietic Progenitor Kinase 1 with Adapter Proteins Crk and CrkL Leads to Synergistic Activation of c-Jun N-Terminal Kinase" Molecular and Cellular Biology, 19(2):1359-1368.
Ling, P. et al. (2001) "Involvement of Hematopoietic Progenitor Kinase 1 in T Cell Receptor Signaling" The Journal of Biological Chemistry, 276(22):18908-18914.
Ling, Q. et al. (2021) "MAP4K1 functions as a tumor promotor and drug mediator for AML via modulation of DNA damage/repair system and MAPK pathway" EBioMedicine, 14 pages.
Linney, I. et al. (2021) "Inhibitors of immuno-oncology target HPK1—a patent review (2016 to 2020)" Expert Opinion on Therapeutic Patents, 33 pages.
Liu, J. et al. (2019) "Critical role of kinase activity of hematopoietic progenitor kinase 1 in anti-tumor immune surveillance" Plos One, 14(3):1-18.
Ma, W. et al. (2001) "Leukocyte-specific adaptor protein Grap2 interacts with hematopoietic progenitor kinase 1 (HPK1) to activate JNK signaling pathway in T lymphocytes" Oncogene, 20:1703-1714.
Mahlab-Aviv, S. et al. (2020) "Spliceosome-Associated microRNAs Signify Breast Cancer Cells and Portray Potential Novel Nuclear Targets" International Journal of Molecular Sciences, 21:1-23.
Malchow, S. et al. (2022) "The HPK1 Inhibitor A?745 Verifies the Potential of Modulating T Cell Kinase Signaling for Immunotherapy" ACS Chem. Biol., 11 pages.
Mallory, K. et al. (2016) "Cyclic-di-GMP binding induces structural rearrangements in the PlzA and PlzC proteins of the Lyme disease and relapsing fever spirochetes: a possible switch mechanism for c-di-GMP-mediated effector functions" Pathogens and Disease, 74(8):1-8.
Mayya, V. et al. (2009) "Quantitative Phosphoproteomic Analysis of T Cell Receptor Signaling Reveals System-Wide Modulation of Protein-Protein Interactions" Science Signaling, 2(84):1-16.
Meng, D. et al. (2020) "S100A14 suppresses metastasis of nasopharyngeal carcinoma by inhibition of NF-kB signaling through degradation of IRAK1" Oncogene, (39)5307-5322.
Metwally, K. et al. (2007) "Synthesis and biological activity of 2,5-diaryl-3-methylpyrimido[4,5-c]quinolin-1(2H)-one derivatives" Bioorganic & Medicinal Chemistry, 15:2434-2440.
Metwally, K. et al. (2013) "Structure-activity relationship investigation of methoxy substitution on anticancer pyrimido[4,5-c]quinolin-1(2H)-ones" Med Chem Res, 22:4481-4491.
Morrissey, KM et al. (2016) "Immunotherapy and Novel Combinations in Oncology: Current Landscape, Challenges, and Opportunities" Clin Transl Sci, 9:89-104.
Navas, V. et al. (2017) "Serine Phosphorylation of SLP76 Is Dispensable for T Cell Development but Modulates Helper T Cell Function" Plos One, 1-17.
Nicolaou, K. et al. (2021) "Design, Synthesis, and Biological Investigation of Thailanstatin A and Spliceostatin D Analogues Containing Tetrahydropyran, Tetrahydrooxazine, and Fluorinated Structural Motifs" The Journal of Organic Chemistry, A-W.
Office Action dated Apr. 15, 2021 for Taiwan Appl. No. 109116856.
Office Action dated Dec. 7, 2021 for Taiwan Appl. No. 109116856.
Offringa, R. et al. (2022) "The expanding role for small molecules in immuno-oncology" Nature, 20 pages.
Palaga, T. et al. (2003) "TCR-Mediated Notch Signaling Regulates Proliferation and IFN-Production in Peripheral T Cells" 171:3019-3024.
Palakurthi, S. et al. (2007) "Screening of 14C-Polyamines in the AT3B-1 Rat Prostate Tumor Model: The Search for a New PET Prostate Imaging Agent" In Vivo, 21:823-828.
Pan, L. et al. (2020) "Expanding the Mitogen-Activated Protein Kinase (MAPK) Universe: An Update on MAP4Ks" Frontiers in Plant Science, 11:1-7.
Patzak, I. et al. (2010) "HPK1 competes with ADAP for SLP-76 binding and via Rap1 negatively affects T-cell adhesion" European Journal of Immunology, 40:3220-3225.
Paul, S. et al. (2013) "A new look at T cell receptor signaling to nuclear factor-kB" Trends in Immunology, 34(6):269-281.
Petasny, M. et al. (2020) "Splicing to Keep Cycling: The Importance of Pre-mRNA Splicing during the Cell Cycle" Trends in Genetics, 1-13.
Rajasekaran, K. et al. (2013) "Signaling by Fyn-ADAP via the Carma1-Bcl-10-MAP3K7 signalosome exclusively regulates inflammatory cytokine production in NK cells" Nature Immunology, 14(11):1127-1139.
Rocha-Perugini, V. et al. (2017) "Role of Drebrin at the Immunological Synapse" Drebrin, Advances in Experimental Medicine and Biology 1006: 271-280.
Rogers, E. et al. (2009) "Rrp1, a cyclic-di-GMP-producing response regulator, is an important regulator of Borrelia burgdorferi core cellular functions" Molecular Microbiology, 71(6):1551-1573.
Sabnis, R. (2021) "Novel Substituted Exomethylene-oxindoles as HPK1 Inhibitors" ACS Med. Chem. Lett. 12:681-682.
Sanchez-Gonzalez, P. et al. (2011) "Quercetin reduces cisplatin nephrotoxicity in rats without compromising its anti-tumour activity" Nephrol Dial Transplant, 26:3484-3495.
Sanlorenzo, M. et al. (2016) "Oncogenic KIT mutations in different exons lead to specific changes in melanocyte phospho-proteome" Journal of Proteomics, 144:140-147.
Sauer, K. et al. (2001) "Hematopoietic Progenitor Kinase 1 Associates Physically and Functionally with the Adaptor Proteins B Cell Linker Protein and SLP-76 in Lymphocytes" The Journal of Biological Chemistry, 276(48):45207-45216.
Sawasdikosol, S. et al. (2003) "Hematopoietic progenitor kinase 1 (HPK1) negatively regulates prostaglandin E2-induced fos gene transcription" Blood, 101(9):3687-3689.

(56) References Cited

OTHER PUBLICATIONS

Sawasdikosol, S. et al. (2007) "Prostaglandin E2 Activates HPK1 Kinase Activity via a PKA-dependent Pathway" The Journal of Biological Chemistry, 282(48):34693-34699.
Sawasdikosol, S. et al. (2012) "HPK1 as a novel target for cancer immunotherapy" Immunology Institute at the Mount Sinai School of Medicine, 4 pages.
Sawasdikosol, S. et al. (2020) "A perspective on HPK1 as a novel immuno-oncology drug target" eLife, 1-15.
Sawasdikosol, S. et al. (2020) "HPK1 Influences Regulatory T Cell Functions" ImmunoHorizons, 4(7)382-391.
Schulze-Luehrmann, J. et al. (2002) "Hematopoietic progenitor kinase 1 supports apoptosis of T lymphocytes" Blood, 100(3):954-960.
Seo, G. et al. (2020) "MAP4K Interactome Reveals STRN4 as a Key STRIPAK Complex Component in Hippo Pathway Regulation" Cell Reports, 32:1-12.e5.
Shi, Y. et al. (2020) "An exon skipping screen identifies antitumor drugs that are potent modulators of premRNA splicing, suggesting new therapeutic applications" Plos One, 15(5):1-19.
Shi, Y. et al. (2021) "Aberrant splicing in neuroblastoma generates RNA-fusion transcripts and provides vulnerability to spliceosome inhibitors" Nucleic Acids Research, 1-13.
Shui, J. et al. (2007) "Hematopoietic progenitor kinase 1 negatively regulates T cell receptor signaling and T cell-mediated immune responses" Nature Immunology, 8(1):84-91.
Si, J. et al. (2020) "Hematopoietic Progenitor Kinase1 (HPK1) Mediates T Cell Dysfunction and Is a Druggable Target for T Cell-Based Immunotherapies" Cancer Cell, 38:1-16.e11.
Siligardi, G. et al. (2012) "The SH3 domain of HS1 protein recognizes lysine-rich polyproline motifs" Amino Acids, 42:1361-1370.
Simon, S. (2013) "Gimme a brake: HPK1 regulates LFA-1 and neutrophil traction" Blood, 121(20):4017-4018.
Soini, L. et al. (2020) "A biophysical and structural analysis of the interaction of BLNK with 14-3-3 proteins" Journal of Structural Biology, 212:1-6.
Song, X. et al. (2020) "Hematopoietic progenitor kinase 1 down-regulates the oncogenic receptor tyrosine kinase AXL in pancreatic cancer" J. Biol. Chem., 295(8):2348-2358.
Tailor, D. et al. (2021) "Y box binding protein 1 inhibition as a targeted therapy for ovarian cancer" Cell Chemical Biology, 22 pages.
Tanaka, N. et al. (2006) "Choroidal Neovascularization in Transgenic Mice Expressing Prokineticin 1: An Animal Model for Age-Related Macular Degeneration" Molecular Therapy, 13(3):609-616.
Tang, L. et al. (2021) "T Cell Exhaustion and CAR-T Immunotherapy in Hematological Malignancies" BioMed Research International, 8 pages.
Taniguchi-Ponciano, K. et al. (2020) "Proteomic and Transcriptomic Analysis Identify Spliceosome as a Significant Component of the Molecular Machinery in the Pituitary Tumors Derived from POU1F1- and NR5A1-Cell Lineages" Genes, 11: 1-14.
Tolba, M. (2020) "Revolutionizing the Landscape of Colorectal Cancer Treatment: The Potential Role of Immune Checkpoint Inhibitors" International Journal of Cancer, 1-29.
Townsend, C. et al. (2020) "Mechanism of protein-guided folding of the active site U2/U6 RNA during spliceosome activation" Science, 1-23.
Vanzyl, E. et al. (2020) "The spliceosome inhibitors isoginkgetin and pladienolide B induce ATF3-dependent cell death" Plos One, 15:1-12.
Vara, B. et al. (2021) "Discovery of Diaminopyrimidine Carboxamide HPK1 Inhibitors as Preclinical Immunotherapy Tool Compounds" ACS Med. Chem. Lett. 12:653-661.
Verma, N. et al. (2020) "Editorial: Adaptor Protein Regulation in Immune Signalling" Frontiers in Immunology, 11:1-3.
Vivier, E. et al. (2013) "ADAPted secretion of cytokines in NK cells" Nature Immunology, 14(11):1108-1110.
Volovitz, I. et al. (2011) "Split Immunity: Immune Inhibition of Rat Gliomas by Subcutaneous Exposure to Unmodified Live Tumor Cells" The Journal of Immunology, 1-11.
Wang, H. et al. (2009) "Proteasome-Mediated Degradation and Functions of Hematopoietic Progenitor Kinase 1 in Pancreatic Cancer" Cancer Res, 69(3):1063-1070.
Wang, H. et al. (2014) "The CUL7/F-box and WD Repeat Domain ontaining 8 (CUL7/Fbxw8) Ubiquitin Ligase Promotes Degradation of Hematopoietic Progenitor Kinase 1" The Journal of Biological Chemistry, 289(7):4009-4017.
Wang, H. et al. (2016) "The emerging roles of F-box proteins in pancreatic tumorigenesis" Seminars in Cancer Biology, 36:88-94.
Wang, H. et al. (2019) "Discovery of (R)?8-(6-Methyl-4-oxo-1,4,5,6-tetrahydropyrrolo[3,4?b]pyrrol-2-yl)-3-(1-methylcyclopropyl)-2-((1-methylcyclopropyl)amino)quinazolin-4(3H)?one, a Potent and Selective Pim-1/2 Kinase Inhibitor for Hematological Malignancies" J. Med. Chem., 62:1523-1540.
Wang, H. et al. (2020) "Abstract 4711: Novel mechanism involved in the regulation ofoncogenic Axl receptor tyrosine kinase in cancer" [downloaded from https://cancerres.aacrjournals.org/content/80/16_Supplement/4711] 4 pages.
Wang, H. et al. (2021) "Drug discovery targeting p21-activated kinase 4 (PAK4): a patent review " Expert Opinion on Therapeutic Patents, 12 pages.
Wang, J. et al. (2017) "HPK1 positive expression associated with longer overall survival in patients with estrogen receptor-positive invasive ductal carcinoma-not otherwise specified" Molecular Medicine Reports, 1-9.
Wang, L. et al. (2018) "EMT- and stroma-related gene expression and resistance to PD-1 blockade in urothelial cancer" Nature Communications, 1-12.
Wang, Q. et al. (2012) "Pdcd4 knockdown up-regulates MAP4K1 expression and activation of AP-1 dependent transcription through c-Myc" Biochimica et Biophysica Acta, 1823:1807-1814.
Wang, S. et al. (2020) "Homeodomain-interacting protein kinase (Hipk) plays roles in nervous system and muscle structure and function" Plos One, 15(3):1-22.
Wang, W. et al. (1997) "Activation of the Hematopoietic Progenitor Kinase-1 (HPK1)-dependent, Stress-activated c-Jun N-terminal Kinase (JNK) Pathway by Transforming Growth Factor b (TGF-b)-activated Kinase (TAK1), a Kinase Mediator of TGF b Signal Transduction" The Journal of Biological Chemistry, 272(36):22771-22775.
Wang, X. et al. (2011) "MEKK3 Regulates IFN-g Production in T Cells through the Rac1/2-Dependent MAPK Cascades" The Journal of Immunology, 186:5791-5800.
Wang, X. et al. (2012) "Attenuation of T Cell Receptor Signaling by Serine Phosphorylation- mediated Lysine 30 Ubiquitination of SLP-76 Protein" The Journal of Biological Chemistry, 287(41): 34091-34100.
Wang, X. et al. (2012) "Down-regulation of B Cell Receptor Signaling by Hematopoietic Progenitor Kinase 1 (HPK1)-mediated Phosphorylation and Ubiquitination of Activated B Cell Linker Protein (BLNK)" The Journal of Biological Chemistry, 287(14):11037-11048.
Wang, Y. et al. (2020) "Pharmacological inhibition of hematopoietic progenitor kinase 1 positively regulates T-cell function" Plos One, 15(12):1-19.
Wen, S. et al. (2005) "Discovery of an MIT-like atracotoxin family: Spider venom peptides that share sequence homology but not pharmacological properties with AVIT family proteins" Peptides, 26:2412-2426.
Wood, K. et al. (2020) "Modelling the developmental spliceosomal craniofacial disorder Burn-McKeown syndrome using induced pluripotent stem cells" Plos One, 15(7):1-30.
Wu, G. et al. (2018) "Inhibition of SF3B1 by molecules targeting the spliceosome results in massive aberrant exon skipping" RNA, 24(8):1056-1066.
Wu, Q. et al. (2020) "DLX6-AS1 promotes cell proliferation, migration and EMT of gastric cancer through FUS-regulated MAP4K1" Cancer Biology & Therapy, 21(1):17-25.

(56) References Cited

OTHER PUBLICATIONS

Yablonski, D. (2019) "Bridging the Gap: Modulatory Roles of the Grb2-Family Adaptor, Gads, in Cellular and Allergic Immune Responses" Frontiers in Immunology, 10:1-19.

Yamamoto, J. et al. (2015) "5-Aminolevulinic acid-induced protoporphyrin IX with multi-dose ionizing irradiation enhances host antitumor response and strongly inhibits tumor growth in experimental glioma in vivo" Molecular Medicine Reports, 11:1813-1819.

Yang, H. et al. (2006) "Tumorigenesis Suppressor Pdcd4 Down-Regulates Mitogen-Activated Protein Kinase Kinase Kinase Kinase 1 Expression to Suppress Colon Carcinoma Cell Invasion" Molecular and Cellular Biology, 26(4):1297-1306.

Yang, L. et al. (2022) "HPK1 inhibitor enhanced tumor response to antiPD-1 immunotherapy in Non-Hodgkin lymphoma" Research Square, 23 pages.

Yankee, T. et al. (2003) "Expression of the Grb2-Related Protein of the Lymphoid System in B Cell Subsets Enhances B Cell Antigen Receptor Signaling Through Mitogen-Activated Protein Kinase Pathways" The Journal of Immunology, 170:349-355.

Yao, Z. et al. (1999) "A Novel Human STE20-related Protein Kinase, HGK, That Specifically Activates the c-Jun N-terminal Kinase Signaling Pathway" The Journal of Biological Chemistry, 274(4):2118-2125.

You, D. et al. (2017) "Critical Role of Hematopoietic Progenitor Kinase 1 in Anittumor Immune Responses" SITC Annual Meeting, Poster P339.

You, D. et al. (2021) "Enhanced antitumor immunity by a novel small molecule HPK1 inhibitor" Journal for ImmunoTherapy of Cancer, 9:1-12.

Yu, E. et al. (2021) "Identification of Potent Reverse Indazole Inhibitors for HPK1" ACS Med. Chem. Lett. 12:459-466.

Yu, J. et al. (2001) "Synergistic Regulation of Immunoreceptor Signaling by SLP-76-Related Adaptor Clnk and Serine/Threonine Protein Kinase HPK-1" Molecular and Cellular Biology, 21(18):6102-6112.

Yurchenko, M. et al. (2010) "CD150 regulates JNK1/2 activation in normal and Hodgkin's lymphoma B cells" Immunology and Cell Biology, 88:565-574.

Zhang, D. et al. (2020) "Intron retention is a hallmark and spliceosome represents a therapeutic vulnerability in aggressive prostate cancer" Nature Communications, 1-19.

Zhang, H. et al. (2022) "Reduced expression of hematopoietic progenitor kinase 1 in T follicular helper cells causes autoimmunity of systemic lupus erythematosus" Lupus, (1):28-38.

Zhang, Q. et al. (2011) "Inhibited expression of hematopoietic progenitor kinase 1 associated with loss of jumonji domain containing 3 promoter binding contributes to autoimmunity in systemic lupus erythematosus" Journal of Autoimmunity, 37:180-189.

Zhang, Q. et al. (2017) "Interactions between hematopoietic progenitor kinase 1 and its adaptor proteins (Review)" Molecular Medicine Reports, 1-11.

Zheng, X. et al. (2020) "Serine/arginine-rich splicing factors: the bridge linking alternative splicing and cancer" International Journal of Biological Sciences, 16(13):2442-2453.

Zhou, G. et al. (1999) "Hematopoietic Progenitor Kinase 1 Is a Component of Transforming Growth Factor b-induced c-Jun N-terminal Kinase Signaling Cascade" The Journal of Biological Chemistry, 274(19):13133-13138.

Zhou, G. et al. (2004) "Protein Phosphatase 4 Is a Positive Regulator of Hematopoietic Progenitor Kinase 1" The Journal of Biological Chemistry, 279(47):49551-49561.

Zhu, Q. et al. (2022) "Hematopoietic Progenitor Kinase 1 in Tumor Immunology: A Medicinal Chemistry Perspective" Journal of Medicinal Chemistry, 26 pages.

\* cited by examiner

SUBSTITUTED ENEOXINDOLES AND USES THEREOF

CROSS REFERENCE

This application is a continuation of U.S. patent application Ser. No. 16/880,134 filed on May 21, 2020, now issued as U.S. Pat. No. 11,453,681, which claims priority to U.S. Provisional Application No. 62/851,875, filed May 23, 2019. The entire contents of these applications are incorporated herein in their entirety for all purposes.

FIELD

This disclosure relates generally to certain eneoxindole compounds, pharmaceutical compositions comprising said compounds, and methods of making and using said compounds and pharmaceutical compositions.

BACKGROUND

Immuno-oncology is an active area of cancer research, highlighted by inhibitor antibodies against the immune checkpoint receptors CTLA4, PD-1 and PD-L1. Targeted disruption of these checkpoint pathways releases the immune cell from key regulatory pathways, promoting an increase in immune responses against cancer cells. Current therapies utilizing these checkpoint inhibitors are highlighted by significant and durable responses to many different cancers. Unfortunately, these responses are often coupled to low overall response rates across patient populations (<25%). Improving these response rates is a formidable goal, and the combination of checkpoint blockade with other immune activating agents or cell based therapies could provide a useful tool for expanding patient responses.

Hematopoietic progenitor kinase 1 (HPK1), a STE20 ser/thr kinase from the germinal center family of kinases, regulates the function of diverse immune populations including T cells, B cells, and dendritic cells (Hu et al., Gens Dev, 1996; Alzabin et al., J Immunol 2009). In T cells, HPK1 negatively regulates T cell receptor (TCR) signaling (Liou et al., Immunity 2000; Sauer et al., JBC 2001) by phosphorylating SLP76 on serine 376. Association of SLP76 with 14-3-3 protein subsequently leads to the disassociation of the signaling complex (Di Bartolo et al., JEM 2007). Further supporting the role of HPK1 as a negative regulator of TCR signaling, murine HPK1 deficient T cells or HPK1 kinase inactive mutant T cells have enhanced ERK ½ activation and effector cytokine secretion upon TCR activation compared to their wild-type counterparts (Shui et al., Nat Immunol 2007; Hernandez et al., Cell Reports 2018). Accordingly, a small molecule inhibitor of HPK1 could offer a method for increasing the response to checkpoint receptor blockade therapy.

SUMMARY

Disclosed herein are compounds of Formula I:

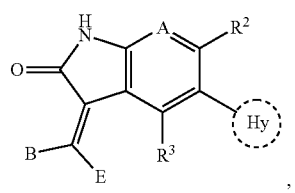

Formula I or pharmaceutically acceptable salts thereof, wherein:
A is N or $CR^1$;
each R', $R^2$, and $R^3$ is independently H, halogen, —CN, —$N(R^{13})_2$, $C_1$-$C_3$ alkyl, $C_1$-$C_3$ haloalkyl, $C_2$-$C_3$ alkynyl, $C_1$-$C_3$ alkoxy, or —$SO_2R^{13}$, wherein the $C_2$-$C_3$ alkynyl is unsubstituted or substituted with 1, 2, or 3 $R^9$ groups;

one of B and E is (G) and the other is J;
J is H, —CN, $C_1$-$C_3$ alkyl, or $C_3$-$C_6$ cycloalkyl; wherein the $C_1$-$C_3$ alkyl or $C_3$-$C_6$ cycloalkyl is unsubstituted or substituted with 1, 2, or 3 $R^{10}$ groups;

(G) is a group of formula

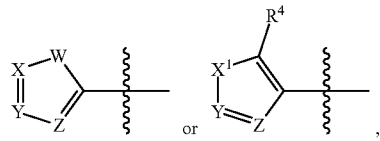

wherein
W is $NR^4$ or S;
X is N or $CR^5$;
Y is N or $CR^6$;
Z is N or $CR^7$;
$X^1$ is NH;
$R^4$ is H;
each $R^5$, $R^6$, and $R^7$ is independently H, halogen, —CN, —$CON(R^8)_2$, —$NR^{13}C(O)R^{13}$, —$SO_2N(R^{13})_2$, $C_1$-$C_3$ alkyl, $C_1$-$C_3$ alkoxy, —$N(R^{13})_2$, $C_3$-$C_6$ cycloalkyl, $C_6$-$C_{10}$ aryl, 5-10 membered heteroaryl having 1, 2, or 3 heteroatoms independently selected from N, O, and S, and 4-6 membered heterocyclyl having 1, 2, or 3 heteroatoms independently selected from N, O, and S; wherein the $C_1$-$C_3$ alkyl, $C_1$-$C_3$ alkoxy, $C_3$-$C_6$ cycloalkyl, $C_6$-$C_{10}$ aryl, 5-10 membered heteroaryl, or 4-6 membered heterocyclyl is unsubstituted or substituted with 1, 2, or 3 $R^{11}$ groups;
or wherein $R^5$ and $R^6$ or $R^6$ and $R^7$ together with atoms to which they are attached form a phenyl or a 5-6 membered heteroaryl having 1 or 2 heteroatoms independently selected from N, O, and S; wherein the phenyl or the 5-6 membered heteroaryl is unsubstituted or substituted with 1, 2, or 3 $R^{11}$ groups;
each $R^8$ is independently H or $C_1$-$C_3$ alkyl, wherein the $C_1$-$C_3$ alkyl is unsubstituted or substituted with 1, 2, or 3 $R^{12}$ groups; or
wherein two $R^8$ groups together with the nitrogen they are attached to form a 4-6 membered heterocyclic ring having 1 or 2 heteroatoms selected from the group consisting of N, O, or S, wherein the 4-6 membered heterocyclic ring is unsubstituted or substituted with 1, 2, or 3 $R^{12}$ groups;
each $R^9$ is independently —$OR^{13}$, $C_1$-$C_3$ alkyl, or $C_3$-$C_6$ cycloalkyl;
each $R^{10}$ and is independently selected from the group consisting of —$OR^{13}$, halogen, CN, —$N(R^8)_2$, —$CON(R^8)_2$, —$N(R^{13})COR^{13}$, —$S(O)_2R^{13}$, $C_1$-$C_3$ alkyl, $C_3$-$C_6$ cycloalkyl, 4-6 membered heterocyclyl having 1, 2, or 3 heteroatoms independently selected from N, O, and S, $C_6$-$C_{10}$ aryl, and 5-10 membered heteroaryl having 1, 2, or 3 heteroatoms independently selected from N, O, and S;

each $R^{12}$ is independently —$OR^{13}$, $C_1$-$C_3$ alkyl, or —$N(R^{13})_2$; wherein the $C_1$-$C_3$ alkyl is unsubstituted or substituted with 1, 2, or 3 groups independently selected from —$OR^{13}$ and —$N(R^{13})_2$;

each $R^{13}$ is independently H or $C_1$-$C_3$ alkyl, wherein the $C_1$-$C_3$ alkyl is unsubstituted or substituted with 1, 2, or 3 $R^{22}$ groups;

each $R^{22}$ is independently selected from the group consisting of halogen, —OH, $C_1$-$C_3$ alkyl, $C_1$-$C_3$ alkoxy, —$NH_2$, —$NH(C_1$-$C_3$ alkyl), —$N(C_1$-$C_3$ alkyl)$_2$ wherein each $C_1$-$C_3$ alkyl is same or different, $C_3$-$C_6$ cycloalkyl, 4-6 membered heterocyclyl with 1, 2, or 3 heteroatoms selected from N, O, and S, $C_6$-$C_{10}$ aryl, and 5-10 membered heteroaryl having 1, 2, or 3 heteroatoms independently selected from N, O, and S; and

is a group of formula:

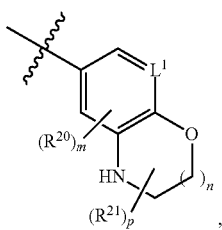

wherein $L^1$ is N or $CR^{19}$;

n is 0, 1 or 2;

m is 0, 1, or 2;

p is 0, 1, 2, 3, 4, 5, or 6;

$R^{19}$ is H, —$OR^{13}$, halogen, CN, —$N(R^{13})_2$, or $C_1$-$C_3$ alkyl;

each $R^{20}$ is independently —$OR^{13}$, halogen, CN, —$N(R^{13})_2$, or $C_1$-$C_3$ alkyl; and each $R^{21}$ is independently —$OR^{13}$, oxo, halogen, CN, —$N(R^{13})_2$, or $C_1$-$C_3$ alkyl;

or two $R^{21}$ groups on same or adjoining atoms are joined together to form a 3-6 membered carbocyclic ring or a 3-6 membered heterocyclic ring having 1 or 2 heteroatoms selected from N, O, and S.

In some embodiments, the compound of Formula I is of a Formula I-Z:

Formula I-Z

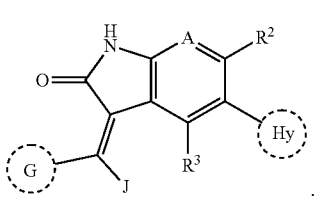

In some embodiments, the compound of Formula I is of a Formula I-E:

Formula I-E

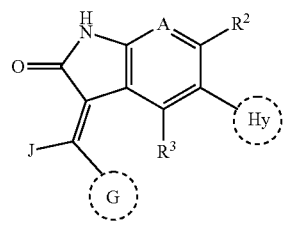

In some embodiments, the compound of Formula I and I-Z is of a Formula II-Z:

Formula II-Z

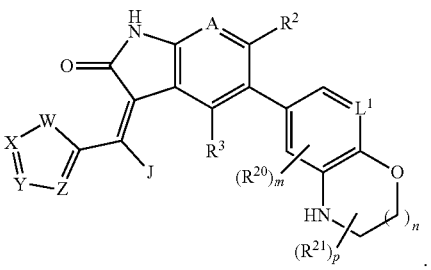

In some embodiments, the compound of Formula I, I-Z, or II-Z is of a Formula IIa-Z:

Formula IIa-Z

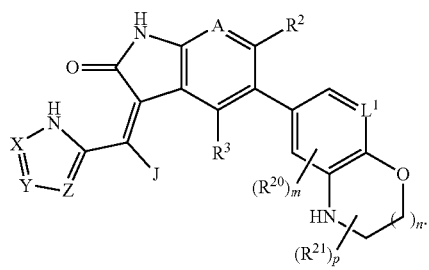

In some embodiments, the compound of Formula I, I-Z, II-Z, and IIa-Z is a compound of Formula IIb-Z:

Formula IIb-Z

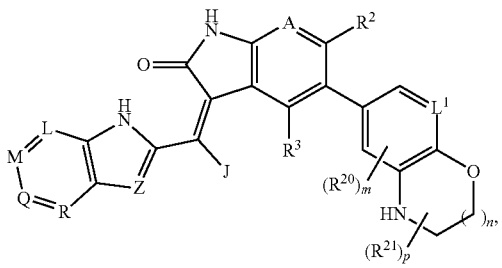

wherein L is N or $CR^{15}$; M is N or $CR^{16}$; Q is N or $CR^{17}$; and R is N or $CR^{18}$; and each $R^{15}$, $R^{16}$, $R^{17}$, and $R^{18}$ is independently selected from the group consisting of H, halogen, CN, —N($R^8$)$_2$, —CON($R^8$)$_2$, —N($R^{13}$)COR$^{13}$, —S(O)$_2$R$^{13}$, $C_1$-$C_3$ alkyl, $C_1$-$C_3$ alkoxy, $C_6$-$C_{10}$ aryl, 5-10 membered heteroaryl having 1, 2, or 3 heteroatoms independently selected from N, O, and S, and 4-6 membered heterocyclyl having 1, 2, or 3 heteroatoms independently selected from N, O, and S.

In some embodiments, the compound of Formula I or I-Z is of Formula III-Z:

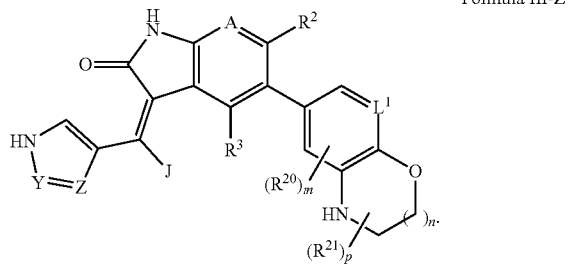

Formula III-Z

In some embodiments, the compound of Formula I, I-Z or III-Z is of a Formula IIIa-Z:

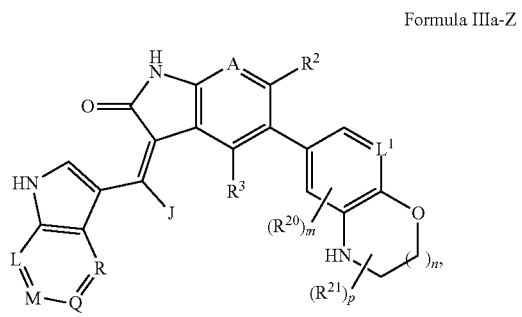

Formula IIIa-Z wherein L is N or CR$^{16}$; M is N or CR$^{16}$; Q is N or CR$^{17}$; and R is N or CR$^{18}$; and each R$^{15}$, R$^{16}$, R$^{17}$, and R$^{18}$ is independently selected from the group consisting of H, halogen, CN, —N($R^8$)$_2$, —CON($R^8$)$_2$, —N($R^{13}$)COR$^{13}$, —S(O)$_2$R$^{13}$, $C_1$-$C_3$ alkyl, $C_1$-$C_3$ alkoxy, $C_6$-$C_{10}$ aryl, 5-10 membered heteroaryl having 1, 2, or 3 heteroatoms independently selected from N, O, and S, and 4-6 membered heterocyclyl having 1, 2, or 3 heteroatoms independently selected from N, O, and S.

Also provided are pharmaceutical compositions comprising a compound disclosed herein, or the pharmaceutically acceptable salt thereof, and a pharmaceutically acceptable excipient or carrier. In some embodiments, the pharmaceutical composition further comprises one or more additional therapeutic agents, or a pharmaceutically acceptable salt thereof.

Also provided are methods of inhibiting hematopoietic progenitor kinase 1 (HPK1) activity in a subject in need thereof, wherein the methods comprise administering to the subject a therapeutically effective amount of a compound of the disclosure, or the pharmaceutically acceptable salt thereof, or the pharmaceutical composition thereof.

Also provided are methods of treating a disease or disorder associated with increased hematopoietic progenitor kinase 1 (HPK1) activity in a subject in need thereof, wherein the methods comprise administering to the subject a therapeutically effective amount of a compound disclosed herein, or the pharmaceutically acceptable salt thereof, or the pharmaceutical composition thereof.

Also provided are methods of increasing T-cell activation in a subject in need thereof, the methods comprising administering to the subject a therapeutically effective amount of a compound of disclosed herein, or the pharmaceutically acceptable salt thereof, or the pharmaceutical composition thereof.

Also provided are methods of treating cancer in a subject in need thereof, comprising administering to the subject a therapeutically effective amount of a compound disclosed herein, or the pharmaceutically acceptable salt thereof, or the pharmaceutical composition thereof. In some embodiments, the cancer is selected from the group consisting of bladder cancer, breast cancer, colorectal cancer, gastric cancer, head and neck squamous cell carcinoma, Hodgkin lymphoma, Merkel-cell carcinoma, mesothelioma, melanoma, non-small cell lung cancer, lung cancer, ovarian cancer, pancreatic cancer, prostate cancer, renal cell carcinoma, small cell lung cancer, transitional cell carcinoma, and urothelial cancer.

Also provided are methods of inhibiting the growth or proliferation of cancer cells in a subject in need thereof, wherein the methods comprise administering to the subject a therapeutically effective amount of a compound disclosed herein, or the pharmaceutically acceptable salt thereof, or the pharmaceutical composition thereof.

Also provided are methods of treating or preventing a hepatitis B virus (HBV) infection in a subject in need thereof, wherein the methods comprise administering to the subject a therapeutically effective amount of a compound disclosed herein, or the pharmaceutically acceptable salt thereof, or the pharmaceutical composition thereof.

Also provided are methods of treating or preventing a human immunodeficiency virus (HIV) infection in a subject in need thereof, wherein the methods comprise administering to the subject a therapeutically effective amount of a compound disclosed herein, or the pharmaceutically acceptable salt thereof, or the pharmaceutical composition there.

In various embodiments, the methods of disclosed herein, further comprise administering a therapeutically effective amount of one or more additional therapeutic agents, or a pharmaceutically acceptable salt thereof.

Also provided are the use of the compounds disclosed herein in a therapy. In some embodiments, the compounds of the disclosure are for use in a method of inhibiting hematopoietic progenitor kinase 1 (HPK1) activity in a subject in need thereof. In some embodiments, the compounds provided herein are for use in a method of treating a disease or disorder associated with increased hematopoietic progenitor kinase 1 (HPK1) activity in a subject in need thereof. In some embodiments, the compounds provided herein are for use in a method of increasing T-cell activation in a subject in need thereof. In some embodiments, the compounds provided herein are for use in a method of treating cancer in a subject in need thereof. In some embodiments, the compounds provided herein are for use in a method of inhibiting the growth or proliferation of cancer cells in a subject in need thereof. In some embodiments, the compounds provided herein are for use in a method of treating or preventing a hepatitis B virus (HBV) infection in a subject in need thereof. In some embodiments, the compounds provided herein are for use in a method of treating or preventing a human immunodeficiency virus (HIV) infection in a subject in need thereof.

In some embodiments, the compounds disclosed herein are used with one or more additional therapeutic agents, or a pharmaceutically acceptable salt thereof.

DETAILED DESCRIPTION

I. Definitions

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present disclosure, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring indicates that the point of attachment for a substituent on the ring can be at any ring atom. For example, $R^a$ in the below structure can be attached to any of the five carbon ring atoms or $R^a$ can replace the hydrogen attached to the nitrogen ring atom:

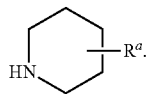

The prefix "$C_{u-v}$" and/or "$C_u$-$C_v$" indicates that the following group has from u to v carbon atoms. For example, "$C_{1-6}$ alkyl" and/or "$C_1$-$C_6$ alkyl" indicates that the alkyl group has from 1 to 6 carbon atoms. Likewise, the term "x-y membered" rings, wherein x and y are numerical ranges, such as "3-12-membered heterocyclyl", refers to a ring containing x-y atoms (e.g. 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula I, II, IIa, IIb, III, or IIIa. Also included are the specific compounds of Examples C1 to C70.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, the term "about X" includes description of "X".

The term "adjoining atoms" as used herein refers to atoms that are immediately next to each other. For example, in "$C^1$-$C^2$-$C^3$-$C^4$" atoms $C^1$ and $C^3$ are adjoining atoms to $C^2$, atoms $C^2$ and $C^4$ are adjoining atoms to $C^3$, atom $C^2$ is adjoining atom to $C_1$, and atom $C^3$ is adjoining atom to $C^4$.

"Alkyl" refers to an unbranched or branched saturated hydrocarbon chain. As used herein, alkyl has 1 to 20 carbon atoms (i.e., $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 4 carbon atoms (i.e., $C_1$-$C_4$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an aliphatic group containing at least one carbon-carbon double bond and having from 2 to 20 carbon atoms (i.e., $C_2$-$C_{20}$ alkenyl), 2 to 8 carbon atoms (i.e., $C_2$-$C_8$ alkenyl), 2 to 6 carbon atoms (i.e., $C_2$-$C_6$ alkenyl), or 2 to 4 carbon atoms (i.e., $C_2$-$C_4$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_2$-$C_{20}$ alkynyl), 2 to 8 carbon atoms (i.e., $C_2$-$C_8$ alkynyl), 2 to 6 carbon atoms (i.e., $C_2$-$C_6$ alkynyl), or 2 to 4 carbon atoms (i.e., $C_2$-$C_4$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(═O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(═O)NR$^y$R$^z$ and an "N-amido" group which refers to the group —NR$^y$C(═O)R$^z$, wherein R$^y$ and R$^z$ are independently selected from the group consisting of hydrogen, alkyl, aryl, haloalkyl, heteroaryl, cycloalkyl, and heterocyclyl; each of which may be optionally substituted.

"Amino" refers to the group —NR$^y$R$^z$ wherein R$^y$ and R$^z$ are independently selected from the group consisting of hydrogen, alkyl, haloalkyl, aryl, heteroaryl, cycloalkyl, and heterocyclyl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_6$-$C_{20}$ aryl), 6 to 12 carbon ring atoms (i.e., $C_6$-$C_{12}$ aryl), or 6 to 10 carbon ring atoms (i.e., $C_6$-$C_{10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_3$-$C_{20}$ cycloalkyl), 3 to 12 ring carbon atoms (i.e., $C_3$-$C_{12}$ cycloalkyl), 3 to 10 ring carbon atoms (i.e., $C_3$-$C_{10}$ cycloalkyl), 3 to 8 ring carbon atoms (i.e., $C_3$-$C_8$ cycloalkyl), or 3 to 6 ring carbon atoms (i.e., $C_3$-$C_6$ cycloalkyl). Examples of cycloalkyl groups include cyclopropyl, cyclobutyl, cyclopentyl, and cyclohexyl.

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., $C_1$-$C_{20}$ heteroaryl), 3 to 12 carbon ring atoms (i.e., $C_3$-$C_{12}$ heteroaryl), or 3 to 8 carbon ring atoms (i.e., $C_3$-$C_8$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" refers to a non-aromatic cyclic alkyl group, with one or more ring heteroatoms independently selected from nitrogen, oxygen and sulfur. As used herein, "heterocyclyl" or "heterocyclic ring" refer to rings that are saturated or partially saturated unless otherwise indicated, e.g., in some embodiments "heterocyclyl" or "heterocyclic ring" refers to rings that are partially saturated where specified. The term "heterocyclyl" or "heterocyclic ring" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., $C_2$-$C_{20}$ heterocyclyl), 2 to 12 carbon ring atoms (i.e., $C_2$-$C_{12}$ heterocyclyl), 2 to 10 carbon ring atoms (i.e., $C_2$-$C_{10}$ heterocyclyl), 2 to 8 carbon ring atoms (i.e., $C_2$-$C_8$ heterocyclyl), 3 to 12 carbon ring atoms (i.e., $C_3$-$C_{12}$ heterocyclyl), 3 to 8 carbon ring atoms (i.e., $C_3$-$C_8$ heterocyclyl), or 3 to 6 carbon ring atoms (i.e., $C_3$-$C_6$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. As used herein, the terms "heterocyclyl", and "heterocyclic ring" are used interchangeably. In some embodiments, a heterocyclyl is substituted with an oxo group.

"Hydroxy" or "hydroxyl" refers to the group —OH.

"Oxo" refers to the group (=O) or (O).

"Sulfonyl" refers to the group —S(O)$_2$R$^c$, where R$^c$ is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, amino, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, amino, alkoxy, halo, oxo, and hydroxyl; "substituted heterocyclyl" refers to a heterocyclyl group having one or more substituents including alkyl, amino, haloalkyl, heterocyclyl, cycloalkyl, aryl, heteroaryl, alkoxy, halo, oxo, and hydroxyl; "substituted aryl" refers to an aryl group having one or more substituents including halo, alkyl, amino, haloalkyl, cycloalkyl, heterocyclyl, heteroaryl, alkoxy, and cyano; "substituted heteroaryl" refers to an heteroaryl group having one or more substituents including halo, amino, alkyl, haloalkyl, cycloalkyl, aryl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

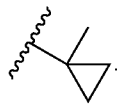

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

A "tautomer" refers to a proton shift from one atom of a molecule to another atom of the same molecule. The present disclosure includes tautomers of any compounds provided herein.

Some of the compounds provided herein exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

A "solvate" is formed by the interaction of a solvent and a compound. Solvates of salts of the compounds provided herein are also provided. Hydrates of the compounds provided herein are also provided.

Any formula or structure provided herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^2$H, $^3$H, $^{13}$C and $^{14}$C are incorporated, are also provided herein. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The present disclosure also includes compounds of Formula I, I-Z, I-E, II-Z, IIa-Z, IIb-Z, III-Z, or IIIa-Z in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I, I-Z, I-E, II-Z, IIa-Z, IIb-Z, III-Z, or IIIa-Z, when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the present disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example, increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, I-Z, I-E, II-Z, IIa-Z, IIb-Z, III-Z, or IIIa-Z.

The concentration of such a heavier isotope, specifically deuterium, may be defined by an isotopic enrichment factor. In the compounds of this disclosure, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure, any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, and the like. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of hematopoietic progenitor kinase 1 (HPK1) activity. The therapeutically effective amount may vary depending on the subject, and the disease or condition being treated, the weight and age of the subject, the severity of the disease or condition, and the manner of administering, which can readily be determined by one of ordinary skill in the art.

The term "inhibition" indicates a decrease in the baseline activity of a biological activity or process. "Inhibition of activity of HPK1" or variants thereof refers to a decrease in HPK1 activity as a direct or indirect response to the presence of a compound of the present disclosure relative to the HPK1 activity in the absence of the compound of the present disclosure. "Inhibition of HPK1" refers to a decrease in HPK1 activity as a direct or indirect response to the presence of a compound provided herein relative to the HPK1 activity in the absence of the compound provided herein. In some embodiments, the inhibition of HPK1 activity may be compared in the same subject prior to treatment, or other subjects not receiving the treatment.

II. Compounds

In one aspect, provided herein is a compound of Formula I:

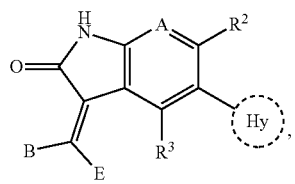

Formula I or a pharmaceutically acceptable salt thereof, wherein:
A is N or $CR^1$;
each $R^1$, $R^2$, and $R^3$ is independently H, halogen, —CN, —N($R^{13}$)$_2$, $C_1$-$C_3$ alkyl, $C_1$-$C_3$ haloalkyl, $C_2$-$C_3$ alkynyl, $C_1$-$C_3$ alkoxy, or —SO$_2R^{13}$, wherein the $C_2$-$C_3$ alkynyl is unsubstituted or substituted with 1, 2, or 3 $R^9$ groups;

one of B and E is  and the other is J;
J is H, —CN, $C_1$-$C_3$ alkyl, or $C_3$-$C_6$ cycloalkyl; wherein the $C_1$-$C_3$ alkyl or $C_3$-$C_6$ cycloalkyl is unsubstituted or substituted with 1, 2, or 3 $R^{10}$ groups;

 is a group of formula

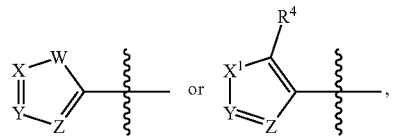

wherein
W is $NR^4$ or S;
X is N or $CR^5$;
Y is N or $CR^6$;
Z is N or $CR^7$;
$X^1$ is NH;
$R^4$ is H;
each $R^5$, $R^6$, and $R^7$ is independently H, halogen, —CN, —CON($R^8$)$_2$, —NR$^{13}$C(O)R$^{13}$, —SO$_2$N($R^{13}$)$_2$, $C_1$-$C_3$ alkyl, $C_1$-$C_3$ alkoxy, —N($R^{13}$)$_2$, $C_3$-$C_6$ cycloalkyl, $C_6$-$C_{10}$ aryl, 5-10 membered heteroaryl having 1, 2, or 3 heteroatoms independently selected from N, O, and S, and 4-6 membered heterocyclyl having 1, 2, or 3 heteroatoms independently selected from N, O, and S; wherein the $C_1$-$C_3$ alkyl, $C_1$-$C_3$ alkoxy, $C_3$-$C_6$ cycloalkyl, $C_6$-$C_{10}$ aryl, 5-10 membered heteroaryl, or 4-6 membered heterocyclyl is unsubstituted or substituted with 1, 2, or 3 $R^{11}$ groups;
or wherein $R^5$ and $R^6$, or $R^6$ and $R^7$ together with atoms to which they are attached form a phenyl or a 5-6 membered heteroaryl having 1 or 2 heteroatoms independently selected from N, O, and S, wherein the phenyl or the 5-6 membered heteroaryl is unsubstituted or substituted with 1, 2, or 3 $R^{11}$ groups;
each $R^8$ is independently H or $C_1$-$C_3$ alkyl, wherein the $C_1$-$C_3$ alkyl is unsubstituted or substituted with 1, 2, or 3 $R^{12}$ groups; or wherein two $R^8$ groups together with the nitrogen they are attached to form a 4-6 membered heterocyclic ring having 1 or 2 heteroatoms selected from the group consisting of N, O, or S, wherein the 4-6 membered heterocyclic ring is unsubstituted or substituted with 1, 2, or 3 $R^{12}$ groups;
each $R^9$ is independently —OR$^{13}$, $C_1$-$C_3$ alkyl, or $C_3$-$C_6$ cycloalkyl;
each $R^{10}$ and $R^{11}$ is independently selected from the group consisting of —OR$^{13}$, halogen, CN, —N($R^8$)$_2$, —CON($R^8$)$_2$, —N($R^{13}$)COR$^{13}$, —S(O)$_2R^{13}$, $C_1$-$C_3$ alkyl, $C_3$-$C_6$ cycloalkyl, 4-6 membered heterocyclyl having 1, 2, or 3 heteroatoms independently selected from N, O, and S, $C_6$-$C_{10}$ aryl, and 5-10 membered heteroaryl having 1, 2, or 3 heteroatoms independently selected from N, O, and S;
each $R^{12}$ is independently —OR$^{13}$, $C_1$-$C_3$ alkyl, or —N($R^{13}$)$_2$; wherein the $C_1$-$C_3$ alkyl is unsubstituted or substituted with 1, 2, or 3 groups independently selected from —OR$^{13}$ and —N($R^{13}$)$_2$,
each $R^{13}$ is independently H or $C_1$-$C_3$ alkyl wherein the $C_1$-$C_3$ alkyl is unsubstituted or substituted with 1, 2, or 3 $R^{22}$ groups;
each $R^{22}$ is independently selected from the group consisting of halogen, —OH, $C_1$-$C_3$ alkyl, $C_1$-$C_3$ alkoxy, —NH$_2$, —NH($C_1$-$C_3$ alkyl), —N($C_1$-$C_3$ alkyl)$_2$ wherein each $C_1$-$C_3$ alkyl is same or different, $C_3$-$C_6$ cycloalkyl, a 4-6 membered heterocyclyl with 1, 2, or 3 heteroatoms selected from N, O, and S, $C_6$-$C_{10}$ aryl, and a 5-10 membered heteroaryl having 1, 2, or 3 heteroatoms independently selected from N, O, and S; and

 is a group of formula:

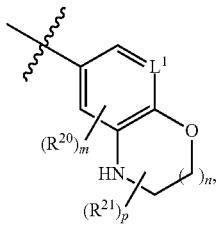

wherein $L^1$ is N or $CR^{19}$;
n is 0, 1 or 2;
m is 0, 1, or 2;
p is 0, 1, 2, 3, 4, 5, or 6;
$R^{19}$ is H, —$OR^{13}$, halogen, CN, —$N(R^{13})_2$, or $C_1$-$C_3$ alkyl;
each $R^{20}$ is independently —$OR^{13}$, halogen, CN, —$N(R^{13})_2$, or $C_1$-$C_3$ alkyl; and
each $R^{21}$ is independently —$OR^{13}$, oxo, halogen, CN, —$N(R^{13})_2$, or $C_1$-$C_3$ alkyl;
or two $R^{21}$ groups on same or adjoining atoms are joined together to form a 3-6 membered carbocyclic ring or a 3-6 membered heterocyclic ring having 1 or 2 heteroatoms selected from N, O, and S.

In some embodiments, the compound of Formula I is of a Formula I-Z:

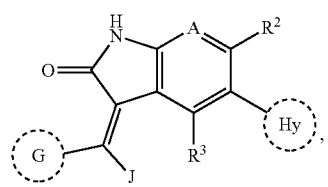

Formula I-Z wherein the variables A, $R^2$, $R^3$, J, Hy, and G are as defined above for Formula I.

In some embodiments, the compound of Formula I is of Formula I-E:

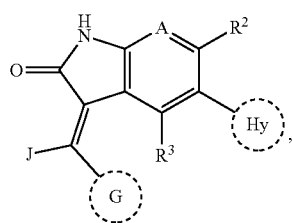

Formula I-E wherein the variables A, $R^2$, $R^3$, J, Hy, and G are as defined above for Formula I.

In some embodiments, of the compounds of Formula I, I-Z, or I-E, G is

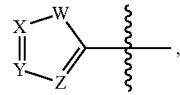

wherein W is NH or S; X is N or $CR^5$; Y is N or $CR^6$; and Z is N or $CR^7$; wherein each $R^5$, $R^6$, and $R^7$ is independently (i) H, (ii) halogen, (iii) —CN, (iv) —$CON(R^8)_2$, (v) —$NR^{13}C(O)R^{13}$, (vi) —$SO_2N(R^{13})_2$, (vii) $C_1$-$C_3$ alkyl, (vii) $C_1$-$C_3$ alkoxy, (ix) —$N(R^{13})_2$, (x) $C_3$-$C_6$ cycloalkyl, (xi) $C_6$-$C_{10}$ aryl, (xii) 5-10 membered heteroaryl having 1, 2, or 3 heteroatoms independently selected from N, O, and S, and (xiii) 4-6 membered heterocyclyl having 1, 2, or 3 heteroatoms independently selected from N, O, and S; wherein the $C_1$-$C_3$ alkyl, $C_1$-$C_3$ alkoxy, $C_3$-$C_6$ cycloalkyl, $C_6$-$C_{10}$ aryl, 5-10 membered heteroaryl, or 4-6 membered heterocyclyl is unsubstituted or substituted with 1, 2, or 3 $R^{11}$ groups;
or wherein $R^5$ and $R^6$, or $R^6$ and $R^7$ together with atoms to which they are attached form (i) a phenyl or (ii) a 5-6 membered heteroaryl having 1 or 2 heteroatoms independently selected from N, O, and S, wherein the phenyl or the 5-6 membered heteroaryl is unsubstituted or substituted with 1, 2, or 3 $R^{11}$ groups;
each $R^8$ is independently H or $C_1$-$C_3$ alkyl, wherein the $C_1$-$C_3$ alkyl is unsubstituted or substituted with 1, 2, or 3 $R^{12}$ groups; or wherein two $R^8$ groups together with the nitrogen they are attached to form a 4-6 membered heterocyclic ring having 1 or 2 heteroatoms selected from the group consisting of N, O, or S, wherein the 4-6 membered heterocyclic ring is unsubstituted or substituted with 1, 2, or 3 $R^{12}$ groups;
each $R^{12}$ is independently —$OR^{13}$, $C_1$-$C_3$ alkyl, or —$N(R^{13})_2$; wherein the $C_1$-$C_3$ alkyl is unsubstituted or substituted with 1, 2, or 3 groups independently selected from —$OR^{13}$ and —$N(R^{13})_2$,
each $R^{11}$ is independently selected from the group consisting of (i) —$OR^{13}$, (ii) halogen, (iii) CN, (iv) —$N(R^8)_2$, (v) —$CON(R^8)_2$, (vi) —$N(R^{13})COR^{13}$, (vii) —$S(O)_2R^{13}$, (viii) $C_1$-$C_3$ alkyl, (ix) $C_3$-$C_6$ cycloalkyl, (x) 4-6 membered heterocyclyl having 1, 2, or 3 heteroatoms independently selected from N, O, and S, (xi) $C_6$-$C_{10}$ aryl, and (xii) 5-10 membered heteroaryl having 1, 2, or 3 heteroatoms independently selected from N, O, and S; and
each $R^{13}$ is independently H or $C_1$-$C_3$ alkyl, wherein the $C_1$-$C_3$ alkyl is unsubstituted or substituted with 1, 2, or 3 $R^{22}$ groups; and
each $R^{22}$ is independently selected from the group consisting of halogen, —OH, $C_1$-$C_3$ alkyl, $C_1$-$C_3$ alkoxy, —$NH_2$, —$NH(C_1$-$C_3$ alkyl), —$N(C_1$-$C_3$ alkyl)$_2$ wherein each $C_1$-$C_3$ alkyl is same or different, $C_3$-$C_6$ cycloalkyl, 4-6 membered heterocyclyl with 1, 2, or 3 heteroatoms selected from N, O, and S, $C_6$-$C_{10}$ aryl, and 5-10 membered heteroaryl having 1, 2, or 3 heteroatoms independently selected from N, O, and S.

In some embodiments of the compounds of Formula I and I-Z, G is

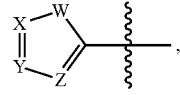

and the compound of Formula I or I-Z is of Formula II-Z:

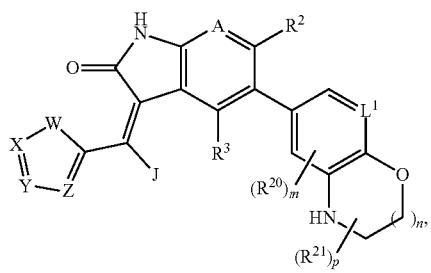

Formula II-Z wherein the variables W, X, Y, Z, J, A, $R^2$, $R^3$, $L^1$, $R^{20}$, $R^{21}$, m, n, and p are as defined above for Formula I.

In some embodiments of the compounds of Formula I, I-Z, I-E, and II-Z, W is NH or S, X is $CR^5$, Y is $CR^6$, and Z is $CR^7$. In some embodiments, W is NH or S, X is N, Y is $CR^6$, and Z is $CR^7$. In some embodiments, W is NH or S, X is $CR^5$, Y is N, and Z is $CR^7$. In some embodiments, W is NH or S, X is $CR^5$, Y is $CR^6$, and Z is N. In some embodiments, W is NH or S, X is N, Y is N, and Z is $CR^7$. In some embodiments, W is NH or S, X is $CR^5$, Y is N, and Z is N. In some embodiments, W is NH or S, X is N, Y is $CR^6$, and Z is N.

In some embodiments of the compounds of Formula I, I-Z, I-E, and II-Z, W is S, X is $CR^5$, Y is $CR^6$, and Z is $CR^7$. In some embodiments, W is S, X is N, Y is $CR^6$, and Z is $CR^7$. In some embodiments, W is S, X is $CR^5$, Y is N, and Z is $CR^7$. In some embodiments, W is S, X is $CR^5$, Y is $CR^6$, and Z is N. In some embodiments, W is S, X is N, Y is N, and Z is $CR^7$. In some embodiments, W is S, X is $CR^5$, Y is N, and Z is N. In some embodiments, W is S, X is N, Y is $CR^6$, and Z is N.

In some embodiments of the compounds of Formula I, I-Z, I-E, and II-Z, W is NH, X is $CR^5$, Y is $CR^6$, and Z is $CR^7$. In some embodiments, W is NH, X is N, Y is $CR^6$, and Z is $CR^7$. In some embodiments, W is NH, X is $CR^5$, Y is N, and Z is $CR^7$. In some embodiments, W is NH, X is $CR^5$, Y is $CR^6$, and Z is N. In some embodiments, W is NH, X is N, Y is N, and Z is $CR^7$. In some embodiments, W is NH, X is $CR^5$, Y is N, and Z is N. In some embodiments, W is NH, X is N, Y is $CR^6$, and Z is N.

In some embodiments of the compounds of Formula I, I-E, and I-Z,  is

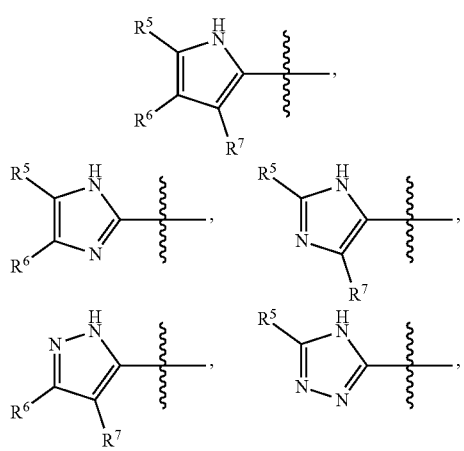

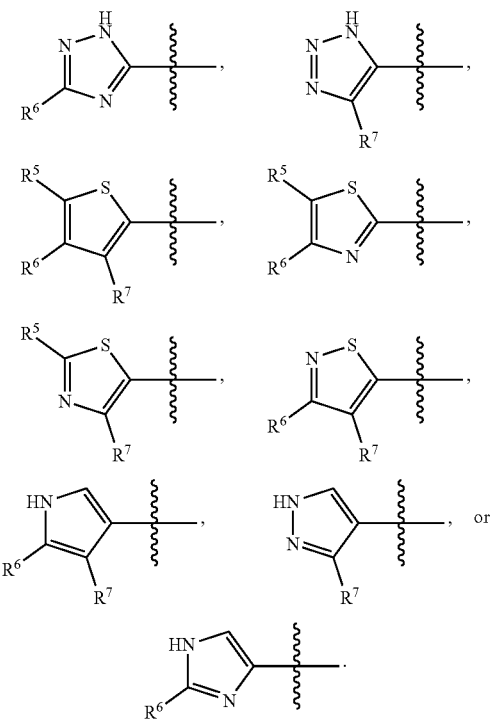

In some embodiments of the compounds of Formula I, I-Z and I-E,  is

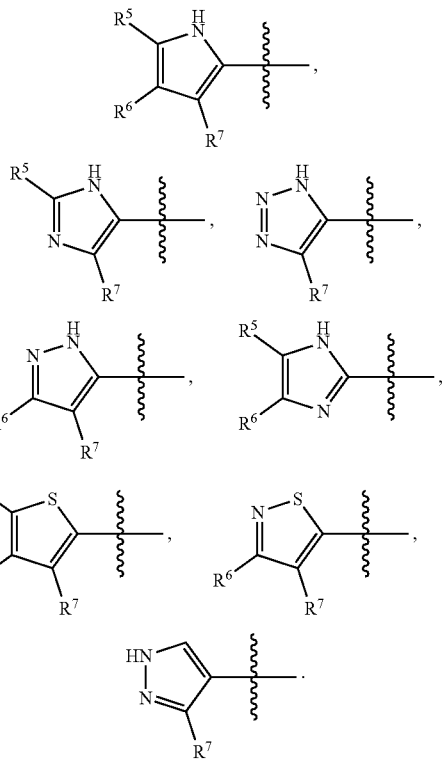

In some embodiments of the compounds of Formula I, I-Z and I-E,  is

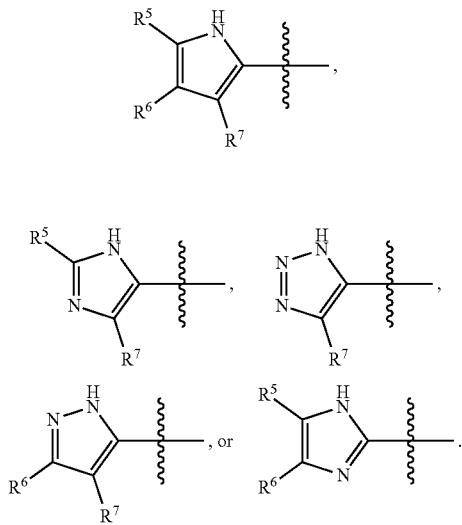

In some embodiments of the compounds of Formula I, I-Z and I-E,  is

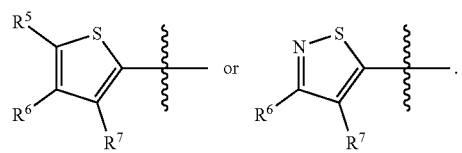

In some embodiments, of the compounds of Formula I, I-Z and I-E  is

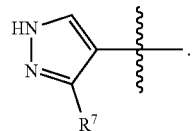

In some embodiments of the compounds of Formula I, I-Z and I-E,  is

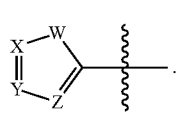

In some embodiments, W is NH. In some embodiments, W is S.

In some embodiments of the compounds of Formula I, I-Z and I-E,  is

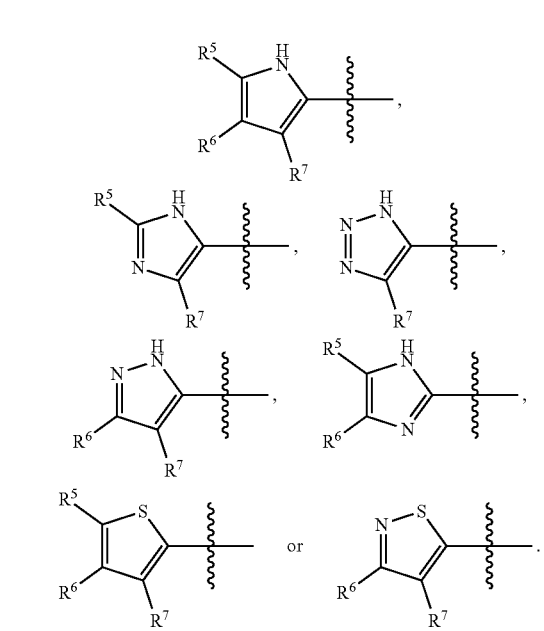

In some embodiments of the compounds of Formula I, I-Z and I-E,  is selected from the group consisting of

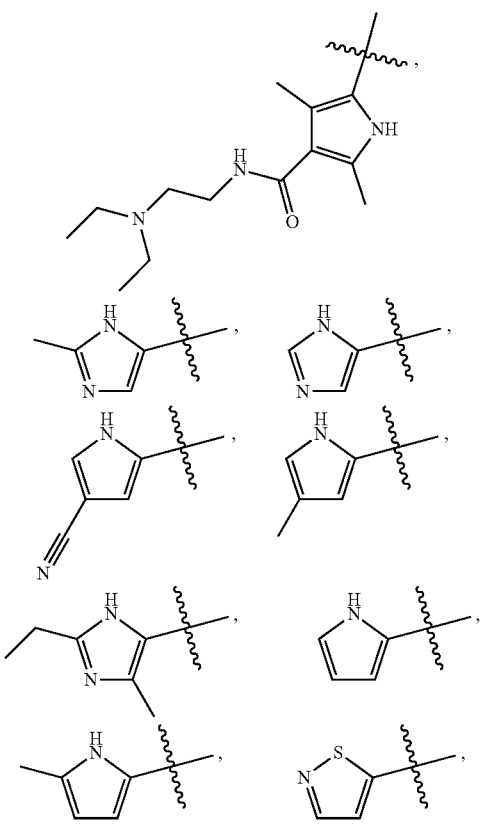

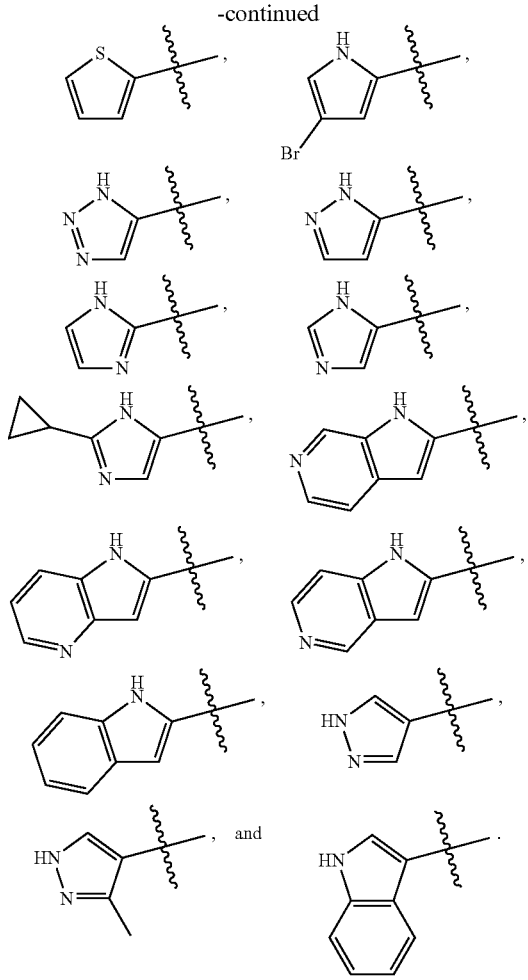
In some embodiments, (G) is selected from the group consisting of
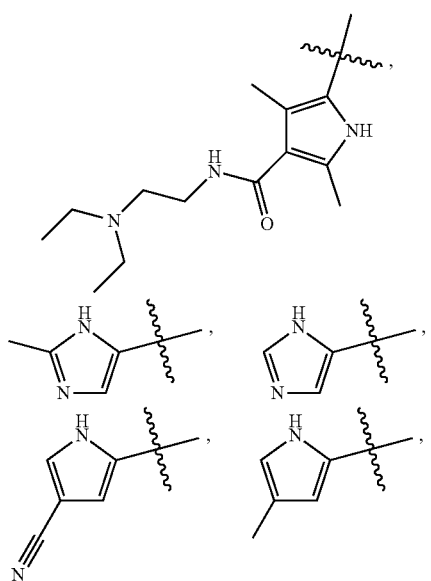
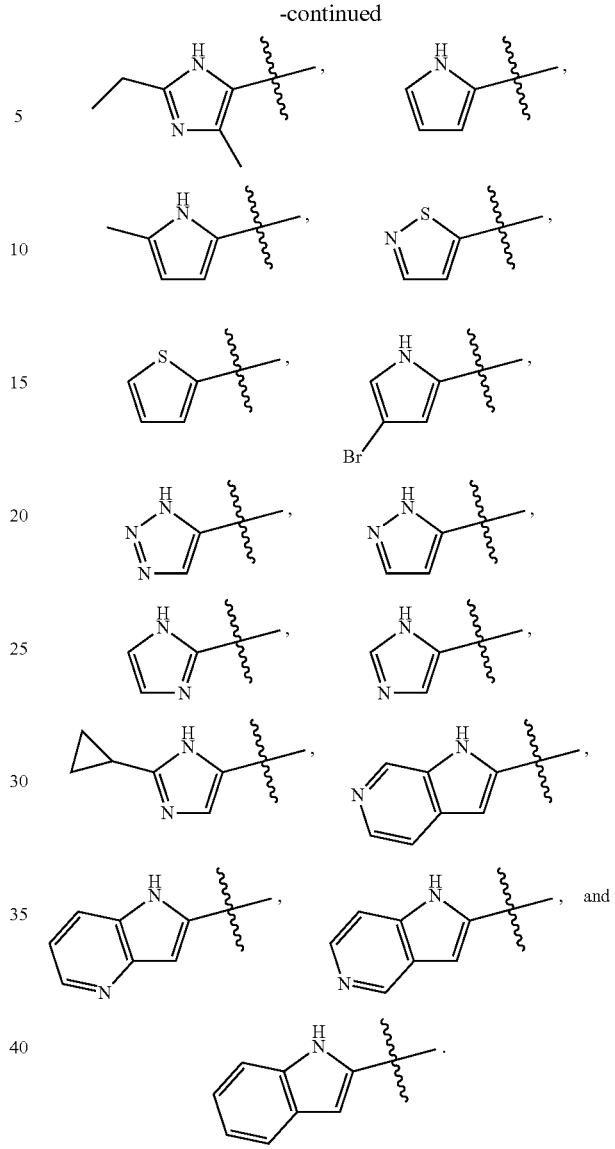
In some embodiments, (G) is selected from the group consisting of -continued

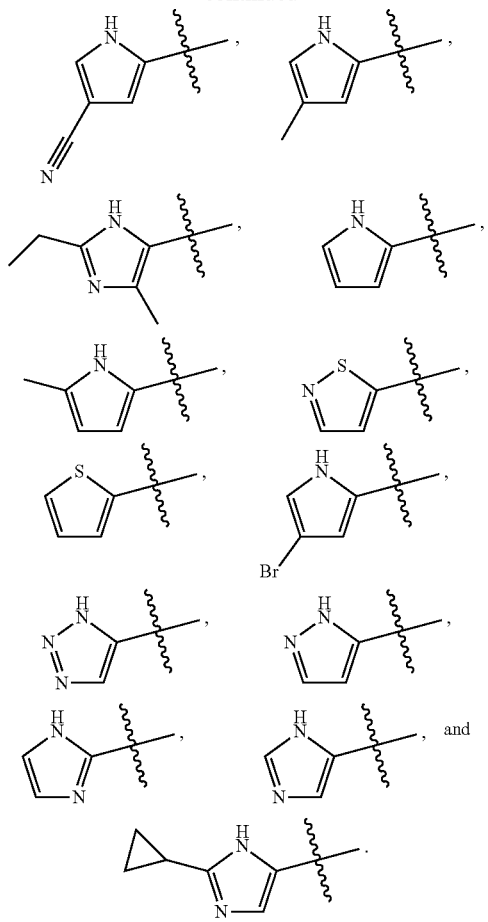

In some embodiments, (G) is selected from the group consisting of

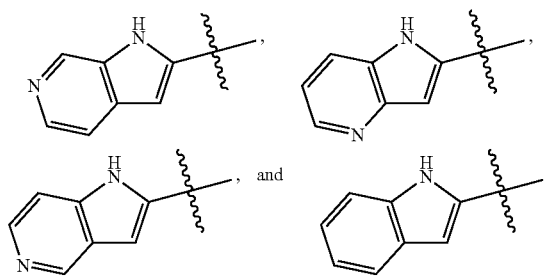

In some embodiments, (G) is selected from the group consisting of

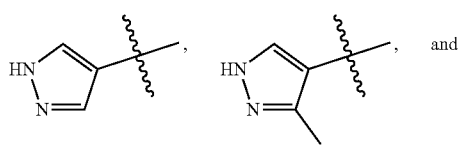

-continued

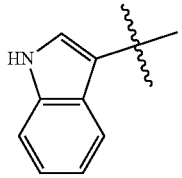

In some embodiments, (G) is

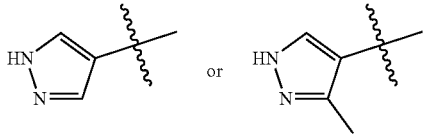

In some embodiments, is

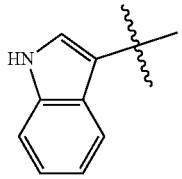

In some embodiments, the compound of Formula I, I-Z, or II-Z is of Formula IIa-Z:

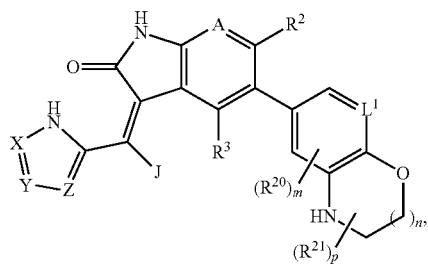

Formula IIa-Z wherein the variables X, Y, Z, J, A, $R^2$, $R^3$, $L^1$, $R^{20}$, $R^{21}$, m, n, and p are as defined above for Formula I.

In some embodiments of the compounds of Formula I, I-Z, I-E, II-Z, and IIa-Z, each $R^5$, $R^6$, and/or $R^7$ is independently (i) H, (ii) halogen, (iii) —CN, (iv) —CON($R^8$)$_2$, (v) —NR$^{13}$C(O)R$^{13}$, (vi) —SO$_2$N(R$^{13}$)$_2$, (vii) $C_1$-$C_3$ alkyl, (viii) $C_1$-$C_3$ alkoxy, (ix) —N(R$^{13}$)$_2$, (x) $C_3$-$C_6$ cycloalkyl, (xi) $C_6$-$C_{10}$ aryl, (xii) 5-10 membered heteroaryl having 1, 2, or 3 heteroatoms independently selected from N, O, and S, and (xiii) 4-6 membered heterocyclyl having 1, 2, or 3 heteroatoms independently selected from N, O, and S; wherein the $C_1$-$C_3$ alkyl, $C_1$-$C_3$ alkoxy, $C_3$-$C_6$ cycloalkyl, $C_6$-$C_{10}$ aryl, 5-10 membered heteroaryl, or 4-6 membered heterocyclyl is unsubstituted or substituted with 1, 2, or 3 $R^{11}$ groups.

In some embodiments for the compound of Formula I, I-Z, I-E, II-Z, and IIa-Z, each $R^5$, $R^6$, and/or IV is independently selected from the group consisting of (i) H, (ii)

halogen, (iii) —CN, (iv) —CON($R^8$)$_2$, (v) —N$R^{13}$C(O)$R^{13}$, (vi) —SO$_2$N($R^{13}$)$_2$, (vii) $C_1$-$C_3$ alkyl, (viii) $C_1$-$C_3$ alkoxy, (ix) —N($R^{13}$)$_2$, (x) $C_3$-$C_6$ cycloalkyl, (xi) $C_6$-$C_{10}$ aryl, (xii) 5-10 membered heteroaryl having 1, 2, or 3 heteroatoms independently selected from N, O, and S, and (xiii) 4-6 membered heterocyclyl having 1, 2, or 3 heteroatoms independently selected from N, O, and S; wherein the $C_1$-$C_3$ alkyl, $C_1$-$C_3$ alkoxy, $C_3$-$C_6$ cycloalkyl, $C_6$-$C_{10}$ aryl, 5-10 membered heteroaryl, or 4-6 membered heterocyclyl is unsubstituted or substituted with one $R^{11}$ group.

In some embodiments for the compound of Formula I, I-Z, I-E, II-Z, and IIa-Z, each $R^5$, $R^6$, and/or $R^7$ is independently selected from the group consisting of (i) H, (ii) halogen, (iii) —CN, (iv) —CON($R^8$)$_2$, (v) —N$R^{13}$C(O)$R^{13}$, (vi) —SO$_2$N($R^{13}$)$_2$, (vii) $C_1$-$C_3$ alkyl, (viii) $C_1$-$C_3$ alkoxy, (ix) —N($R^{13}$)$_2$, (x) $C_3$-$C_6$ cycloalkyl, (xi) $C_6$-$C_{10}$ aryl, (xii) 5-10 membered heteroaryl having 1, 2, or 3 heteroatoms independently selected from N, O, and S, and (xiii) 4-6 membered heterocyclyl having 1, 2, or 3 heteroatoms independently selected from N, O, and S; wherein the $C_1$-$C_3$ alkyl, $C_1$-$C_3$ alkoxy, $C_3$-$C_6$ cycloalkyl, $C_6$-$C_{10}$ aryl, 5-10 membered heteroaryl, or 4-6 membered heterocyclyl is unsubstituted.

In some embodiments for the compound of Formula I, I-Z, I-E, II-Z, and IIa-Z, each $R^5$, $R^6$, and/or $R^7$ is independently selected from the group consisting of (i) H, (ii) halogen, (iii) —CN, (iv) —CON($R^8$)$_2$, (v) —N$R^{13}$C(O)$R^{13}$, (vi) —SO$_2$N($R^{13}$)$_2$, (vii) $C_1$-$C_3$ alkyl, (viii) —N($R^{13}$)$_2$, (ix) $C_3$-$C_6$ cycloalkyl, and (x) 5-10 membered heteroaryl having 1, 2, or 3 heteroatoms independently selected from N, O, and S; wherein the $C_1$-$C_3$ alkyl, $C_3$-$C_6$ cycloalkyl or 5-10 membered heteroaryl is unsubstituted; each $R^8$ is independently H or $C_1$-$C_3$ alkyl, wherein the $C_1$-$C_3$ alkyl is unsubstituted or substituted with 1, 2, or 3 $R^{12}$ groups; or wherein two $R^8$ groups together with the nitrogen they are attached to form a 4-6 membered heterocyclic ring having 1 or 2 heteroatoms selected from the group consisting of N, O, or S, wherein the 4-6 membered heterocyclic ring is unsubstituted or substituted with one $R^{12}$ group; each $R^{12}$ is independently —O$R^{13}$, $C_1$-$C_3$ alkyl, or —N($R^{13}$)$_2$, wherein the $C_1$-$C_3$ alkyl is unsubstituted or substituted with —O$R^{13}$ or —N($R^{13}$)$_2$; and each $R^{13}$ is independently H or $C_1$-$C_3$ alkyl.

In some embodiments for the compound of Formula I, I-Z, I-E, II-Z, and IIa-Z, each $R^5$, $R^6$, and/or $R^7$ is independently selected from the group consisting of (i) H, (ii) halogen, (iii) —CN, (iv) —CON($R^8$)$_2$, (v) $C_1$-$C_3$ alkyl, and (vi) $C_3$-$C_6$ cycloalkyl, wherein the $C_1$-$C_3$ alkyl or $C_3$-$C_6$ cycloalkyl is unsubstituted; each $R^8$ is independently H or $C_1$-$C_3$ alkyl, wherein the $C_1$-$C_3$ alkyl is unsubstituted or substituted with one $R^{12}$ group; $R^{12}$ is —O$R^{13}$, $C_1$-$C_3$ alkyl, or —N($R^{13}$)$_2$; and each $R^{13}$ is independently H or $C_1$-$C_3$ alkyl.

In some embodiments for the compound of Formula I, I-Z, I-E, II-Z, and IIa-Z, each $R^5$, $R^6$, and/or $R^7$ is independently selected from the group consisting of H, Br, —CN, —CONH$R^8$, $C_1$-$C_3$ alkyl, and $C_3$-$C_6$ cycloalkyl, wherein the $C_1$-$C_3$ alkyl or $C_3$-$C_6$ cycloalkyl is unsubstituted; $R^8$ is $C_1$-$C_3$ alkyl, wherein the $C_1$-$C_3$ alkyl is unsubstituted or substituted with one $R^{12}$ group; $R^{12}$ is —O$R^{13}$ or —N($R^{13}$)$_2$; and each $R^{13}$ is independently $C_1$-$C_3$ alkyl. In some embodiments, each $R^5$, $R^6$, and/or $R^7$ is independently selected from the group consisting of H, Br, —CN, —CONHCH$_2$CH$_2$N(CH$_2$CH$_3$)$_2$, CH$_3$, and cyclopropyl.

In some embodiments of the compounds of Formula I, I-Z, I-E, and II-Z, W is NH, X is C$R^5$, Y is C$R^6$, and Z is C$R^7$; wherein each $R^5$, $R^6$, and $R^7$ is independently selected from the group consisting of (i) H, (ii) halogen, (iii) —CN, (iv) —CON($R^8$)$_2$, (v) $C_1$-$C_3$ alkyl, and (vi) $C_3$-$C_6$ cycloalkyl, wherein the $C_1$-$C_3$ alkyl or $C_3$-$C_6$ cycloalkyl is unsubstituted; each $R^8$ is independently H or $C_1$-$C_3$ alkyl, wherein the $C_1$-$C_3$ alkyl is unsubstituted or substituted with one group; $R^{12}$ is —O$R^{13}$, $C_1$-$C_3$ alkyl, or —N($R^{13}$)$_2$; and each $R^{13}$ is independently H or $C_1$-$C_3$ alkyl. In some embodiments, W is NH, X is C$R^5$, Y is C$R^6$, and Z is C$R^7$, wherein each $R^5$, $R^6$, and $R^7$ is independently selected from the group consisting of H, Br, —CN, —CONH$R^8$, $C_1$-$C_3$ alkyl and $C_3$-$C_6$ cycloalkyl, wherein the $C_1$-$C_3$ alkyl or $C_3$-$C_6$ cycloalkyl is unsubstituted; $R^8$ is $C_1$-$C_3$ alkyl, wherein the $C_1$-$C_3$ alkyl is unsubstituted or substituted with one $R^{12}$ group; $R^{12}$ is —O$R^{13}$ or —N($R^{13}$)$_2$; and each $R^{13}$ is independently $C_1$-$C_3$ alkyl. In some embodiments, W is NH, X is C$R^5$, Y is C$R^6$, and Z is C$R^7$; wherein each $R^5$, $R^6$, and $R^7$ is independently selected from the group consisting of H, Br, —CN, —CONHCH$_2$CH$_2$N(CH$_2$CH$_3$)$_2$, CH$_3$, and cyclopropyl.

In some embodiments of the compounds of Formula I, I-Z, I-E, and II-Z, W is NH, X is N, Y is C$R^6$, and Z is C$R^7$; wherein each $R^6$ and $R^7$ is independently selected from the group consisting of (i) H, (ii) halogen, (iii) —CN, (iv) —CON($R^8$)$_2$, (v) $C_1$-$C_3$ alkyl, and (vi) $C_3$-$C_6$ cycloalkyl; wherein the $C_1$-$C_3$ alkyl or $C_3$-$C_6$ cycloalkyl is unsubstituted; each $R^8$ is independently H or $C_1$-$C_3$ alkyl, wherein the $C_1$-$C_3$ alkyl is unsubstituted or substituted with one group; $R^{12}$ is —O$R^{13}$, $C_1$-$C_3$ alkyl, or —N($R^{13}$)$_2$; and each $R^{13}$ is independently H or $C_1$-$C_3$ alkyl. In some embodiments, W is NH, X is N, Y is C$R^6$, and Z is C$R^7$; wherein each $R^6$ and $R^7$ is independently selected from the group consisting of (i) H, (ii) Br, (iii) —CN, (iv) —CONH$R^8$, (v) $C_1$-$C_3$ alkyl and (vi) $C_3$-$C_6$ cycloalkyl, wherein the $C_1$-$C_3$ alkyl or $C_3$-$C_6$ cycloalkyl is unsubstituted; $R^8$ is $C_1$-$C_3$ alkyl, wherein the $C_1$-$C_3$ alkyl is unsubstituted or substituted with one $R^{12}$ group; $R^{12}$ is —O$R^{13}$ or —N($R^{13}$)$_2$; and each $R^{13}$ is independently $C_1$-$C_3$ alkyl. In some embodiments, W is NH, X is N, Y is C$R^6$, and Z is C$R^7$; wherein each $R^6$ and $R^7$ is independently selected from the group consisting of H, Br, —CN, —CONHCH$_2$CH$_2$N(CH$_2$CH$_3$)$_2$, CH$_3$, and cyclopropyl.

In some embodiments of the compounds of Formula I, I-Z, I-E, and II-Z, W is NH, X is C$R^5$, Y is N, and Z is C$R^7$; wherein each $R^5$ and $R^7$ is independently selected from the group consisting of (i) H, (ii) halogen, (iii) —CN, (iv) —CON($R^8$)$_2$, (v) $C_1$-$C_3$ alkyl, and (vi) $C_3$-$C_6$ cycloalkyl; wherein the $C_1$-$C_3$ alkyl or $C_3$-$C_6$ cycloalkyl is unsubstituted; each $R^8$ is independently H or $C_1$-$C_3$ alkyl, wherein the $C_1$-$C_3$ alkyl is unsubstituted or substituted with one $R^{12}$ group; $R^{12}$ is —O$R^{13}$, $C_1$-$C_3$ alkyl, or —N($R^{13}$)$_2$; and each $R^{13}$ is independently H or $C_1$-$C_3$ alkyl. In some embodiments, W is NH, X is C$R^5$, Y is N, and Z is C$R^7$; wherein each $R^5$ and $R^7$ is independently (i) H, (ii) Br, (iii) —CN, (iv) —CONH$R^8$, (v) $C_1$-$C_3$ alkyl or (vi) $C_3$-$C_6$ cycloalkyl, wherein the $C_1$-$C_3$ alkyl or $C_3$-$C_6$ cycloalkyl is unsubstituted; $R^8$ is $C_1$-$C_3$ alkyl, wherein the $C_1$-$C_3$ alkyl is unsubstituted or substituted with one $R^{12}$ group; $R^{12}$ is —O$R^{13}$ or —N($R^{13}$)$_2$; and each $R^{13}$ is independently $C_1$-$C_3$ alkyl. In some embodiments, W is NH, X is C$R^5$, Y is N, and Z is C$R^7$; wherein each $R^5$ and $R^7$ is independently selected from the group consisting of H, Br, —CN, —CONHCH$_2$CH$_2$N(CH$_2$CH$_3$)$_2$, CH$_3$, and cyclopropyl.

In some embodiments of the compounds of Formula I, I-Z, I-E, and II-Z, W is NH, X is C$R^5$, Y is C$R^6$, and Z is N; wherein each $R^5$ and $R^6$ is independently selected from the group consisting of (i) H, (ii) halogen, (iii) —CN, (iv) —CON($R^8$)$_2$, (v) $C_1$-$C_3$ alkyl, and (vi) $C_3$-$C_6$ cycloalkyl; wherein the $C_1$-$C_3$ alkyl or $C_3$-$C_6$ cycloalkyl is unsubstituted; each $R^8$ is independently H or $C_1$-$C_3$ alkyl, wherein the $C_1$-$C_3$ alkyl is unsubstituted or substituted with one $R^{12}$ group; $R^{12}$ is —$OR^{13}$, $C_1$-$C_3$ alkyl, or —$N(R^{13})_2$; and each $R^{13}$ is independently H or $C_1$-$C_3$ alkyl. In some embodiments, W is NH, X is $CR^5$, Y is $CR^6$, and Z is N; wherein each $R^5$ and $R^6$ is independently selected from the group consisting of (i) H, (ii) Br, (iii) —CN, (iv) —$CONHR^8$, (v) $C_1$-$C_3$ alkyl or (vi) $C_3$-$C_6$ cycloalkyl, wherein the $C_1$-$C_3$ alkyl or $C_3$-$C_6$ cycloalkyl is unsubstituted; $R^8$ is $C_1$-$C_3$ alkyl, wherein the $C_1$-$C_3$ alkyl is unsubstituted or substituted with one $R^{12}$ group; $R^{12}$ is —$OR^{13}$ or —$N(R^{13})_2$; and each $R^{13}$ is independently $C_1$-$C_3$ alkyl. In some embodiments, W is NH, X is $CR^5$, Y is $CR^6$, and Z is N; wherein each $R^5$ and $R^6$ is independently selected from the group consisting of H, Br, —CN, —$CONHCH_2CH_2N(CH_2CH_3)_2$, $CH_3$, and cyclopropyl.

In some embodiments of the compounds of Formula I, I-Z, I-E, and II-Z, W is NH, X is N, Y is N, and Z is $CR^7$; wherein $R^7$ is selected from the group consisting of (i) H, (ii) halogen, (iii) —CN, (vi) —$CON(R^8)_2$, (v) $C_1$-$C_3$ alkyl, and (vi) $C_3$-$C_6$ cycloalkyl; wherein the $C_1$-$C_3$ alkyl or $C_3$-$C_6$ cycloalkyl is unsubstituted; each $R^8$ is independently H or $C_1$-$C_3$ alkyl, wherein the $C_1$-$C_3$ alkyl is unsubstituted or substituted with one $R^{12}$ group; $R^{12}$ is —$OR^{13}$, $C_1$-$C_3$ alkyl, or —$N(R^{13})_2$; and each $R^{13}$ is independently H or $C_1$-$C_3$ alkyl. In some embodiments, W is NH, X is N, Y is N, and Z is $CR^7$; wherein $R^7$ is selected from the group consisting of (i) H, (ii) Br, (iii) —CN, (iv) —$CONHR^8$, (v) $C_1$-$C_3$ alkyl or (vi) $C_3$-$C_6$ cycloalkyl, wherein the $C_1$-$C_3$ alkyl or $C_3$-$C_6$ cycloalkyl is unsubstituted; $R^8$ is $C_1$-$C_3$ alkyl, wherein the $C_1$-$C_3$ alkyl is unsubstituted or substituted with one $R^{12}$ group; $R^{12}$ is —$OR^{13}$ or —$N(R^{13})_2$; and each $R^{13}$ is independently $C_1$-$C_3$ alkyl. In some embodiments, W is NH, X is N, Y is N, and Z is $CR^7$; wherein $R^7$ is selected from the group consisting of H, Br, —CN, —$CONHCH_2N(CH_2CH_3)_2$, $CH_3$, and cyclopropyl.

In some embodiments of the compounds of Formula I, I-Z, I-E, and II-Z, W is NH, X is N, Y is $CR^6$, and Z is N; wherein $R^6$ is selected from the group consisting of (i) H, (ii) halogen, (iii) —CN, (iv) —$CON(R^8)_2$, (v) $C_1$-$C_3$ alkyl, and (vi) $C_3$-$C_6$ cycloalkyl; wherein the $C_1$-$C_3$ alkyl or $C_3$-$C_6$ cycloalkyl is unsubstituted; each $R^8$ is independently H or $C_1$-$C_3$ alkyl, wherein the $C_1$-$C_3$ alkyl is unsubstituted or substituted with one $R^{12}$ group; $R^{12}$ is —$OR^{13}$, $C_1$-$C_3$ alkyl, or —$N(R^{13})_2$; and each $R^{13}$ is independently H or $C_1$-$C_3$ alkyl. In some embodiments, W is NH, X is N, Y is $CR^6$, and Z is N; wherein $R^6$ is selected from the group consisting of (i) H, (ii) Br, (iii) —CN, (iv) —$CONHR^8$, (v) $C_1$-$C_3$ alkyl or (vi) $C_3$-$C_6$ cycloalkyl, wherein the $C_1$-$C_3$ alkyl or $C_3$-$C_6$ cycloalkyl is unsubstituted; $R^8$ is $C_1$-$C_3$ alkyl, wherein the $C_1$-$C_3$ alkyl is unsubstituted or substituted with one $R^{12}$ group; $R^{12}$ is —$OR^{13}$ or —$N(R^{13})_2$; and each $R^{13}$ is independently $C_1$-$C_3$ alkyl. In some embodiments, W is NH, X is N, Y is $CR^6$, and Z is N; wherein $R^6$ is selected from the group consisting of H, Br, —CN, —$CONHCH_2N(CH_2CH_3)_2$, $CH_3$, and cyclopropyl.

In some embodiments of the compounds of Formula I, I-Z, I-E, and II-Z, W is NH, X is $CR^5$, Y is N, and Z is N; wherein $R^5$ is selected from the group consisting of (i) H, (ii) halogen, (iii) —CN, (iv) —$CON(R^8)_2$, (v) $C_1$-$C_3$ alkyl, and (vi) $C_3$-$C_6$ cycloalkyl; wherein the $C_1$-$C_3$ alkyl or $C_3$-$C_6$ cycloalkyl is unsubstituted; each $R^8$ is independently H or $C_1$-$C_3$ alkyl, wherein the $C_1$-$C_3$ alkyl is unsubstituted or substituted with one $R^{12}$ group; $R^{12}$ is —$OR^{13}$, $C_1$-$C_3$ alkyl, or —$N(R^{13})_2$; and each $R^{13}$ is independently H or $C_1$-$C_3$ alkyl. In some embodiments, W is NH, X is $CR^5$, Y is N, and Z is N; wherein $R^5$ is selected from the group consisting of H, Br, —CN, —$CONHR^8$, $C_1$-$C_3$ alkyl or $C_3$-$C_6$ cycloalkyl, wherein the $C_1$-$C_3$ alkyl or $C_3$-$C_6$ cycloalkyl is unsubstituted; $R^8$ is $C_1$-$C_3$ alkyl, wherein the $C_1$-$C_3$ alkyl is unsubstituted or substituted with one $R^{12}$ group; $R^{12}$ is —$OR^{13}$ or —$N(R^{13})_2$; and each $R^{13}$ is independently $C_1$-$C_3$ alkyl. In some embodiments, W is NH, X is $CR^5$, Y is N, and Z is N; wherein $R^5$ is selected from the group consisting of H, Br, —CN, —$CONHCH_2CH_2N(CH_2CH_3)_2$, $CH_3$, and cyclopropyl.

In some embodiments of the compounds of Formula I, I-Z, I-E, II-Z, and IIa-Z, each $R^5$, $R^6$, and $R^7$ is independently H, halogen, —CN, —$CON(R^8)_2$, —$NR^{13}C(O)R^{13}$, —$SO_2N(R^{13})_2$, $C_1$-$C_3$ alkyl, 5-6 membered heteroaryl having 1 or 2 heteroatoms independently selected from N, O and S, or $C_3$-$C_6$ cycloalkyl; wherein the $C_1$-$C_3$ alkyl or the $C_3$-$C_6$ cycloalkyl is unsubstituted or substituted with 1, 2, or 3 $R^{11}$ groups. In some embodiments, each $R^5$, $R^6$, and $R^7$ is independently H, halogen, —CN, —$CON(R^8)_2$, —$SO_2N(R^{13})_2$, $C_1$-$C_3$ alkyl, or $C_3$-$C_6$ cycloalkyl; wherein the $C_1$-$C_3$ alkyl or the $C_3$-$C_6$ cycloalkyl is unsubstituted or substituted with 1, 2, or 3 $R^{11}$ groups. In some embodiments, each $R^5$, $R^6$ and $R^7$ is independently H, Br, CN, —$CON(R^8)_2$, —$SO_2N(R^{13})_2$, $C_1$-$C_3$ alkyl, or $C_3$-$C_6$ cycloalkyl; wherein the $C_1$-$C_3$ alkyl or the $C_3$-$C_6$ cycloalkyl is unsubstituted. In some embodiments, each $R^5$, $R^6$ and $R^7$ is independently H, CN, Br, —$CONHCH_2CH_2N(CH_2CH_3)_2$, —$CONH(CH_3)$, —$SO_2NHCH_3$, —$CH_3$, —$CH_2CH_3$, or cyclopropyl.

In some embodiments of the compounds of Formula I, I-Z, I-E, II-Z, and IIa-Z, $R^5$ is H, $C_1$-$C_3$ alkyl, or $C_3$-$C_6$ cycloalkyl. In some embodiments, $R^5$ is H, —$CH_3$, —$CH_2CH_3$, or cyclopropyl.

In some embodiments of the compounds of Formula I, I-Z, I-E, II-Z, and IIa-Z, $R^6$ is H, halogen, —CN, $C_1$-$C_3$ alkyl, or $CON(R^8)_2$. In some embodiments, $R^6$ is H, Br, CN, $C_1$-$C_3$ alkyl, or —$CONHCH_2CH_2N(CH_2CH_3)_2$.

In some embodiments of the compounds of Formula I, I-Z, I-E, II-Z, and IIa-Z, $R^7$ is H or $CH_3$.

In some embodiments of the compounds of Formula I, I-Z, I-E, II-Z, and IIa-Z, each $R^5$, $R^6$, and $R^7$ is H.

In some embodiments, of the compounds of Formula I, I-Z, I-E, II-Z, and IIa-Z, X is $CR^5$ and Y is $CR^6$, wherein $R^5$ and $R^6$ together with atoms to which they are attached form (i) a phenyl or (ii) a 5 or 6 membered heteroaryl having 1 or 2 heteroatoms independently selected from N, O, and S; wherein the phenyl or the 5 or 6 membered heteroaryl is unsubstituted or substituted with 1, 2, or 3 $R^{11}$ groups. In some embodiments, the phenyl or the 5 or 6 membered heteroaryl is unsubstituted or substituted with one $R^{11}$ group. In some embodiments, the phenyl or the 5 or 6 membered heteroaryl is unsubstituted.

In some embodiments, of the compounds of Formula I, I-Z, I-E, II-Z, and IIa-Z, X is $CR^5$ and Y is $CR^6$, wherein $R^5$ and $R^6$ together with atoms to which they are attached form (i) a phenyl or (ii) a 5 or 6 membered heteroaryl having 1 or 2 heteroatoms independently selected from N and S; wherein the phenyl or the 5 or 6 membered heteroaryl is unsubstituted or substituted with 1, 2, or 3 $R^{11}$ groups. In some embodiments, the phenyl or the 5 or 6 membered heteroaryl is unsubstituted or substituted with one $R^{11}$ group. In some embodiments, the phenyl or the 5 or 6 membered heteroaryl is unsubstituted.

In some embodiments, of the compounds of Formula I, I-Z, I-E, II-Z, and IIa-Z, X is $CR^5$ and Y is $CR^6$, wherein $R^5$ and $R^6$ together with atoms to which they are attached form (i) phenyl, (ii) pyridyl or (iii) thiozolyl; wherein the (i) phenyl, (ii) pyridyl or (iii) thiozolyl is unsubstituted or substituted with 1, 2, or 3 $R^{11}$ groups. In some embodiments, the phenyl, pyridyl or thiozolyl is unsubstituted or substituted with one $R^{11}$ group. In some embodiments, the phenyl, pyridyl or thiozolyl is unsubstituted.

In some embodiments, the compound of Formula I, I-Z, II-Z, and IIa-Z is a compound of Formula IIb-Z:

Formula IIb-Z

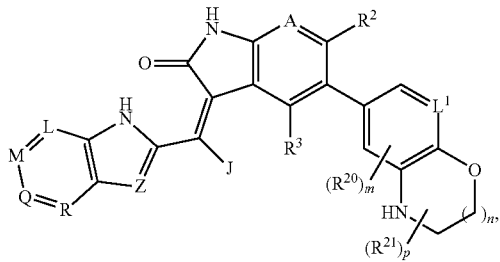

wherein the variables Z, J, A, $R^2$, $R^3$, $L^1$, $R^{20}$, $R^{21}$, m, n, and p are as defined above for Formula I;

L is N or $CR^{15}$;
M is N or $CR^{16}$;
Q is N or $CR^{17}$; and
R is N or $CR^{18}$;

wherein each $R^{15}$, $R^{16}$, $R^{17}$, and $R^{18}$ is independently selected from the group consisting of H, halogen, CN, —N$(R^8)_2$, —CON$(R^8)_2$, —N$(R^{13})$COR$^{13}$, —S(O)$_2$R$^{13}$, $C_1$-$C_3$ alkyl, $C_1$-$C_3$ alkoxy, $C_6$-$C_{10}$ aryl, 5-10 membered heteroaryl having 1, 2, or 3 heteroatoms independently selected from N, O, and S, and 4-6 membered heterocyclyl having 1, 2, or 3 heteroatoms independently selected from N, O, and S.

In some embodiments of the compounds of Formula I and I-Z,  is a group of formula

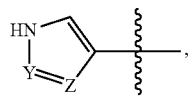

and the compound is of Formula III-Z:

Formula III-Z

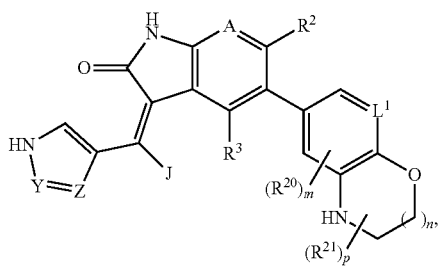

wherein the variables Y, Z, J, A, $R^2$, $R^3$, $L^1$, $R^{20}$, $R^{21}$, m, n, and p are as defined above for Formula I.

In some embodiments of the compounds of Formula I, I-Z, I-E, II-Z, IIa-Z, and III-Z, Y is $CR^6$ and Z is $CR^7$, wherein $R^6$ and $R^7$ together with atoms to which they are attached form (i) a phenyl or (ii) a 5 or 6 membered heteroaryl having 1 or 2 heteroatoms independently selected from N, O, and S; wherein the phenyl or the 5 or 6 membered heteroaryl is unsubstituted or substituted with 1, 2, or 3 $R^{11}$ groups. In some embodiments, the phenyl or the 5 or 6 membered heteroaryl is unsubstituted or substituted with one $R^{11}$ group. In some embodiments, the phenyl or the 5 or 6 membered heteroaryl is unsubstituted.

In some embodiments, of the compounds of Formula I, I-Z, I-E, II-Z, IIa-Z, and III-Z, Y is $CR^6$ and Z is $CR^7$, wherein $R^6$ and $R^7$ together with atoms to which they are attached form (i) a phenyl or (ii) a 5 or 6 membered heteroaryl having 1 or 2 heteroatoms independently selected from N and S; wherein the phenyl or the 5 or 6 membered heteroaryl is unsubstituted or substituted with 1, 2, or 3 $R^{11}$ groups. In some embodiments, the phenyl or the 5 or 6 membered heteroaryl is unsubstituted or substituted with one $R^{11}$ group. In some embodiments, the phenyl or the 5 or 6 membered heteroaryl is unsubstituted.

In some embodiments of the compounds of Formula I, I-Z, I-E, II-Z, IIa-Z, and III-Z, Y is $CR^6$ and Z is $CR^7$, wherein $R^6$ and $R^7$ together with atoms to which they are attached form a (i) phenyl, (ii) pyridyl or (iii) thiozolyl; wherein the phenyl, pyridyl or thiozolyl is unsubstituted or substituted with 1, 2, or 3 $R^{11}$ groups. In some embodiments, the phenyl, pyridyl or thiozolyl is unsubstituted or substituted with one $R^{11}$ group. In some embodiments, the phenyl, pyridyl or thiozolyl is unsubstituted.

In some embodiments, of the compounds of Formula I, I-Z, I-E, II-Z, IIa-Z, and III-Z, $R^{11}$ is selected from the group consisting of (i) CN, (ii) —N$(R^8)_2$, (iii) —N$(R^{13})$COR$^{13}$, and (iv) 4-6 membered heterocyclyl having 1, 2, or 3, heteroatoms independently selected from N, O, and S; wherein each $R^{13}$ is independently H or $C_1$-$C_3$ alkyl. In some embodiments, $R^{11}$ is selected from the group consisting of (i) —CN, (ii) —NH$_2$, (iii) —NHCOR$^{13}$, and (iv) 6 membered heterocyclyl having 1 or 2 heteroatoms independently selected from N and O; wherein $R^{13}$ is $C_1$-$C_3$ alkyl. In some embodiments, $R^{11}$ is selected from the group consisting of CN, —NH$_2$, —NHCOCH$_3$, and morpholinyl. In some embodiments, of the compounds provided herein $R^{11}$ is absent.

In some embodiments the compound of Formula I, I-Z or III-Z, is a compound of Formula IIIa-Z:

Formula IIIa-Z

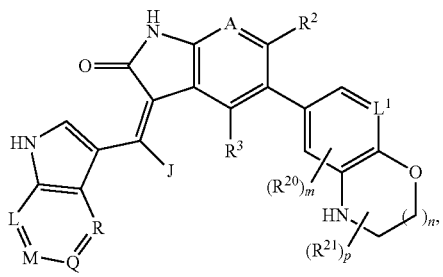

wherein the variables J, A, $R^2$, $R^3$, $L^1$, $R^{20}$, $R^{21}$, m, n, and p are as defined above for Formula I; and L, M, Q, and R are as defined above for Formula IIb-Z.

In some embodiments of the compounds of Formula IIb-Z and IIIa-Z, L is $CR^{15}$, M is $CR^{16}$, Q is $CR^{17}$, and R is $CR^{18}$; wherein each $R^{15}$, $R^{16}$, $R^{17}$, and $R^{18}$ is independently selected from the group consisting of (i) H, (ii) halogen, (iii) CN, (iv) —N$(R^8)_2$, (v) —CON$(R^8)_2$, (vi) —N$(R^{13})$COR$^{13}$, (vii) —S(O)$_2$R$^{13}$, (viii) C$_1$-C$_3$ alkyl, (ix) C$_1$-C$_3$ alkoxy, (x) C$_6$-C$_{10}$ aryl, (xi) 5-10 membered heteroaryl having 1, 2, or 3 heteroatoms independently selected from N, O, and S, and (xii) 4-6 membered heterocyclyl having 1, 2, or 3 heteroatoms independently selected from N, O, and S. In some embodiments, L is CRIB, is CR$^{16}$, Q is CR$^{17}$, and R is CR$^{11}$; wherein each R$^{15}$, R$^{16}$, R$^{17}$, and R$^{18}$ is independently (i) H, (ii) CN, (iii) NH$_2$, or (vi) NHCOCH$_3$. In some embodiments, L is CR$^{15}$, M is CR$^{16}$, Q is CR$^{17}$, and R is CR$^{18}$; wherein each R$^{15}$, R$^{16}$, R$^{17}$, and R$^{18}$ is H.

In some embodiments of the compounds of Formula IIb-Z and IIIa-Z, L is N, M is CR$^{16}$, Q is CR$^{17}$, and R is CR$^{18}$; wherein each R$^{16}$, R$^{17}$, and R$^{18}$ is independently selected from the group consisting of (i) H, (ii) halogen, (iii) CN, (iv) —N(R$^8$)$_2$, (v) —CON(R$^8$)$_2$, (vi) —N(R$^{13}$)COR$^{13}$, (vii) —S(O)$_2$R$^{13}$, (viii) C$_1$-C$_3$ alkyl, (ix) C$_1$-C$_3$ alkoxy, (x) C$_6$-C$_{10}$ aryl, (xi) 5-10 membered heteroaryl having 1, 2, or 3 heteroatoms independently selected from N, O, and S, and (xii) 4-6 membered heterocyclyl having 1, 2, or 3 heteroatoms independently selected from N, O, and S. In some embodiments, L is N, M is CR$^{16}$, Q is CR$^{17}$, and R is CR$^{11}$; wherein each R$^{16}$, R$^{17}$, and R$^{11}$ is independently (i) H, (ii) CN, (iii) NH$_2$, or (iv) NHCOCH$_3$. In some embodiments, L is N, M is CR$^{16}$, is CR$^{17}$, and R is CR$^{11}$; wherein each R$^{16}$, R$^{17}$, and R$^{18}$ is H.

In some embodiments of the compounds of Formula IIb-Z and IIIa-Z, L is CR$^{15}$, M is N, Q is CR$^{17}$, and R is CR$^{11}$; wherein each R$^{15}$, R$^{17}$, and R$^{11}$ is independently selected from the group consisting of (i) H, (ii) halogen, (iii) CN, (iv) —N(R$^8$)$_2$, (v) —CON(R$^8$)$_2$, (vi) —N(R$^{13}$)COR$^{13}$, (vii) —S(O)$_2$R$^{13}$, (viii) C$_1$-C$_3$ alkyl, (ix) C$_1$-C$_3$ alkoxy, (x) C$_6$-C$_{10}$ aryl, (xi) 5-10 membered heteroaryl having 1, 2, or 3 heteroatoms independently selected from N, O, and S, and (xii) 4-6 membered heterocyclyl having 1, 2, or 3 heteroatoms independently selected from N, O, and S. In some embodiments, L is CR$^{15}$, M is N, Q is CR$^{17}$, and R is CR$^{18}$; wherein each R$^{15}$, R$^{17}$, and R$^{18}$ is independently (i) H, (ii) CN, (iii) NH$_2$, or (iv) NHCOCH$_3$. In some embodiments, L is CR$^{15}$, M is N, Q is CR$^{17}$, and R is CR$^{11}$; wherein each R$^{15}$, R$^{17}$, and R$^{11}$ is H.

In some embodiments of the compounds of Formula IIb-Z and IIIa-Z, L is CR$^{15}$, M is CR$^{16}$, Q is N, and R is CR$^{11}$; wherein each R$^{15}$, R$^{16}$, and R$^{18}$ is independently selected from the group consisting of (i) H, (ii) halogen, (iii) CN, (iv) —N(R$^8$)$_2$, (v) —CON(R$^8$)$_2$, (vi) —N(R$^{13}$)COR$^{13}$, (vii) —S(O)$_2$R$^{13}$, (viii) C$_1$-C$_3$ alkyl, (ix) C$_1$-C$_3$ alkoxy, (x) C$_6$-C$_{10}$ aryl, (xi) 5-10 membered heteroaryl having 1, 2, or 3 heteroatoms independently selected from N, O, and S, and (xii) 4-6 membered heterocyclyl having 1, 2, or 3 heteroatoms independently selected from N, O, and S. In some embodiments, L is CR$^{15}$, M is CR$^{16}$, Q is N, and R is CR$^{11}$; wherein each R$^{15}$, R$^{16}$, and R$^{18}$ is independently H, CN, NH$_2$, or NHCOCH$_3$. In some embodiments, L is CR$^{15}$, M is CR$^{16}$, Q is N, and R is CR$^{18}$; wherein each R$^{15}$, R$^{16}$, and R$^{18}$ is H.

In some embodiments of the compounds of Formula IIb-Z and IIIa-Z, L is CR$^{15}$, M is CR$^{16}$, Q is CR$^{17}$, and R is N; wherein each R$^{15}$, R$^{16}$, and R$^{17}$ is independently selected from the group consisting of (i) H, (ii) halogen, (iii) CN, (iv) —N(R$^8$)$_2$, (v) —CON(R$^8$)$_2$, (vi) —N(R$^{13}$)COR$^{13}$, (vii) —S(O)$_2$R$^{13}$, (viii) C$_1$-C$_3$ alkyl, (ix) C$_1$-C$_3$ alkoxy, (x) C$_6$-C$_{10}$ aryl, (xi) 5-10 membered heteroaryl having 1, 2, or 3 heteroatoms independently selected from N, O, and S, and (xii) 4-6 membered heterocyclyl having 1, 2, or 3 heteroatoms independently selected from N, O, and S. In some embodiments, L is CR$^{15}$, M is CR$^{16}$, Q is CR$^{17}$, and R is N; wherein each R$^{15}$, R$^{16}$, and R$^{17}$ is independently H, CN, NH$_2$, or NHCOCH$_3$. In some embodiments, L is CR$^{15}$, M is CR$^{16}$, Q is CR$^{17}$, and R is N; wherein each R$^{15}$, R$^{16}$, and R$^{17}$ is H.

In some embodiments of the compounds of Formula IIb-Z and IIIa-Z, each R$^{15}$, R$^{16}$, R$^{17}$, and R$^{18}$ is independently selected from the group consisting of H, CN, —N(R$^8$)$_2$, and —N(R$^{13}$)COR$^{13}$. In some embodiments, R$^{15}$, R$^{16}$, R$^{17}$, and R$^{18}$ are each H.

In some embodiments of the compounds of Formula I, I-Z, I-E, II-Z, IIa-Z, IIb-Z, III-Z, and IIIa-Z, each R$^8$ is independently H or C$_1$-C$_3$ alkyl, wherein the C$_1$-C$_3$ alkyl is unsubstituted or substituted with 1, 2, or 3 R$^{12}$ groups. In some embodiments, R$^8$ is H or C$_1$-C$_3$ alkyl, wherein the C$_1$-C$_3$ alkyl is unsubstituted substituted with one R$^{12}$ group. In some embodiments, R$^8$ is H or C$_1$-C$_3$ alkyl, wherein the C$_1$-C$_3$ alkyl is unsubstituted. In some embodiments, R$^8$ is H. In some embodiments, R$^8$ is C$_1$-C$_3$ alkyl. In some embodiments, R$^8$ is H or C$_1$-C$_3$ alkyl substituted with —N(R$^{13}$)$_2$, wherein R$^{13}$ is H or C$_1$-C$_3$ alkyl. In some embodiments, R$^8$ is H or C$_1$-C$_3$ alkyl substituted with —N(CH$_2$CH$_3$)$_2$.

In some embodiments of the compounds of Formula I, I-Z, I-E, II-Z, IIa-Z, IIb-Z, III-Z, and IIIa-Z, two R$^8$ groups together with the nitrogen they are attached to form a 4-6 membered heterocyclic ring having 1 or 2 heteroatoms selected from the group consisting of N, O, or S, wherein the 4-6 membered heterocyclic ring is unsubstituted or substituted with 1, 2, or 3 R$^{12}$ groups.

In some embodiments of the compounds of Formula I, I-Z, I-E, II-Z, IIa-Z, IIb-Z, III-Z, and IIIa-Z, two R$^8$ groups together with the nitrogen they are attached to form a 4-6 membered heterocyclic ring having 1 or 2 heteroatoms selected from the group consisting of N, O, or S, wherein the 4-6 membered heterocyclic ring is unsubstituted or substituted with one R$^{12}$ group.

In some embodiments of the compounds of Formula I, I-Z, I-E, II-Z, IIa-Z, IIb-Z, III-Z, and IIIa-Z, two R$^8$ groups together with the nitrogen they are attached to form a 4-6 membered heterocyclic ring having 1 or 2 heteroatoms selected from the group consisting of N, O, or S, wherein the 4-6 membered heterocyclic ring is unsubstituted.

In some embodiments of the compounds of Formula I, I-Z, I-E, II-Z, IIa-Z, IIb-Z, III-Z, and IIIa-Z, two R$^8$ groups together with the nitrogen they are attached to form a 6 membered heterocyclic ring having 2 heteroatoms selected from the group consisting of N, O, or S, wherein the 6 membered heterocyclic ring is unsubstituted or substituted with one R$^{12}$ group.

In some embodiments of the compounds of Formula I, I-Z, I-E, II-Z, IIa-Z, IIb-Z, III-Z, and IIIa-Z, two R$^8$ groups together with the nitrogen they are attached to form a 6 membered heterocyclic ring having 2 heteroatoms selected from N and S, wherein the 6 membered heterocyclic ring is unsubstituted or substituted with one R$^{12}$ group.

In some embodiments of the compounds of Formula I, I-Z, I-E, II-Z, IIa-Z, IIb-Z, III-Z, and IIIa-Z, each R$^{12}$ is independently —OR$^{13}$, C$_1$-C$_3$ alkyl, or —N(R$^{13}$)$_2$; wherein each R$^{13}$ is independently H or C$_1$-C$_3$ alkyl.

In some embodiments of the compounds of Formula I, I-Z, I-E, II-Z, IIa-Z, IIb-Z, III-Z, and IIIa-Z, A is N or CR$^1$, and each R$^1$, R$^2$, and R$^3$ is independently selected from the group consisting of (i) H, (ii) halogen, (iii) —CN, (iv) —N(R$^{13}$)$_2$, (v) C$_1$-C$_3$ alkyl, (vi) C$_2$-C$_3$ alkynyl, (vii) C$_1$-C$_3$ alkoxy, or -(viii) SO$_2$R$^{13}$, wherein the C$_2$-C$_3$ alkynyl is unsubstituted or substituted with 1, 2, or 3 R$^9$ groups; each R$^9$ is independently —OR$^{13}$, C$_1$-C$_3$ alkyl, or C$_3$-C$_6$ cycloalkyl; and each R$^{13}$ is independently H or C$_1$-C$_3$ alkyl.

In some embodiments of the compounds of Formula I, I-Z, I-E, II-Z, IIa-Z, IIb-Z, III-Z, and IIIa-Z, A is N or $CR^1$, and each $R^1$, $R^2$, and $R^3$ is independently selected from (i) H, (ii) halogen, (iii) —CN, (iv) $C_1$-$C_3$ alkyl, (v) $C_2$-$C_3$ alkynyl, (vi) $C_1$-$C_3$ alkoxy, or (vii) —$SO_2R^{13}$, wherein the $C_2$-$C_3$ alkynyl is unsubstituted or substituted with one, two or three $R^9$ groups; each $R^9$ is independently —$OR^{13}$, $C_1$-$C_3$ alkyl, or $C_3$-$C_6$ cycloalkyl; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, A is N or $CR^1$, and each $R^1$, $R^2$, and $R^3$ is independently selected from the group consisting of H, F, Cl, —CN, —$CH_3$, —$OCH_3$, $C_2$-$C_3$ alkynyl, or —$SO_2R^{13}$, wherein the $C_2$-$C_3$ alkynyl is unsubstituted or substituted with one, two or three $R^9$ groups; each $R^9$ is independently —OH, —$CH_3$, or cyclopropyl.

In some embodiments of the compounds of Formula I, I-Z, I-E, II-Z, IIa-Z, IIb-Z, III-Z, and IIIa-Z, A is N or $CR^1$; and each $R^1$, $R^2$, and $R^3$ is independently selected from the group consisting of H, halogen, and $C_1$-$C_3$ alkyl. In some embodiments, A is N or $CR^1$, and each $R^1$, $R^2$, and $R^3$ is independently selected from H, F, Cl, and $C_1$-$C_3$ alkyl. In some embodiments, A is N or $CR^1$, and each $R^1$, $R^2$, and $R^3$ is independently selected from H, F, Cl and $CH_3$.

In some embodiments of the compounds of Formula I, I-Z, I-E, II-Z, IIa-Z, IIb-Z, III-Z, and IIIa-Z, A is N or $CR^1$; wherein $R^1$ is H, halogen, —CN, —$N(R^{13})_2$, $C_1$-$C_3$ alkyl, $C_2$-$C_3$ alkynyl, $C_1$-$C_3$ alkoxy, or —$SO_2R^{13}$, wherein the $C_2$-$C_3$ alkynyl is unsubstituted or substituted with 1, 2, or 3 $R^9$ groups; each $R^9$ is independently —$OR^{13}$, $C_1$-$C_3$ alkyl, or $C_3$-$C_6$ cycloalkyl; and each $R^{13}$ is independently H or $C_1$-$C_3$ alkyl. In some embodiments, A is N or $CR^1$; wherein $R^1$ is H, halogen or $C_1$-$C_3$ alkyl. In some embodiments, A is N or $CR^1$; wherein $R^1$ is H, F, Cl or $C_1$-$C_3$ alkyl. In some embodiments, A is N or $CR^1$; wherein $R^1$ is H, F, Cl or $CH_3$.

In some embodiments of the compounds of Formula I, I-Z, I-E, II-Z, IIa-Z, IIb-Z, III-Z, and IIIa-Z, A is $CR^1$; wherein $R^1$ is H, halogen, —CN, —$N(R^{13})_2$, $C_1$-$C_3$ alkyl, $C_2$-$C_3$ alkynyl, $C_1$-$C_3$ alkoxy, or —$SO_2R^{13}$, wherein the $C_2$-$C_3$ alkynyl is unsubstituted or substituted with 1, 2, or 3 $R^9$ groups; each $R^9$ is independently —$OR^{13}$, $C_1$-$C_3$ alkyl, or $C_3$-$C_6$ cycloalkyl; and each $R^{13}$ is independently H or $C_1$-$C_3$ alkyl. In some embodiments, A is $CR^1$; wherein $R^1$ is H, halogen or $C_1$-$C_3$ alkyl. In some embodiments, A is $CR^1$; wherein $R^1$ is H, F, Cl or $C_1$-$C_3$ alkyl. In some embodiments, A is $CR^1$; wherein $R^1$ is H, F, Cl or $CH_3$.

In some embodiments of the compounds of Formula I, I-Z, I-E, II-Z, IIa-Z, IIb-Z, III-Z, and IIIa-Z, A is N.

In some embodiments of the compounds of Formula I, I-Z, I-E, II-Z, IIa-Z, IIb-Z, III-Z, and IIIa-Z, $R^2$ is (i) H, (ii) halogen, (iii) —CN, (iv) —$N(R^{13})_2$, (v) $C_1$-$C_3$ alkyl, (vi) $C_2$-$C_3$ alkynyl, (vii) $C_1$-$C_3$ alkoxy, or (viii) —$SO_2R^{13}$, wherein the $C_2$-$C_3$ alkynyl is unsubstituted or substituted with 1, 2, or 3 $R^9$ groups; each $R^9$ is independently —$OR^{13}$, $C_1$-$C_3$ alkyl, or $C_3$-$C_6$ cycloalkyl; and each $R^{13}$ is independently H or $C_1$-$C_3$ alkyl. In some embodiments, $R^2$ is (i) H, (ii) halogen, (iii) —CN, (iv) $C_1$-$C_3$ alkyl, (v) $C_2$-$C_3$ alkynyl, (vi) $C_1$-$C_3$ alkoxy, or (vii) —$SO_2R^{13}$, wherein the $C_2$-$C_3$ alkynyl is unsubstituted or substituted with 1, 2, or 3 $R^9$ groups; each $R^9$ is independently —$OR^{13}$, $C_1$-$C_3$ alkyl, or $C_3$-$C_6$ cycloalkyl; and each $R^{13}$ is independently H or $C_1$-$C_3$ alkyl. In some embodiments, $R^2$ is H, F, Cl, —CN, —$CH_3$, —$OCH_3$, $C_2$-$C_3$ alkynyl, or —$SO_2R^{13}$ wherein the $C_2$-$C_3$ alkynyl is unsubstituted or substituted with one, two or three $R^9$ groups; each $R^9$ is independently —OH, —$CH_3$, or cyclopropyl. In some embodiments, $R^2$ is H, F, Cl or $C_1$-$C_3$ alkyl. In some embodiments, $R^2$ is H, F, Cl or $CH_3$.

In some embodiments of the compounds of Formula I, I-Z, I-E, II-Z, IIa-Z, IIb-Z, III-Z, and IIIa-Z, $R^3$ is (i) H, (ii) halogen, (iii) —CN, (iv) —$N(R^{13})_2$, (v) $C_1$-$C_3$ alkyl, (vi) $C_2$-$C_3$ alkynyl, (vii) $C_1$-$C_3$ alkoxy, or (viii) —$SO_2R^{13}$, wherein the $C_2$-$C_3$ alkynyl is unsubstituted or substituted with 1, 2, or 3 $R^9$ groups; each $R^9$ is independently —$OR^{13}$, $C_1$-$C_3$ alkyl, or $C_3$-$C_6$ cycloalkyl; and each $R^{13}$ is independently H or $C_1$-$C_3$ alkyl. In some embodiments, $R^3$ is H or $C_1$-$C_3$ alkyl. In some embodiments, $R^3$ is H or —$CH_3$. In some embodiments, $R^3$ is H. In some embodiments, $R^3$ is $C_1$-$C_3$ alkyl. In some embodiments, $R^3$ is —$CH_3$.

In some embodiments of the compounds of Formula I, I-Z, I-E, II-Z, IIa-Z, IIb-Z, III-Z, and IIIa-Z, each $R^1$, $R^2$, and $R^3$ is independently H, halogen, $C_1$-$C_3$ alkyl, or $C_2$-$C_3$ alkynyl, wherein the $C_2$-$C_3$ alkynyl is unsubstituted or substituted with 1, 2, or 3 $R^9$ groups. In some embodiments, each $R^1$, $R^2$, and $R^3$ is independently H, F, Cl, $C_1$-$C_3$ alkyl, or $C_2$-$C_3$ alkynyl, wherein the $C_2$-$C_3$ alkynyl is unsubstituted or substituted with 1, 2, or 3 groups independently selected from the group consisting of OH, $CH_3$, and cyclopropyl.

In some embodiments of the compounds of Formula I, I-Z, I-E, II-Z, IIa-Z, IIb-Z, III-Z, and IIIa-Z, both $R^1$ and $R^3$ are H.

In some embodiments of the compounds of Formula I, I-Z, I-E, II-Z, IIa-Z, IIb-Z, III-Z, and IIIa-Z, $R^2$ is H, halogen, CN, —$N(R^{13})_2$, $C_1$-$C_3$ alkoxy, $C_1$-$C_3$ alkyl, or $C_2$-$C_3$ alkynyl, wherein the $C_2$-$C_3$ alkynyl is unsubstituted or substituted with 1, 2, or 3 $R^9$ groups. In some embodiments, $R^2$ is H, halogen, $C_1$-$C_3$ alkyl, or $C_2$-$C_3$ alkynyl, wherein the $C_2$-$C_3$ alkynyl is unsubstituted or substituted with 1, 2, or 3 $R^9$ groups. In some embodiments, $R^2$ is H, Cl, F, —$CH_3$, —CN, —$NH_2$, —$SO_2CH_3$, —$OCH_3$,

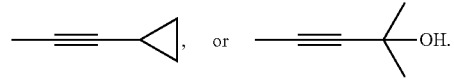

In some embodiments, $R^2$ is H, Cl, F, or $CH_3$.

In some embodiments of the compounds of Formula I, I-Z, I-E, II-Z, IIa-Z, IIb-Z, III-Z, and IIIa-Z, $R^9$ is —OH, $CH_3$, or cyclopropyl.

In some embodiments of the compounds of Formula I, I-Z, I-E, II-Z, IIa-Z, IIb-Z, III-Z, and IIIa-Z, $R^1$ is H, halogen or $C_1$-$C_3$ alkyl. In some embodiments, $R^1$ is H, F, Cl, or $CH_3$.

In some embodiments of the compounds of Formula I, I-Z, I-E, II-Z, IIa-Z, IIb-Z, III-Z, and IIIa-Z, $R^1$ is F or Cl and $R^2$ is H.

In some embodiments of the compounds of Formula I, I-Z, I-E, II-Z, IIa-Z, IIb-Z, III-Z, and IIIa-Z, $R^1$ is F or Cl; $R^2$ is H; and $R^3$ is H or $C_1$-$C_3$ alkyl. In some embodiments, $R^1$ is F or Cl; $R^2$ is H; and $R^3$ is $CH_3$.

In some embodiments of the compounds of Formula I, I-Z, I-E, II-Z, IIa-Z, IIb-Z, III-Z, and IIIa-Z, $R^1$ is $CH_3$; $R^2$ is H; and $R^3$ is H.

In some embodiments of the compounds of Formula I, I-Z, I-E, II-Z, IIa-Z, IIb-Z, III-Z, and IIIa-Z, $R^1$, $R^2$, and $R^3$ is H.

In some embodiments of the compounds of Formula I, I-Z, I-E, II-Z, IIa-Z, IIb-Z, III-Z, and IIIa-Z, J is H, —CN, $C_1$-$C_3$ alkyl, or $C_3$-$C_6$ cycloalkyl, wherein the $C_1$-$C_3$ alkyl or $C_3$-$C_6$ cycloalkyl is unsubstituted or substituted with 1, 2, or 3 $R^{10}$ groups; each $R^{10}$ is independently selected from the group consisting of (i) —$OR^{13}$, (ii) halogen, (iii) CN, (iv) —$N(R^8)_2$, (v) —$CON(R^8)_2$, (vi) —$N(R^{13})COR^{13}$, (vii) —$S(O)_2R^{13}$, (viii) $C_1$-$C_3$ alkyl, (ix) $C_3$-$C_6$ cycloalkyl, (x)

4-6 membered heterocyclyl having 1, 2, or 3 heteroatoms independently selected from N, O, and S, (xi) $C_6$-$C_{10}$ aryl, and (xii) 5-10 membered heteroaryl having 1, 2, or 3 heteroatoms independently selected from N, O, and S; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, J is H, —CN, $C_1$-$C_3$ alkyl, or $C_3$-$C_6$ cycloalkyl, wherein the $C_1$-$C_3$ alkyl or $C_3$-$C_6$ cycloalkyl is unsubstituted or substituted with one $R^{10}$ group; $R^{10}$ is selected from the group consisting of (i) —$OR^{13}$, (ii) halogen, (iii) CN, (iv) —$N(R^8)_2$, (v) —$CON(R^8)_2$, (vi) —$N(R^{13})COR^{13}$, (vii) —$S(O)_2R^{13}$, (viii) $C_1$-$C_3$ alkyl, (ix) $C_3$-$C_6$ cycloalkyl, (x) 4-6 membered heterocyclyl having 1, 2, or 3 heteroatoms independently selected from N, O, and S, (xi) $C_6$-$C_{10}$ aryl, and (xii) 5-10 membered heteroaryl having 1, 2, or 3 heteroatoms independently selected from N, O, and S; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, J is H or $C_1$-$C_3$ alkyl, wherein the $C_1$-$C_3$ alkyl is unsubstituted or substituted with one $R^{10}$ group; $R^{10}$ is selected from the group consisting of (i) —$OR^{13}$, (®1) halogen, (iii) CN, (iv) —$N(R^8)_2$, (v) —$CON(R^8)_2$, (vi) —$N(R^{13})COR^{13}$, (vii) —$S(O)_2R^{13}$, (viii) $C_1$-$C_3$ alkyl, (ix) $C_3$-$C_6$ cycloalkyl, (x) 4-6 membered heterocyclyl having 1, 2, or 3 heteroatoms independently selected from N, O, and S, (xi) $C_6$-$C_{10}$ aryl, and (xii) 5-10 membered heteroaryl having 1, 2, or 3 heteroatoms independently selected from N, O, and S; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, J is H or $C_1$-$C_3$ alkyl, wherein the $C_1$-$C_3$ alkyl is unsubstituted or substituted with 1, 2, or 3 $R^{10}$ group; $R^{10}$ is selected from the group consisting of (i) —$OR^{13}$, (®1) halogen, (iii) CN, (iv) —$N(R^8)_2$, (v) $C_1$-$C_3$ alkyl, and (vi) $C_3$-$C_6$ cycloalkyl; wherein each $R^{13}$ is independently H or $C_1$-$C_3$ alkyl. In some embodiments, J is H or $C_1$-$C_3$ alkyl, wherein the $C_1$-$C_3$ alkyl is unsubstituted or substituted with 1, 2, or 3 $R^{10}$ group; and $R^{10}$ is selected from the group consisting of (i) —OH, (ii) halogen, (iii) CN, (iv) —$NH_2$, (v) $C_1$-$C_3$ alkyl, and (vi) $C_3$-$C_6$ cycloalkyl.

In some embodiments of the compounds of Formula I, I-Z, I-E, II-Z, IIa-Z, IIb-Z, III-Z, and IIIa-Z, J is H, —CN, unsubstituted $C_1$-$C_3$ alkyl, or unsubstituted $C_3$-$C_6$ cycloalkyl. In some embodiments, J is H, unsubstituted $C_1$-$C_3$ alkyl, or unsubstituted $C_3$-$C_6$ cycloalkyl. In some embodiments, J is H or unsubstituted $C_1$-$C_3$ alkyl. In some embodiments, J is H, methyl or ethyl. In some embodiments, J is H. In some embodiments, J is $C_1$-$C_3$ alkyl. In some embodiments, J is methyl or ethyl.

In some embodiments of the compounds of Formula I, I-Z, and I-E,  is selected from the group consisting of

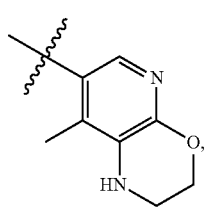 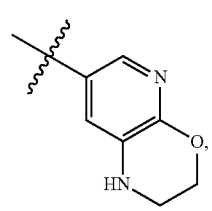

-continued

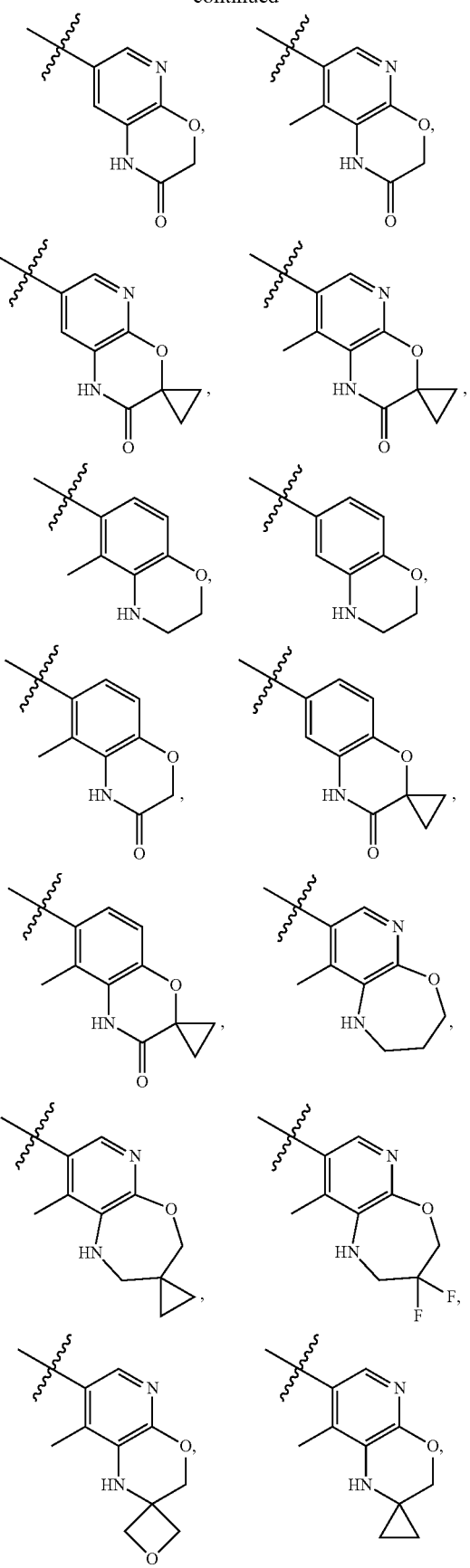

-continued
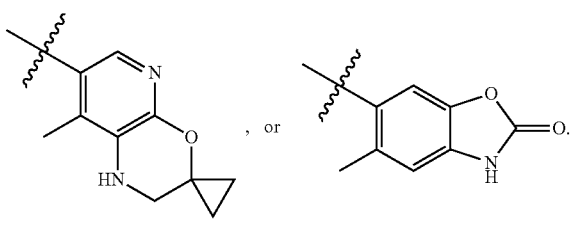 , or
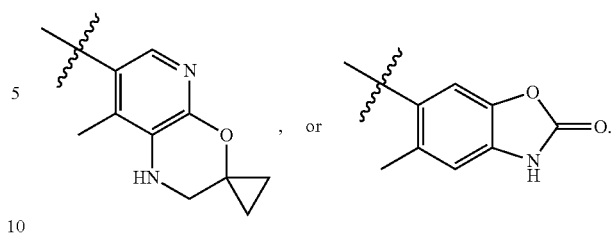 , or
In some embodiments, (Hy) is
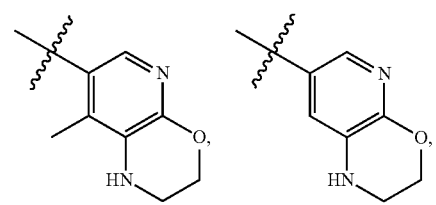
In some embodiments, (Hy) is
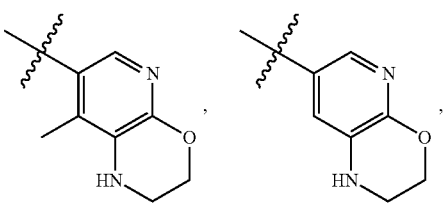
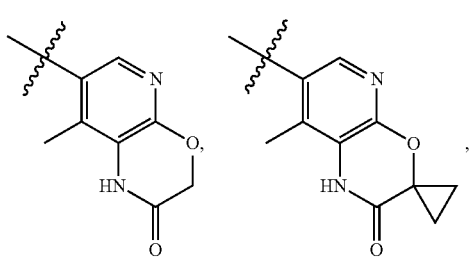
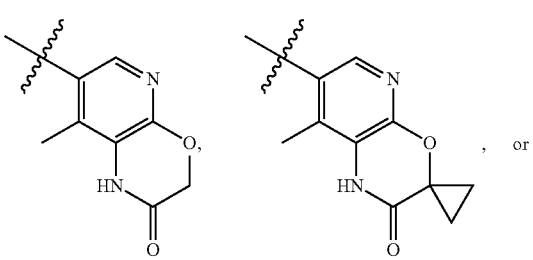 , or
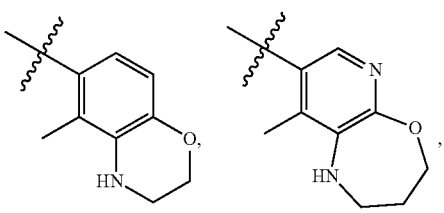
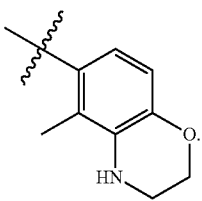
In some embodiments, (Hy) is
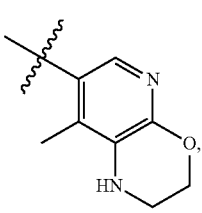
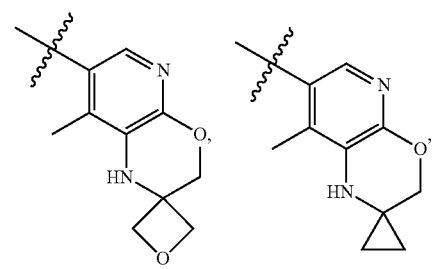
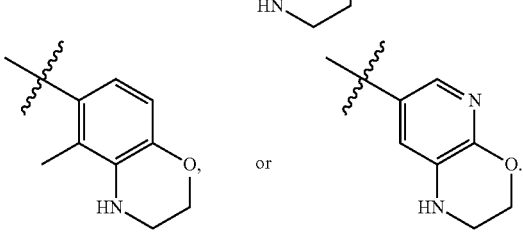 or In some embodiments,  or

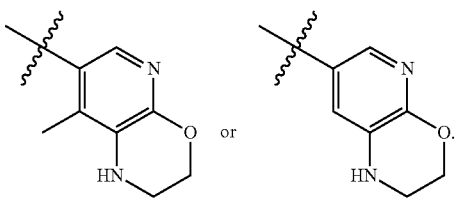 [SMILES: *c1cnc2c(c1C)NCCO2 ; *c1cnc2c(c1)NCCO2]

In some embodiments  is

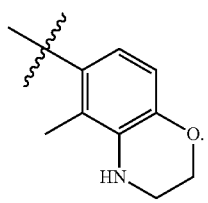 [SMILES: *c1ccc2c(c1C)NCCO2]

In some embodiments,  is

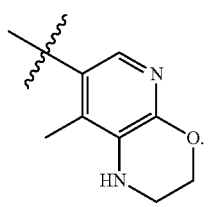 [SMILES: *c1cnc2c(c1C)NCCO2]

In some embodiments,  is

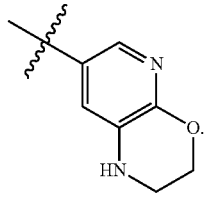 [SMILES: *c1cnc2c(c1)NCCO2]

In some embodiments of the compounds of Formula I, I-Z, I-E, II-Z, IIa-Z, IIb-Z, III-Z, and IIIa-Z, $L^1$ is N or $CR^{19}$, wherein $R^{19}$ is H, —$OR^{13}$, halogen, CN, —$N(R^{13})_2$, or $C_1$-$C_3$ alkyl; and each $R^{13}$ is independently H or $C_1$-$C_3$ alkyl. In some embodiments, $L^1$ is N or $CR^{19}$, wherein $R^{19}$ is H or $C_1$-$C_3$ alkyl. In some embodiments, $L^1$ is N or $CR^{19}$, wherein $R^{19}$ is H or $CH_3$. In some embodiments, $L^1$ is N or $CR^{19}$, wherein $R^{19}$ is H.

In some embodiments of the compounds of Formula I, I-Z, I-E, II-Z, IIa-Z, IIb-Z, III-Z, and IIIa-Z, $L^1$ is $CR^{19}$, wherein $R^{19}$ is H, —$OR^{13}$, halogen, CN, —$N(R^{13})_2$, or $C_1$-$C_3$ alkyl; and wherein each $R^{13}$ is independently H or $C_1$-$C_3$ alkyl. In some embodiments, $L^1$ is $CR^{19}$, wherein $R^{19}$ is H or $C_1$-$C_3$ alkyl. In some embodiments, $L^1$ is $CR^{19}$, wherein $R^{19}$ is H or $CH_3$. In some embodiments, $L^1$ is $CR^{19}$, wherein $R^{19}$ is H.

In some embodiments of the compounds of Formula I, I-Z, I-E, II-Z, IIa-Z, IIb-Z, III-Z, and IIIa-Z, $L^1$ is N.

In some embodiments of the compounds of Formula I, I-Z, I-E, II-Z, IIa-Z, IIb-Z, III-Z, and IIIa-Z, n is 1. In some embodiments, n is 0. In some embodiments, n is 2.

In some embodiments of the compounds of Formula I, I-Z, I-E, II-Z, IIa-Z, IIb-Z, III-Z, and IIIa-Z, n is 1 and $L^1$ is $CR^{19}$; wherein $R^{19}$ is H or $C_1$-$C_3$ alkyl, for example, $R^{19}$ is H or $CH_3$, or $R^{19}$ is H. In some embodiments, n is 0 and $L^1$ is $CR^{19}$; wherein $R^{19}$ is H or $C_1$-$C_3$ alkyl, for example, $R^{19}$ is H or $CH_3$, or $R^{19}$ is H. In some embodiments, n is 2 and $L^1$ is $CR^{19}$; wherein $R^{19}$ is H or $C_1$-$C_3$ alkyl, for example, $R^{19}$ is H or $CH_3$, or $R^{19}$ is H.

In some embodiments of the compounds of Formula I, I-Z, I-E, II-Z, IIa-Z, IIb-Z, III-Z, and IIIa-Z, n is 1 and $L^1$ is N. In some embodiments, n is 0 and $L^1$ is N. In some embodiments, n is 2 and $L^1$ is N.

In some embodiments of the compounds of Formula I, I-Z, I-E, II-Z, IIa-Z, IIb-Z, III-Z, and IIIa-Z, m is 0, 1, 2, or 3; each $R^{20}$ is independently —$OR^{13}$, halogen, CN, —$N(R^{13})_2$, or $C_1$-$C_3$ alkyl; and each $R^{13}$ is independently H or $C_1$-$C_3$ alkyl. In some embodiments, m is 0, 1, 2, or 3; and each $R^{20}$ is independently $C_1$-$C_3$ alkyl. In some embodiments, m is 0 or 1; and $R^{20}$ is $C_1$-$C_3$ alkyl. In some embodiments, m is 0. In some embodiments, m is 1; and $R^{20}$ is $C_1$-$C_3$ alkyl. In some embodiments, m is 0 or 1 and $R^{20}$ is $CH_3$. In some embodiments, m is 1 and $R^{20}$ is $CH_3$.

In some embodiments of the compounds of Formula I, I-Z, I-E, II-Z, IIa-Z, IIb-Z, III-Z, and IIIa-Z, $L^1$ is $CR^{19}$ or N; n is 1; m is 0; and p is 0. In some embodiments, $L^1$ is $CR^{19}$ or N; n is 0; m is 0; and p is 0. In some embodiments, $L^1$ is $CR^{19}$ or N; n is 2; m is 0; and p is 0. In some embodiments, $L^1$ N; n is 1; m is 0; and p is 0. In some embodiments, $L^1$ is N; n is 0; m is 0; and p is 0. In some embodiments, $L^1$ is N; n is 2; m is 0; and p is 0.

In some embodiments of the compounds of Formula I, I-Z, I-E, II-Z, IIa-Z, IIb-Z, III-Z, and IIIa-Z, $L^1$ is $CR^{19}$; n is 1; m is 0; and p is 0; $R^{19}$ is H, —$OR^{13}$, halogen, CN, —$N(R^{13})_2$, or $C_1$-$C_3$ alkyl; and each $R^{13}$ is independently H or $C_1$-$C_3$ alkyl. In some embodiments, $L^1$ is $CR^{19}$; n is 1; m is 0; and p is 0; wherein $R^{19}$ is H, —OH, halogen, CN, —$NH_2$, or $C_1$-$C_3$ alkyl. In some embodiments, $L^1$ is $CR^{19}$; n is 1; m is 0; p is 0; and $R^{19}$ is H.

In some embodiments of the compounds of Formula I, I-Z, I-E, II-Z, IIa-Z, IIb-Z, III-Z, and IIIa-Z, $L^1$ is $CR^{19}$; n is 0; m is 0; and p is 0; wherein $R^{19}$ is H, —$OR^{13}$, halogen, CN, —$N(R^{13})_2$, or $C_1$-$C_3$ alkyl; and each $R^{13}$ is independently H or $C_1$-$C_3$ alkyl. In some embodiments, $L^1$ is $CR^{19}$; n is 0; m is 0; and p is 0; wherein $R^{19}$ is H, —OH, halogen, CN, —$NH_2$, or $C_1$-$C_3$ alkyl. In some embodiments of the compounds of Formula I, II, IIa, IIb, and IIIa, $L^1$ is $CR^{19}$; n is 0; m is 0; p is 0; and $R^{19}$ is H.

In some embodiments of the compounds of I, I-Z, I-E, II-Z, IIa-Z, IIb-Z, III-Z, and IIIa-Z, $L^1$ is $CR^{19}$; n is 2; m is 0; and p is 0; wherein $R^{19}$ is H, —$OR^{13}$, halogen, CN, —$N(R^{13})_2$, or $C_1$-$C_3$ alkyl; and each $R^{13}$ is independently H or $C_1$-$C_3$ alkyl. In some embodiments, $L^1$ is $CR^{19}$; n is 2; m is 0; and p is 0; wherein $R^{19}$ is H, —OH, halogen, CN, —$NH_2$, or $C_1$-$C_3$ alkyl. In some embodiments of the compounds of Formula I, II, IIa, IIb, III, and IIIa, $L^1$ is $CR^{19}$; n is 2; m is 0; p is 0; and $R^{19}$ is H.

In some embodiments of the compounds of Formula I, I-Z, I-E, II-Z, IIa-Z, IIb-Z, III-Z, and IIIa-Z, $L^1$ is N; n is 1; m is 1; and p is 0; wherein $R^{20}$ is —$OR^{13}$, halogen, CN, —N(R$^{13}$)$_2$, or C$_1$-C$_3$ alkyl; and each R$^{13}$ is independently H or C$_1$-C$_3$ alkyl. In some embodiments, L$^1$ is N; n is 1; m is 1; and p is 0; wherein R$^{20}$ is —OH, halogen, CN, —NH$_2$, or C$_1$-C$_3$ alkyl. In some embodiments, L$^1$ is N; n is 1; m is 1; p is 0; and R$^{20}$ is C$_1$-C$_3$ alkyl. In some embodiments, L$^1$ is N; n is 1; m is 1; p is 0; and R$^{20}$ is CH$_3$.

In some embodiments of the compounds of Formula I, I-Z, I-E, II-Z, IIa-Z, IIb-Z, III-Z, and IIIa-Z, L$^1$ is N; n is 0; m is 1; and p is 0; wherein R$^{20}$ is —OR$^{13}$, halogen, CN, —N(R$^{13}$)$_2$, and C$_1$-C$_3$ alkyl; and each R$^{13}$ is independently H or C$_1$-C$_3$ alkyl. In some embodiments, L$^1$ is N; n is 0; m is 1; and p is 0; and R$^{20}$ is —OH, halogen, CN, —NH$_2$, or C$_1$-C$_3$ alkyl. In some embodiments, L$^1$ is N; n is 0; m is 1; p is 0; and R$^{20}$ is C$_1$-C$_3$ alkyl. In some embodiments, L$^1$ is N; n is 0; m is 1; p is 0; and R$^{20}$ is CH$_3$.

In some embodiments of the compounds of Formula I, I-Z, I-E, II-Z, IIa-Z, IIb-Z, III-Z, and IIIa-Z, L$^1$ is N; n is 2; m is 1; and p is 0; wherein R$^{20}$ is —OR$^{13}$, halogen, CN, —N(R$^{13}$)$_2$, or C$_1$-C$_3$ alkyl; and each R$^{13}$ is independently H or C$_1$-C$_3$ alkyl. In some embodiments, L$^1$ is N; n is 2; m is 1; and p is 0; R$^{20}$ is —OH, halogen, CN, —NH$_2$, or C$_1$-C$_3$ alkyl. In some embodiments, L$^1$ is N; n is 2; m is 1; p is 0; and R$^{20}$ is C$_1$-C$_3$ alkyl. In some embodiments, L$^1$ is N; n is 2; m is 1; p is 0; and R$^{20}$ is CH$_3$.

In some embodiments of the compounds of Formula I, I-Z, I-E, II-Z, IIa-Z, IIb-Z, III-Z, and IIIa-Z, L$^1$ is CR$^{19}$; n is 1; m is 1; and p is 0; wherein R$^{19}$ is H, —OR$^{13}$, halogen, CN, —N(R$^{13}$)$_2$, or C$_1$-C$_3$ alkyl; R$^{20}$ is —OR$^{13}$, halogen, CN, —N(R$^{13}$)$_2$, or C$_1$-C$_3$ alkyl; and each R$^{13}$ is independently H or C$_1$-C$_3$ alkyl. In some embodiments, L$^1$ is CR$^{19}$; n is 1; m is 1; and p is 0; wherein R$^{19}$ is H, —OH, halogen, CN, —NH$_2$, or C$_1$-C$_3$ alkyl; R$^{20}$ is —OH, halogen, CN, —NH$_2$, or C$_1$-C$_3$ alkyl. In some embodiments, L$^1$ is CR$^{19}$; n is 1; m is 1; and p is 0; wherein R$^{19}$ is H and R$^{20}$ is —OH, halogen, CN, —NH$_2$, or C$_1$-C$_3$ alkyl. In some embodiments, L$^1$ is CR$^{19}$; n is 1; m is 1; and p is 0; wherein R$^{19}$ is H and R$^{20}$ is C$_1$-C$_3$ alkyl. In some embodiments, L$^1$ is CR$^{19}$; n is 1; m is 1; p is 0; wherein R$^{19}$ is H and R$^{20}$ is CH$_3$.

In some embodiments of the compounds of Formula I, I-Z, I-E, II-Z, IIa-Z, IIb-Z, III-Z, and IIIa-Z, L$^1$ is CR$^{19}$; n is 0; m is 1; and p is 0; wherein R$^{19}$ is H, —OR$^{13}$, halogen, CN, —N(R$^{13}$)$_2$, or C$_1$-C$_3$ alkyl; R$^{20}$ is —OR$^{13}$, halogen, CN, —N(R$^{13}$)$_2$, or C$_1$-C$_3$ alkyl; and each R$^{13}$ is independently H or C$_1$-C$_3$ alkyl. In some embodiments, L$^1$ is CR$^{19}$; n is 0; m is 1; and p is 0; wherein R$^{19}$ is H, —OH, halogen, CN, —NH$_2$, or C$_1$-C$_3$ alkyl; R$^{20}$ is —OH, halogen, CN, —NH$_2$, or C$_1$-C$_3$ alkyl. In some embodiments, L$^1$ is CR$^{19}$; n is 0; m is 1; and p is 0; wherein R$^{19}$ is H and R$^{20}$ is —OH, halogen, CN, —NH$_2$, or C$_1$-C$_3$ alkyl. In some embodiments, L$^1$ is CR$^{19}$; n is 0; m is 1; p is 0; R$^{19}$ is H and R$^{20}$ is C$_1$-C$_3$ alkyl. In some embodiments, L$^1$ is CR$^{19}$; n is 0; m is 1; p is 0; R$^{19}$ is H and R$^{20}$ is CH$_3$.

In some embodiments of the compounds of Formula I, I-Z, I-E, II-Z, IIa-Z, IIb-Z, III-Z, and IIIa-Z, L$^1$ is CR$^{19}$; n is 2; m is 1; and p is 0; wherein R$^{19}$ is H, —OR$^{13}$, halogen, CN, —N(R$^{13}$)$_2$, or C$_1$-C$_3$ alkyl; R$^{20}$ is —OR$^{13}$, halogen, CN, —N(R$^{13}$)$_2$, or C$_1$-C$_3$ alkyl; and each R$^{13}$ is independently H or C$_1$-C$_3$ alkyl. In some embodiments, L$^1$ is CR$^{19}$; n is 2; m is 1; and p is 0; wherein R$^{19}$ is H, —OH, halogen, CN, —NH$_2$, or C$_1$-C$_3$ alkyl; R$^{20}$ is —OH, halogen, CN, —NH$_2$, or C$_1$-C$_3$ alkyl. In some embodiments, L$^1$ is CR$^{19}$; n is 2; m is 1; and p is 0; wherein R$^{19}$ is H and R$^{20}$ is —OH, halogen, CN, —NH$_2$, or C$_1$-C$_3$ alkyl. In some embodiments, L$^1$ is CR$^{19}$; n is 2; m is 1; p is 0; R$^{19}$ is H and R$^{20}$ is C$_1$-C$_3$ alkyl. In some embodiments, L$^1$ is CR$^{19}$; n is 2; m is 1; p is 0; R$^{19}$ is H and R$^{20}$ is CH$_3$.

In some embodiments of the compounds of I, I-Z, I-E, II-Z, IIa-Z, IIb-Z, III-Z, and IIIa-Z, L$^1$ is CR$^{19}$ or N; n is 0, 1, or 2; m is 0 or 1; and p is 0, 1, 2, or 3; wherein R$^{19}$ is H, —OR$^{13}$, halogen, CN, —N(R$^{13}$)$_2$ or C$_1$-C$_3$ alkyl; R$^{20}$ is —OR$^{13}$, halogen, CN, —N(R$^{13}$)$_2$ or C$_1$-C$_3$ alkyl; each R$^{21}$ is independently —OR$^{13}$, oxo, halogen, CN, —N(R$^{13}$)$_2$ or C$_1$-C$_3$ alkyl; or two R$^{21}$ groups on same or adjoining atoms are joined together to form a 3-6 membered carbocyclic ring or a 3-6 membered heterocyclic ring; and each R$^{13}$ is independently H or C$_1$-C$_3$ alkyl.

In some embodiments of the compounds of Formula I, I-Z, I-E, II-Z, IIa-Z, IIb-Z, III-Z, and IIIa-Z, L$^1$ is CR$^{19}$ or N; n is 0, 1, or 2; m is 0 or 1; and p is 0, 1, 2, or 3; wherein R$^{19}$ is H; R$^{20}$ is —OR$^{13}$, halogen, CN, —N(R$^{13}$)$_2$, or C$_1$-C$_3$ alkyl; each R$^{21}$ is independently —OR$^{13}$, oxo, halogen, CN, —N(R$^{13}$)$_2$ or C$_1$-C$_3$ alkyl; or two R$^{21}$ groups on same or adjoining atoms are joined together to form a 3-6 membered carbocyclic ring or a 3-6 membered heterocyclic ring; and each R$^{13}$ is independently H or C$_1$-C$_3$ alkyl.

In some embodiments of the compounds of Formula I, I-Z, I-E, II-Z, IIa-Z, IIb-Z, III-Z, and IIIa-Z, L$^1$ is CR$^{19}$ or N; n is 0, 1, or 2; m is 0 or 1; and p is 0, 1, 2, or 3; wherein R$^{19}$ is H; R$^{20}$ is C$_1$-C$_3$ alkyl; each R$^{21}$ is independently —OR$^{13}$, oxo, halogen, CN, —N(R$^{13}$)$_2$ or C$_1$-C$_3$ alkyl; or two R$^{21}$ groups on same or adjoining atoms are joined together to form a 3-6 membered carbocyclic ring or a 3-6 membered heterocyclic ring; and each R$^{13}$ is independently H or C$_1$-C$_3$ alkyl.

In some embodiments of the compounds of Formula I, I-Z, I-E, II-Z, IIa-Z, IIb-Z, III-Z, and IIIa-Z, L$^1$ is CR$^{19}$ or N; n is 0, 1, or 2; m is 0; and p is 0, 1, 2, or 3; wherein R$^{19}$ is H; each R$^{21}$ is independently —OR$^{13}$, oxo, halogen, CN, —N(R$^{13}$)$_2$ or C$_1$-C$_3$ alkyl; or two R$^{21}$ groups on same or adjoining atoms are joined together to form a 3-6 membered carbocyclic ring or a 3-6 membered heterocyclic ring; and each R$^{13}$ is independently H or C$_1$-C$_3$ alkyl. In some embodiments, L$^1$ is CR$^{19}$ or N; n is 0, 1, or 2; m is 0; and p is 0, 1, 2, or 3; wherein R$^{19}$ is H; and each R$^{21}$ is independently —OH, oxo, halogen, CN, —NH$_2$, or C$_1$-C$_3$ alkyl; or two R$^{21}$ groups on same or adjoining atoms are joined together to form a 3-6 membered carbocyclic ring or a 3-6 membered heterocyclic ring.

In some embodiments of the compounds of Formula I, I-Z, I-E, II-Z, IIa-Z, IIb-Z, III-Z, and IIIa-Z, L$^1$ is CR$^{19}$ or N; n is 0, 1, or 2; m is 1; and p is 0, 1, 2, or 3; wherein R$^{19}$ is H; R$^{20}$ is C$_1$-C$_3$ alkyl; and each R$^{21}$ is independently —OH, oxo, halogen, CN, —NH$_2$ or C$_1$-C$_3$ alkyl; or two R$^{21}$ groups on same or adjoining atoms are joined together to form a 3-6 membered carbocyclic ring or a 3-6 membered heterocyclic ring.

In some embodiments of the compounds of Formula I, I-Z, I-E, II-Z, IIa-Z, IIb-Z, III-Z, and IIIa-Z, L$^1$ is CR$^{19}$ or N; n is 0, 1, or 2; m is 1; and p is 0, 1, 2, or 3; wherein R$^{19}$ is H; R$^{20}$ is CH$_3$; and each R$^{21}$ is independently —OH, oxo, halogen, CN, —NH$_2$ or C$_1$-C$_3$ alkyl; or two R$^{21}$ groups on same or adjoining atoms are joined together to form a 3-6 membered carbocyclic ring or a 3-6 membered heterocyclic ring.

In some embodiments of the compounds of Formula I, I-Z, I-E, II-Z, IIa-Z, IIb-Z, III-Z, and IIIa-Z, L$^1$ is CR$^{19}$ or N; n is 1; m is 0 or 1; and p is 0, 1, 2, or 3; wherein R$^{19}$ is H, —OR$^{13}$, halogen, CN, —N(R$^{13}$)$_2$, or C$_1$-C$_3$ alkyl; R$^{20}$ is —OR$^{13}$, halogen, CN, —N(R$^{13}$)$_2$, or C$_1$-C$_3$ alkyl; each R$^{21}$ is independently —OR$^{13}$, oxo, halogen, CN, —N(R$^{13}$)$_2$ or C$_1$-C$_3$ alkyl; or two R$^{21}$ groups on same or adjoining atoms are joined together to form a 3-6 membered carbocyclic ring or a 3-6 membered heterocyclic ring; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, $L^1$ is $CR^{19}$ or N; n is 1; m is 0 or 1; and p is 0, 1, 2, or 3; wherein $R^{19}$ is H; $R^{20}$ is —$OR^{13}$, halogen, CN, —$N(R^{13})_2$, or $C_1$-$C_3$ alkyl; each $R^{21}$ is independently —$OR^{13}$, oxo, halogen, CN, —$N(R^{13})_2$ or $C_1$-$C_3$ alkyl; or two $R^{21}$ groups on same or adjoining atoms are joined together to form a 3-6 membered carbocyclic ring or a 3-6 membered heterocyclic ring; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, $L^1$ is $CR^{19}$ or N; n is 1; m is 0 or 1; and p is 0, 1, 2, or 3; wherein $R^{19}$ is H; $R^{20}$ is $C_1$-$C_3$ alkyl; each $R^{21}$ is independently —$OR^{13}$, oxo, halogen, CN, —$N(R^{13})_2$, or $C_1$-$C_3$ alkyl; or two $R^{21}$ groups on same or adjoining atoms are joined together to form a 3-6 membered carbocyclic ring or a 3-6 membered heterocyclic ring; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, $L^1$ is $CR^{19}$ or N; n is 1; m is 0; and p is 0, 1, 2, or 3; wherein $R^{19}$ is H; each $R^{21}$ is independently —$OR^{13}$, oxo, halogen, CN, —$N(R^{13})_2$ or $C_1$-$C_3$ alkyl; or two $R^{21}$ groups on same or adjoining atoms are joined together to form a 3-6 membered carbocyclic ring or a 3-6 membered heterocyclic ring; and each $R^{13}$ is independently H or $C_1$-$C_3$ alkyl. In some embodiments, $L^1$ is $CR^{19}$ or N; n is 0, 1, or 2; m is 0; and p is 0, 1, 2, or 3; wherein $R^{19}$ is H; and each $R^{21}$ is independently —OH, oxo, halogen, CN, —$NH_2$ or $C_1$-$C_3$ alkyl; or two $R^{21}$ groups on same or adjoining atoms are joined together to form a 3-6 membered carbocyclic ring or a 3-6 membered heterocyclic ring.

In some embodiments of the compounds of the compounds of Formula I, I-Z, I-E, II-Z, IIa-Z, IIb-Z, III-Z, and IIIa-Z, $L^1$ is $CR^{19}$ or N; n is 1; m is 1; and p is 0, 1, 2, or 3; wherein $R^{19}$ is H; $R^{20}$ is $C_1$-$C_3$ alkyl; each $R^{21}$ is independently —OH, oxo, halogen, CN, —$NH_2$ or $C_1$-$C_3$ alkyl; or two $R^{21}$ groups on same or adjoining atoms are joined together to form a 3-6 membered carbocyclic ring or a 3-6 membered heterocyclic ring.

In some embodiments of the compounds of Formula I, I-Z, I-E, II-Z, IIa-Z, IIb-Z, III-Z, and IIIa-Z, $L^1$ is $CR^{19}$ or N; n is 1; m is 1; and p is 0, 1, 2, or 3; wherein $R^{19}$ is H; $R^{20}$ is $CH_3$; each $R^{21}$ is independently —OH, oxo, halogen, CN, —$NH_2$, or $C_1$-$C_3$ alkyl; or two $R^{21}$ groups on same or adjoining atoms are joined together to form a 3-6 membered carbocyclic ring or a 3-6 membered heterocyclic ring.

In some embodiments of the compounds of Formula I, I-Z, I-E, II-Z, IIa-Z, IIb-Z, III-Z, and IIIa-Z, $L^1$ is $CR^{19}$ or N; n is 1; m is 1; and p is 0, 1, 2, or 3; wherein $R^{19}$ is H, —$OR^{13}$, halogen, CN, —$N(R^{13})_2$, or $C_1$-$C_3$ alkyl; $R^{20}$ is —$OR^{13}$, halogen, CN, —$N(R^{13})_2$, or $C_1$-$C_3$ alkyl; each $R^{21}$ is independently —$OR^{13}$, oxo, halogen, CN, —$N(R^{13})_2$ or $C_1$-$C_3$ alkyl; or two $R^{21}$ groups on same or adjoining atoms are joined together to form a 3-6 membered carbocyclic ring or a 3-6 membered heterocyclic ring; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, $L^1$ is $CR^{19}$ or N; n is 0; m is 1; and p is 0, 1, 2, or 3; wherein $R^{19}$ is H, —$OR^{13}$, halogen, CN, —$N(R^{13})_2$, or $C_1$-$C_3$ alkyl; $R^{20}$ is —$OR^{13}$, halogen, CN, —$N(R^{13})_2$, or $C_1$-$C_3$ alkyl; each $R^{21}$ is independently —$OR^{13}$, oxo, halogen, CN, —$N(R^{13})_2$ or $C_1$-$C_3$ alkyl; or two $R^{21}$ groups on same or adjoining atoms are joined together to form a 3-6 membered carbocyclic ring or a 3-6 membered heterocyclic ring; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, $L^1$ is $CR^{19}$ or N; n is 2; m is 1; and p is 0, 1, 2, or 3; wherein $R^{19}$ is H, —$OR^{13}$, halogen, CN, —$N(R^{13})_2$, or $C_1$-$C_3$ alkyl; $R^{20}$ is —$OR^{13}$, halogen, CN, —$N(R^{13})_2$, or $C_1$-$C_3$ alkyl; each $R^{21}$ is independently —$OR^{13}$, oxo, halogen, CN, —$N(R^{13})_2$ or $C_1$-$C_3$ alkyl; or two $R^{21}$ groups on same or adjoining atoms are joined together to form a 3-6 membered carbocyclic ring or a 3-6 membered heterocyclic ring; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, $L^1$ is $CR^{19}$ or N; n is 1; m is 1; and p is 1; wherein $R^{19}$ is H, —$OR^{13}$, halogen, CN, —$N(R^{13})_2$ or $C_1$-$C_3$ alkyl; $R^{20}$ is —$OR^{13}$, halogen, CN, —$N(R^{13})_2$, or $C_1$-$C_3$ alkyl; $R^{21}$ is independently —$OR^{13}$, oxo, halogen, CN, —$N(R^{13})_2$ or $C_1$-$C_3$ alkyl; and each $R^{13}$ is independently H or $C_1$-$C_3$ alkyl. In some embodiments, $L^1$ is $CR^{19}$ or N; n is 1; m is 1; and p is 1; wherein $R^{19}$ is H; $R^{20}$ is —$OR^{13}$, halogen, CN, —$N(R^{13})_2$, or $C_1$-$C_3$ alkyl; $R^{21}$ is independently —$OR^{13}$, oxo, halogen, CN, —$N(R^{13})_2$ or $C_1$-$C_3$ alkyl; and each $R^{13}$ is independently H or $C_1$-$C_3$ alkyl. In some embodiments, $L^1$ is $CR^{19}$ or N; n is 1; m is 1; and p is 1; wherein $R^{19}$ is H; $R^{20}$ is $C_1$-$C_3$ alkyl; $R^{21}$ is independently —$OR^{13}$, oxo, halogen, CN, —$N(R^{13})_2$ or $C_1$-$C_3$ alkyl; and each $R^{13}$ is independently H or $C_1$-$C_3$ alkyl. In some embodiments, $L^1$ is $CR^{19}$; n is 1; m is 1; and p is 1; wherein $R^{19}$ is H; $R^{20}$ is $CH_3$; $R^{21}$ is —$OR^{13}$, oxo, halogen, CN, —$N(R^{13})_2$ or $C_1$-$C_3$ alkyl; and each $R^{13}$ is independently H or $C_1$-$C_3$ alkyl. In some embodiments, $L^1$ is $CR^{19}$; n is 1; m is 1; and p is 1; wherein $R^{19}$ is H; $R^{20}$ is $CH_3$; $R^{21}$ is —OH, oxo, halogen, CN, —$NH_2$ or $C_1$-$C_3$ alkyl. In some embodiments, $L^1$ is $CR^{19}$; n is 1; m is 1; and p is 1; wherein $R^{19}$ is H; $R^{20}$ is $CH_3$; and $R^{21}$ is oxo.

In some embodiments of the compounds of Formula I, I-Z, I-E, II-Z, IIa-Z, IIb-Z, III-Z, and IIIa-Z, $L^1$ is N; n is 1; m is 1; and p is 1; $R^{20}$ is $C_1$-$C_3$ alkyl; $R^{21}$ is —$OR^{13}$, oxo, halogen, CN, —$N(R^{13})_2$ or $C_1$-$C_3$ alkyl; and each $R^{13}$ is independently H or $C_1$-$C_3$ alkyl. In some embodiments, $L^1$ is N; n is 1; m is 1; and p is 1; $R^{20}$ is $CH_3$; $R^{21}$ is —$OR^{13}$, oxo, halogen, CN, —$N(R^{13})_2$ or $C_1$-$C_3$ alkyl; and each $R^{13}$ is independently H or $C_1$-$C_3$ alkyl. In some embodiments, $L^1$ is N; n is 1; m is 1; and p is 1; wherein $R^{20}$ is $CH_3$; $R^{21}$ is —OH, oxo, halogen, CN, —$NH_2$ or $C_1$-$C_3$ alkyl. In some embodiments, $L^1$ is N; n is 1; m is 1; and p is 1; wherein $R^{20}$ is $CH_3$; and $R^{21}$ is oxo.

In some embodiments of the compounds of Formula II, I-Z, I-E, II-Z, IIa-Z, IIb-Z, III-Z, and IIIa-Z, $L^1$ is $CR^{19}$ or N; n is 2; m is 1; and p is 0, 1, 2, or 3; wherein $R^{19}$ is H, —$OR^{13}$, halogen, CN, —$N(R^{13})_2$, or $C_1$-$C_3$ alkyl; $R^{20}$ is —$OR^{13}$, halogen, CN, —$N(R^{13})_2$, or $C_1$-$C_3$ alkyl; each $R^{21}$ is independently —$OR^{13}$, oxo, halogen, CN, —$N(R^{13})_2$ or $C_1$-$C_3$ alkyl; or two $R^{21}$ groups on same or adjoining atoms are joined together to form a 3-6 membered carbocyclic ring or a 3-6 membered heterocyclic ring; and each $R^{13}$ is independently H or $C_1$-$C_3$ alkyl.

In some embodiments of the compounds of Formula I, I-Z, I-E, II-Z, IIa-Z, IIb-Z, III-Z, and IIIa-Z, m is 0 or 1; and p is 0, 1, 2, or 3. In some embodiments, m is 0 or 1; p is 0, 1, 2, or 3; $R^{20}$ is $C_1$-$C_3$ alkyl; and each $R^{21}$ is independently a halogen or oxo; or two $R^{21}$ groups on same atoms are joined together to form a 3-6 membered carbocyclic ring or a 3-6 membered heterocyclic ring having 1 or 2 heteroatoms selected from N, O, and S.

In some embodiments of the compounds of Formula I, I-Z, I-E, II-Z, IIa-Z, IIb-Z, III-Z, and IIIa-Z, m is 0. In some embodiments, m is 1.

In some embodiments of the compounds of Formula I, I-Z, I-E, II-Z, IIa-Z, IIb-Z, III-Z, and IIIa-Z, $R^{20}$ is $CH_3$.

In some embodiments of the compounds of Formula I, I-Z, I-E, II-Z, IIa-Z, IIb-Z, III-Z, and IIIa-Z, p is 0.

In some embodiments of the compounds of Formula I, I-Z, I-E, II-Z, IIa-Z, IIb-Z, III-Z, and IIIa-Z, p is 2. In some embodiments, p is 2 and the two $R^{21}$ groups are on same atom and are joined together to form a 3-6 membered carbocyclic ring or a 3-6 membered heterocyclic ring having 1 or 2 heteroatoms selected from N, O, and S.

In some embodiments of the compounds of Formula I, I-Z, I-E, II-Z, IIa-Z, IIb-Z, III-Z, and IIIa-Z, m is 1; $R^{20}$ is $C_1$-$C_3$ alkyl; p is 2; and the two $R^{21}$ groups are on same atom and are joined together to form a 3-6 membered carbocyclic ring.

In some embodiments of the compounds of Formula I, I-Z, I-E, II-Z, IIa-Z, IIb-Z, III-Z, and IIIa-Z, p is 1. In some embodiments, p is 1 and $R^{21}$ is oxo.

In some embodiments of the compounds of Formula I, I-Z, I-E, II-Z, IIa-Z, IIb-Z, III-Z, and IIIa-Z, n is 0. In some embodiments, n is 1. In some embodiments, n is 2.

In some embodiments, the compound of Formula I, I-Z, II-Z, IIa-Z, or IIb-Z, is selected from the group consisting of

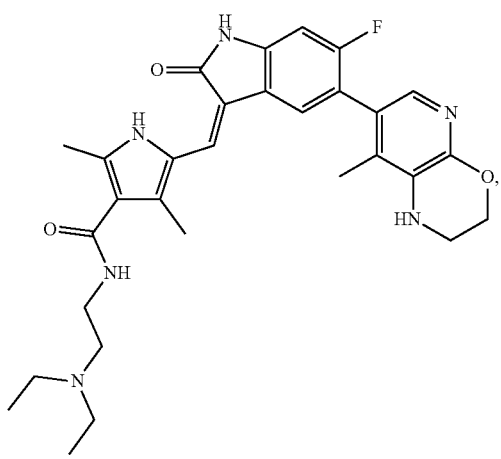

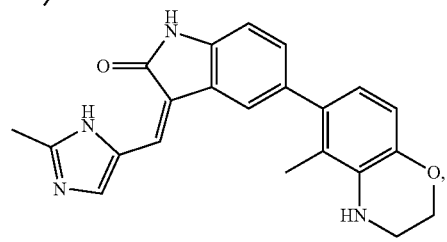

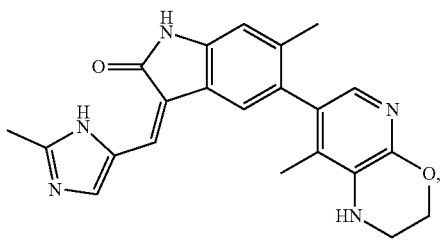

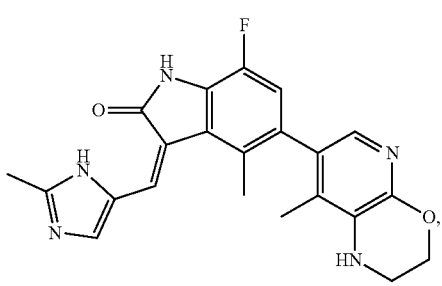

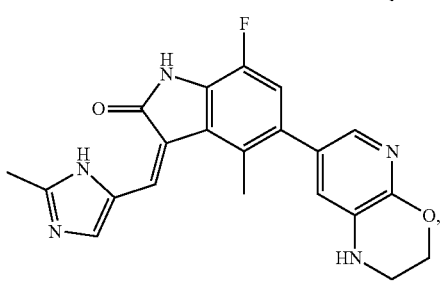

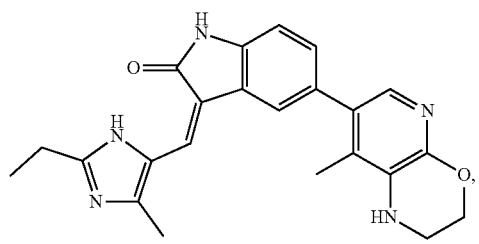

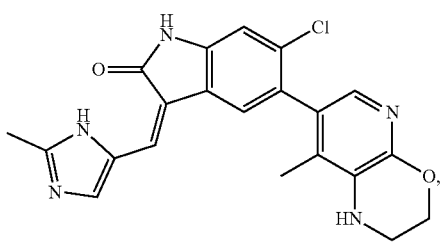

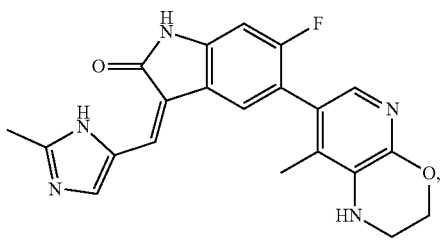

-continued
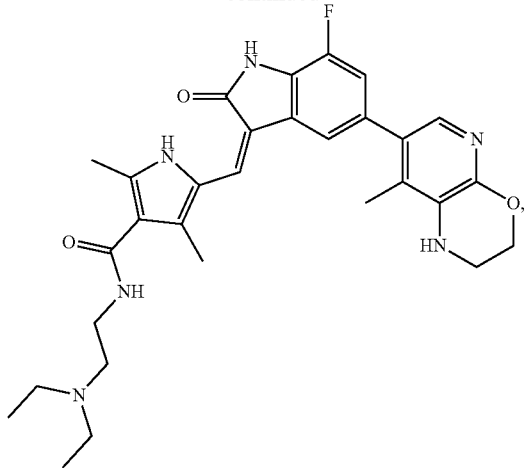
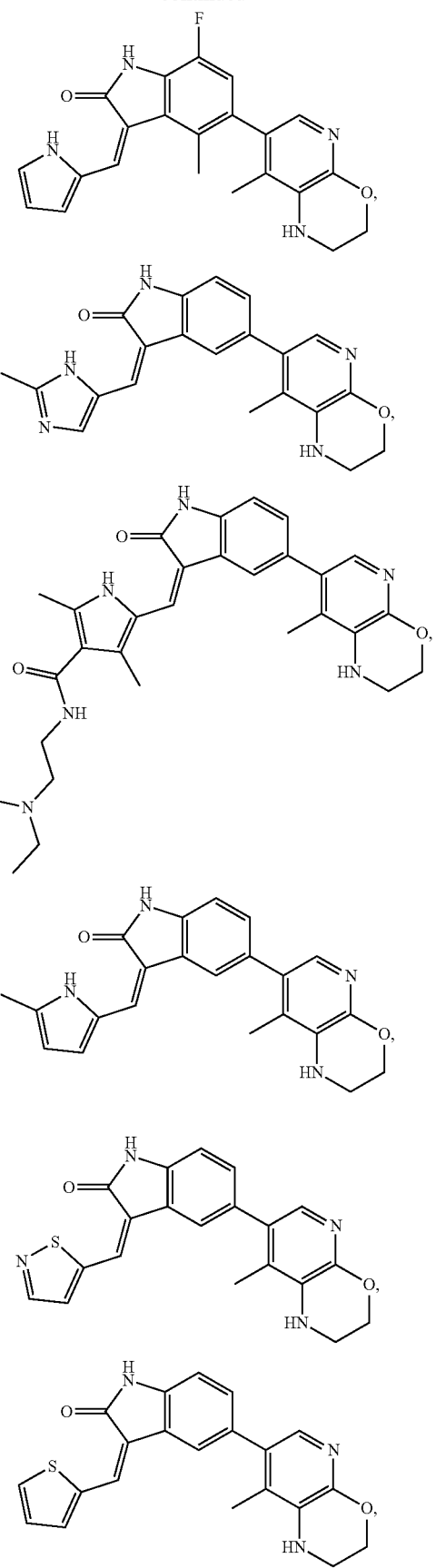

-continued
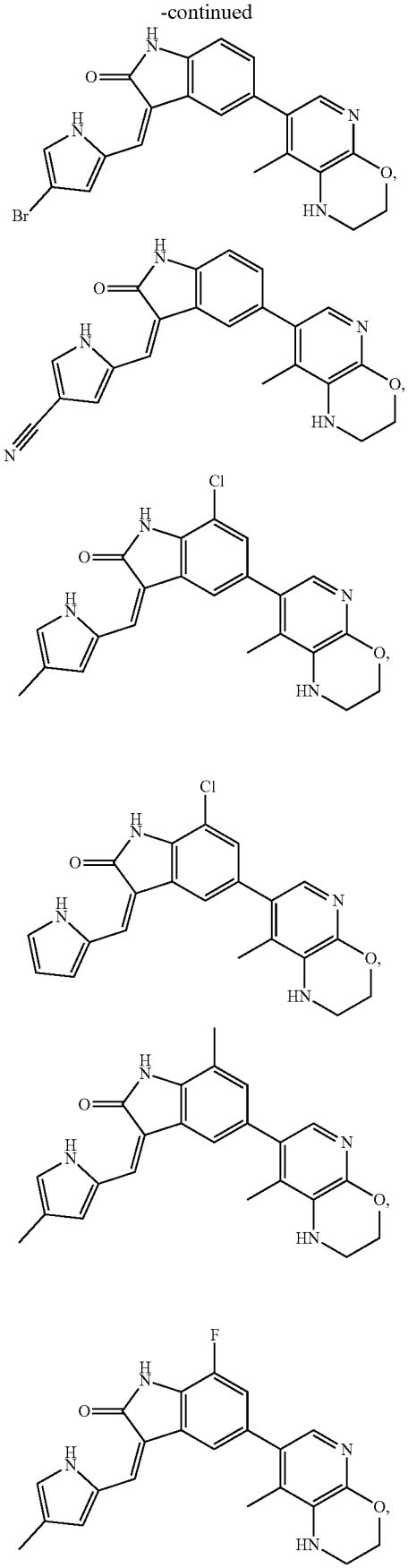
-continued
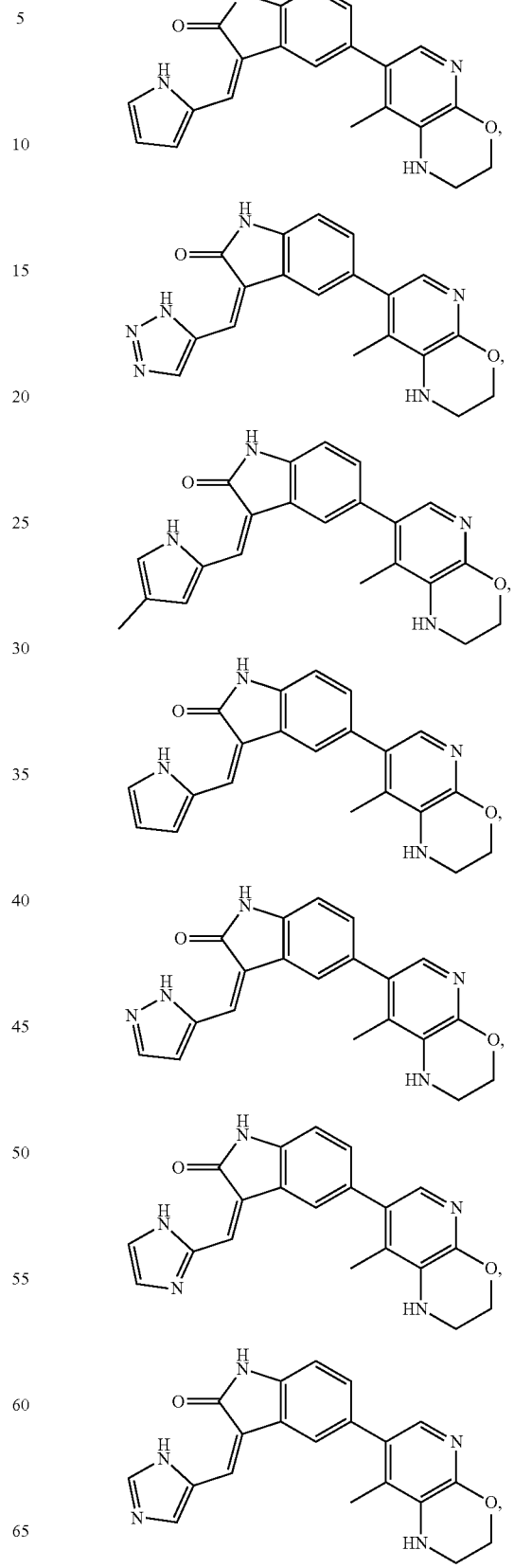

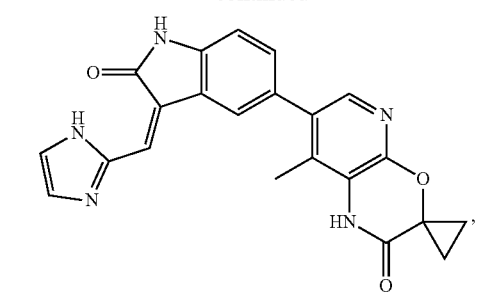
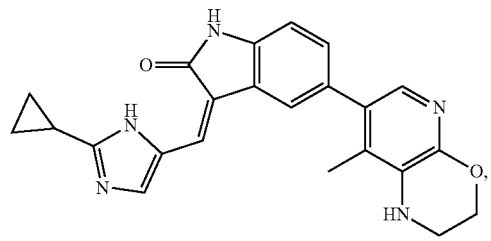
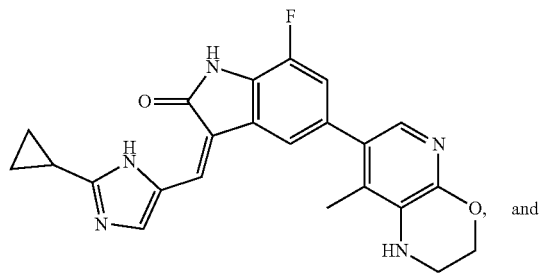
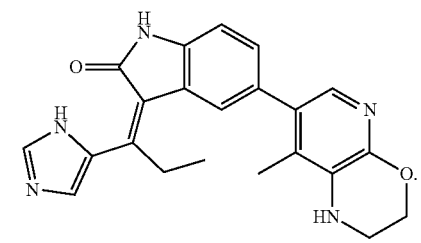
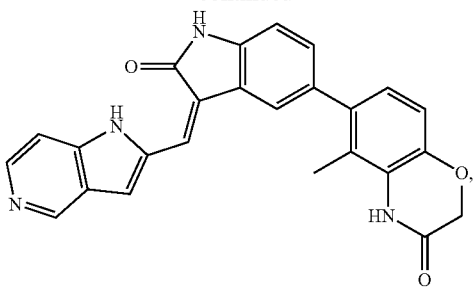
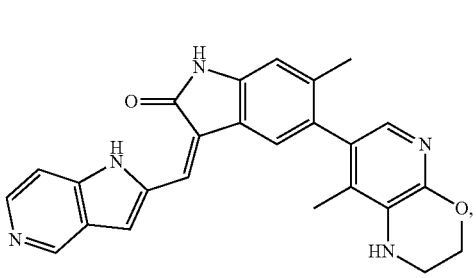
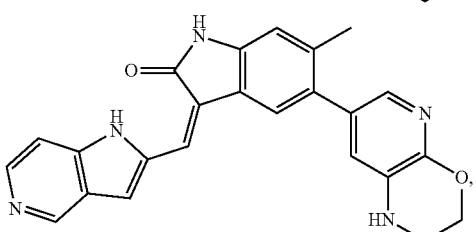
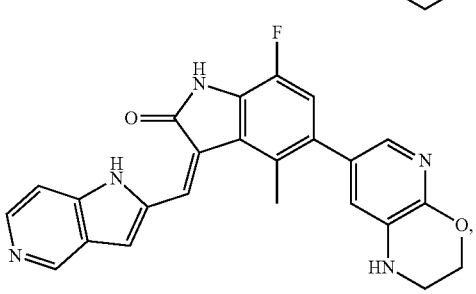
In some embodiments, the compound of Formula I, I-Z, II-Z, IIa-Z, or IIb-Z is selected from the group consisting of
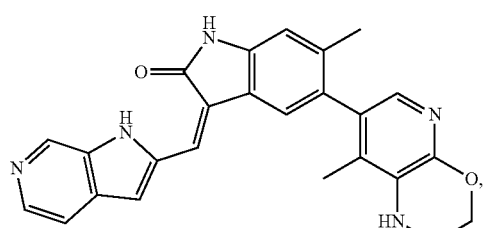
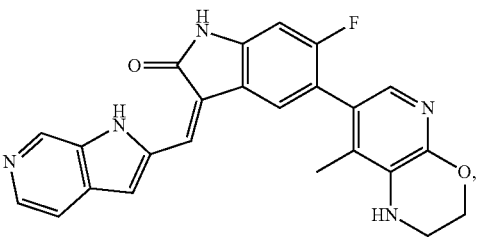
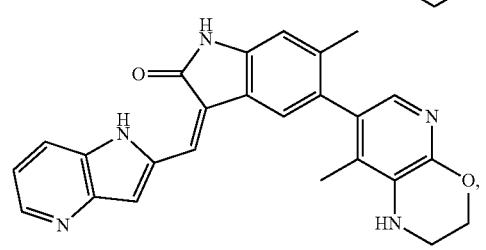
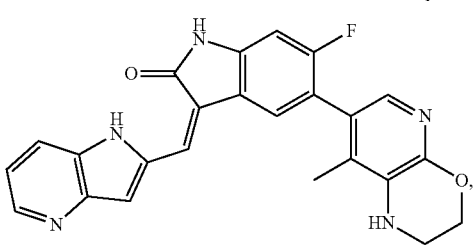

-continued
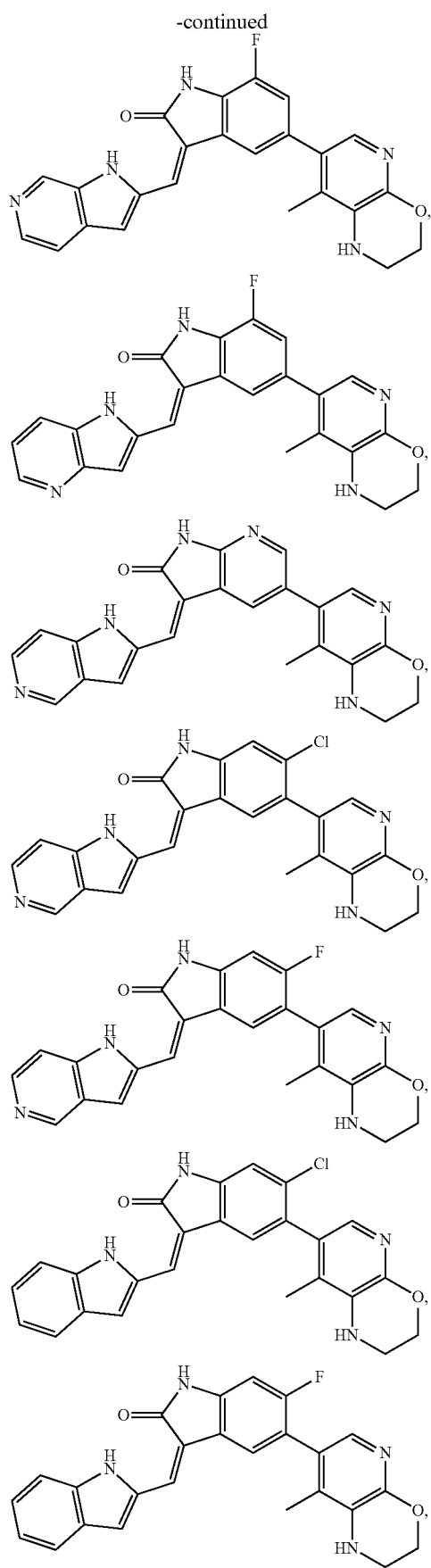
-continued
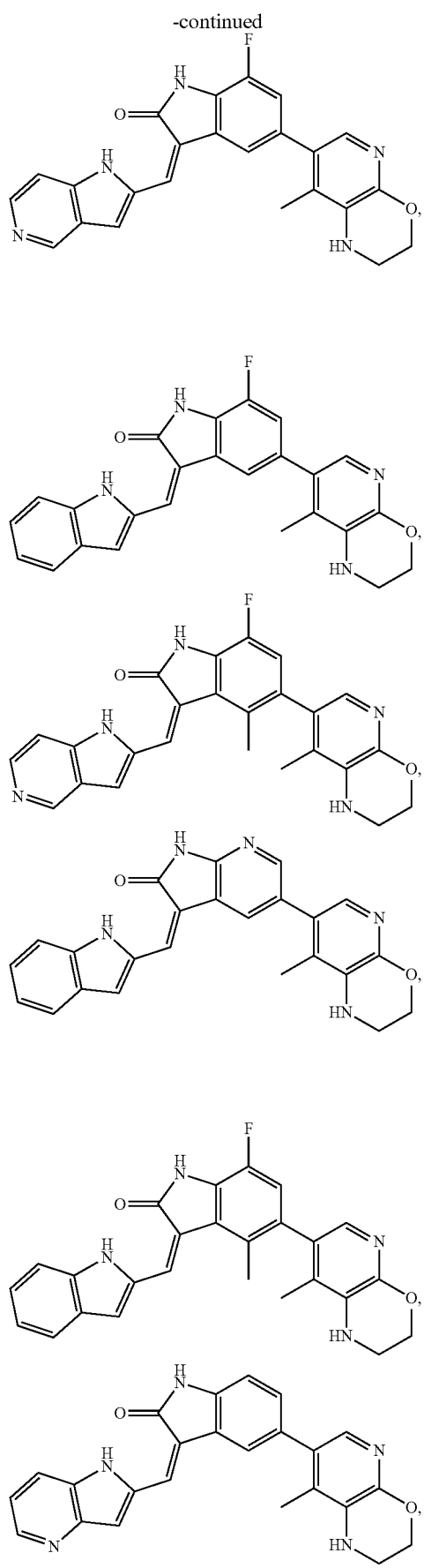

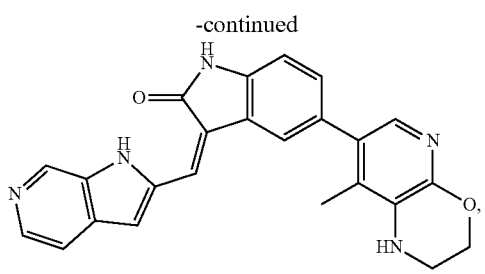
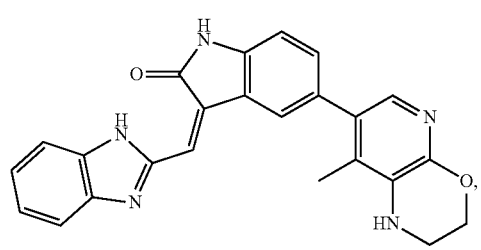
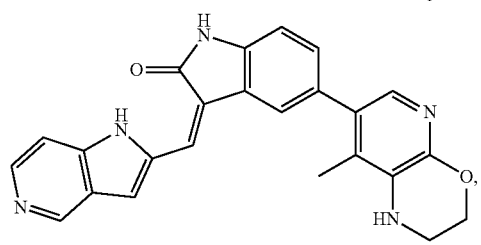
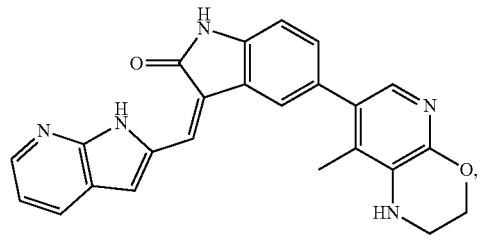
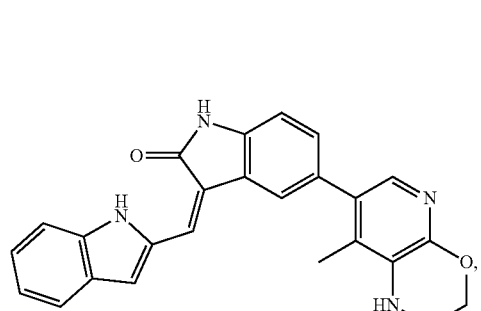
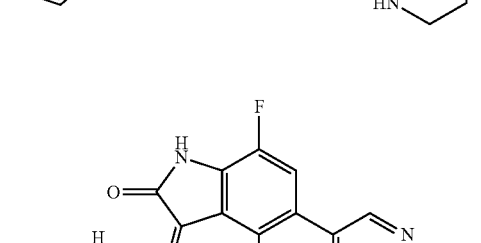
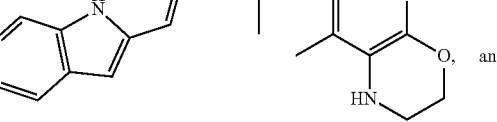, and
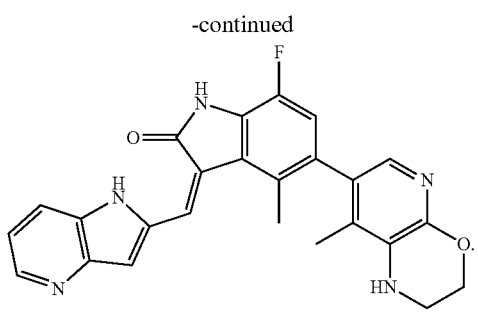
In some embodiments, the compound of Formula I, I-Z, or III-Z is selected from the group consisting of:
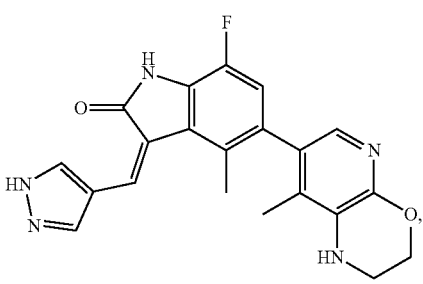
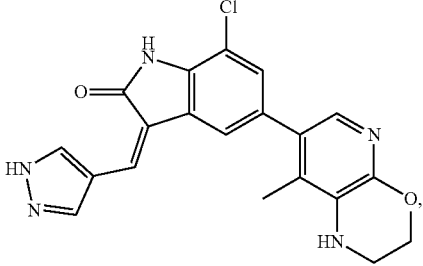
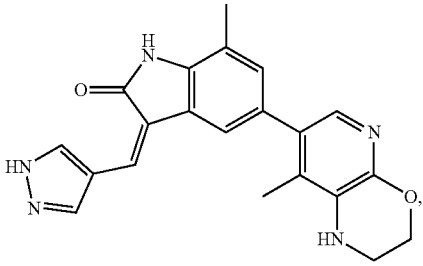
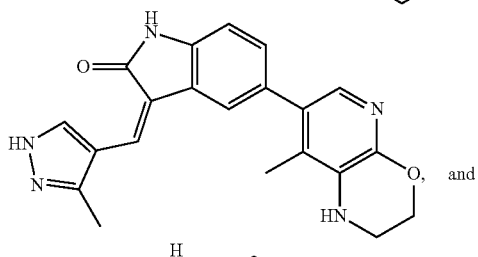, and
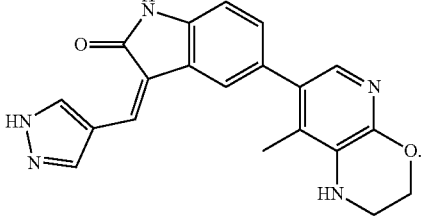

In some embodiments, the compound of Formula I, I-Z, III-Z, or IIIa-Z is

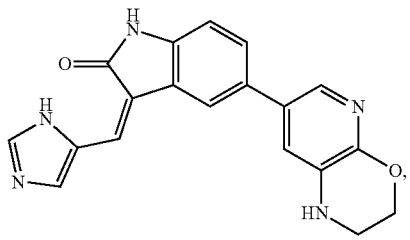 [SMILES: O=C1Nc2ccc(-c3cnc4c(c3)NCCO4)cc2/C1=C/c1cnc[nH]1]

or a pharmaceutically acceptable salt thereof.

In some embodiments, the compound of Formula I, I-Z, III-Z, or IIIa-Z is

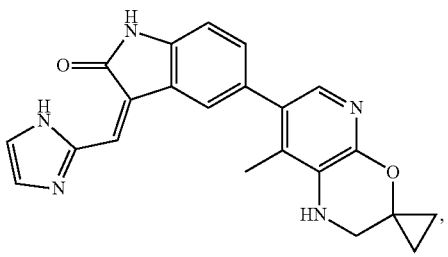 [SMILES: Cc1c(-c2ccc3c(c2)/C(=C/c2ncc[nH]2)C(=O)N3)cnc2c1NCC1(CC1)O2]

or a pharmaceutically acceptable salt thereof.

In some embodiments, the compound of Formula I, I-Z, III-Z, or IIIa-Z is:

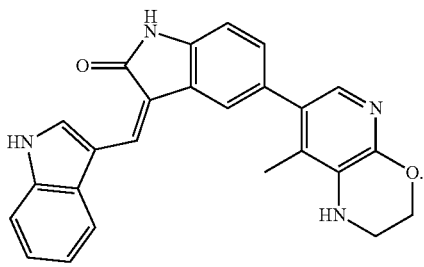 [SMILES: Cc1c(-c2ccc3c(c2)/C(=C/c2c[nH]c4ccccc24)C(=O)N3)cnc2c1NCCO2]

III. Compositions and Kits

Compounds provided herein are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants.

In one aspect, provided herein are pharmaceutical compositions comprising a compound provided herein (e.g., a compound of Formula I, I-Z, I-E, II-Z, IIa-Z, IIb-Z, III-Z, and IIIa-Z), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or a pharmaceutically acceptable salt thereof.

In some embodiments, the one or more additional therapeutic agents include agents that are therapeutic for a hepatitis B virus (HBV) infection, human immunodeficiency virus (HIV) infection, cancer, or a hyper-proliferative disease. In some embodiments, the one or more additional therapeutic agents include PD1 inhibitors and/or PDL1 inhibitors. In some embodiments, the one or more additional therapeutic agents that are therapeutic for HBV infection include PDL1 inhibitors and/or PDL1 inhibitors. In some embodiments, the one or more additional therapeutic agents that are therapeutic for cancer or hyper-proliferative disease include PD1 inhibitors and/or PDL1 inhibitors.

In some embodiments, the one or more additional therapeutic agents include agents that are therapeutic for HBV infection. In some embodiments, the one or more additional therapeutic agents is selected from the group consisting of: adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In some embodiments, the one or more additional therapeutic agents include agents that are therapeutic for HIV infection. In some embodiments, the one or more additional therapeutic agents is selected from the group consisting of 4'-ethynyl-2-fluoro-2'-deoxyadenosine, bictegravir or a pharmaceutically acceptable salt thereof, abacavir sulfate, tenofovir, tenofovir disoproxil, tenofovir disoproxil fumarate, tenofovir disoproxil hemifumarate, tenofovir alafenamide, tenofovir alafenamide hemifumarate, emtricitabine, and lamivudine, or a pharmaceutically acceptable salt of any of the foregoing, or any combinations thereof.

In some embodiments, the one or more additional therapeutic agents include PD1 inhibitors and/or PDL1 inhibitors. In some embodiments, the one or more additional therapeutic agents is selected from the group consisting of nivolumab, lambrolizumab, pembrolizumab, pidilizumab, PDR001, TSR-001, atezolizumab, durvalumab, or avelumab, or a pharmaceutically acceptable salt of any of the foregoing, or any combinations thereof.

In some embodiments, the one or more additional therapeutic agents include agents that are therapeutic for cancer or hyper-proliferative disease. In some embodiments, the one or more additional therapeutic agents is selected from the group consisting of: rituxan, doxorubicin, gemcitabine, pidilizumab, TSR-042, BMS-986016, ruxolitinib, N-(cyanomethyl)-4-[2-(4-morpholinoanilino)pyrimidin-4-yl]benzamide, XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5-carbonitrile, and ipilimumab, or a pharmaceutically acceptable salt of any of the foregoing, or any combinations thereof.

In some embodiments, the one or more additional therapeutic agents is selected from the group consisting of idelalisib, tirabrutinib, momelotinib, and entospletinib, or a pharmaceutically acceptable salt of any of the foregoing, or any combinations thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds provided herein. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The compounds provided herein can be comprised in a kit. In one aspect, provided herein are kits that comprise a compound provided herein, (e.g., a compound of Formula I, I-E, II-Z, IIa-Z, IIb-Z, III-Z, or IIIa-Z), or a pharmaceutically acceptable salt, stereoisomer, prodrug, or solvate thereof, and suitable packaging. In some embodiments, the kit further comprises instructions for use. In some embodiments, the kit comprises a compound provided herein (e.g., a compound of Formula I, I-Z, I-E, II-Z, IIa-Z, IIb-Z, III-Z, or IIIa-Z), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (e.g., one, two, three, four, one or two, one to three, or one to four) additional therapeutic agents, or a pharmaceutically acceptable salt thereof.

In one aspect, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

IV. Methods

The methods provided herein may be applied to cell populations in vivo or ex vivo. "In vivo" means within a living individual, as within an animal or human. In this context, the methods provided herein may be used therapeutically in an individual. "Ex vivo" means outside of a living individual. Examples of ex vivo cell populations include in vitro cell cultures and biological samples including fluid or tissue samples obtained from individuals. Such samples may be obtained by suitable methods. Exemplary biological fluid samples include blood, cerebrospinal fluid, urine, and saliva. Exemplary tissue samples include tumors and biopsies thereof. In this context, the present disclosure may be used for a variety of purposes, including therapeutic and experimental purposes. For example, the present disclosure may be used ex vivo to determine the optimal schedule and/or dosing of administration of a HPK1 inhibitor for a given indication, cell type, individual, and other parameters. Information gleaned from such use may be used for experimental purposes or in the clinic to set protocols for in vivo treatment. Other ex vivo uses for which the present disclosure may be suited are described below or will become apparent to those skilled in the art. The selected compounds may be further characterized to examine the safety or tolerance dosage in human or non-human subjects.

In one aspect, the present disclosure provides methods of inhibiting HPK1 activity in a subject in need thereof, comprising administering to the subject a therapeutically effective amount of a compound provided herein (e.g., a compound of Formula I, I-Z, I-E, II-Z, IIa-Z, IIb-Z, III-Z, or IIIa-Z), or a pharmaceutically acceptable salt thereof, or a pharmaceutical composition provided herein.

In one aspect, the present disclosure provides methods of treating a disease or disorder associated with increased HPK1 activity in a subject in need thereof, comprising administering to the subject a therapeutically effective amount of a compound provided herein, or a pharmaceutically acceptable salt thereof, or a pharmaceutical composition provided herein.

In one aspect, the present disclosure provides methods of increasing T-cell activation in a subject in need thereof, comprising administering to the subject a therapeutically effective amount of a compound provided herein (e.g., a compound of Formula I, I-Z, I-E, II-Z, IIa-Z, IIb-Z, III-Z, or IIIa-Z), or a pharmaceutically acceptable salt thereof, or a pharmaceutical composition provided herein.

In one aspect, the present disclosure provides methods of treating cancer in a subject in need thereof, comprising administering to the subject a therapeutically effective amount of a compound provided herein (e.g., a compound of Formula I, I-Z, I-E, II-Z, IIa-Z, IIb-Z, III-Z, or IIIa-Z), or a pharmaceutically acceptable salt thereof, or a pharmaceutical composition provided herein.

In some embodiments, the cancer is selected from the group consisting of bladder cancer, breast cancer, colorectal cancer, gastric cancer, head and neck squamous cell carcinoma, Hodgkin lymphoma, Merkel-cell carcinoma, mesothelioma, melanoma, non-small cell lung cancer, lung cancer, ovarian cancer, pancreatic cancer, prostate cancer, renal cell carcinoma, small cell lung cancer, transitional cell carcinoma, urothelial cancer. In some embodiments, the cancer is a solid tumor.

In one aspect, the present disclosure provides methods of inhibiting the growth or proliferation of cancer cells in a subject in need thereof, comprising administering to the subject a therapeutically effective amount of a compound provided herein (e.g., a compound of Formula I, I-Z, I-E, II-Z, IIa-Z, IIb-Z, III-Z, or IIIa-Z), or a pharmaceutically acceptable salt thereof, or a pharmaceutical composition provided herein.

In some embodiments, the above methods further comprise administering a therapeutically effective amount of one or more additional therapeutic agents, or a pharmaceutically acceptable salt thereof.

In some embodiments, the one or more additional therapeutic agents is selected from the group consisting of: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, OX40 agonists, GITR agonists, CD27 agonists, CD28 agonists, CD40 agonists, CD137 agonists, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C—X—C chemokine receptor type 4 (CXCR-4) inhibitors, B7-H3 inhibitors, CD73 inhibitors, inhibitory RNA, IL2/15/17 fusion proteins, MKNK½ inhibitors, JAK inhibitors, and PI3K inhibitors, or a pharmaceutically acceptable salt of any of the foregoing, or any combinations thereof.

In some embodiments, the one or more additional therapeutic agents is selected from the group consisting of: rituxan, doxorubicin, gemcitabine, nivolumab, pembrolizumab, pidilizumab, PDR001, TSR-001, atezolizumab, durvalumab, avelumab, pidilizumab, TSR-042, BMS-986016, ruxolitinib, N-(cyanomethyl)-4-[2-(4-morpholinoanilino) pyrimidin-4-yl]benzamide, XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5-carbonitrile, and ipilimumab, or a pharmaceutically acceptable salt of any of the foregoing, or any combinations thereof.

In some embodiments, the one or more additional therapeutic agents is selected from the group consisting of idelalisib, tirabrutinib, momelotinib, and entospletinib, or a pharmaceutically acceptable salt of any of the foregoing, or any combinations thereof.

In one aspect, the present disclosure provides methods of treating or preventing a hepatitis B virus (HBV) infection in a subject in need thereof, comprising administering to the subject a therapeutically effective amount of a compound provided herein (e.g., a compound of Formula I, I-Z, I-E, II-Z, IIa-Z, IIb-Z, III-Z, or IIIa-Z), or a pharmaceutically acceptable salt thereof, or a pharmaceutical composition provided herein.

In some embodiments, the method of treating or preventing a HBV infection further comprises administering a therapeutically effective amount of one or more additional therapeutic agents, or a pharmaceutically acceptable salt thereof.

In some embodiments, the one or more additional therapeutic agents is selected from the group consisting of HBV combination drugs, HBV vaccines, HBV DNA polymerase inhibitors, immunomodulators, toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucleotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1 agonists, Bruton's tyrosine kinase (BTK) inhibitors, KDM inhibitors, HBV replication inhibitors, arginase inhibitors, and other HBV drugs, or a pharmaceutically acceptable salt of any of the foregoing, or any combinations thereof.

In some embodiments, the one or more additional therapeutic agents is selected from the group consisting of adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In some embodiments, the one or more additional therapeutic agents is selected from the group consisting of entecavir, adefovir, tenofovir disoproxil fumarate, tenofovir alafenamide, tenofovir, tenofovir disoproxil, tenofovir alafenamide fumarate, tenofovir alafenamide hemifumarate, telbivudine and lamivudine, or a pharmaceutically acceptable salt of any of the foregoing, or any combinations thereof.

In some embodiments, the one or more additional therapeutic agents is selected from the group consisting of tenofovir alafenamide, tenofovir alafenamide fumarate, and tenofovir alafenamide hemifumarate, or a pharmaceutically acceptable salt of any of the foregoing, or any combinations thereof.

In one aspect, the present disclosure provides methods of treating or preventing a human immunodeficiency virus (HIV) infection in a subject in need thereof, comprising administering to the subject a therapeutically effective amount of a compound provided herein (e.g., a compound of Formula I, I-Z, I-E, II-Z, IIa-Z, IIb-Z, III-Z, or IIIa-Z), or a pharmaceutically acceptable salt thereof, or a pharmaceutical composition provided herein.

In some embodiments, the method of treating or preventing a HIV infection further comprises administering a therapeutically effective amount of one or more additional therapeutic agents, or a pharmaceutically acceptable salt thereof.

In some embodiments, the one or more additional therapeutic agents is selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the one or more additional therapeutic agents is selected from the group consisting of 4'-ethynyl-2-fluoro-2'-deoxyadenosine, bictegravir, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof.

In some embodiments, the one or more additional therapeutic agents is selected from the group consisting of 4'-ethynyl-2-fluoro-2'-deoxyadenosine, bictegravir, tenofovir alafenamide, tenofovir alafenamide fumarate and tenofovir alafenamide hemifumarate, or a pharmaceutically acceptable salt of any of the foregoing, or any combinations thereof.

In some embodiments, the one or more additional therapeutic agents is selected from the group consisting of 4'-ethynyl-2-fluoro-2'-deoxyadenosine, bictegravir, tenofovir disoproxil, tenofovir disoproxil hemifumarate, and tenofovir disoproxil fumarate, or a pharmaceutically acceptable salt of any of the foregoing, or any combinations thereof.

In some embodiments, the one or more additional therapeutic agents is selected from the group consisting of emtricitabine and lamivudine, or a pharmaceutically acceptable salt of each thereof.

In some embodiments, the one or more additional therapeutic agents is emtricitabine or a pharmaceutically acceptable salt thereof.

In some embodiments, the method of treating or preventing a HIV infection further comprises administering one or more additional therapeutic agents selected from the group consisting of 4'-ethynyl-2-fluoro-2'-deoxyadenosine, bictegravir, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof, and further comprises administering another therapeutic agent selected from the group consisting of emtricitabine and lamivudine, or a pharmaceutically acceptable salt of each thereof.

In some embodiments, the method of treating or preventing a HIV infection further comprises administering one or more additional therapeutic agents selected from the group consisting of 4'-ethynyl-2-fluoro-2'-deoxyadenosine, bictegravir, tenofovir alafenamide, and tenofovir alafenamide hemifumarate, or a pharmaceutically acceptable salt of any of the foregoing, or any combinations thereof, and further comprises administering another therapeutic agent selected from the group consisting of emtricitabine and lamivudine, or a pharmaceutically acceptable salt of each thereof.

In some embodiments, the method of treating or preventing a HIV infection further comprises administering one or more additional therapeutic agents selected from the group consisting of 4'-ethynyl-2-fluoro-2'-deoxyadenosine, bictegravir, tenofovir disoproxil, tenofovir disoproxil fumarate, and tenofovir disoproxil hemifumarate, or a pharmaceutically acceptable salt of any of the foregoing, or any combinations thereof, and further comprises administering another therapeutic agent selected from the group consisting of emtricitabine and lamivudine, or a pharmaceutically acceptable salt thereof.

In some embodiments, the methods described herein comprise administering a therapeutically effective amount of a compound provided herein (e.g., a compound of Formula I, I, I-Z, I-E, II-Z, IIa-Z, IIb-Z, III-Z, or IIIa-Z), or a pharmaceutically acceptable salt thereof. In some embodiments, the methods described herein comprise administering a therapeutically effective amount of a pharmaceutical composition provided herein.

In one aspect, provided herein is a compound disclosed herein, or a pharmaceutically acceptable salt thereof, for use in therapy.

In one aspect, provided herein is a compound disclosed herein, or a pharmaceutically acceptable salt thereof, for use in a method of inhibiting hematopoietic progenitor kinase 1 (HPK1) activity in a subject in need thereof.

In one aspect, provided herein is a compound disclosed herein, or a pharmaceutically acceptable salt thereof, for use in a method of treating a disease or disorder associated with increased hematopoietic progenitor kinase 1 (HPK1) activity in a subject in need thereof.

In one aspect, provided herein is a compound disclosed herein, or a pharmaceutically acceptable salt thereof, for use in a method of increasing T-cell activation in a subject in need thereof.

In one aspect, provided herein is a compound disclosed herein, or a pharmaceutically acceptable salt thereof, for use in a method of treating cancer in a subject in need thereof.

In some embodiments, the cancer is selected from the group consisting of bladder cancer, breast cancer, colorectal cancer, gastric cancer, head and neck squamous cell carcinoma, Hodgkin lymphoma, Merkel-cell carcinoma, mesothelioma, melanoma, non-small cell lung cancer, lung cancer, ovarian cancer, pancreatic cancer, prostate cancer, renal cell carcinoma, small cell lung cancer, transitional cell carcinoma, and urothelial cancer. In some embodiments, the cancer is a solid tumor.

In one aspect, provided herein is a compound disclosed herein, or a pharmaceutically acceptable salt thereof, for use in a method of inhibiting the growth or proliferation of cancer cells in a subject in need thereof.

In some embodiments, the use in a method of inhibiting the growth or proliferation of cancer cells in a subject in need thereof further comprises administering a therapeutically effective amount of one or more additional therapeutic agents, or a pharmaceutically acceptable salt thereof.

In some embodiments, the use in a method of inhibiting the growth or proliferation of cancer cells in a subject in need thereof further comprises administering one or more additional therapeutic agents selected from the group consisting of: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, OX40 agonists, GITR agonists, CD27 agonists, CD28 agonists, CD40 agonists, CD137 agonists, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C—X—C chemokine receptor type 4 (CXCR-4) inhibitors, B7-H3 inhibitors, CD73 inhibitors, inhibitory RNA, IL2/15/17 fusion proteins, MKNK½ inhibitors, JAK inhibitors, and PI3K inhibitors, or a pharmaceutically acceptable salt of any of the foregoing, or any combinations thereof.

In some embodiments, the use in a method of inhibiting the growth or proliferation of cancer cells in a subject in need thereof further comprises administering one or more additional therapeutic agents selected from the group consisting of: rituxan, doxorubicin, gemcitabine, nivolumab, pembrolizumab, pidilizumab, PDR001, TSR-001, atezolizumab, durvalumab, avelumab, pidilizumab, TSR-042, BMS-986016, ruxolitinib, N-(cyanomethyl)-4-[2-(4-morpholinoanilino)pyrimidin-4-yl]benzamide, XL147, BKM120, GDC-0941, BAY80-6946, PX-866, CH5132799, XL756, BEZ235, and GDC-0980, wortmannin, LY294002, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5-carbonitrile, and ipilimumab, or a pharmaceutically acceptable salt of any of the foregoing, or any combinations thereof.

In some embodiments, the use in a method of inhibiting the growth or proliferation of cancer cells in a subject in need thereof further comprises administering one or more additional therapeutic agents selected from the group consisting of idelalisib, tirabrutinib, momelotinib, and entospletinib, or a pharmaceutically acceptable salt of any of the foregoing, or any combinations thereof.

In one aspect, provided herein is a compound disclosed herein, or a pharmaceutically acceptable salt thereof, for use in a method of treating or preventing a hepatitis B virus (HBV) infection in a subject in need thereof.

In some embodiments, the use in a method of treating or preventing a hepatitis B virus (HBV) infection in a subject in need thereof further comprises administering a therapeutically effective amount of one or more additional therapeutic agents, or a pharmaceutically acceptable thereof.

In some embodiments, the use in a method of treating or preventing a hepatitis B virus (HBV) infection in a subject in need thereof further comprises administering one or more additional therapeutic agents selected from the group consisting of HBV combination drugs, HBV vaccines, HBV DNA polymerase inhibitors, immunomodulators, toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1 agonists, Bruton's tyrosine kinase (BTK) inhibitors, KDM inhibitors, HBV replication inhibitors, arginase inhibitors, and other HBV drugs, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reafferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of entecavir, adefovir, tenofovir disoproxil fumarate, tenofovir alafenamide, tenofovir, tenofovir disoproxil, tenofovir alafenamide fumarate, tenofovir alafenamide hemifumarate, telbivudine and lamivudine, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of tenofovir alafenamide, tenofovir alafenamide fumarate, and tenofovir alafenamide hemifumarate, or a pharmaceutically acceptable salt of any of the foregoing, or any combinations thereof.

In one aspect, provided herein is a compound disclosed herein, or a pharmaceutically acceptable salt thereof, for use in a method of treating or preventing a human immunodeficiency virus (HIV) infection in a subject in need thereof.

In some embodiments, the use in a method of treating or preventing a hepatitis B virus (HBV) infection in a subject in need thereof further comprises administering one or more additional therapeutic agents, or a pharmaceutically acceptable salt thereof.

In some embodiments, the use in a method of treating or preventing a hepatitis B virus (HBV) infection in a subject in need thereof further comprises administering one or more additional therapeutic agents selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of 4'-ethynyl-2-fluoro-2'-deoxyadenosine, bictegravir, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of 4'-ethynyl-2-fluoro-2'-deoxyadenosine, bictegravir, tenofovir alafenamide, tenofovir alafenamide fumarate or tenofovir alafenamide hemifumarate, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of 4'-ethynyl-2-fluoro-2'-deoxyadenosine, bictegravir, or a pharmaceutically acceptable salt thereof, tenofovir disoproxil, tenofovir disoproxil hemifumarate or tenofovir disoproxil fumarate, or a pharmaceutically acceptable salt of any of the foregoing, or any combinations thereof.

In some embodiments, the uses described herein comprise administering a therapeutically effective amount of a compound provided herein (e.g., a compound of Formula I, I-Z, I-E, II-Z, IIa-Z, IIb-Z, III-Z, or IIIa-Z), or a pharmaceutically acceptable salt thereof.

V. Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 1000 mg/kg, for example, between about 0.1 and 700 mg/kg, between about 0.1 and 500 mg/kg, between about 0.1 and 300 mg/Kg or between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I, I-E, II-Z, IIa-Z, IIb-Z, III-Z, or IIIa-Z, or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 µg to about 30 mg per day, or from about 30 µg to about 300 µg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I, I-Z, I-E, II-Z, IIa-Z, IIb-Z, III-Z, or IIIa-Z are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound provided herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1 mg and 1,000 mg, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, or 1000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

The frequency of dosage of the compound of the present disclosure will be determined by the needs of the individual patient and can be, for example, once per day or twice, or more times, per day. Administration of the compound continues for as long as necessary to treat the HBV infection, HIV infection, cancer, hyper-proliferative disease, or any other indication described herein. For example, a compound can be administered to a human being infected with HBV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles may be alternated with resting periods of about 1 to 28 days, commonly about 7 days or about 14 days, between cycles. The treatment cycles, in other embodiments, may also be continuous.

VI. Combination Therapy

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

Co-administration includes administration of unit dosages of the compounds disclosed herein before or after administration of unit dosages of one or more additional therapeutic agents. The compounds disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In some embodiments a compound of Formula I, I-Z, I-E, II-Z, IIa-Z, IIb-Z, III-Z, or IIIa-Z, is formulated as a tablet, which may optionally contain one or more other compounds useful for treating the disease being treated. In certain embodiments, the tablet can contain another active ingredient for treating a HBV infection, HIV infection, cancer, or a hyper-proliferative disease. In some embodiments, such tablets are suitable for once daily dosing.

Also provided herein are methods of treatment in which a compound of Formula I, I-Z, I-E, II-Z, IIa-Z, IIb-Z, III-Z, or IIIa-Z, or pharmaceutically acceptable salt thereof, is given to a patient in combination with one or more additional therapeutic agents or therapy. In some embodiments, the total daily dosage of a compound of Formula I, I-Z, I-E, II-Z, IIa-Z, IIb-Z, III-Z, or IIIa-Z, or a pharmaceutically acceptable salt thereof, may be about 300 mg/day administered in a single dose for a human subject.

HBV Combination Therapy

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In certain embodiments, a compound of Formula I, I-Z, I-E, II-Z, IIa-Z, IIb-Z, III-Z, or IIIa-Z is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPER-VAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, AB-506, RO-6871765, AIC-649, and IR-103.

Toll-like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, and ND-1.1.

Examples of TLR7 modulators include GS-9620 (vesatolimod), GSK-2245035, imiquimod, resiquimod, DSR-6434, DSP-3025, IMO-4200, MCT-465, MEDI-9197, 3M-051, SB-9922, 3M-052, Limtop, D, telratolimod, SP-0509, TMX-30X, TMX-202, RG-7863, RG-7795, LHC-165, RG-7854, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, GS-9688 and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), US20130251673 (Novira Therapeutics), US Pat. No. 9670205, US20160289229 U.S. patent application Ser. No. 15/692,161, and U.S. patent application Ser. No. 15/692,093.

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (Bristol Myers Squibb), WO2015057655 (Eisai Co Ltd), WO2017001307 (Roche), WO2018005586 (Bristol Myers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO201804163 (Roche), WO2018038877 (3M Co), WO2015057659 (Eisai Co Ltd), WO2017202704 (Roche), WO2018026620 (Bristol Myers Squibb), WO2016029077 (Janus Biotherapeutics), WO201803143 (Merck), WO2016096778 (Roche), WO2017190669 (Shanghai De Novo Pharmatech), U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), WO2015023958 (University of Kansas)

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin interferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404, RG-6004.

Short Interfering RNAs (siRNA) and ddRNAi

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucelotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Examples of farnesoid x receptor agonist such as EYP-001, GS-9674, EDP-305, MET-409, Tropifexor, AKN-083, RDX-023, BWD-100, LMB-763, INV-3, NTX-023-1, EP-024297 and GS-8670

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies include HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience)

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include GS-4882, AB-423, AT-130, GLS4, NVR-1221, NVR-3778, AL-3778, BAY 41-4109, morphothiadine mesilate, ARB-168786, ARB-880, JNJ-379, RG-7907, HEC-72702, AB-506, ABI-H0731, JNJ-440, ABI-H2158 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Retinoic Acid-Inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-Dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include cemiplimab, nivolumab, pembrolizumab, pidilizumab, BGB-108, STI-A1014, SHR-1210, PDR-001, PF-06801591, IBI-308, GB-226, STI-1110, JNJ-63723283, CA-170, durvalumab, atezolizumab and mDX-400, JS-001, Camrelizumab, Sintilimab, Sintilimab, tislelizumab, BCD-100, BGB-A333 JNJ-63723283, GLS-010 (WBP-3055), CX-072, AGEN-2034, GNS-1480 (Epidermal growth factor receptor antagonist; Programmed cell death ligand 1 inhibitor), CS-1001, M-7824 (PD-L1/TGF-0 bifunctional fusion protein), Genolimzumab, BMS-936559.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, GS-4224, CX-072, and BMS-936559.

Examples of PD-1 inhibitors include the compounds disclosed in WO2017112730 (Incyte Corp), WO2017087777 (Incyte Corp), WO2017017624, WO2014151634 (Bristol Myers Squibb Co), WO201317322 (Bristol Myers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (Bristol Myers Squibb Co), WO20161266460 (Bristol Myers Squibb Co), WO2017087678 (Bristol Myers Squibb Co), WO2016149351 (Bristol Myers Squibb Co), WO2015033299 (Aurigene Discovery Technologies Ltd), WO2015179615 (Eisai Co Ltd; Eisai Research Institute), WO2017066227 (Bristol Myers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (Bristol Myers Squibb Co), WO2015033303 (Aurigene Discovery Technologies Ltd), WO2017205464 (Incyte Corp), WO2016019232 (3M Co; Individual; Texas A&M University System), WO2015160641 (Bristol Myers Squibb Co), WO2017079669 (Incyte Corp), WO2015033301 (Aurigene Discovery Technologies Ltd), WO2015034820 (Bristol Myers Squibb Co), WO2018073754 (Aurigene Discovery Technologies Ltd), WO2016077518 (Bristol Myers Squibb Co), WO2016057624 (Bristol Myers Squibb Co), WO2018044783 (Incyte Corp), WO2016100608 (Bristol Myers Squibb Co), WO2016100285 (Bristol Myers Squibb Co), WO2016039749 (Bristol Myers Squibb Co), WO2015019284 (Cambridge Enterprise Ltd), WO2016142894 (Aurigene Discovery Technologies Ltd), WO2015134605 (Bristol Myers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (Bristol Myers Squibb Co), WO2013144704 (Aurigene Discovery Technologies Ltd), WO2018013789 (Incyte Corp), WO2017176608 (Bristol Myers Squibb Co), WO2018009505 (Bristol Myers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), WO2018026971 (Arising International).

Other examples of PD-1 and/or PDL-1 inhibitors include the compounds disclosed in U.S. Provisional Ser. Nos. 62/630,187, 62/640,534, 62/736,116, and 62/747,029.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), GSK-2879552, and RG-6016.

STING Agonists

Examples of STING agonists include SB-11285, AdVCA0848, STINGVAX, and the compounds disclosed in WO 2018065360 ("Biolog Life Science Institute Forschungslabor und Biochemica-Vertrieb GmbH, Germany), WO 2018009466 (Aduro Biotech), WO 2017186711 (Invivo-Gen), WO 2017161349 (Immune Sensor), WO 2017106740 (Aduro Biotech), US 20170158724 (Glaxo Smithkiline), WO 2017075477 (Aduro Biotech), US 20170044206 (Merck), WO 2014179760 (University of California), WO2018098203 (Janssen), WO2018118665 (Merck), WO2018118664 (Merck), WO2018100558 (Takeda), WO2018067423 (Merck), WO2018060323 (Boehringer).

Non-Nucleoside Reverse Transcriptase Inhibitors (NNRTI)

Examples of NNRTI include the compounds disclosed in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene therapy and cell therapy includes the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Gene Editors

Examples of genome editing systems include a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X PreSI, PreS2, S, P or SP gene refers to (1) reducing or eliminating PreC, C, X PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreSI, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X PreSI, PreS2, S, P and/or SP gene(s) is performed by targeting the gene(s) within HBV cccDNA and/or integrated HBV DNA.

CAR-T Cell Therapy

CAR T cell therapy includes a population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

TCR T cell therapy includes T cells expressing HBV-specific T cell receptors. TCR-T cells are engineered to target HBV derived peptides presented on the surface of virus-infected cells. In some embodiments, the T-cells express HBV surface antigen (HBsAg)-specific TCR. Examples of TCR-T therapy directed to treatment of HBV include LTCR-H2-1.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, a compound disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics). US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

HIV Combination Therapy

In certain embodiments, a method for treating or preventing an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, the compounds disclosed herein are formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, or any combinations thereof.

In certain embodiments, such tablets are suitable for once daily dosing.

In some embodiments, the additional therapeutic agent may be an anti-HIV agent. In some embodiments, the additional therapeutic agent is selected from the group consisting of HIV combination drugs, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T), latency reversing agents, compounds that target the HIV capsid (including capsid inhibitors), immune-based therapies, phosphatidylinositol 3-kinase (PI3K) inhibitors, alpha-4/beta-7 antagonists, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and other HIV therapeutic agents, or any combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, or any combinations thereof.

HIV Combination Drugs

Examples of combination drugs include ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812, or any combinations thereof.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, and elsulfavirine (VM-1500).

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, DS-003 (BMS-599793), gp120 inhibitors, and CXCR4 inhibitors.

Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide $C_{25}P$, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176, BMS-986197, GSK-3640254 and GSK-2838232.

Latency Reversing Agents

Examples of latency reversing agents include histone deacetylase (HDAC) inhibitors, proteasome inhibitors such as velcade, and ixazomib citrate, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), AM-0015, ALT-803, NIZ-985, NKTR-255, IL-15 modulating antibodies, JQ1, disulfiram, amphotericin B, and ubiquitin inhibitors such as largazole analogs, APH-0812, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, GS-6207, AVI-621, AVI-101, AVI-201, AVI-301, and AVI-CAN1-15 series.

HIV Long Acting Agents

Examples of drugs that are being developed as long acting regimens: cabotegravir LA, rilpivirine LA, cabotegravir LA+rilpivirine LA, any integrase LA, VM-1500A-LAI, maraviroc (LAI), tenofovir implant, MK-8591 implant, long-acting dolutegravir, long acting raltegravir+lamivudine.

Immune-Based Therapies

Examples of immune-based therapies include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107; interleukin-15/Fc fusion protein; AM-0015, ALT-803, NIZ-985, NKTR-255, NKTR-262, NKTR-214, normferon; peginterferon alfa-2a;

peginterferon alfa-2b; recombinant interleukin-15; Xmab-24306, RPI-MN; GS-9620; STING modulators; RIG-I modulators; NOD2 modulators; STING modulators, RIG-I modulators, NOD2 modulators, SB-9200, and IR-103.

Examples of TLR agonists include vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod, RO-7020531.

Examples of TLR8 modulators include motolimod, resiquimod, 3M-051, 3M-052, MCT-465, IMO-4200, VTX-763, VTX-1463 and those disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 9,670,205 (Gilead Sciences Inc.), US20160289229 (Gilead Sciences Inc.), U.S. patent application Ser. No. 15/692,161 (Gilead Sciences Inc.), and U.S. patent application Ser. No. 15/692,093 (Gilead Sciences Inc.)

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4 Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bispecific antibodies, trispecific antibodies, multivalent antibodies, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, CD3 bispecific antibodies, CD16 bispecific antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66.

Further examples include bavituximab, UB-421, C2F5, 2G12, C4E10, C2F5+C2G12+C4E10, 8ANC195, 3BNC117, 3BNC117-LS, D1D2, 3BNC60, 10-1074, 10-1074-LS, GS-9722, DH411-2, BG18, PGT145, PGT121, PGT122, PGT-151, PGT-133, PGT-135, PGT-128, MDXO10 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PG9, PG16, 8ANC195, 2Dm2m, 4Dm2m, 6Dm2m, VRC01, VRC-01-LS, PGDM1400, A32, 7B2, 10E8, 10E8VLS, 3810109, 10E8v4, 10E8.4/iMab, VRC-01/PGDM-1400/ 10E8v4, IMC-HIV, iMabm36, 10E8v4/PGT121-VRC01, eCD4-Ig, IOMA, CAP256-VRC26.25, DRVIA7, SAR-441236, VRC-07-523, VRC07-523LS, VRC-HIVMAB080-00-AB, VRC-HIVMAB060-00-AB, P2G12, and VRC07. Example of HIV bispecific antibodies include MGD014, TMB-bispecific.

Additional examples of HIV bispecific antibodies include MGD014.

Pharmacokinetic Enhancers

Examples of pharmacokinetic enhancers include cobicistat and ritonavir.

HIV Vaccines

Examples of HIV vaccines include peptide vaccines, recombinant subunit protein vaccines, live vector vaccines using viral vectors such as arenavirus, lymphocytic choriomeningitis virus (LCMV), pichinde virus, modified vaccinia Ankara virus (MVA), adenovirus, adeno-associated virus (AAV), vesicular stomatitis virus (VSV) and Chimpanzee adenovirus (ChAd), DNA vaccines, CD4-derived peptide vaccines, vaccine combinations, BG505 SOSIP.664 gp140, rgp120 (AIDSVAX), ALVAC HIV, (vCP1521)/AIDSVAX B/E (gp120) (RV144), monomeric gp120 HIV-1 subtype C vaccine, Remune, ITV-1, Contre Vir, Ad4-Env145NFL, Ad5-ENVA-48, HB-500, DCVax-001 (CDX-2401), Vacc-4x, Vacc-C5, Vacc-CRX, VVX-004, VAC-3S, multiclade DNA recombinant adenovirus-5 (rAd5), rAd5 gag-pol env A/B/C vaccine, Pennvax-G, Pennvax-GP/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), Paxvax, EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI, DNA.HTI and MVA.HTI, VRC-HIVDNA016-00-VP+ VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, arenavirus vector-based immunotherapies (Vaxwave, TheraT), MVA-BN HIV-1 vaccine regimen, MVA.tHIVconsv4, MVA.tHIVconsv3, UBI HIV gp120, mRNA based prophylactic vaccines, TBL-1203HI, VRC-HIVRGP096-00-VP, VAX-3S, HIV MAG DNA vaccine.

Additional HIV Therapeutic Agents

Examples of additional HIV therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

Examples of other drugs for treating HIV include acemannan, alisporivir, astodrimer, BanLec, CC-11050, deferiprone, Gamimune, griffithsin, metenkefalin, naltrexone, Prolastin, REP 9, RPI-MN, Vorapaxar, VSSP, Hlviral, SB-728-T, 1,5-dicaffeoylquinic acid, rHIV7-shl-TAR-CCR5RZ, AAV-eCD4-Ig gene therapy, MazF gene therapy, MK-8527, BlockAide, PSC-RANTES, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

Gene Therapy and Cell Therapy

Gene therapy and cell therapy include the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Examples of dendritic cell therapy include AGS-004.

Gene Editors

Examples of gene editing systems include a CRISPR/Cas9 system, a zinc finger nuclease system, a TALEN system, a homing endonucleases system, and a meganuclease system.

Examples of HIV targeting CRISPR/Cas9 systems include EBT101.

CAR-T Cell Therapy

CAR-T cell therapy includes a population of immune effector cells engineered to express a chimeric antigen receptor (CAR), wherein the CAR comprises an HIV antigen-binding domain. The HIV antigens include an HIV envelope protein or a portion thereof, gp120 or a portion thereof, a CD4 binding site on gp120, the CD4-induced binding site on gp120, N glycan on gp120, the V2 of gp120, and the membrane proximal region on gp41. In some embodiments, the immune effector cell is a T cell or an NK cell. In some embodiments, the T cell is a CD4+ T cell, a CD8+ T cell, or a combination thereof.

Examples of HIV CAR-T cell therapy include VC-CAR-T, anti-CD4 CART cell therapy, autologous hematopoietic stem cells genetically engineered to express a CD4 CAR and the C46 peptide.

TCR-T Cell Therapy

TCR-T cell therapy includes T cells engineered to target HIV derived peptides present on the surface of virus-infected cells.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide hemifumarate, or bictegravir.

In a particular embodiment, a compound disclosed herein, or a pharmaceutically acceptable salt thereof, is combined with tenofovir, tenofovir disoproxil, tenofovir disoproxil fumarate, tenofovir alafenamide, tenofovir alafenamide hemifumarate, or bictegravir.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide hemifumarate, and bictegravir and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, tenofovir alafenamide hemifumarate, and bictegravir and a second additional therapeutic agent, wherein the second additional therapeutic agent is emtricitabine.

A compound as disclosed herein may be combined with one or more additional therapeutic agents in any dosage amount of the compound (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of Formula I, I-Z, I-E, II-Z, IIa-Z, IIb-Z, III-Z, or IIIa-Z) may be combined with the agents provided herein in any dosage amount of the compound (e.g., from 1 mg to 500 mg of compound) as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of Formula I, I-Z, I-E, II-Z, IIa-Z, IIb-Z, III-Z, or IIIa-Z) may be combined with the agents provided herein in any dosage amount of the compound (e.g., from 1 mg to 500 mg of compound) as if each combination of dosages were specifically and individually listed.

Cancer and/or Hyper-Proliferative Disease Combination Therapy

In one embodiment, the compound provided herein may be employed with other therapeutic methods of cancer treatment. Preferably, combination therapy with chemotherapeutic, hormonal, antibody, surgical and/or radiation treatments are contemplated.

In some embodiments, the further anti-cancer therapy is surgery and/or radiotherapy. In some embodiments, the further anti-cancer therapy is at least one additional cancer medicament.

In some embodiments, there is provided a combination comprising a compound of Formula I, I-Z, I-E, II-Z, IIa-Z, IIb-Z, III-Z, or IIIa-Z, or a pharmaceutically acceptable salt thereof and at least one further cancer medicament.

In some embodiments, there is provided a combination comprising a compound of Formula I, I-Z, I-E, II-Z, IIa-Z, IIb-Z, III-Z, or IIIa-Z, or a pharmaceutically acceptable salt thereof and at least one further cancer medicament, for use in therapy.

In some embodiments, there is provided the use of a combination comprising a compound of Formula I, I-Z, I-E, II-Z, IIa-Z, IIb-Z, III-Z, or IIIa-Z, or a pharmaceutically acceptable salt thereof and at least one cancer medicament, in the manufacture of a medicament for the treatment of cancer.

Examples of further cancer medicaments include intercalating substances such as anthracycline, doxorubicin, idarubicin, epirubicin, and daunorubicin; topoisomerase inhibitors such as irinotecan, topotecan, camptothecin, lamellarin D, etoposide, teniposide, mitoxantrone, amsacrine, ellipticines and aurintricarboxylic acid; nitrosourea compounds such as carmustine (BCNU), lomustine (CCNU), and streptozocin; nitrogen mustards such as cyclophosphamide, mechlorethamine, uramustine, bendamustine, melphalan, chlorambucil, mafosfamide, trofosfamid and ifosfamide; alkyl sulfonates such as busulfan and treosulfan; alkylating agents such as procarbazin, dacarbazin, temozolomid and thiotepa; platinum analogues such as cisplatin, carboplatin, nedaplatin, oxaliplatin, satraplatin, and triplatin tetranitrate; microtubule disruptive drugs such as vinblastine, colcemid and nocodazole; antifolates like methotrexate, aminopterin, dichloromethotrexat, pemetrexed, raltitrexed and pralatrexate: purine analogues like azathioprine, mercaptopurine, thioguanine, fludarabine, fludarabine phosphate, pentostatin and cladribine; pyrimidine analogues like 5-fluorouracil, floxuridine, cytarabine, 6-azauracil, gemcitabine; steroids such as gestagene, androgene, glucocorticoids, dexamethasone, prednisolone, and prednisone; anti-cancer antibodies such as monoclonal antibodies, e.g., alemtuzumab, apolizumab, cetuximab, epratuzumab, galiximab, gemtuzumab, ipilimumab, labetuzumab, panitumumab, rituximab, trastuzumab, nimotuzumab, mapatumumab, matuzumab, rhMab ICR62 and pertuzumab, radioactively labeled antibodies and antibody-drug conjugates; anti-cancer peptides such as radioactively labeled peptides and peptide-drug conjugates; and taxane and taxane analogues such as paclitaxel and docetaxel.

In certain embodiments, a method for treating or preventing a cancer or hyper-proliferative disease in a human or animal having or at risk of having the cancer or hyper-proliferative disease is provided, comprising administering to the human or animal a therapeutically effective amount of a compound of Formula I, I-Z, I-E, II-Z, IIa-Z, IIb-Z, III-Z, or IIIa-Z as disclosed herein, or a pharmaceutically acceptable salt thereof, in combination with a therapeutically effective amount of one or more (e.g., one, two, three, one or two, or one to three) additional therapeutic agents. In one embodiment, a method for treating a cancer or hyper-proliferative disease in a human or animal having or at risk of having the cancer or hyper-proliferative disease is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating a cancer or hyper-proliferative disease, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating cancer or hyper-proliferative disease.

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, a gene modifier or editor (such as CRISPR/Cas9, zinc finger nucleases or synthetic nucleases, TALENs), a CAR (chimeric antigen receptor) T-cell immunotherapeutic agent, an engineered T cell receptor (TCR-T), or any combination thereof. These therapeutic agents may be in the forms of compounds, antibodies, polypeptides, or polynucleotides. In one embodiment, provided herein is a product comprising a compound described herein and an additional therapeutic agent as a combined preparation for simultaneous, separate, or sequential use in therapy.

The one or more additional therapeutic agents include, but are not limited to, an inhibitor, agonist, antagonist, ligand, modulator, stimulator, blocker, activator or suppressor of a gene, ligand, receptor, protein, or factor. Non-limiting examples of additional therapeutic agents include:

Abelson murine leukemia viral oncogene homolog 1 gene (ABL, such as ABL1), Acetyl-CoA carboxylase (such as ACC½), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C—C motif) receptor (such as CCR2, CCR4, CCR5, CCR8), chemokine (C—X—C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), CISH (Cytokine-inducible SH2-containing protein), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, (CEACAM6), CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, C-type lectin domain protein 9A (CLEC9A), Cyclin D1, Cyclin G1, cyclin-dependent kinases (CDK, such as CDK1, CDK1B, CDK2-9), cyclooxygenase (such as COX1, COX2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Death receptor 5 (DR5, TRAILR2), Death receptor 4 (DR4, TRAILR1), Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (Ep-CAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase, (FASN), Ferritin, FGF-2 ligand, FGF-5 ligand, fibroblast growth factor (FGF, such as FGF1, FGF2, FGF4), Fibronectin, Fms-related tyrosine kinase 3 (Flt3), Fms-like tyrosine kinase-3 ligand (FLT3L), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (HOT), Heme oxygenase 2 (H02), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, HLA class I antigen alpha G (HLA-G), Non-classical HLA, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1α), Imprinted Maternally Expressed Transcript (H19) gene, mitogen-activated protein kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, GI, G2, K, M), Immunoglobulin Fc receptor, Immunoglobulin gamma Fc receptor (such as I, III, IIIA), indoleamine 2,3-dioxygenase (IDO, such as IDO1 and IDO2), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukocyte immunoglobulin-like receptor subfamily B member 1 (ILT2), Leukocyte immunoglobulin-like receptor subfamily B member 2 (ILT4), Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), 5-Lipoxygenase (5-LOX), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, NLRP3 (NACHT LRR PYD domain protein 3) modulators, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly (ADP ribose) polymerase (PARP, such as PARP1, PARP2, PARP3, PARP7, and mono-PARPs), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), Prostaglandin E2 synthase, prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Secreted phospholipase A2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Suppressor of cytokine signaling modulators (SOCS), Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tumor specific neoantigens, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E21 (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase, Mer (Mer tyrosine kinase receptor modulators), YAP (Yes-associated protein modulators), Wee-1 protein kinase, Wilms' tumor antigen 1, Wilms' tumor protein, WW domain containing transcription regulator protein 1 (TAZ), X-linked inhibitor of apoptosis protein, Zinc finger protein transcription factor, or any combinations thereof.

Non-limiting examples of additional therapeutic agents may be categorized by their mechanism of action into, for example, the following groups:

- anti-metabolites/anti-cancer agents, such as pyrimidine analogs floxuridine, capecitabine, cytarabine, CPX-351 (liposomal cytarabine, daunorubicin), and TAS-118;
- purine analogs, folate antagonists (such as pralatrexate), and related inhibitors;
- antiproliferative/antimitotic agents including natural products, such as *vinca* alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);
- DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide;
- DNA-hypomethylating agents, such as guadecitabine (SGI-110) and ASTX727;
- antibiotics such as dactinomycin, daunorubicin, doxorubicin, idarubicin, anthracyclines, mitoxantrone, bleomycins, and plicamycin (mithramycin);
- enzymes such as L-asparaginase which systemically metabolizes L-asparagine and deprives cells which do not have the capacity to synthesize their own asparagine;
- antiplatelet agents;
- DNAi oligonucleotides targeting Bcl-2, such as PNT2258;
- agents that activate or reactivate latent human immunodeficiency virus (HIV), such as panobinostat and romidepsin;
- asparaginase stimulators, such as crisantaspase (Erwinase®) and GRASPA (ERY-001, ERY-ASP), and calaspargase pegol;
- pan-Trk, ROS1 and ALK inhibitors, such as entrectinib and TPX-0005;
- anaplastic lymphoma kinase (ALK) inhibitors, such as alectinib and ceritinib;
- antiproliferative/antimitotic alkylating agents, such as nitrogen mustard cyclophosphamide and analogs (melphalan, chlorambucil, hexamethylmelamine, thiotepa), alkyl nitrosoureas (carmustine) and analogs, streptozocin, and triazenes (dacarbazine);
- antiproliferative/antimitotic antimetabolites, such as folic acid analogs (methotrexate);
- platinum coordination complexes (cisplatin, oxiloplatinim, and carboplatin), procarbazine, hydroxyurea, mitotane, and aminoglutethimide;
- hormones, hormone analogs (estrogen, tamoxifen, goserelin, bicalutamide, and nilutamide), and aromatase inhibitors (letrozole and anastrozole);
- anticoagulants such as heparin, synthetic heparin salts, and other inhibitors of thrombin;
- fibrinolytic agents such as tissue plasminogen activator, streptokinase, urokinase, aspirin, dipyridamole, ticlopidine, and clopidogrel;
- antimigratory agents;
- antisecretory agents (breveldin);
- immunosuppressives, such as tacrolimus, sirolimus, azathioprine, and mycophenolate;
- growth factor inhibitors, and vascular endothelial growth factor inhibitors;
- fibroblast growth factor inhibitors, such as FPA14;
- anti-VEGFR antibodies, such as IMC-3C5, GNR-011, LYN-00101, and tanibirumab;
- anti-VEGF/DDL4 antibodies, such as ABT-165;
- anti-cadherins antibodies, such as HKT-288;
- anti-CD70 antibodies, such as AMG-172;
- anti-leucine-rich repeat containing 15 (LRRC15) antibodies, such as ABBV-085 and ARGX-110;
- angiotensin receptor blockers and nitric oxide donors;
- antisense oligonucleotides, such as AEG35156, IONIS-KRAS-2.5Rx, EZN-3042, RX-0201, IONIS-AR-2.5Rx, BP-100 (prexigebersen), and IONIS-STAT3-2.5Rx;
- DNA interference oligonucleotides, such as PNT2258 and AZD-9150;
- anti-ANG-2 antibodies, such as MEDI3617, and LY3127804;
- anti-ANG-1/ANG-2 antibodies, such as AMG-780;
- anti-MET/EGFR antibodies, such as LY3164530;
- anti-EGFR antibodies, such as ABT-414, AMG-595, necitumumab, ABBV-221, depatuxizumab mafodotin (ABT-414), tomuzotuximab, ABT-806, vectibix, modotuximab, and RM-1929;
- anti-CSF1R antibodies, such as emactuzumab, LY3022855, AMG-820, and FPA-008 (cabiralizumab);
- anti-CD40 antibodies, such as RG7876, SEA-CD40, APX-005M, and ABBV-428;
- anti-endoglin antibodies, such as TRC105 (carotuximab);
- anti-CD45 antibodies, such as 131I-BC8 (lomab-B);
- anti-HER3 antibodies, such as LJM716, and GSK2849330;
- anti-HER2 antibodies, such as margetuximab, MEDI4276, and BAT-8001;
- anti-HLA-DR antibodies, such as IMMU-114;
- anti-IL-3 antibodies, such as JNJ-56022473;
- anti-OX40 antibodies, such as MEDI6469, MEDI6383, MEDI0562 (tavolixizumab), MOXR0916, PF-04518600, RG-7888, GSK-3174998, INCAGN1949, BMS-986178, GBR-8383, and ABBV-368;
- anti-EphA3 antibodies, such as KB-004;
- anti-CD20 antibodies, such as obinutuzumab, IGN-002;
- anti-CD20/CD3 antibodies, such as RG7828;
- anti-CD37 antibodies, such as AGS67E, and otlertuzumab (TRU-016);
- anti-ENPP3 antibodies, such as AGS-16C3F;
- anti-FGFR-3 antibodies, such as LY3076226, and B-701;
- anti-FGFR-2 antibodies, such as GAL-F2;
- anti-C5 antibodies, such as ALXN-1210;
- anti-CD27 antibodies, such as varlilumab (CDX-1127);
- anti-TROP-2 antibodies, such as IMMU-132
- anti-NKG2a antibodies, such as monalizumab;
- anti-VISTA antibodies, such as HMBD-002;
- anti-PVRIG antibodies, such as COM-701;
- anti-EpCAM antibodies, such as VB4-845;
- anti-BCMA antibodies, such as GSK-2857916
- anti-CEA antibodies, such as RG-7813;
- anti-cluster of differentiation 3 (CD3) antibodies, such as MGD015;
- anti-folate receptor alpha antibodies, such as IMGN853;
- MCL-1 inhibitors, such as AMG-176, S-64315, AZD-5991, 483-LM, A-1210477, UMI-77, and JKY-5-037;
- epha2 inhibitors, such as MM-310;

anti LAG-3 antibodies, such as relatlimab (ONO-4482), LAG-525, MK-4280, and REGN-3767, INCAGN2385;
raf kinase/VEGFR inhibitors, such as RAF-265;
polycomb protein (EED) inhibitors, such as MAK683;
anti-fibroblast activation protein (FAP)/IL-2R antibodies, such as RG7461;
anti-fibroblast activation protein (FAP)/TRAIL-R2 antibodies, such as RG7386;
anti-fucosyl-GM1 antibodies, such as BMS-986012;
p38 MAP kinase inhibitors, such as ralimetinib;
PRMT1 inhibitors, such as MS203;
Sphingosine kinase 2 (SK2) inhibitors, such as opaganib;
FLT3-ITD inhibitors, such as BCI-332;
FLT3-ITD/Mer tyrosine kinase inhibitors, such as MRX-2843;
Nuclear erythroid 2-related factor 2 stimulators, such as omaveloxolone (RTA-408);
Tropomyosin receptor kinase (TRK) inhibitors, such as LOXO-195, and ONO-7579;
anti-ICOS antibodies, such as JTX-2011, and GSK3359609;
anti-DR5 (TRAIL2) antibodies, such as DS-8273, CTB-006, INBRX-109, GEN-1029;
anti-Carcinoembryonic-antigen-related-cell-adhesion-molecule-6 (CEACAM6, CD66C) antibodies, such as BAY-1834942, NEO-201 (CEACAM ⅝);
anti-GD2 antibodies, such as APN-301;
anti-interleukin-17 (IL-17) antibodies, such as CJM-112;
anti-carbonic anhydrase IX antibodies, such as TX-250;
anti-CD38-attenukine, such as TAK573;
anti-Mucin 1 antibodies, such as gatipotuzumab;
anti-FTL3 antibodies, such as Flysyn, ASP-1235;
anti-FLT3/CD3 BiTE antibodies, such as AMG-427;
Mucin 1 inhibitors, such as GO-203-2C;
MARCKS protein inhibitors, such as BIO-11006;
Folate antagonists, such as arfolitixorin;
Galectin-3 inhibitors, such as GR-MD-02;
Phosphorylated P68 inhibitors, such as RX-5902;
CD95/TNF modulators, such as ofranergene obadenovec;
PI3K/Akt/mTOR inhibitors, such as ABTL-0812;
pan-PIM kinase inhibitors, such as INCB-053914;
PIM/FLT3 kinase inhibitors, such as MEN-1703 (SEL-24);
IL-12 gene stimulators, such as EGEN-001, and tavokinogene telseplasmid;
Heat shock protein HSP90 inhibitors, such as TAS-116, and PEN-866;
VEGF/HGF antagonists, such as MP-0250;
SYK tyrosine kinase/FLT3 tyrosine kinase inhibitors, such as TAK-659 (mivavotinib);
SYK tyrosine kinase/JAK tyrosine kinase inhibitors, such as ASN-002;
JAK3/JAK1/TBK1 kinase inhibitors, such as CS-12912;
FLT3 tyrosine kinase inhibitor, such as FF-10101, HM-43239, SKI-G-801;
FLT3 tyrosine kinase agonist, such as CDX-301;
EGFR/FLT3/ABL tyrosine kinase inhibitors, such as SKLB-1028;
FLT3/MEK1 inhibitors, such as E-6201;
IL-24 antagonist, such as AD-IL24;
NLRP3 (NACHT LRR PYD domain protein 3) modulators, such as BMS-986299;
RIG-I agonists, such as RGT-100;
Aerolysin stimulators, such as topsalysin;
P-Glycoprotein 1 inhibitors, such as HM-30181A;
CSF-1 antagonists, such as ARRY-382, and BLZ-945;
CCR8 inhibitors, such as 1-309, SB-649701, HG-1013, RAP-310;
anti-Mesothelin antibodies, such as SEL-403;
Thymidine kinase stimulators, such as aglatimagene besadenovec;
Polo-like kinase 1 inhibitors, such as PCM-075;
TLR-7 agonists, such as TMX-101 (imiquimod);
NEDD8 inhibitors, such as pevonedistat (MLN-4924), and TAS-4464;
Pleiotropic pathway modulators, such as avadomide (CC-122);
FoxM1 inhibitors, such as thiostrepton;
Anti-MUC1 antibodies, such as Mab-AR-20.5;
anti-CD38 antibodies, such as isatuximab, and MOR-202;
UBA1 inhibitors, such as TAK-243;
Src tyrosine kinase inhibitors, such as VAL-201;
VDAC/HK inhibitors, such as VDA-1102;
BRAF/PI3K inhibitors, such as ASN-003;
Elf4a inhibitors, such as rohinitib, eFT226;
TP53 gene stimulators, such as ad-p53;
PD-L1/EGFR inhibitors, such as GNS-1480 (lazertinib);
PD-1/CTLA-4 inhibitors, such as PF-06936308;
Retinoic acid receptor alpha (RARα) inhibitors, such as SY-1425;
SIRT3 inhibitors, such as YC8-02;
Stromal cell-derived factor 1 ligand inhibitors, such as olaptesed pegol (NOX-A12);
IL-4 receptor modulators, such as MDNA-55;
Arginase-I stimulators, such as pegzilarginase;
Topoisomerase I inhibitor/hypoxia inducible factor-1 alpha inhibitors, such as PEG-SN38 (firtecan pegol);
Hypoxia inducible factor-1 alpha inhibitors, such as PT-2977, and PT-2385;
CD122 agonists such as NKTR-214;
TLR7/TLR8 agonist, such as NKTR-262;
TLR7 agonists, such as DS-0509, GS-9620, LHC-165, TMX-101 (imiquimod);
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
Menin and mixed lineage leukemia (MLL) inhibitors such as KO-539;
Liver x receptor agonists, such as RGX-104;
IL-10 agonists, such as AM-0010;
EGFR/ErbB-2 inhibitors, such as varlitinib;
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
Glucocorticoid receptor antagonists, such as relacorilant (CORT-125134);
Second mitochondria-derived activator of caspases (SMAC) protein inhibitors, such as BI-891065;
Lactoferrin modulators, such as LTX-315;
Kit tyrosine kinase/PDGF receptor alpha antagonists such as DCC-2618;
KIT inhibitors, such as PLX-9486;
Exportin 1 inhibitors, such as eltanexor;
EGFR/ErbB2/Ephb4 inhibitors, such as tesevatinib;
anti-CD33 antibodies, such as IMGN-779;
anti-KMA antibodies, such as MDX-1097;
anti-TIM-3 antibodies, such as TSR-022, LY-3321367, and MBG-453;

anti-CD55 antibodies, such as PAT-SC1;
anti-PSMA antibodies, such as ATL-101;
anti-CD100 antibodies, such as VX-15;
anti-EPHA3 antibodies, such as fibatuzumab;
anti-Erbb antibodies, such as CDX-3379, HLX-02, and seribantumab;
anti-APRIL antibodies, such as BION-1301;
Anti-Tigit antibodies, such as BMS-986207, AGEN-1307, and RG-6058;
anti-TIM-3 antibodies, such as INCAGN-2390;
CHST15 gene inhibitors, such as STNM-01;
RAS inhibitors, such as NEO-100;
Somatostatin receptor antagonist, such as OPS-201;
CEBPA gene stimulators, such as MTL-501;
DKK3 gene modulators, such as MTG-201;
Chemokine (CXCR1/CXCR2) inhibitors, such as SX-682;
p70s6k inhibitors, such as MSC2363318A;
methionine aminopeptidase 2 (MetAP2) inhibitors, such as M8891, and APL-1202;
arginine N-methyltransferase 5 inhibitors, such as GSK-3326595;
anti-programmed cell death protein 1 (anti-PD-1) antibodies, such as nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317 (tislelizumab), GLS-010 (WBP-3055), AK-103 (HX-008), CS-1003, HLX-10, MGA-012, BI-754091, REGN-2810 (cemiplimab), AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, AK-105, PD1-PIK, BAT-1306, BAT-1306, and anti-programmed death-ligand 1 (anti-PD-L1) antibodies such as BMS-936559, atezolizumab (MPDL3280A), durvalumab (MED14736), avelumab, CK-301, (MSB0010718C), MEDI0680, CX-072, CBT-502, PDR-001 (spartalizumab), TSR-042 (dostarlimab), MSB-2311, JTX-4014, BGB-A333, SHR-1316, CS-1001 (WBP-3155, KN-035, IBI-308, (sintilimab), HLX-20, KL-A167, STI-A1014, STI-A1015 (IMC-001), BCD-135, FAZ-053, TQB-2450, and MDX1105-01;
PD-L1/VISTA antagonists such as CA-170;
PD-1/PD-L1 inhibitors, such as INCB086550, GS-4224;
anti-PD-L1/TGFβ antibodies, such as M7824;
anti-transferrin antibodies, such as CX-2029;
anti-IL-8 (Interleukin-8) antibodies, such as HuMax-Inflam;
ATM (ataxia telangiectasia) inhibitors, such as AZD0156;
CHK1 inhibitors, such as GDC-0575, LY2606368 (prexasertib), SRA737, and RG7741 (CHK½);
CXCR4 antagonists, such as BL-8040, LY2510924, burixafor (TG-0054), X4P-002, and X4P-001-10;
EXH2 inhibitors, such as GSK2816126;
HER2 inhibitors, such as neratinib, and tucatinib (ONT-380);
KDM1 inhibitors, such as ORY-1001, IMG-7289, INCB-59872, and GSK-2879552;
CXCR2 antagonists, such as AZD-5069;
GM-CSF antibodies, such as lenzilumab;
DNA dependent protein kinase inhibitors, such as MSC2490484A (nedisertib), VX-984, and AsiDNA (DT-01);
protein kinase C (PKC) inhibitors, such as LXS-196, and sotrastaurin;
Selective estrogen receptor downregulators (SERD), such as fulvestrant (Faslodex®), RG6046, RG6047, elacestrant (RAD-1901) and AZD9496;
Selective estrogen receptor covalent antagonists (SERCAs), such as H3B-6545;
selective androgen receptor modulator (SARM), such as GTX-024, and darolutamide;
transforming growth factor-beta (TGF-beta) kinase antagonists, such as galunisertib;
anti-transforming growth factor-beta (TGF-beta) antibodies, such as LY3022859, NIS793, and XOMA 089;
bispecific antibodies, such as MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLECl2A), MCLA-128 (HER2/HER3), JNJ-0819, JNJ-7564 (CD3/heme), AMG-757 (DLL3-CD3), MGD-013 (PD-1/LAG-3), FS-118 (LAG-3/PD-L1) MGD-019 (PD-1/CTLA-4), KN-046 (PD-1/CTLA-4), MEDI-5752 (CTLA-4/PD-1), RO-7121661 (PD-1/TIM-3), XmAb-20717 (PD-1/CTLA-4), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MGD-009 (CD3/B7H3), AGEN1223, IMCgp100 (CD3/gp100 T-cell engager) and AGEN-1423, ATOR-1015 (CTLA-4/OX40), LY-3415244 (TIM3/PDL1), INHIBRX-105 (4-1BB/PDL1), faricimab (VEGF-A/ANG-2), FAP-4-IBBL (4-1BB/FAP), XmAb-13676 (CD3/CD20), TG-1801 (CD19/CD47), XmAb-18087 (SSTR2/CD3), catumaxomab (CD3/EpCAM), SAR-156597 (IL4/IL13), EMB-01 (EGFR/cMET), REGN-4018 (MUC16/CD3), RG-7828 (CD20/CD3), CC-93269 (CD3/BCMA), REGN-5458 (CD3/BCMA), navicixizumab (DLL4/VEGF), GRB-1302 (CD3/Erbb2), vanucizumab (VEGF-A/ANG-2), GRB-1342 (CD38/CD3), GEM-333 (CD3/CD33), IMM-0306 (CD47/CD20);
Mutant selective EGFR inhibitors, such as PF-06747775, EGF816 (nazartinib), ASP8273, ACEA-0010, and BI-1482694;
Anti-GITR (glucocorticoid-induced tumor necrosis factor receptor-related protein) antibodies, such as MEDI1873, FPA-154, INCAGN-1876, TRX-518, BMS-986156, MK-1248, and GWN-323;
anti-delta-like protein ligand 3 (DDL3) antibodies, such as rovalpituzumab tesirine;
anti-clusterin antibodies, such as AB-16B5;
anti-Ephrin-A4 (EFNA4) antibodies, such as PF-06647263;
anti-RANKL antibodies, such as denosumab;
anti-mesothelin antibodies, such as BMS-986148, and Anti-MSLN-MMAE;
anti-sodium phosphate cotransporter 2B (NaP2B) antibodies, such as lifastuzumab
anti-c-Met antibodies, such as ABBV-399;
Adenosine A2A receptor antagonists, such as CPI-444, AZD-4635, preladenant, and PBF-509;
Alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);

IDH1 inhibitors such as AG-120, and AG-881 (IDH1 and IDH2), IDH-305, and BAY-1436032;
interleukin-3 receptor (IL-3R) modulators, such as SL-401;
Arginine deiminase stimulators, such as pegargiminase (ADI-PEG-20);
antibody-drug conjugates, such as MLN0264 (anti-GCC, guanylyl cyclase C), T-DM1 (trastuzumab emtansine, Kadcycla, SYD985), milatuzumab-doxorubicin (hCD74-DOX), brentuximab vedotin, DCDT2980S, polatuzumab vedotin (RG-7596), SGN-CD70A, SGN-CD19A, inotuzumab ozogamicin (CMC-544), lorvotuzumab mertansine, SAR3419, isactuzumab govitecan, enfortumab vedotin (ASG-22ME), ASG-15ME, DS-8201 ((trastuzumab deruxtecan), 225Ac-lintuzumab, U3-1402, 177Lu-tetraxetan-tetuloma, tisotumab vedotin, anetumab ravtansine, CX-2009, SAR-566658, W-0101, polatuzumab vedotin, ABBV-085, gemtuzumab ozogamicin, ABT-414, glembatumumab vedotin (CDX-011), labetuzumab govitecan (IMMU-130), sacituzumab govitecan (IMMU-132), lifastuzumab vedotin, (RG-7599), milatuzumab-doxorubicin (IMMU-110), indatuximab ravtansine (BT-062), pinatuzumab vedotin (RG-7593), SGN-LIV1A, SGN-CD33A, SAR566658, MLN2704, SAR408701, rovalpituzumab tesirine, ABBV-399, AGS-16C3F, ASG-22ME, AGS67E, AMG 172, AMG 595, AGS-15E, BAY1129980, BAY1187982, BAY94-934 (anetumab ravtansine), GSK2857916, Humax-TF-ADC (tisotumab vedotin), IMGN289, IMGN529, IMGN853 (mirvetuximab soravtansine), LOP628, PCA062, MDX-1203, MEDI-547, PF-06263507, PF-06647020, PF-06647263, PF-06664178, RG7450, RG7458, RG7598, SAR566658, SGN-CD33A;
claudin-18 inhibitors, such as claudiximab;
β-catenin inhibitors, such as CWP-291;
anti-CD73 antibodies, such as MEDI-9447 (oleclumab), CPX-006, IPH-53, NZV-930, and BMS-986179;
CD73 antagonists, such as AB-680, PSB-12379, PSB-12441, PSB-12425, and −708;
CD39/CD73 antagonists, such as PBF-1662;
chemokine receptor 2 (CCR) inhibitors, such as PF-04136309, CCX-872, and BMS-813160 (CCR2/CCR5)
thymidylate synthase inhibitors, such as ONX-0801;
ALK/ROS1 inhibitors, such as lorlatinib;
tankyrase inhibitors, such as G007-LK;
Mdm2 p53-binding protein inhibitors, such as CMG-097, and HDM-201;
c-PIM inhibitors, such as PIM447;
BRAF inhibitors, such as dabrafenib, vemurafenib, encorafenib (LGX818), and PLX8394;
sphingosine kinase-2 (SK2) inhibitors, such as Yeliva® (ABC294640);
cell cycle inhibitors, such as selumetinib (MEK½), and sapacitabine;
AKT inhibitors such as MK-2206, ipatasertib, afuresertib, AZD5363, ARQ-092, capivasertib, and triciribine;
anti-CTLA-4 (cytotoxic T-lymphocyte protein-4) antibodies, such as tremelimumab, ipilimumab (BMS-734016), AGEN-1884, BMS-986218, AGEN1181, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BA-3071;
CTLA-4 (cytotoxic T-lymphocyte protein-4) inhibitors, such as BPI-002;
TLR-3 agonist/interferon inducers, such as Poly-ICLC (NSC-301463)
c-MET inhibitors, such as AMG-337, savolitinib, tivantinib (ARQ-197), capmatinib, and tepotinib, ABT-700, AG213, AMG-208, JNJ-38877618 (OMO-1), merestinib, and HQP-8361;
c-Met/VEGFR inhibitors, such as BMS-817378, and TAS-115;
c-Met/RON inhibitors, such as BMS-777607;
c-Met/VEGF2/AXL/RON/Mer/FLT3 inhibitors, such as CT-053 (ningetinib);
c-Kit/VEGFR2/PDGFR/VEGFR3/FLT1/FLT3 inhibitors, such as SHR-1020 (famitinib L-malate);
BRAF/EGFR inhibitors, such as BGB-283;
bcr/abl inhibitors, such as rebastinib, and asciminib;
MNK1/MNK2 inhibitors, such as eFT-508;
mTOR inhibitor/cytochrome P450 3A4 stimulators, such as TYME-88
lysine-specific demethylase-1 (LSD1) inhibitors, such as CC-90011;
Pan-RAF inhibitors, such as LY3009120, LXH254, and TAK-580;
Raf/MEK inhibitors, such as RG7304;
CSF1R/KIT and FLT3 inhibitors, such as pexidartinib (PLX3397);
kinase inhibitors, such as vandetanib;
E selectin antagonists, such as GMI-1271;
differentiation inducers, such as tretinoin;
epidermal growth factor receptor (EGFR) inhibitors, such as osimertinib (AZD-9291);
topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), and irofulven (MGI-114);
corticosteroids, such as cortisone, dexamethasone, hydrocortisone, methylprednisolone, prednisone, and prednisolone;
growth factor signal transduction kinase inhibitors;
nucleoside analogs, such as DFP-10917;
Ax1 inhibitors, such as BGB-324 (bemcentinib), and SLC-0211;
BET inhibitors, such as INCB-054329, INCB057643, TEN-010, AZD-5153, ABT-767, BMS-986158, CC-90010, GSK525762 (molibresib), NHWD-870, ODM-207, GSK-2820151, GSK-121015TA, ZBC246, ZBC260, ZEN3694, FT-1101, RG-6146, CC-90010, mivebresib, BI-894999, PLX-2853, PLX-51107, CPI-0610, and GS-5829;
PARP inhibitors, such as olaparib, rucaparib, veliparib, talazoparib, ABT-767, and BGB-290, fluzolepali (SHR-3162), niraparib (JNJ-64091742), bendamustine hydrochloride;
IMP-4297, SC-10914, IDX-1197, HWH-340, CK-102, simmiparib;
PARP/Tankyrase inhibitors such as 2X-121 (e-7499)
Proteasome inhibitors, such as ixazomib, carfilzomib (Kyprolis®), and marizomi;
Glutaminase inhibitors, such as CB-839 (telaglenastat);
Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131; bacterial vector vaccines such as CRS-207/GVAX, axalimogene filolisbac (ADXS11-

001); adenovirus vector vaccines such as nadofaragene firadenovec; autologous Gp96 vaccine; dendritic cells vaccines, such as CVactm, stapuldencel-T, eltrapuldencel-T, SL-701, BSK01TM, rocapuldencel-T (AGS-003), DCVAC, CVac™, stapuldencel-T, eltrapuldencel-T, SL-701, BSK01™, ADXS31-142; oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, PF-06753512, VBI-1901, TG-4010, ProscaVax™; tumor cell vaccines, such as Vigil@(IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; and GI-4000; 10-103; Neoantigen peptide vaccines, such as AGEN-2017, GEN-010, NeoVax, RG-6180, GEN-009, PGV-001 (TLR-3 agonist), GRANITE-001, NEO-PV-01; Peptide vaccines that target heat shock proteins, such as PhosphoSynVax™; Vitespen (HSPPC-96-C);

anti-DLL4 (delta like ligand 4) antibodies, such as demcizumab;

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);

interferon gamma ligand modulators, such as interferon gamma (OH-6000, Ogamma 100);

IL-6 receptor modulators, such as tocilizumab, siltuximab, and AS-101 (CB-06-02, IVX-Q-101);

Telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacitidine;

DNA gyrase inhibitors, such as pixantrone and sobuzoxane;

Bcl-2 family protein inhibitors, such as ABT-263, venetoclax (ABT-199), ABT-737, and AT-101;

Notch inhibitors, such as LY3039478 (crenigacestat), tarextumab (anti-Notch2/3), and BMS-906024;

anti-myostatin inhibitors, such as landogrozumab;

hyaluronidase stimulators, such as PEGPH-20;

Wnt pathway inhibitors, such as SM-04755, PRI-724, and WNT-974;

gamma-secretase inhibitors, such as PF-03084014, MK-0752, and RO-4929097;

Grb-2 (growth factor receptor bound protein-2) inhibitors, such as BP T001;

TRAIL pathway-inducing compounds, such as ONC201, and ABBV-621;

Focal adhesion kinase inhibitors, such as VS-4718, defactinib, and GSK2256098;

hedgehog inhibitors, such as saridegib, sonidegib (LDE225), glasdegib and vismodegib;

Aurora kinase inhibitors, such as alisertib (MLN-8237), and AZD-2811, AMG-900, barasertib, and ENMD-2076;

HSPB1 modulators (heat shock protein 27, HSP27), such as brivudine, and apatorsen;

ATR inhibitors, such as BAY-937, AZD6738, AZD6783, VX-803, VX-970 (berzosertib) and VX-970;

mTOR inhibitors, such as sapanisertib and vistusertib (AZD2014), and ME-344;

mTOR/PI3K inhibitors, such as gedatolisib, GSK2141795, omipalisib, and RG6114;

Hsp90 inhibitors, such as AUY922, onalespib (AT13387), SNX-2112, and SNX5422;

Murine double minute (mdm2) oncogene inhibitors, such as DS-3032b, RG7775, AMG-232, HDM201, and idasanutlin (RG7388);

CD137 agonists, such as urelumab, (PF-05082566), AGEN2373, ADG-106, and utomilumab (PF-05082566);

STING agonists, such as ADU-S100 (MIW-815), SB-11285, MK-1454, SR-8291, AdVCA0848, GSK-532, SYN-STING, MSA-1, and SR-8291;

FGFR inhibitors, such as FGF-401, INCB-054828, BAY-1163877, AZD4547, JNJ-42756493, LY2874455, and Debio-1347;

fatty acid synthase (FASN) inhibitors, such as TVB-2640;

Anti-KIR monoclonal antibodies, such as lirilumab (IPH-2102), and IPH-4102;

Antigen CD19 inhibitors, such as MOR208, MEDI-551, AFM-11, and inebilizumab;

CD44 binders, such as A6;

protein phosphatease 2A (PP2A) inhibitors, such as LB-100;

CYP17 inhibitors, such as seviteronel (VT-464), ASN-001, ODM-204, CFG920, and abiraterone acetate;

RXR agonists, such as IRX4204;

hedgehog/smoothened (hh/Smo) antagonists, such as taladegib, and patidegib;

complement C3 modulators, such as Imprime PGG;

IL-15 agonists, such as ALT-803, NKTR-255, and hetIL-15;

EZH2 (enhancer of zeste homolog 2) inhibitors, such as tazemetostat, CPI-1205, and GSK-2816126;

Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, and OBP-301;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819

PLK inhibitors of PLK 1, 2, and 3, such as volasertib (PLK1);

WEE1 inhibitors, such as AZD1775 (adavosertib);

Rho kinase (ROCK) inhibitors, such as AT13148, and KD025;

ERK inhibitors, such as GDC-0994, LY3214996, and MK-8353;

IAP inhibitors, such as ASTX660, debio-1143, birinapant, APG-1387, and LCL-161;

RNA polymerase inhibitors, such as lurbinectedin (PM-1183), and CX-5461;

Tubulin inhibitors, such as PM-184, BAL-101553 (lisavanbulin), OXI-4503, fluorapacin (AC-0001), and plinabulin;

Toll-like receptor 4 (TL4) agonists, such as G100, GSK1795091, and PEPA-10;

Elongation factor 1 alpha 2 inhibitors, such as plitidepsin;

CD95 inhibitors, such as APG-101, APO-010, and asunercept;

WT1 inhibitors, such as DSP-7888;

splicing factor 3B subunit1 (SF3B1) inhibitors, such as H3B-8800

PDGFR alpha/KIT mutant-specific inhibitors such as BLU-285;

SHP-2 inhibitors, such as TNO155 (SHP-099), and RMC-4550;

Microbiome modulators, such as SER-401, EDP-1503, MRx-0518; and retinoid Z receptor gamma (RORγ) agonists, such as LYC-55716;

In some embodiments, provided herein are methods of treating or preventing a cancer or hyper-proliferative disease in a human or animal having or at risk of having the cancer or hyper-proliferative disease is provided, comprising administering to the human or animal a therapeutically effective amount of a compound of Formula I, I-Z, I-E, II-Z, IIa-Z, IIb-Z, III-Z, or IIIa-Z as disclosed herein, or a pharmaceutically acceptable salt thereof, in combination with a therapeutically effective amount of one or more (e.g., one, two, three, one or two, or one to three) additional therapeutic agents selected from the group consisting of apoptosis signal-regulating kinase (ASK) inhibitors; Bruton's tyrosine kinase (BTK) inhibitors; cluster of differentiation 47 (CD47) inhibitors; cyclin-dependent kinase (CDK) inhibitors; discoidin domain receptor (DDR) inhibitors; histone deacetylase (HDAC) inhibitors; indoleamine-pyrrole-2,3-dioxygenase (IDO1) inhibitors; Janus kinase (JAK) inhibitors; lysyl oxidase-like protein (LOXL) inhibitors; matrix metalloprotease (MMP) inhibitors; mitogen-activated protein kinase (MEK) inhibitors; phosphatidylinositol 3-kinase (PI3K) inhibitors; spleen tyrosine kinase (SYK) inhibitors; toll-like receptor 8 (TLR8) inhibitors; toll-like receptor 9 (TLR9) inhibitors; tyrosine-kinase inhibitors (TKIs), or a pharmaceutically acceptable salt of any of the foregoing, or any combinations thereof. Non-limiting examples include:

MCL-1 inhibitors, such as AMG-176, AMG-397, S-64315, and AZD-5991, 483-LM, A-1210477, UMI-77, JKY-5-037; Examples of MCL1 inhibitors include, but are not limited to, those described in WO-2018183418, WO-2016033486, and WO-2017147410;

SHP-2 inhibitors, such as TNO155 (SHP-099), RMC-4550, JAB-3068, RMC-4630; Examples of SHP2 inhibitors include, but are not limited to, those described in WO-2018172984 and WO-2017211303;

Hematopoietic Progenitor Kinase 1 (HPK1) inhibitors; Examples of Hematopoietic Progenitor Kinase 1 (HPK1) inhibitors include, but are not limited to, those described in WO-2018183956, WO-2018183964, WO-2018167147, WO-2018183964, WO-2016205942, WO-2018049214, WO-2018049200, WO-2018049191, WO-2018102366, WO-2018049152 and WO-2016090300;

Apoptosis Signal-Regulating Kinase (ASK) Inhibitors: ASK inhibitors include ASK1 inhibitors. Examples of ASK1 inhibitors include, but are not limited to, those described in WO 2011/008709 (Gilead Sciences) and WO 2013/112741 (Gilead Sciences);

Bruton's Tyrosine Kinase (BTK) Inhibitors: Examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, and TAS-5315;

Cluster of Differentiation 47 (CD47) inhibitors: Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621;

Cyclin-dependent Kinase (CDK) Inhibitors: CDK inhibitors include inhibitors of CDK 1, 2, 3, 4, 6, 7 and 9, such as abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, and TG-02;

Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations);

Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat;

Indoleamine-pyrrole-2,3-dioxygenase (IDO1) inhibitors: Examples of IDO1 inhibitors include, but are not limited to, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, and LY-3381916;

Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019;

Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics);

Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555), GS-5745 (andecaliximab) and those described in WO 2012/027721 (Gilead Biologics);

Mitogen-activated Protein Kinase (MEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, and refametinib;

Phosphatidylinositol 3-kinase (PI3K) Inhibitors: PI3K inhibitors include inhibitors of PI3Kγ, PI3Kδ, PI3Kβ, PI3Kα, and/or pan-PI3K. Examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences);

Spleen Tyrosine Kinase (SYK) Inhibitors: Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), GS-9876, and those described in U.S. Pat. No. 8,450,321 (Gilead Connecticut) and those described in U.S. 2015/0175616;

Toll-like receptor 8 (TLR8) inhibitors: Examples of TLR8 inhibitors include, but are not limited to, E-6887, IMO-4200, IMO-8400, IMO-9200, MCT-465, MEDI-9197, motolimod, resiquimod, GS-9688, VTX-1463, and VTX-763;

Toll-like receptor 9 (TLR9) inhibitors: Examples of TLR9 inhibitors include, but are not limited to, AST-008, IMO-2055, IMO-2125, lefitolimod, litenimod, MGN-1601, and PUL-042; and Tyrosine-kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody).

As used herein, the term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer. Examples of chemotherapeutic agents include but are not limited to:

alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylomithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above.

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Anti-Hormonal Agents

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, and ODM-204.

Examples of progesterone receptor antagonist include onapristone.

Anti-Angiogenic Agents

Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, $\alpha,\alpha'$-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, and inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Immunotherapeutic Agents

Examples of immunotherapeutic agents include but are not limited to therapeutic antibodies suitable for treating patients. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. In some embodiments, a combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

Cancer Gene Therapy and Cell Therapy

Cancer gene therapy and cell therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; and genetic approaches to modify cellular activity to further alter endogenous immune responsiveness against cancer.

Gene Editors

Examples of genome editing system include a CRISPR/Cas9 system, a zinc finger nuclease system, a TALEN system, a homing endonucleases system, and a meganuclease system.

CAR-T Cell Therapy and TCR-T Cell Therapy

CAR-T cell therapy includes a population of immune effector cells engineered to express a chimeric antigen receptor (CAR), wherein the CAR comprises a tumor antigen-binding domain. The immune effector cell is a T cell or an NK cell. TCR-T cell therapy includes TCR-T cells that are engineered to target tumor derived peptides present on the surface of tumor cells. Cells can be autologous or allogeneic.

In some embodiments, the CAR comprises an antigen binding domain, a transmembrane domain, and an intracellular signaling domain.

In some embodiments, the intracellular domain comprises a primary signaling domain, a costimulatory domain, or both of a primary signaling domain and a costimulatory domain.

In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12.

In some embodiments, the costimulatory domain comprises a functional domain of one or more proteins selected from the group consisting of CD27, CD28, 4-1BB (CD137), OX40, CD30, CD40, PD-1, ICOS, lymphocyte function-associated antigen-1 (LFA-I), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 11, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R u, ITGAI, VLA1, CD49a, ITGA4, IA4, CD49D, ITGA6, VLA-6, CD49f, ITGAD, CD11d, ITGAE, CD103, ITGAL, CD1 1a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain binds a tumor antigen.

In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvIII); ganglioside G2 (GD2); ganglioside GD3 (aNeuSAc(2-8)aNeuSAc(2-3)bD-Gaip(1-4)bDGIcp(1-1)Cer); TNF receptor family member B cell maturation (BCMA); Tn antigen ((Tn Ag) or (GaINAcu-Ser/Thr)); prostate-specific membrane antigen (PSMA); Receptor tyrosine kinase-like orphan receptor 1 (RORI); Fms-Like, Tyrosine Kinase 3 (FLT3); Tumor-associated glycoprotein 72 (TAG72); CD38; CD44v6; Carcinoembryonic antigen (CEA); Epithelial cell adhesion molecule (EP-CAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y)antigen; CD24; Platelet-derived growth factor receptor beta (PDGFR-beta); Stage-specificembryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murineleukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeuSAc(2-3)bDGalp(1-4)bDGlcp(1-1)Cer); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-1a); Melanomaassociated antigen 1 (MAGE-A1); ETS translocation-variant gene 6, located on chromosome 12p (ETV6-AML); sperm protein 17 (SPA17); X Antigen Family, Member 1A (XAGE1); angiopoietinbinding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, and Fc Receptor-like 5 (FcRL5).

Non limiting examples of cell therapies include Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CART cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

In some embodiments, the tumor targeting antigen includes: Alpha-fetoprotein, such as ET-1402, and AFP-TCR; Anthrax toxin receptor 1, such as anti-TEM8 CAR T-cell therapy; B cell maturation antigens (BCMA), such as bb-2121, UCART-BCMA, ET-140, KITE-585, MCM-998, LCAR-B38M, CART-BCMA, SEA-BCMA, BB212, UCART-BCMA, ET-140, P-BCMA-101, and AUTO-2 (APRIL-CAR; Anti-CLL-1 antibodies, such as KITE-796; Anti-PD-L1-CAR tank cell therapy, such as KD-045; B7 homolog 6, such as CAR-NKp30 and CAR-B7H6; B-lymphocyte antigen CD19, such as TBI-1501, CTL-119 huCART-19 T cells, JCAR-015 U.S. Pat. No. 7,446,190, JCAR-014, JCAR-017, (WO2016196388, WO2016033570, WO2015157386), axicabtagene ciloleucel (KTE-C19), U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, and IM19 CAR-T; B-lymphocyte antigen CD20, such as ACTR707; B-lymphocyte antigen CD19/B-lymphocyte antigen 22, such as TC-310; B-lymphocyte cell antigen 22, such as UCART-22, and JCAR-018 (WO2016090190); NY-ESO-1, such as GSK-3377794, and TBI-1301; Carbonic anhydrase, such as DC-Ad-GMCAIX; Caspase 9 suicide gene, such as CaspaCIDe DLI, and BPX-501; CCR5, such as SB-728; CDw123, such as MB-102, and UCART-123; CD20m such as CBM-C20.1; CD4, such as ICG-122; CD30, such as CART30 (CBM-C30.1; CD33, such as CIK-CAR.CD33; CD38, such as T-007, and UCART-38; CD40 ligand, such as BPX-201; CEACAM protein 4 modulators, such as MG7-CART; Claudin 6, such as CSG-002; EBV targeted, such as CMD-003; MUC16, such as autologous 4H111-28z/fnL-12/ EFGRt T cell; Endonuclease, such as PGN-201; Epstein-Barr virus specific T-lymphocytes, such as TT-10; Erbb2, such as CST-102 and CIDeCAR; Ganglioside (GD2), such as 4SCAR-GD2; folate hydrolase 1 (FOLH1, Glutamate carboxypeptidase II, PSMA) such as CIK-CAR.PSMA, CART-PSMA-TGFBRDN, and P-PSMA-101; Glypican-3 (GPC3), such as TT-16 and GLYCAR; Hepatocyte growth factor receptor, such as anti-cMet RNA CAR T; Human papillomavirus E7 protein, such as KITE-439; Immunoglobulin gamma Fc receptor III, such as ACTR087; IL-12, such as DC-RTS-IL-12; IL-12 agonist/mucin 16, such as JCAR-020; IL-13 alpha 2, such as MB-101; IL-2, such as CST-101; K-Ras GTPase, such as anti-KRAS G12V mTCR cell therapy; Neural cell adhesion molecule L1 L1CAM (CD171), such as JCAR-023; Latent membrane protein 1/Latent membrane protein 2, such as Ad5f35-LMPd1-2-transduced autologous dendritic cells; Melanoma associated antigen 10, such as MAGE-A10C796T and MAGE-A10 TCR; Melanoma associated antigen 3/Melanoma associated antigen 6 (MAGE A3/A6) such as KITE-718; Mesothelin, such as CSG-MESO and TC-210; NKG2D, such as NKR-2; Ntrkr1 tyrosine kinase receptor, such as JCAR-024; PRAM, such as BPX-701 and IMCgp100; T-lymphocyte, such as TT-12; Tumor infiltrating lymphocytes, such as LN-144 and LN-145; and Wilms tumor protein, such as JTCR-016, WT1-CTL.

Lymphoma or Leukemia Combination Therapy

In some embodiments, the additional therapeutic agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, flgrastim, flavopiridol, fludarabine, FR (fludarabine and rituximab), geldanamycin (17-AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R-MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCl-779), thalidomide, therapeutic allogeneic lymphocytes, thiotepa, tipifamib, vincristine, vincristine sulfate, vinorelbine ditartrate, SAHA (suberanilohydroxamic acid, or suberoyl, anilide, and hydroxamic acid), vemurafenib (Zelboraf®), and venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The above-mentioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and non-myeloablative allogeneic hematopoietic stem cell transplantation.

Non-Hodgkin's Lymphomas Combination Therapy

In some embodiments, the additional therapeutic agents are suitable for treating non-Hodgkin's lymphomas (NHL), especially those of B cell origin, which include monoclonal antibodies, standard chemotherapy approaches (e.g., CHOP, CVP, FCM, MCP, and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP, R-FCM, R-CVP, and R-MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

In some embodiments, the additional therapeutic agents are suitable for treating mantle cell lymphoma (MCL), which include combination chemotherapies such as CHOP, hyperCVAD, and FCM. These regimens can also be supplemented with the monoclonal antibody rituximab to form combination therapies R-CHOP, hyperCVAD-R, and R-FCM. Any of the above-mentioned therapies may be combined with stem cell transplantation or ICE in order to treat MCL.

Other examples of therapeutic agents suitable for treating MCL include:
- immunotherapy, such as monoclonal antibodies (like rituximab) and cancer vaccines, such as GTOP-99, which are based on the genetic makeup of an individual patient's tumor;
- radioimmunotherapy, wherein a monoclonal antibody is combined with a radioisotope particle, such as iodine-131 tositumomab (BEXXAR®), yttrium-90 ibritumomab tiuxetan (ZEVALIN®), and BEXXAR® in sequential treatment with CHOP;
- autologous stem cell transplantation coupled with high-dose chemotherapy, administering proteasome inhibitors such as bortezomib (VELCADE® or PS-341), or administering antiangiogenesis agents such as thalidomide, especially in combination with rituximab;
- drugs that lead to the degradation of Bcl-2 protein and increase cancer cell sensitivity to chemotherapy, such as oblimersen, in combination with other chemotherapeutic agents;
- mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents;
- other agents such as flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17-AAG).

Waldenstrom's Macroglobulinemia Combination Therapy

In some embodiments, the additional therapeutic agents are suitable for treating Waldenstrom's Macroglobulinemia (WM), which include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combinations thereof.

Other examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

In some embodiments, the additional therapeutic agents are suitable for treating diffuse large B-cell lymphoma (DLBCL), which include cyclophosphamide, doxorubicin, vincristine, prednisone, anti-CD20 monoclonal antibodies, etoposide, bleomycin, many of the agents listed for WM, and any combination thereof, such as ICE and R-ICE.

Chronic Lymphocytic Leukemia Combination Therapy

In some embodiments, the additional therapeutic agents are suitable for treating chronic lymphocytic leukemia (CLL), which include chlorambucil, cyclophosphamide, fludarabine, pentostatin, cladribine, doxorubicin, vincristine, prednisone, prednisolone, alemtuzumab, many of the agents listed for WM, and combination chemotherapy and chemo-immunotherapy, including the following common combination regimens: CVP, R-CVP, ICE, R-ICE, FCR, and FR.

Myelofibrosis Combination Therapy

In some embodiments, the additional therapeutic agents are suitable for treating myelofibrosis, which include hedgehog inhibitors, histone deacetylase (HDAC) inhibitors, and tyrosine kinase inhibitors. Non-limiting examples of hedgehog inhibitors are saridegib and vismodegib.

Examples of HDAC inhibitors include, but are not limited to, pracinostat and panobinostat.

Non-limiting examples of tyrosine kinase inhibitors include lestaurtinib, bosutinib, imatinib, gilteritinib, radotinib, and cabozantinib.

Hyperproliferative Disease Combination Therapy

In some embodiments, the additional therapeutic agents are suitable for treating a hyper-proliferative disease, which include gemcitabine, nab-paclitaxel, and gemcitabine/nab-paclitaxel with a JAK inhibitor and/or PI3K6 inhibitor.

Bladder Cancer Combination Therapy

In some embodiments, the additional therapeutic agents are suitable for treating bladder cancer, which include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combinations thereof.

Breast Cancer Combination Therapy

In some embodiments, the additional therapeutic agents are suitable for treating breast cancer, which include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

In some embodiments, the additional therapeutic agents are suitable for treating triple negative breast cancer, which include cyclophosphamide, docetaxel, doxorubicin, epirubicin, fluorouracil, paclitaxel, and combinations thereof.

Colorectal Cancer Combination Therapy

In some embodiments, the additional therapeutic agents are suitable for treating colorectal cancer, which include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy

In some embodiments, the additional therapeutic agents are suitable for treating castration-resistant prostate cancer, which include abiraterone, cabazitaxel, docetaxel, enzalutamide, prednisone, sipuleucel-T, and any combinations thereof.

Esophageal and Esophagogastric Junction Cancer Combination Therapy

In some embodiments, the additional therapeutic agents are suitable for treating esophageal and esophagogastric junction cancer, which include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

In some embodiments, the additional therapeutic agents are suitable for treating gastric cancer, which include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head & Neck Cancer Combination Therapy

In some embodiments, the additional therapeutic agents are suitable for treating head & neck cancer, which include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

In some embodiments, the additional therapeutic agents are suitable for treating hepatobiliary cancer, which include capecitabine, cisplatin, fluoropyrimidine, 5-fluorourcil, gemecitabine, oxaliplatin, sorafenib, and any combinations thereof.

Hepatocellular Carcinoma Combination Therapy

In some embodiments, the additional therapeutic agents are suitable for treating hepatocellular carcinoma, which include capecitabine, doxorubicin, gemcitabine, sorafenib, and any combinations thereof.

Non-Small Cell Lung Cancer Combination Therapy

In some embodiments, the additional therapeutic agents are suitable for treating non-small cell lung cancer (NSCLC), which include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

In some embodiments, the additional therapeutic agents are suitable for treating small cell lung cancer (SCLC), which include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Melanoma Combination Therapy

In some embodiments, the additional therapeutic agents are suitable for treating melanoma, which include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy

In some embodiments, the additional therapeutic agents are suitable for treating ovarian cancer, which include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcibabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

In some embodiments, the additional therapeutic agents are suitable for treating pancreatic cancer, which include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy

In some embodiments, the additional therapeutic agents are suitable for treating renal cell carcinoma, which include axitinib, bevacizumab, cabozantinib, erlotinib, everolimus, levantinib, nivolumab, pazopanib, sorafenib, sunitinib, temsirolimus, and any combinations thereof.

VI. Compound Preparation

Some embodiments of the present disclosure are directed to processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in the schemes below, and the particular examples that follow.

List of Abbreviations and Acronyms

| Abbreviation | Meaning |
| --- | --- |
| ° C. | Degree Celsius |
| Ac | Acetyl |
| MeCN | Acetonitrile |
| AcOH | Acetic acid |
| ATP | Adenosine triphosphate |
| Boc | tert-butyloxycarbonyl |
| br | Broad |
| ca | circa |
| Cy | cyclohexyl |
| d | Doublet or deuterated |
| DCM or CH$_2$Cl$_2$ | Dichloromethane |
| dd | Doublet of doublets |
| DMF | Dimethylformamide |
| DMSO | Dimethylsulfoxide |
| dppf | 1,1'-Bis(diphenylphosphino)ferrocene |
| dt | Doublet-triplet |
| equiv | Equivalents |
| Et | Ethyl |

-continued

| Abbreviation | Meaning |
| --- | --- |
| EA or EtOAc | Ethyl acetate |
| g | Grams |
| Hal | Halogen |
| HPLC | High pressure liquid chromatography |
| hr or h or hrs | Hours |
| Hz | Hertz |
| J | Coupling constant (MHz) |
| K$_2$CO$_3$ | Potassium carbonate |
| Kg or kg | Kilogram |
| L | Liter |
| LCMS or LC-MS | Liquid chromatography-mass spectrometry |
| M | Molar |
| m | multiplet |
| M+ | Mass peak |
| M + H | Mass peak plus hydrogen |
| Me | Methyl |
| MeOH | Methanol |
| mg | Milligram |
| MHz | Megahertz |
| ml or mL | Milliliter |
| mM | Millimolar |
| mmol | Millimole |
| mol | Mole |
| MS | Mass spectroscopy |
| Ms | methanesulfonyl |
| N | Normal |
| NaH | Sodium hydride |
| NBS | N-Bromosuccinimide |
| n-Bu or Bu | Butyl |
| NH$_4$Cl | Ammonium Chloride |
| NMR | Nuclear magnetic resonance |
| NMP | N-methylpyrrolidinone |
| Pd-C/ Pd/C | Palladium on Carbon |
| PE | Petroleum ether |
| Ph | Phenyl |
| q | Quartet |
| RT or rt | Room temperature |
| s | Singlet |
| sat. | Saturated |
| sec | second(s) |
| t | Triplet |
| t-Bu or tert-Bu or t-butyl | tert-Butyl |
| TFA | Trifluoroacetic acid |
| THF | Tetrahydrofuran |
| δ | Chemical shift (ppm) |
| μL or μl | Microliter |
| μM | Micromolar |

Synthesis of the Compounds

The compounds of the present application may be prepared using the methods disclosed herein and modifications thereof, which will be apparent given the disclosure herein. Known synthetic methods may be used in addition to the procedures described herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure.

Compounds were named using ChemBioDraw Ultra Version 14.0.

When production of starting materials is not particularly described, the compounds are either known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. The methods or features described in various Examples may be combined or adapted in various ways to provide additional ways of making the compounds described herein.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. Group labels (e.g. $R^1$, $R^a$, $R^b$) used in the reaction schemes herein are for illustrative purposes only and unless otherwise specified do not necessarily match by name or function the labels used elsewhere to describe compounds of Formula I, I-Z, I-E, II-Z, IIa-Z, IIb-Z, III-Z, or IIIa-Z or aspects or fragments thereof.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are known in the art. For example, numerous protecting groups are described in T. W. Greene and G. M. Wuts (1999) Protecting Groups in Organic Synthesis, 3$^{rd}$ Edition, Wiley, New York, and references cited therein.

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present invention are inert organic solvents, and the reactions are carried out under an inert gas, preferably nitrogen or argon.

Reaction Scheme I

The compounds of Formula I or I-Z may be prepared using methods similar to those shown in Reaction Scheme I.

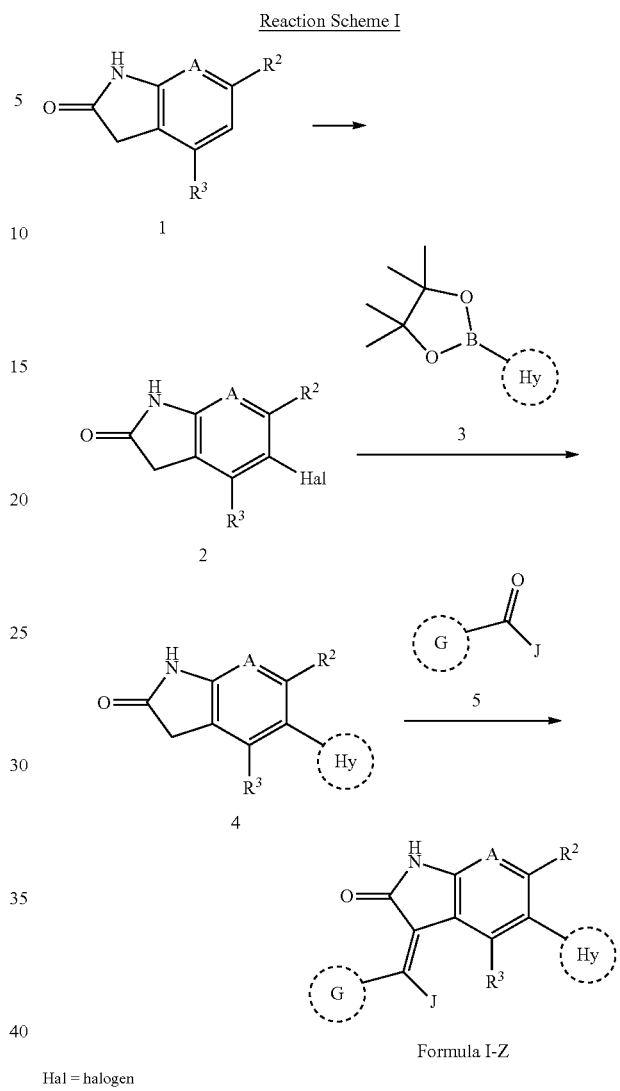

Hal = halogen

Step 1—Preparation of a Compound of Formula 2

The compounds of formula 2 are commercially available or can be made by halogenating compounds 1 by methods known in the art. Compounds 1 are commercially available or can be made by methods known in the art. Compounds 1 may be mixed in a suitable solvent, such as TFA, in the presence of NBS. After stirring at temperatures between 0° C. and 100° C. for between 10 min and 24 h or until reaction is complete, the reaction is allowed to equilibrate to room temperature. The compound of formula 2 can be obtained by filtration, precipitation, or extraction. To extract the compounds of formula 2, an organic solvent such as ethyl acetate may be added, followed by washing with water and brine. The organic phase can be concentrated to obtain the compounds of formula 2. The compounds of formula 2 may be purified by any suitable methods, such as chromatography on silica gel, trituration, precipitation, or crystallization.

Step 2—Preparation of a Compound of Formula 4

The compounds of formula 4 may be prepared by combining compounds of formula 2 and formula 3. The compounds of formula 3 are commercially available or may be prepared by borylating the corresponding iodide, bromide, or chloride by methods known in the art. A compound of formula 2 and formula 3 may be mixed in a suitable solvent, such as DMF, in the presence of an appropriate base, such as potassium carbonate, palladium catalyst, such as PdCl$_2$ (dppf), and co-solvent, such as water. After stirring at a temperature between 23° C. and 110° C. for between 10 min and 24 h or until the reaction is complete, the reaction is allowed to cool to room temperature. To extract the compounds of formula 4, an organic solvent, such as ethyl acetate may be added, followed by washing with water and brine. The organic phase can be concentrated to obtain the compounds of formula 4. The compounds of formula 4 may be purified by a suitable method, such as chromatography on silica gel, trituration, precipitation, or crystallization.

Step 3—Preparation of a Compound of Formula I

The compounds of Formula I or I-Z can be made by combining the compounds of formula 4 and compounds of formula 5. Compound of formula 5 are commercially available or can be prepared by methods known in the art. Compounds of formula 4 and 5 may be combined in a suitable solvent, such as ethanol, in the presence of a suitable amine, such as piperidine or pyrrolidine. After stirring at a temperature between 60° C. and 155° C., with or without the use of a microwave reactor, for between 15 min and 24 hours, the reaction is allowed to cool to room temperature. The crude residue is dissolved in a suitable solvent mixture, such as 1:1 dichloromethane:TFA and stirred at temperatures between 23° C. and 100° C. for 15 minutes to 24 hours. The mixtures are then cooled to room temperature. Compounds of Formula I may be isolated by concentration under reduced pressure, and may be purified by a suitable method, such as chromatography on silica gel, reverse phase chromatography, trituration, precipitation, or crystallization.

Reaction Scheme II

The compounds of Formula IIb-Z may be prepared using methods similar to those shown in Reaction Scheme II.

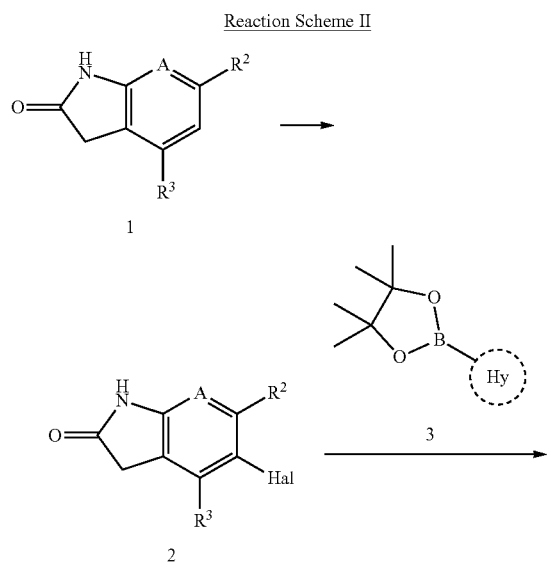

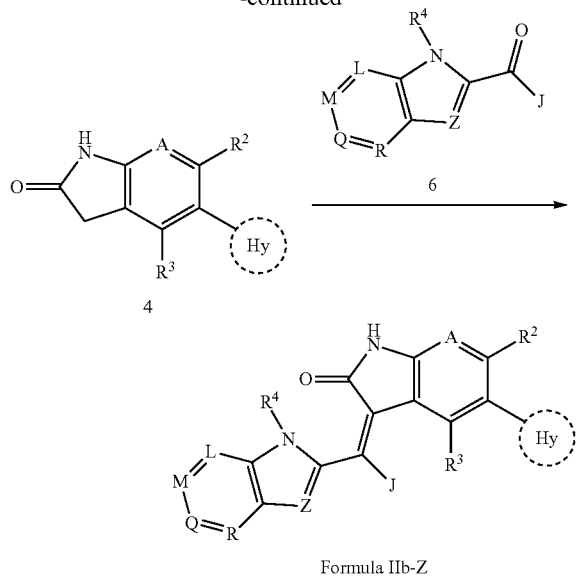

Formula IIb-Z

Step 1—Preparation of a Compound of Formula 2

The compounds of formula 2 are commercially available or can be made as described above for Reaction Scheme I.

Step 2—Preparation of a Compound of Formula 4

The compounds of formula 4 may be prepared by combining compounds of formula 2 and formula 3 as described above for Reaction Scheme I. The compounds of formula 3 are commercially available or may be prepared as described above for Reaction Scheme I.

Step 3—Preparation of a Compound of Formula IIb-Z

The compounds of Formula IIb-Z can be made by combining the compounds of formula 4 and compounds of formula 6. Compound of formula 6 are commercially available or can be prepared by methods known in the art. Compounds of formula 4 and 6 may be combined in a suitable solvent, such as ethanol, in the presence of a suitable amine, such as piperidine or pyrrolidine. After stirring at a temperature between 60° C. and 155° C., with or without the use of a microwave reactor, for between 15 min and 24 hours, the reaction is allowed to cool to room temperature. The crude residue is dissolved in a suitable solvent mixture, such as 1:1 dichloromethane:TFA and stirred at temperatures between 23° C. and 100° C. for 15 minutes to 24 hours. The mixtures are then cooled to room temperature. Compounds of Formula IIb-Z may be isolated by concentration under reduced pressure. The compound of Formula IIb-Z may be purified by any suitable methods, such as chromatography on silica gel, reverse phase chromatography, trituration, precipitation, or crystallization.

Reaction Scheme III

The compounds of Formula IIIa may be prepared using methods similar to those shown in Reaction Scheme III.

Reaction Scheme III

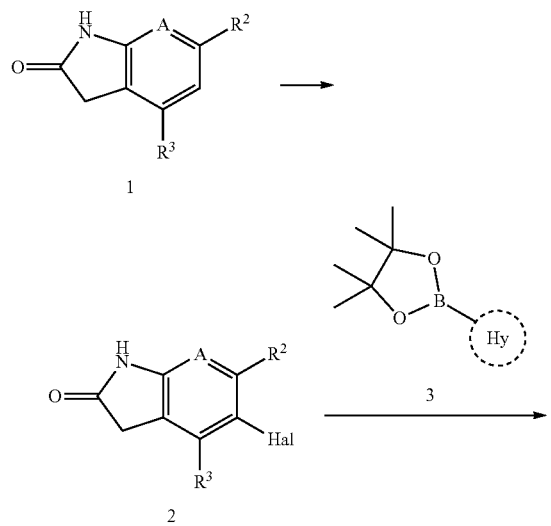

Step 3—Preparation of a Compound of Formula IIa-Z

The compounds of Formula IIIa-Z can be made by combining the compounds of formula 4 and compounds of formula 7. Compound of formula 7 are commercially available or can be prepared by methods known in the art. Compounds of formula 4 and 7 may be combined in a suitable solvent, such as ethanol, in the presence of a suitable amine, such as piperidine or pyrrolidine. After stirring at a temperature between 60° C. and 155° C., with or without the use of a microwave reactor, for between 15 min and 24 hours, the reaction is allowed to cool to room temperature. The crude residue is dissolved in a suitable solvent mixture, such as 1:1 dichloromethane:TFA and stirred at temperatures between 23° C. and 100° C. for 15 minutes to 24 hours. The mixtures are then cooled to room temperature. Compounds of Formula IIIa-Z may be isolated by concentration under reduced pressure. The compounds of Formula IIIa-Z may be purified by any suitable methods known in the art, such as chromatography on silica gel, reverse phase chromatography, trituration, precipitation, or crystallization.

General Procedures

Procedure 1: General Preparation of Intermediate 13 and Related Compounds

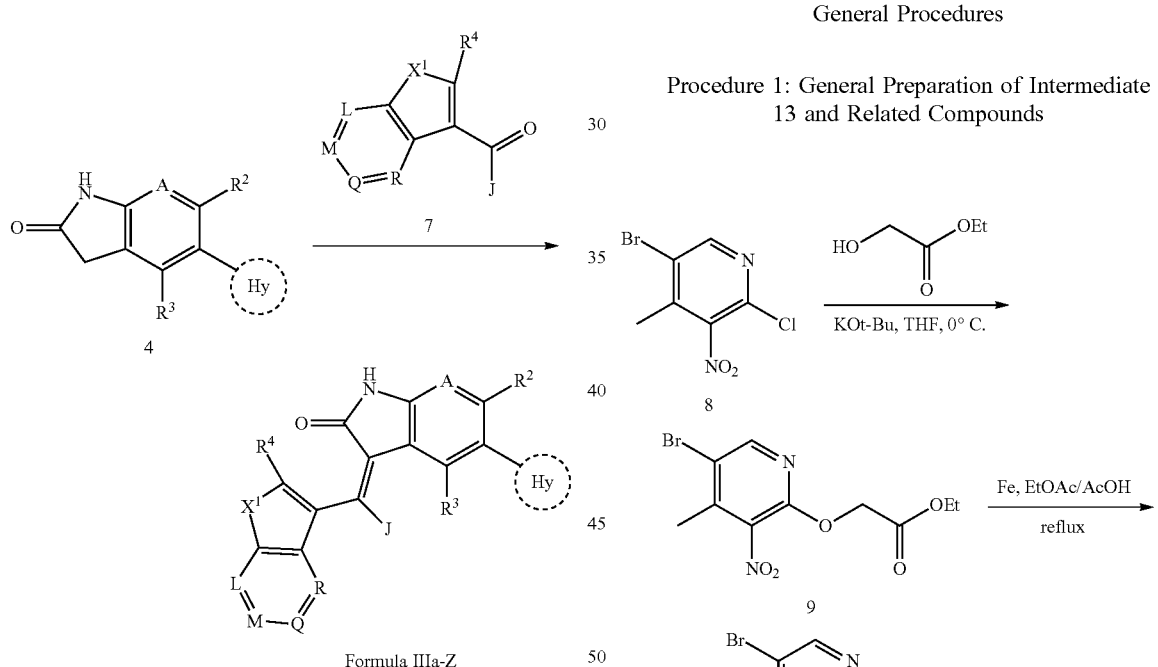

Step 1—Preparation of a Compound of Formula 2

The compounds of formula 2 are commercially available or can be made as described above for Reaction Scheme I.

Step 2—Preparation of a Compound of Formula 4

The compounds of formula 4 may be prepared by combining compounds of formula 2 and formula 3 as described above for Reaction Scheme I. The compounds of formula 3 are commercially available or may be prepared as described above for Reaction Scheme I.

-continued

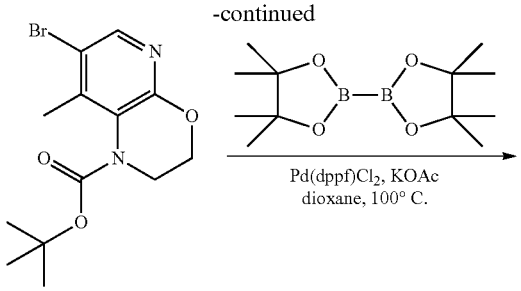

12

B. Preparation of 7-bromo-8-methyl-1H-pyrido[2,3-b][1,4]oxazin-2(3H)-one (10)

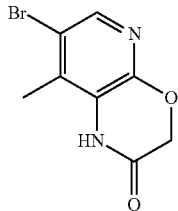

9 (1.3 g, 4.07 mmol, 1.0 equiv.) and iron metal (1.14 g, 20.4 mmol, 5.0 equiv.) were dissolved in EtOAc (10 mL) and AcOH (5 mL). A reflux condenser was fitted and the reaction vessel was heated to 85° C. After 16 hours, the reaction mixture was cooled to room temperature and basified with saturated sodium carbonate solution. The aqueous layer was extracted with EtOAc (4×20 mL). The combined organic layers were dried over sodium sulfate and concentrated in vacuo to afford 10 which was used without further purification. LCMS-ESI$^+$ (m/z): [M+H]$^+$ calcd for $C_8H_8BrN_2O_2$: 243.0; found: 243.1.

C. Preparation of 7-bromo-8-methyl-2,3-dihydro-1H-pyrido[2,3-b][1,4]oxazine (11)

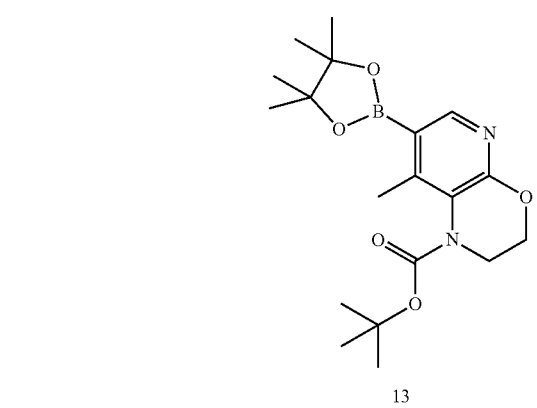

13

A. Preparation of ethyl 2-((5-bromo-4-methyl-3-nitropyridin-2-yl)oxy)acetate (9)

A vial with a stir bar was charged with 10 (331 mg, 1.36 mmol, 1.0 equiv.) then sealed. The vessel was cooled to 0° C. and a THF solution of borane (4.54 mL, 0.9 M, 3 equiv.) was added slowly through the septum. The sealed vessel was then heated to 50° C. After 30 minutes, the vessel was cooled to room temperature then saturated NaHCO$_3$ was added dropwise until gas evolution ceased. The aqueous layer was then extracted with EtOAc (4×5 mL). The combined organic layers were dried over sodium sulfate and concentrated in vacuo to afford 11 which was used without further purification. LCMS-ESI$^+$ (m/z): [M+H]$^+$ calcd for $C_8H_{10}BrN_2O$: 229.0; found: 229.1.

D. Preparation of tert-butyl 7-bromo-8-methyl-2,3-dihydro-1H-pyrido[2,3-b][1,4]oxazine-1-carboxylate (12)

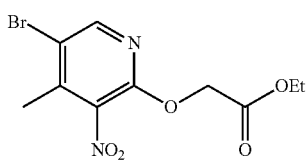 [SMILES: CCOC(=O)COc1ncc(Br)c(C)c1[N+](=O)[O-]]

Ethyl glycolate (13.17 mL, 139.2 mmol, 7.0 equiv.) was dissolved in THF (5 mL) and cooled to 0° C. Potassium tert-butoxide (13.39 g, 119.3 mmol, 6.0 equiv.) was added to the solution in 3 portions. After an additional 5 minutes at 0° C., 8 (5.0 g, 19.88 mmol, 1.0 equiv.) was added. After 2 minutes of stirring at 0° C. the reaction was quenched by the addition of 15 mL of saturated ammonium chloride. The aqueous layer was then extracted with EtOAc (4×30 mL). The combined organic layers were dried over sodium sulfate and concentrated in vacuo. The crude product was purified by column chromatography (EtOAc/Hexanes 0-50%) to afford 9. LCMS-ESI$^+$ (m/z): [M+H]$^+$ calcd for $C_{10}H_{12}BrN_2O_5$: 319.0; found: 319.1.

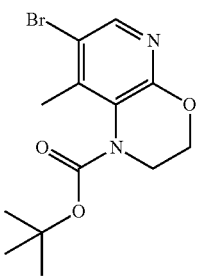 [SMILES: Cc1c(Br)cnc2c1N(C(=O)OC(C)(C)C)CCO2]

11 (630 mg, 2.75 mmol, 1.0 equiv.) was dissolved in THF (10 mL) and cooled to 0° C. To this solution was added a 1.5

M solution of LiHMDS in THF (5.5 mL, 8.25 mmol, 3 equiv.) dropwise over 5 minutes. After 10 minutes at 0° C., Boc$_2$O (1.8 g, 8.25 mmol, 3.0 equiv.) was added in a single portion. The reaction mixture was allowed to warm to room temperature. After 15 minutes, the reaction was quenched by the addition of saturated ammonium chloride (10 mL). The aqueous layer was extracted with EtOAc (4×15 mL). The combined organic layers were dried over sodium sulfate and concentrated in vacuo. The crude oil was purified by column chromatography (EtOAc/Hexanes 0-50%) to afford 12. LCMS-ESI$^+$ (m/z): [M+H]$^+$ calcd for C$_{13}$H$_{18}$BrN$_2$O$_3$: 329.0; found: 329.2.

E. Preparation of tert-butyl 8-methyl-7-(4,4,5,5-tetramethyl-1,3,2-dioxaborolan-2-yl)-2,3-dihydro-1H-pyrido[2,3-b][1,4]oxazine-1-carboxylate (13)

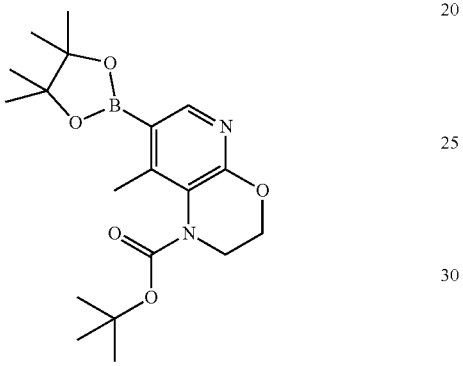

A screw cap vial with a stir bar was charged with 12 (227 mg, 0.84 mmol, 1.0 equiv.), dipinacoldiboron (427 mg, 1.68 mmol, 2.0 equiv.), Pd(dppf)Cl$_2$·CH$_2$Cl$_2$ (137.4 mg, 0.17 mmol, 20 mol %) and KOAc (289 mg, 2.94 mmol, 3.5 equiv.). The vial was sealed and dioxane (4 mL) was added via syringe. The reaction vessel was then placed under vacuum until gas evolution was observed and then refilled with argon. The vessel was evacuated and refilled four times in total. The reaction vessel was then heated to 100° C. for 2 hours. The reaction mixture was then filtered through celites and concentrated in vacuo. The crude material was purified by column chromatography (EtOAc/Hexanes 0-20%) to afford 13. LCMS-ESI$^+$ (m/z): [M+H]$^+$ calcd for C$_{19}$H$_{30}$BN$_2$O$_5$: 377.2; found: 377.3.

Procedure 2: General Preparation of Intermediate 14 and Related Compounds

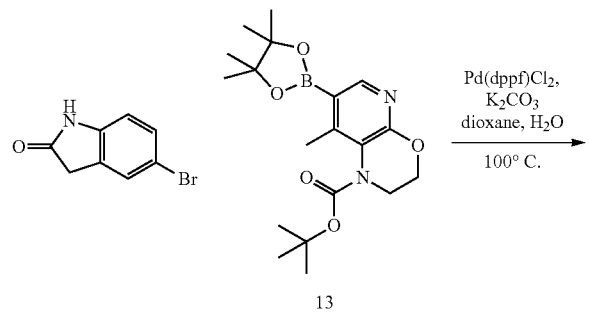

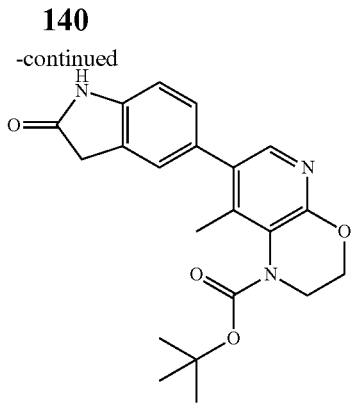

14

A. Preparation of tert-butyl 8-methyl-7-(2-oxoindolin-5-yl)-2,3-dihydro-1H-pyrido[2,3-b][1,4]oxazine-1-carboxylate (14)

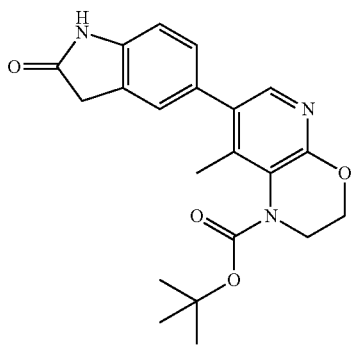 [SMILES: Cc1c(-c2ccc3c(c2)CC(=O)N3)cnc2c1N(C(=O)OC(C)(C)C)CCO2]

A mixture of 13 (400 mg, 1.2 mmol, 1.35 equiv.) and 5-bromoindolin-2-one (166 mg, 0.79 mmol) was dissolved with dioxane (6 mL) and water (0.6 mL) in a 40 mL vial. To the vessel were added potassium carbonate (218 mg, 1.58 mmol, 2.0 equiv.) and Pd(dppf)Cl$_2$ (65.6 mg, 0.08 mmol, 10 mol %), and nitrogen was bubbled through the mixture for 2 minutes. After stirring for 2 hours at 100° C., or until complete by LCMS analysis, the reaction mixture was cooled to room temperature, diluted with ethyl acetate, and filtered through celite. The filtrate was washed once with water and once with brine. The organic layer was dried over magnesium sulfate, filtered, and concentrated under vacuum. The crude residue was purified by silica gel chromatography using a 0-10% MeOH in DCM eluent to afford 14. LCMS-ESI$^+$ (m/z): [M+H]$^+$ calcd for C$_{21}$H$_{24}$N$_3$O$_4$: 382.2; found: 382.3.

Procedure 3: General Preparation of Intermediate 15 and Related Compounds

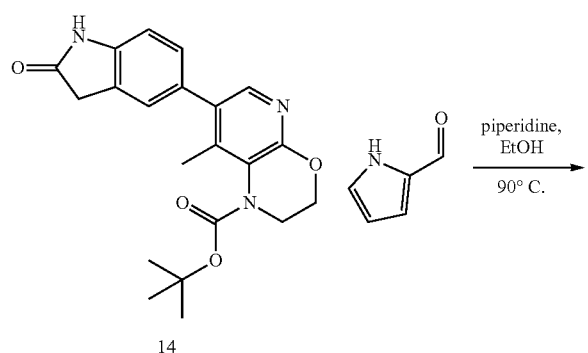

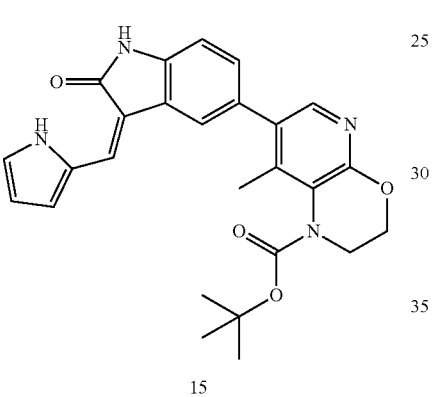

A. Preparation of tert-butyl (Z)-7-(3-((1H-pyrrol-2-yl)methylene)-2-oxoindolin-5-yl)-8-methyl-2,3-dihydro-1H-pyrido[2,3-b][1,4]oxazine-1-carboxylate (15)

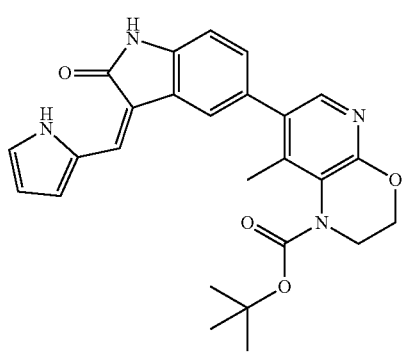 [SMILES: Cc1c(-c2ccc3c(c2)/C(=C/c2ccc[nH]2)C(=O)N3)cnc2c1N(C(=O)OC(C)(C)C)CCO2]

In an oven-dried 2-dram vial were added 14 (35 mg, 0.09 mmol), 1H-pyrrole-2-carbaldehyde, ethanol (1 mL), and piperidine (1 drop). The vessel was heat to 90° C. for 30 minutes. Upon cooling to room temperature, the contents were concentrated under vacuum and using without further purification.

Procedure 4: General Preparation of Intermediate 17 and Related Compounds

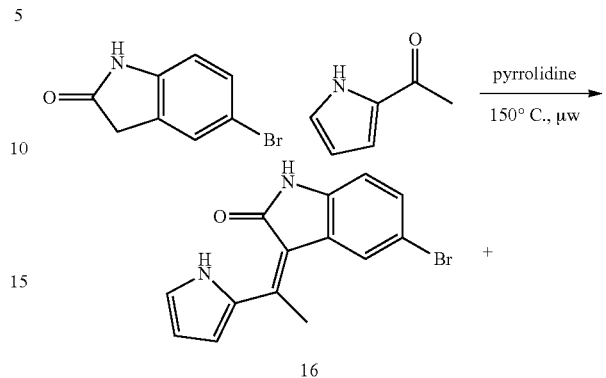

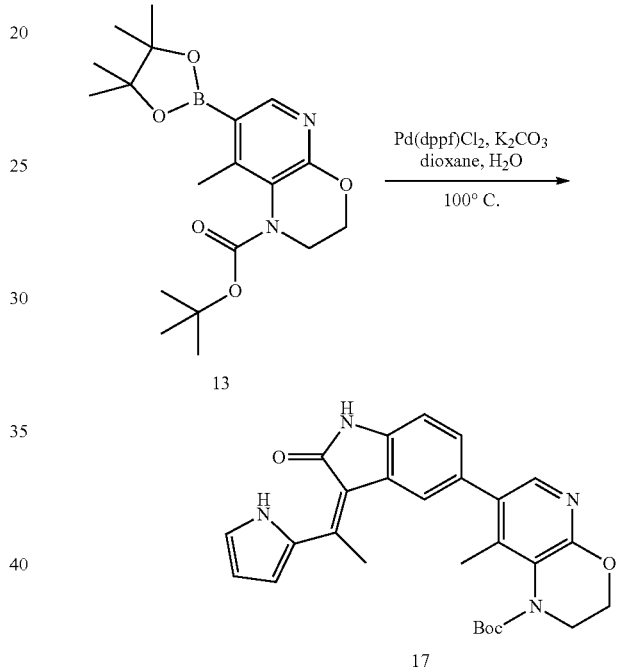

A. Preparation of (Z)-3-(1-(1H-pyrrol-2-yl)ethylidene)-5-bromoindolin-2-one (16)

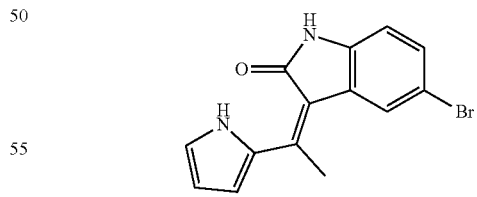

To a microwave vial were added 5-bromoindolin-2-one (0.24 mmol, 50 mg) and 1-(1H-pyrrol-2-yl)ethan-1-one (0.31 mmol, 34 mg) with pyrrolidine (1 mL) and heated in a microwave reactor for 1 hour at 150° C. The reaction mixture was concentrated under reduced pressure and purified by reversed phase HPLC to give (Z)-3-(1-(1H-pyrrol-2-yl)ethylidene)-5-bromoindolin-2-one (16). LCMS-ESI$^+$ (m/z): [M+H]$^+$ calcd for $C_{14}H_{11}BrN_2O$: 302.0; found: 302.2.

B. Preparation of tert-butyl (Z)-7-(3-(1-(1H-pyrrol-2-yl)ethylidene)-2-oxoindolin-5-yl)-8-methyl-2,3-dihydro-1H-pyrido[2,3-b][1,4]oxazine-1-carboxylate (17)

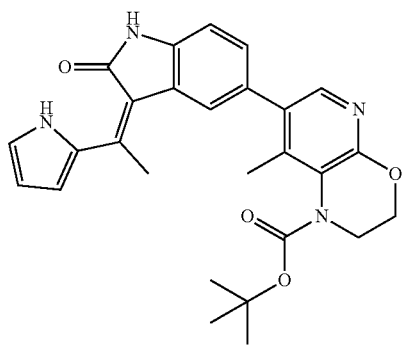 [SMILES: C/C(=C1/C(=O)Nc2ccc(-c3cnc4c(c3C)N(C(=O)OC(C)(C)C)CCO4)cc21)c1ccc[nH]1]

(Z)-3-(1-(1H-pyrrol-2-yl)ethylidene)-5-bromoindolin-2-one (16) (18 mg, 0.06 mmol), tert-butyl 8-methyl-7-(4,4,5,5-tetramethyl-1,3,2-dioxaborolan-2-yl)-2,3-dihydro-1H-pyrido[2,3-b][1,4]oxazine-1-carboxylate (13) (28 mg, 0.08 mmol), potassium carbonate (41 mg, 0.17 mmol), and Pd(dppf)Cl$_2$ (4.8 mg, 0.006 mmol) were combined with dioxane (3 mL) and H$_2$O (0.3 mL). The mixture was purged with nitrogen gas and heated at 100° C. on heating block for 30 min. The reaction mixture was diluted with ethyl acetate, filtered through a pad of celite, concentrated, and purified by reversed phase HPLC to give (Z)-3-(1-(1H-pyrrol-2-yl)ethylidene)-5-bromoindolin-2-one (17). LCMS-ESI$^+$ (m/z): [M+H]$^+$ calcd for C$_{27}$H$_{28}$N$_4$O$_4$: 472.2; found: 472.2.

Procedure 5: General procedure for Boc deprotection ((Z)-3-((1H-pyrrol-2-yl)methylene)-5-(8-methyl-2,3-dihydro-1H-pyrido[2,3-b][1,4]oxazin-7-yl)indolin-2-one) (Example 29)

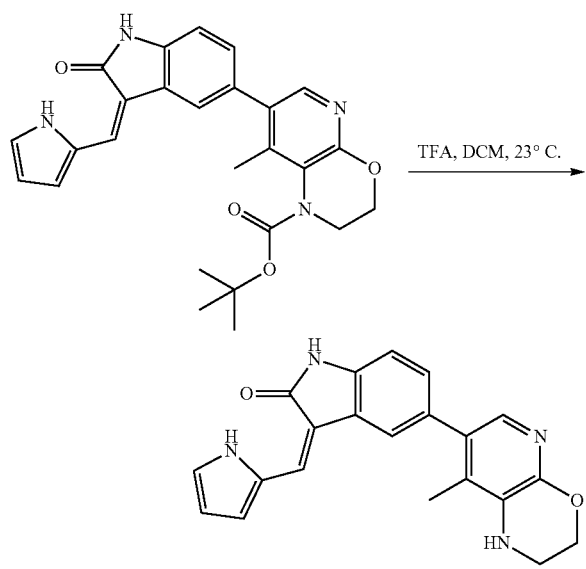

To a 2-dram vial was added unpurified 15 (20 mg), TFA (1 mL) and DCM (1 mL). The mixture was stirred at room temperature for 30 minutes. The solution was concentrated under vacuum and purified by reverse phase HPLC. LCMS-ESI$^+$ (m/z): [M+H]$^+$ calcd for C$_{21}$H$_{19}$N$_4$O$_2$: 359.1; found: 359.2.

EXAMPLES

Example 1: (Z)-N-(2-(diethylamino)ethyl)-5-((6-fluoro-5-(8-methyl-2,3-dihydro-1H-pyrido[2,3-b][1,4]oxazin-7-yl)-2-oxoindolin-3-ylidene)methyl)-2,4-dimethyl-1H-pyrrole-3-carboxamide (C1)

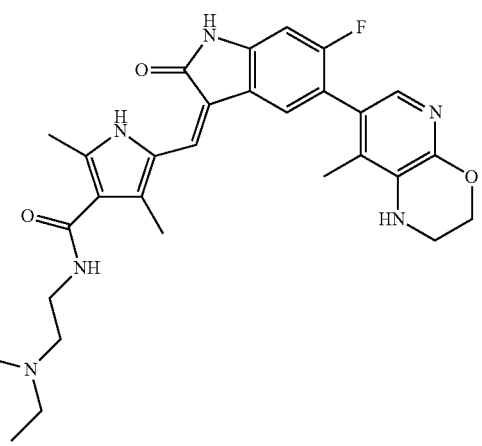

This compound was prepared as outlined above in procedures 1, 2, 3, and 5 using commercially available intermediates 5-bromo-6-fluoroindolin-2-one and N-(2-(diethylamino)ethyl)-5-formyl-2,4-dimethyl-1H-pyrrole-3-carboxamide.

$^1$H NMR (400 MHz, Methanol-d4) δ 7.60 (s, 1H), 7.57 (d, J=7.0 Hz, 1H), 7.43 (s, 1H), 6.81 (d, J=9.8 Hz, 1H), 4.51 (t, J=4.4 Hz, 2H), 3.72 (t, J=6.1 Hz, 2H), 3.56 (s, 2H), 3.35 (dd, J=15.3, 7.0 Hz, 8H), 2.52 (s, 3H), 2.44 (s, 3H), 2.08 (d, J=1.6 Hz, 3H), 1.37 (t, J=7.3 Hz, 6H). LCMS-ESI$^+$ (m/z): [M+H]$^+$ calcd for C$_{30}$H$_{35}$FN$_6$O$_3$: 547.3; found: 547.6.

Example 2: (Z)-3-((2-methyl-1H-imidazol-5-yl)methylene)-5-(5-methyl-3,4-dihydro-2H-benzo[b][1,4]oxazin-6-yl)indolin-2-one (C2)

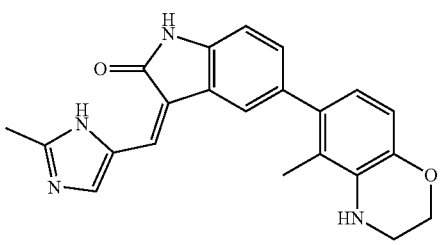

This compound was prepared as outlined above in procedures 2, 3, and 5 using commercially available intermediate 2-methyl-TH-imidazole-5-carbaldehyde and (5-methyl-3,4-dihydro-2H-benzo[b][1,4]oxazin-6-yl)boronic acid.

$^1$H NMR (400 MHz, Methanol-d4) δ 7.93 (s, 1H), 7.69 (s, 1H), 7.54 (s, 1H), 7.18 (d, J=7.8 Hz, 1H), 6.97 (d, J=8.0 Hz, 1H), 6.63 (d, J=8.2 Hz, 1H), 6.52 (d, J=8.3 Hz, 1H), 4.22-4.15 (m, 2H), 3.49-3.42 (m, 3H), 2.76 (s, 3H), 2.02 (s, 3H). LCMS-ESI⁺ (m/z): [M+H]⁺ calcd for C$_{22}$H$_{20}$N$_4$O$_2$: 373.2; found: 373.4.

Example 3: (Z)-6-methyl-3-((2-methyl-1H-imidazol-5-yl)methylene)-5-(8-methyl-2,3-dihydro-1H-pyrido[2,3-b][1,4]oxazin-7-yl)indolin-2-one (C3)

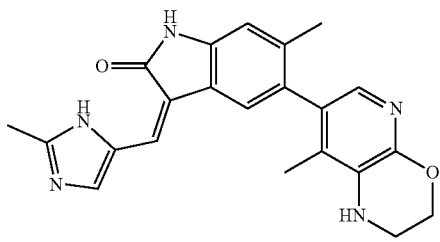 [SMILES: Cc1ncc(/C=C2\C(=O)Nc3cc(C)c(-c4cnc5c(c4C)NCCO5)cc32)[nH]1]

This compound was prepared as outlined above in procedures 1, 2, 3, and 5 using commercially available intermediates 5-bromo-6-methylindolin-2-one and 2-methyl-1H-imidazole-5-carbaldehyde.

¹H NMR (400 MHz, Methanol-d4) δ 7.94 (s, 1H), 7.63 (s, 1H), 7.45 (s, 1H), 7.37 (s, 1H), 6.96 (s, 1H), 4.60 (t, J=4.5 Hz, 2H), 3.61 (td, J=4.3, 2.4 Hz, 2H), 2.76 (s, 3H), 2.12 (s, 3H), 2.01 (s, 3H). LCMS-ESI⁺ (m/z): [M+H]⁺ calcd for C$_{22}$H$_{22}$N$_5$O$_2$: 388.2; found: 388.2.

Example 4: (Z)-7-fluoro-4-methyl-3-((2-methyl-1H-imidazol-5-yl)methylene)-5-(8-methyl-2,3-dihydro-1H-pyrido[2,3-b][1,4]oxazin-7-yl)indolin-2-one (C4)

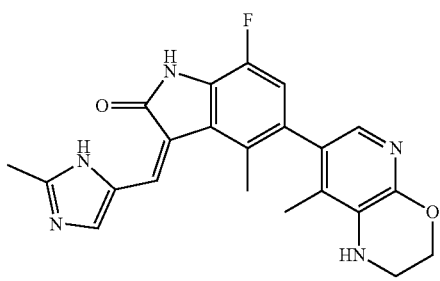 [SMILES: Cc1ncc(/C=C2\C(=O)Nc3c(F)cc(-c4cnc5c(c4C)NCCO5)c(C)c32)[nH]1]

A. Preparation of 7-fluoro-4-methylindolin-2-one (18)

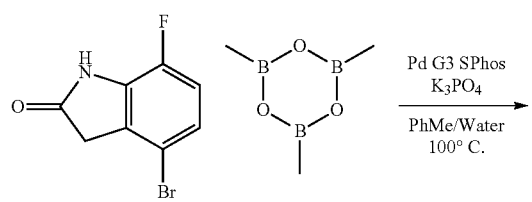

-continued

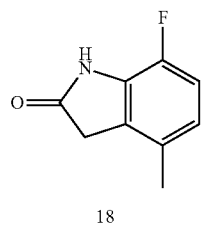

18

To a 40 mL vial was added commercially available 4-bromo-7-fluoroindolin-2-one (400.0 mg, 1.74 mmol, 1.0 equiv.), 2,4,6-trimethyl-1,3,5,2,4,6-trioxatriborinane (327 mg, 0.37 mL, 2.6 mmol, 1.5 equiv.), Pd G3 SPhos (27.1 mg, 0.03 mmol, 0.02 equiv.), and potassium phosphate tribasic (737.3 mg, 3.48 mmol, 2.0 equiv.). The vial was then charged with a stir bar, toluene (3.6 mL), and water (0.4 mL) sequentially. The vial was then sealed with a teflon cap. The sealed vessel was then subjected to four cycles of evacuation until gas evolution from solution was observed and refilling with argon. The vessel was then heated to 100° C. for 1 hour. After cooling to room temperature, the reaction mixture was diluted with ethyl acetate (2 mL) and water (1 mL). The organic layer was separated, and the aqueous layer was extracted twice more with ethyl acetate. The combined organic layers were dried over sodium sulfate and concentrated in vacuo. Purification by silica gel chromatography (EtOAc/Hexanes) afforded 7-fluoro-4-methylindolin-2-one (18). LCMS-ESI⁺ (m/z): [M+H]⁺ calcd for C$_9$H$_8$FNO: 166.1; found: 166.1.

B. Preparation of 5-bromo-7-fluoro-4-methylindolin-2-one

To 40 mL vial was added 7-fluoro-4-methylindolin-2-one (18) (100 mg, 0.61 mmol, 1 equiv.), a stir bar, and MeCN (3 mL) sequentially. The vial was cooled to 0° C. NBS (129.3 mg, 0.73 mmol, 1.2 equiv.) was then added in a single portion and the reaction was allowed to warm to room temperature overnight. Water was then added to the reaction and a beige precipitate formed. The precipitate was isolated by vacuum filtration then washed sequentially with water, hexanes, and ether. The solids were further dried under vacuum to afford 5-bromo-7-fluoro-4-methylindolin-2-one (19). LCMS-ESI⁺ (m/z): [M+H]⁺ calcd for C$_9$H$_7$BrFNO: 244.0; found: 244.2.

C. Preparation of (Z)-7-fluoro-4-methyl-3-((2-methyl-1H-imidazol-5-yl)methylene)-5-(8-methyl-2,3-dihydro-TH-pyrido[2,3-b][1,4]oxazin-7-yl)indolin-2-one (C4)

This compound was prepared as outlined above in procedures 1, 2, 3, and 5 using 7-fluoro-4-methylindolin-2-one (19) and commercially available intermediate 2-methyl-TH-imidazole-5-carbaldehyde.

$^1$H NMR (400 MHz, Methanol-d4) δ 8.16 (s, 1H), 7.85 (s, 1H), 7.39 (s, 1H), 7.03 (d, J=9.9 Hz, 1H), 4.61 (t, J=4.5 Hz, 2H), 3.62 (td, J=4.3, 2.0 Hz, 2H), 2.78 (s, 3H), 2.34 (s, 3H), 2.02 (s, 3H). LCMS-ESI$^+$ (m/z): [M+H]$^+$ calcd for $C_{22}H_{21}FN_5O_2$: 406.2; found: 406.1.

Example 5: (Z)-5-(2,3-dihydro-TH-pyrido[2,3-b][1,4]oxazin-7-yl)-7-fluoro-4-methyl-3-((2-methyl-TH-imidazol-5-yl)methylene)indolin-2-one (C5)

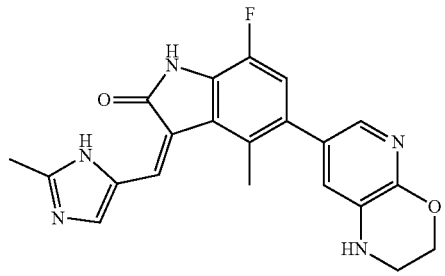 [SMILES: Cc1ncc(/C=C2\C(=O)Nc3c(F)cc(-c4cnc5c(c4)NCCO5)c(C)c32)[nH]1]

This compound was prepared as outlined above for (Z)-7-fluoro-4-methyl-3-((2-methyl-1H-imidazol-5-yl)methylene)-5-(8-methyl-2,3-dihydro-H-pyrido[2,3-b][1,4]oxazin-7-yl)indolin-2-one using commercially available intermediate (2,3-dihydro-1H-pyrido[2,3-b][1,4]oxazin-7-yl)boronic acid.

$^1$H NMR (400 MHz, Methanol-d4) δ 8.16 (s, 1H), 7.85 (s, 1H), 7.38 (d, J=2.0 Hz, 1H), 7.12 (d, J=2.0 Hz, 1H), 7.08 (d, J=10.2 Hz, 1H), 4.59-4.49 (m, 2H), 3.53-3.48 (m, 2H), 2.77 (s, 3H), 2.49 (s, 3H). LCMS-ESI$^+$ (m/z): [M+H]$^+$ calcd for $C_{21}H_{19}FN_5O_2$: 392.1; found: 392.1.

Example 6: (Z)-3-((2-ethyl-4-methyl-1H-imidazol-5-yl)methylene)-5-(8-methyl-2,3-dihydro-1H-pyrido[2,3-b][1,4]oxazin-7-yl)indolin-2-one (C6)

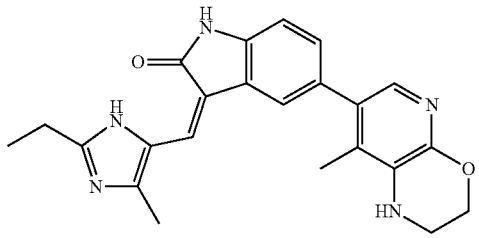 [SMILES: CCc1nc(C)c(/C=C2\C(=O)Nc3ccc(-c4cnc5c(c4C)NCCO5)cc32)[nH]1]

This compound was prepared as outlined above in procedures 1, 2, 3, and 5 using commercially available intermediate 2-ethyl-4-methyl-1H-imidazole-5-carbaldehyde.

$^1$H NMR (400 MHz, Methanol-d4) δ 7.78 (d, J=5.6 Hz, 2H), 7.40 (s, 1H), 7.27-7.22 (m, 1H), 7.06 (d, J=8.0 Hz, 1H), 4.50 (t, J=4.4 Hz, 2H), 3.59-3.52 (m, 2H), 3.08 (q, J=7.6 Hz, 2H), 2.59 (s, 3H), 2.15 (s, 3H), 1.48 (t, J=7.6 Hz, 3H). LCMS-ESI$^+$ (m/z): [M+H]$^+$ calcd for $C_{23}H_{24}N_5O_2$: 402.2; found: 402.5.

Example 7: (Z)-6-chloro-3-((2-methyl-1H-imidazol-5-yl)methylene)-5-(8-methyl-2,3-dihydro-1H-pyrido[2,3-b][1,4]oxazin-7-yl)indolin-2-one (C7)

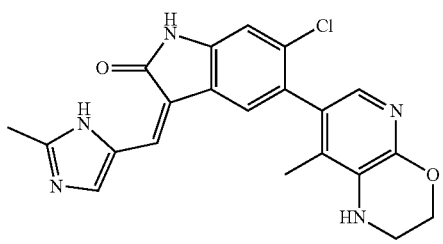 [SMILES: Cc1ncc(/C=C2\C(=O)Nc3cc(Cl)c(-c4cnc5c(c4C)NCCO5)cc32)[nH]1]

This compound was prepared as outlined above in procedures 1, 2, 3, and 5 using commercially available intermediates 5-bromo-6-chloroindolin-2-one and 2-methyl-1H-imidazole-5-carbaldehyde.

$^1$H NMR (400 MHz, Methanol-d4) δ 7.99 (s, 1H), 7.72 (s, 1H), 7.62 (s, 1H), 7.36 (s, 1H), 7.15 (s, 1H), 4.52 (t, J=4.5 Hz, 2H), 3.56 (q, J=4.6 Hz, 2H), 2.76 (s, 3H), 2.01 (s, 3H). LCMS-ESI$^+$ (m/z): [M+H]$^+$ calcd for $C_{21}H_{19}ClN_5O_2$: 408.1; found: 408.9.

Example 8: (Z)-6-fluoro-3-((2-methyl-1H-imidazol-5-yl)methylene)-5-(8-methyl-2,3-dihydro-1H-pyrido[2,3-b][1,4]oxazin-7-yl)indolin-2-one (C8)

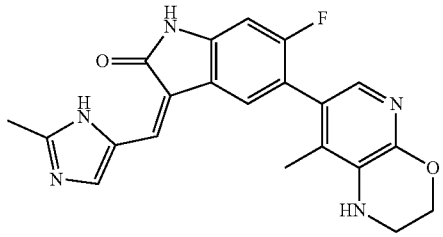 [SMILES: Cc1ncc(/C=C2\C(=O)Nc3cc(F)c(-c4cnc5c(c4C)NCCO5)cc32)[nH]1]

This compound was prepared as outlined above in procedures 1, 2, 3, and 5 using commercially available intermediates 5-bromo-6-fluoroindolin-2-one and 2-methyl-1H-imidazole-5-carbaldehyde.

$^1$H NMR (400 MHz, Methanol-d4) δ 7.96 (s, 1H), 7.69 (s, 1H), 7.61 (d, J=7.0 Hz, 1H), 7.40 (s, 1H), 6.86 (d, J=9.5 Hz, 1H), 4.49 (t, J=4.5 Hz, 2H), 3.54 (s, 2H), 2.76 (s, 3H), 2.05 (d, J=1.8 Hz, 3H). LCMS-ESI$^+$ (m/z): [M+H]$^+$ calcd for $C_{21}H_{19}FN_5O_2$: 392.1; found: 392.4.

Example 9: (Z)-N-(2-(diethylamino)ethyl)-5-((7-fluoro-5-(8-methyl-2,3-dihydro-1H-pyrido[2,3-b][1,4]oxazin-7-yl)-2-oxoindolin-3-ylidene)methyl)-2,4-dimethyl-1H-pyrrole-3-carboxamide (C9)

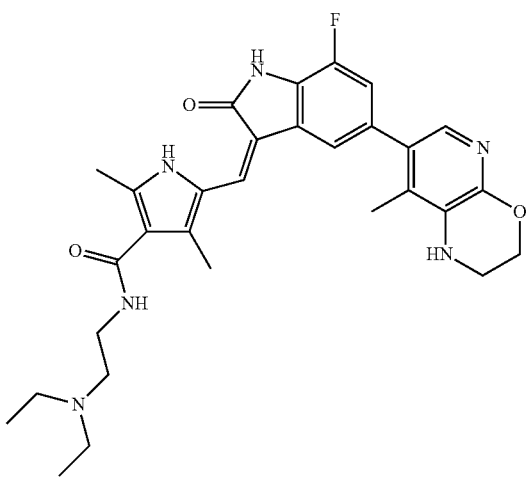 [SMILES: CCN(CC)CCNC(=O)c1c(C)[nH]c(/C=C2\C(=O)Nc3c(F)cc(-c4cnc5c(c4C)NCCO5)cc32)c1C]

This compound was prepared as outlined above in procedures 1, 2, 3, and 5 using commercially available intermediates 5-bromo-7-fluoroindolin-2-one and N-(2-(diethylamino)ethyl)-5-formyl-2,4-dimethyl-1H-pyrrole-3-carboxamide.

$^1$H NMR (400 MHz, Methanol-d4) δ 7.69 (s, 1H), 7.46-7.41 (m, 2H), 6.93 (d, J=10.6 Hz, 1H), 4.52 (t, J=4.4 Hz, 2H), 3.72 (t, J=6.1 Hz, 2H), 3.56 (t, J=4.5 Hz, 2H), 3.36 (dd, J=16.0, 7.0 Hz, 6H), 2.53 (s, 3H), 2.46 (s, 3H), 2.17 (s, 3H), 1.38 (t, J=7.3 Hz, 6H). LCMS-ESI$^+$ (m/z): [M+H]$^+$ calcd for $C_{30}H_{36}FN_6O_3$: 547.3; found: 547.6.

Example 10: (Z)-7-fluoro-3-((2-methyl-1H-imidazol-5-yl)methylene)-5-(8-methyl-2,3-dihydro-1H-pyrido[2,3-b][1,4]oxazin-7-yl)indolin-2-one (C10)

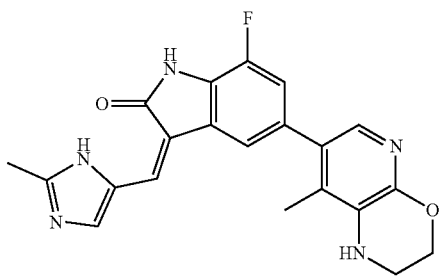 [SMILES: Cc1ncc(/C=C2\C(=O)Nc3c(F)cc(-c4cnc5c(c4C)NCCO5)cc32)[nH]1]

This compound was prepared as outlined above in procedures 1, 2, 3, and 5 using commercially available intermediates 5-bromo-7-fluoroindolin-2-one and 2-methyl-1H-imidazole-5-carbaldehyde.

$^1$H NMR (400 MHz, Methanol-d4) δ 8.01 (s, 1H), 7.83 (s, 1H), 7.49 (d, J=1.3 Hz, 1H), 7.43 (s, 1H), 7.14 (dd, J=10.5, 1.4 Hz, 1H), 4.56-4.47 (m, 2H), 3.56 (dd, J=5.1, 3.9 Hz, 2H), 2.77 (s, 3H), 2.16 (s, 3H). LCMS-ESI$^+$ (m/z): [M+H]$^+$ calcd for $C_{21}H_{19}FN_5O_2$: 392.1; found: 392.4.

Example 11: (Z)-3-(1-(1H-imidazol-5-yl)ethylidene)-5-(8-methyl-2,3-dihydro-1H-pyrido[2,3-b][1,4]oxazin-7-yl)indolin-2-one (C11)

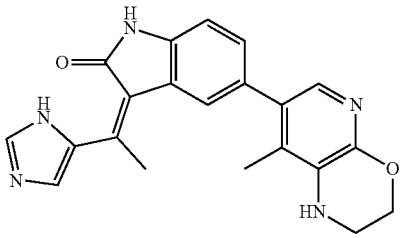 [SMILES: C/C(=C1/C(=O)Nc2ccc(-c3cnc4c(c3C)NCCO4)cc21)c1cnc[nH]1]

This compound was prepared as outline in procedures 4 and 5 using commercially available intermediate 1-(1H-imidazol-5-yl)ethan-1-one.

$^1$H NMR (400 MHz, Methanol-d4) δ 8.93 (d, J=1.2 Hz, 1H), 8.20 (d, J=1.2 Hz, 1H), 7.71 (s, 1H), 7.44 (s, 1H), 7.32-7.27 (m, 1H), 7.10 (d, J=8.0 Hz, 1H), 4.51 (d, J=4.5 Hz, 2H), 3.57 (t, J=4.5 Hz, 2H), 2.80 (s, 3H), 2.16 (s, 3H). LCMS-ESI$^+$ (m/z): [M+H]$^+$ calcd for $C_{21}H_{20}N_5O_2$: 374.2; found: 374.1.

Example 12: (Z)-5-((7-fluoro-4-methyl-5-(8-methyl-2,3-dihydro-1H-pyrido[2,3-b][1,4]oxazin-7-yl)-2-oxoindolin-3-ylidene)methyl)-1H-pyrrole-3-carbonitrile (C12)

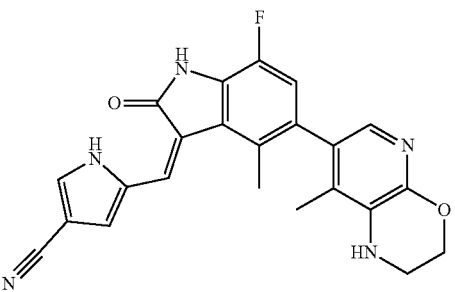 [SMILES: Cc1c(-c2cc(F)c3c(c2C)/C(=C/c2cc(C#N)c[nH]2)C(=O)N3)cnc2c1NCCO2]

This compound was prepared as outlined above for (Z)-7-fluoro-4-methyl-3-((2-methyl-1H-imidazol-5-yl)methylene)-5-(8-methyl-2,3-dihydro-1H-pyrido[2,3-b][1,4]oxazin-7-yl)indolin-2-one using commercially available intermediate 5-formyl-1H-pyrrole-3-carbonitrile.

$^1$H NMR (400 MHz, Methanol-d4) δ 14.12 (s, 1H), 7.85-7.71 (m, 2H), 7.40 (s, 1H), 7.19 (t, J=1.8 Hz, 1H), 6.92 (d, J=10.0 Hz, 1H), 4.62 (t, J=4.6 Hz, 2H), 3.70-3.55 (m, 2H), 2.32 (s, 3H), 2.03 (s, 3H). LCMS-ESI$^+$ (m/z): [M+H]$^+$ calcd for $C_{23}H_{19}FN_5O_2$: 416.1; found: 416.1.

Example 13: (Z)-7-fluoro-4-methyl-3-((4-methyl-1H-pyrrol-2-yl)methylene)-5-(8-methyl-2,3-dihydro-1H-pyrido[2,3-b][1,4]oxazin-7-yl)indolin-2-one (C13)

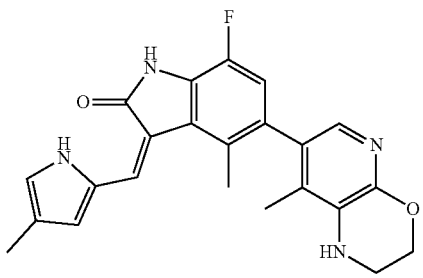 [SMILES: Cc1c[nH]c(/C=C2\C(=O)Nc3c(F)cc(-c4cnc5c(c4C)NCCO5)c(C)c32)c1]

This compound was prepared as outlined above for (Z)-7-fluoro-4-methyl-3-((2-methyl-1H-imidazol-5-yl)methylene)-5-(8-methyl-2,3-dihydro-1H-pyrido[2,3-b][1,4]oxazin-7-yl)indolin-2-one using commercially available 4-methyl-1H-pyrrole-2-carbaldehyde.

$^1$H NMR (400 MHz, Methanol-d4) δ 13.34 (s, 1H), 7.78 (s, 1H), 7.38 (s, 1H), 7.09 (s, 1H), 6.81 (d, J=10.1 Hz, 1H), 6.69 (s, 1H), 4.62 (t, J=4.5 Hz, 2H), 3.63 (td, J=4.3, 2.5 Hz, 2H), 2.31 (s, 3H), 2.15 (s, 3H), 2.03 (s, 3H). LCMS-ESI$^+$ (m/z): [M+H]$^+$ calcd for $C_{23}H_{22}FN_4O_2$: 405.2; found: 405.1.

Example 14: (Z)-3-((1H-pyrrol-2-yl)methylene)-7-fluoro-4-methyl-5-(8-methyl-2,3-dihydro-1H-pyrido[2,3-b][1,4]oxazin-7-yl)indolin-2-one (C14)

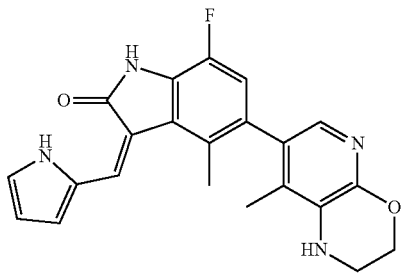 [SMILES: Cc1c(-c2cc(F)c3c(c2C)/C(=C/c2ccc[nH]2)C(=O)N3)cnc2c1NCCO2]

This compound was prepared as outlined above for (Z)-7-fluoro-4-methyl-3-((2-methyl-1H-imidazol-5-yl)methylene)-5-(8-methyl-2,3-dihydro-1H-pyrido[2,3-b][1,4]oxazin-7-yl)indolin-2-one.

$^1$H NMR (400 MHz, Methanol-d4) δ 13.55 (s, 1H), 7.86 (s, 1H), 7.38 (s, 1H), 7.28 (td, J=2.7, 1.3 Hz, 1H), 6.88 (dt, J=3.6, 1.5 Hz, 1H), 6.82 (d, J=10.1 Hz, 1H), 6.39 (dt, J=3.7, 2.3 Hz, 1H), 4.67-4.52 (m, 2H), 3.62 (td, J=4.3, 2.4 Hz, 2H), 2.32 (s, 3H), 2.02 (s, 3H). LCMS-ESI$^+$ (m/z): [M+H]$^+$ calcd for $C_{22}H_{20}FN_4O_2$: 391.2; found: 391.1.

Example 15: (Z)-3-((2-methyl-1H-imidazol-5-yl)methylene)-5-(8-methyl-2,3-dihydro-1H-pyrido[2,3-b][1,4]oxazin-7-yl)indolin-2-one (C15)

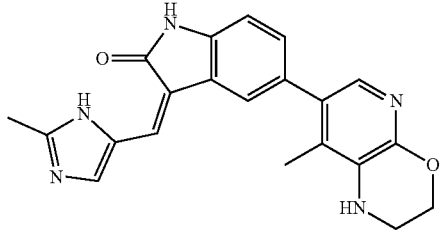

This compound was prepared as outlined above in procedures 1, 2, 3, and 5 using commercially available intermediate 2-methyl-1H-imidazole-5-carbaldehyde.

$^1$H NMR (400 MHz, Methanol-d4) δ 7.94 (s, 1H), 7.75 (s, 1H), 7.62 (d, J=1.6 Hz, 1H), 7.38 (s, 1H), 7.25 (dd, J=8.0, 1.6 Hz, 1H), 7.05 (d, J=8.1 Hz, 1H), 4.52-4.42 (m, 2H), 3.57-3.48 (m, 2H), 2.75 (s, 3H), 2.12 (s, 3H). LCMS-ESI$^+$ (m/z): [M+H]$^+$ calcd for $C_{21}H_{20}N_5O_2$: 374.2; found: 374.4.

Example 16: (Z)-N-(2-(diethylamino)ethyl)-2,4-dimethyl-5-((5-(8-methyl-2,3-dihydro-1H-pyrido[2,3-b][1,4]oxazin-7-yl)-2-oxoindolin-3-ylidene)methyl)-1H-pyrrole-3-carboxamide (C16)

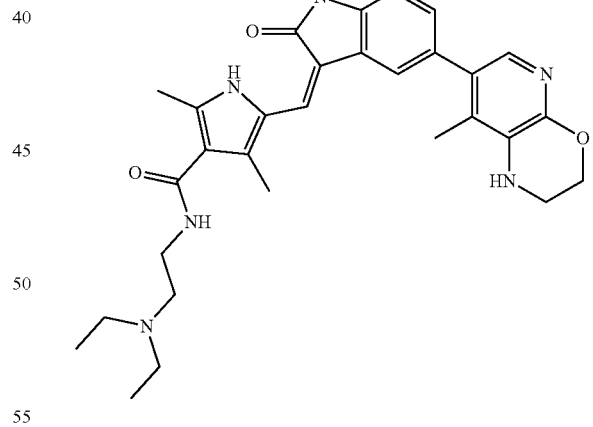

This compound was prepared as outlined above in procedures 1, 2, 3, and 5 using commercially available intermediates and N-(2-(diethylamino)ethyl)-5-formyl-2,4-dimethyl-1H-pyrrole-3-carboxamide.

$^1$H NMR (400 MHz, Methanol-d4) δ 7.64 (s, 1H), 7.59 (d, J=1.6 Hz, 1H), 7.42 (s, 1H), 7.11-7.07 (m, 1H), 7.01 (d, J=8.0 Hz, 1H), 4.52 (t, J=4.5 Hz, 2H), 3.72 (t, J=6.1 Hz, 2H), 3.57 (t, J=4.4 Hz, 2H), 3.36 (dd, J=15.6, 6.9 Hz, 6H), 2.53 (s, 3H), 2.46 (s, 3H), 2.16 (s, 3H), 1.38 (t, J=7.3 Hz, 6H). LCMS-ESI$^+$ (m/z): [M+H]$^+$ calcd for $C_{30}H_{36}FN_6O_3$: 529.3; found: 529.7.

Example 17: (Z)-3-((5-methyl-1H-pyrrol-2-yl)methylene)-5-(8-methyl-2,3-dihydro-1H-pyrido[2,3-b][1,4]oxazin-7-yl)indolin-2-one (C17)

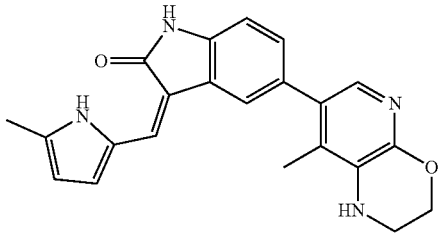 [SMILES: Cc1ccc(/C=C2\C(=O)Nc3ccc(-c4cnc5c(c4C)NCCO5)cc32)[nH]1]

This compound was prepared as outlined above in procedures 1, 2, 3, and 5 using commercially available intermediate 5-methyl-1H-pyrrole-2-carbaldehyde.

$^1$H NMR (400 MHz, Methanol-d4) δ 7.55 (s, 1H), 7.47 (s, 1H), 7.41 (s, 1H), 7.07-6.99 (m, 2H), 6.76 (s, 1H), 6.13 (d, J=3.3 Hz, 1H), 4.53 (t, J=4.5 Hz, 2H), 3.57 (t, J=4.5 Hz, 2H), 2.40 (s, 3H), 2.17 (s, 3H). LCMS-ESI$^+$ (m/z): [M+H]$^+$ calcd for $C_{22}H_{21}N_4O_2$: 373.2; found: 373.4.

Example 18: (Z)-3-(isothiazol-5-ylmethylene)-5-(8-methyl-2,3-dihydro-1H-pyrido[2,3-b][1,4]oxazin-7-yl)indolin-2-one (C18)

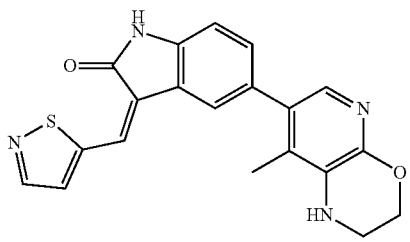 [SMILES: Cc1c(-c2ccc3c(c2)/C(=C/c2ccns2)C(=O)N3)cnc2c1NCCO2]

This compound was prepared as outlined above in procedures 1, 2, 3, and 5 using commercially available intermediate isothiazole-5-carbaldehyde.

$^1$H NMR (400 MHz, Methanol-d4) δ 8.53 (d, J=1.8 Hz, 1H), 8.15 (s, 1H), 7.72 (ddd, J=15.9, 1.8, 0.6 Hz, 2H), 7.44 (s, 1H), 7.26 (dd, J=8.0, 1.7 Hz, 1H), 7.04 (dd, J=8.0, 0.6 Hz, 1H), 4.60-4.51 (m, 2H), 3.63-3.54 (m, 2H), 2.19 (s, 3H). LCMS-ESI$^+$ (m/z): [M+H]$^+$ calcd for $C_{20}H_{16}N_4O_2S$: 377.1; found: 377.4.

Example 19: (E and Z)-5-(8-methyl-2,3-dihydro-1H-pyrido[2,3-b][1,4]oxazin-7-yl)-3-(thiophen-2-ylmethylene)indolin-2-one (C19)

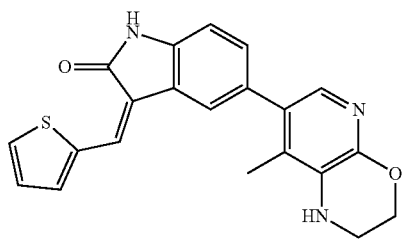 [SMILES: Cc1c(-c2ccc3c(c2)/C(=C/c2cccs2)C(=O)N3)cnc2c1NCCO2]

This compound was prepared as outlined above in procedures 1, 2, 3, and 5 using commercially available intermediate thiophene-2-carbaldehyde.

Mixture of 2 isomers; HPLC tR=4.22 min/4.40 min. LCMS-ESI$^+$ (m/z): [M+H]$^+$ calcd for $C_{21}H_{18}N_3O_2S$: 376.1; found: 376.4.

Example 20: (Z)-3-((4-bromo-1H-pyrrol-2-yl)methylene)-5-(8-methyl-2,3-dihydro-1H-pyrido[2,3-b][1,4]oxazin-7-yl)indolin-2-one (C20)

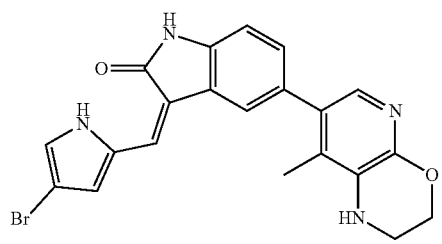 [SMILES: Cc1c(-c2ccc3c(c2)/C(=C/c2cc(Br)c[nH]2)C(=O)N3)cnc2c1NCCO2]

This compound was prepared as outlined above in procedures 1, 2, 3, and 5 using commercially available intermediate 4-bromo-1H-pyrrole-2-carbaldehyde.

$^1$H NMR (400 MHz, Methanol-d4) δ 7.58 (s, 1H), 7.49 (s, 1H), 7.34 (s, 1H), 7.20 (s, 1H), 7.08 (d, J=9.6 Hz, 1H), 6.98 (d, J=8.1 Hz, 1H), 6.79 (s, 1H), 4.39 (s, 2H), 3.57 (s, 2H), 2.08 (s, 3H). LCMS-ESI$^+$ (m/z): [M+H]$^+$ calcd for $C_{21}H_{18}BrN_4O_2$: 437.1; found: 437.3.

Example 21: (Z)-5-((5-(8-methyl-2,3-dihydro-1H-pyrido[2,3-b][1,4]oxazin-7-yl)-2-oxoindolin-3-ylidene)methyl)-1H-pyrrole-3-carbonitrile (C21)

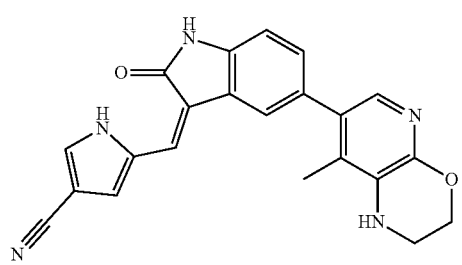 [SMILES: Cc1c(-c2ccc3c(c2)/C(=C/c2cc(C#N)c[nH]2)C(=O)N3)cnc2c1NCCO2]

This compound was prepared as outlined above in procedures 1, 2, 3, and 5 using commercially available intermediate 5-formyl-1H-pyrrole-3-carbonitrile.

$^1$H NMR (400 MHz, Methanol-d4) δ 7.75 (s, 1H), 7.65 (d, J=2.7 Hz, 1H), 7.56 (s, 1H), 7.38 (s, 1H), 7.15 (d, J=8.4 Hz, 1H), 7.07 (s, 1H), 7.01 (d, J=8.1 Hz, 1H), 4.47 (t, J=4.4 Hz, 2H), 3.54 (t, J=4.4 Hz, 2H), 2.13 (s, 3H). LCMS-ESI$^+$ (m/z): [M+H]$^+$ calcd for $C_{22}H_{18}N_5O_2$: 384.1; found: 384.4.

Example 22: (Z)-7-chloro-3-((4-methyl-1H-pyrrol-2-yl)methylene)-5-(8-methyl-2,3-dihydro-1H-pyrido[2,3-b][1,4]oxazin-7-yl)indolin-2-one (C22)

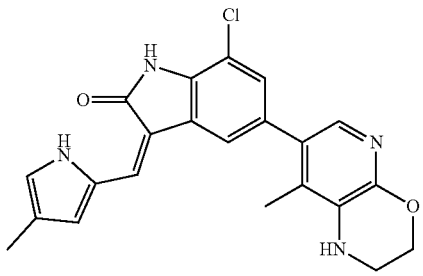

This compound was prepared as outlined above in procedures 1, 2, 3, and 5 using commercially available intermediates 4-methyl-1H-pyrrole-2-carbaldehyde and 5-bromo-7-chloroindolin-2-one.

$^1$H NMR (400 MHz, Methanol-d4) δ 7.61 (s, 1H), 7.43 (d, J=1.5 Hz, 1H), 7.40 (s, 1H), 7.12-7.03 (m, 2H), 6.68 (s, 1H), 4.48 (t, J=4.4 Hz, 2H), 3.54 (t, J=4.5 Hz, 2H), 2.14 (d, J=2.6 Hz, 3H). LCMS-ESI$^+$ (m/z): [M+H]$^+$ calcd for $C_{22}H_{20}ClN_4O_2$: 407.1; found: 407.9.

Example 23: (Z)-3-((1H-pyrrol-2-yl)methylene)-7-chloro-5-(8-methyl-2,3-dihydro-1H-pyrido[2,3-b][1,4]oxazin-7-yl)indolin-2-one (C23)

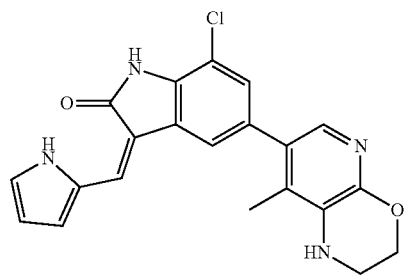

This compound was prepared as outlined above in procedures 1, 2, 3, and 5 using commercially available intermediate 5-bromo-7-chloroindolin-2-one.

$^1$H NMR (400 MHz, Methanol-d4) δ 7.71 (s, 1H), 7.47 (d, J=1.5 Hz, 1H), 7.42 (s, 1H), 7.30 (d, J=3.5 Hz, 1H), 7.11 (d, J=1.4 Hz, 1H), 6.87 (dt, J=3.7, 1.8 Hz, 1H), 6.39 (dt, J=3.7, 2.3 Hz, 1H), 4.55-4.46 (m, 2H), 3.56 (t, J=4.5 Hz, 2H), 2.16 (s, 3H). LCMS-ESI$^+$ (m/z): [M+H]$^+$ calcd for $C_{21}H_{18}ClN_4O_2$: 393.1; found: 393.8.

Example 24: (Z)-7-methyl-3-((4-methyl-1H-pyrrol-2-yl)methylene)-5-(8-methyl-2,3-dihydro-1H-pyrido[2,3-b][1,4]oxazin-7-yl)indolin-2-one (C24)

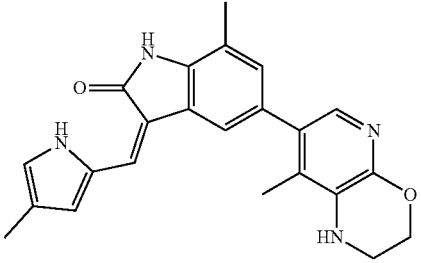 [SMILES: Cc1c[nH]c(/C=C2\C(=O)Nc3c(C)cc(-c4cnc5c(c4C)NCCO5)cc32)c1]

This compound was prepared as outlined above in procedures 1, 2, 3, and 5 using commercially available intermediates 4-methyl-1H-pyrrole-2-carbaldehyde and 5-bromo-7-methylindolin-2-one.

$^1$H NMR (400 MHz, Methanol-d4) δ 7.53 (s, 1H), 7.41 (s, 1H), 7.33 (s, 1H), 7.05 (s, 1H), 6.91 (s, 1H), 6.62 (s, 1H), 4.56 (t, J=4.5 Hz, 2H), 3.59 (t, J=4.5 Hz, 2H), 2.33 (s, 3H), 2.19 (s, 3H), 2.14 (s, 3H). LCMS-ESI$^+$ (m/z): [M+H]$^+$ calcd for $C_{23}H_{23}N_4O_2$: 387.2; found: 387.5.

Example 25: (Z)-7-fluoro-3-((4-methyl-1H-pyrrol-2-yl)methylene)-5-(8-methyl-2,3-dihydro-1H-pyrido[2,3-b][1,4]oxazin-7-yl)indolin-2-one (C25)

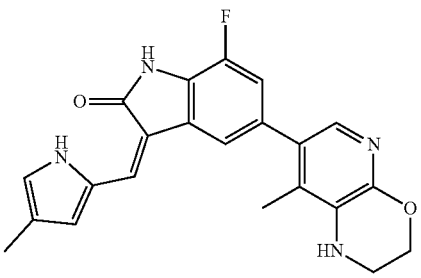 [SMILES: Cc1c[nH]c(/C=C2\C(=O)Nc3c(F)cc(-c4cnc5c(c4C)NCCO5)cc32)c1]

This compound was prepared as outlined above in procedures 1, 2, 3, and 5 using commercially available intermediates 4-methyl-1H-pyrrole-2-carbaldehyde and 5-bromo-7-fluoroindolin-2-one.

$^1$H NMR (400 MHz, Methanol-d4) δ 7.61 (s, 1H), 7.43 (s, 1H), 7.34 (d, J=1.3 Hz, 1H), 7.09 (d, J=2.4 Hz, 1H), 6.92 (dd, J=10.7, 1.4 Hz, 1H), 6.68 (s, 1H), 4.58-4.49 (m, 2H), 3.62-3.53 (m, 2H), 2.16 (d, J=13.2 Hz, 6H). LCMS-ESI$^+$ (m/z): [M+H]$^+$ calcd for $C_{22}H_{20}FN_4O_2$: 391.2; found: 391.4.

Example 26: (Z)-3-((1H-pyrrol-2-yl)methylene)-7-fluoro-5-(8-methyl-2,3-dihydro-1H-pyrido[2,3-b][1,4]oxazin-7-yl)indolin-2-one (C26)

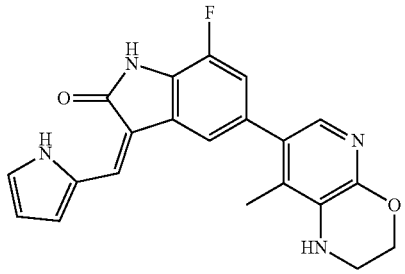 [SMILES: Cc1c(-c2cc(F)c3c(c2)/C(=C/c2ccc[nH]2)C(=O)N3)cnc2c1NCCO2]

This compound was prepared as outlined above in procedures 1, 2, 3, and 5 using commercially available intermediate 5-bromo-7-fluoroindolin-2-one.

$^1$H NMR (400 MHz, Methanol-d4) δ 7.71 (s, 1H), 7.44 (s, 1H), 7.37 (d, J=1.4 Hz, 1H), 7.29 (d, J=3.2 Hz, 1H), 6.94 (dd, J=10.7, 1.4 Hz, 1H), 6.87 (dt, J=3.7, 1.6 Hz, 1H), 6.39 (dt, J=3.7, 2.3 Hz, 1H), 4.54 (dd, J=4.9, 4.0 Hz, 2H), 3.61-3.52 (m, 2H), 2.18 (s, 3H). LCMS-ESI$^+$ (m/z): [M+H]$^+$ calcd for $C_{21}H_{18}FN_4O_2$: 377.1; found: 377.4.

Example 27: (Z)-3-((1H-1,2,3-triazol-5-yl)methylene)-5-(8-methyl-2,3-dihydro-1H-pyrido[2,3-b][1,4]oxazin-7-yl)indolin-2-one (C27)

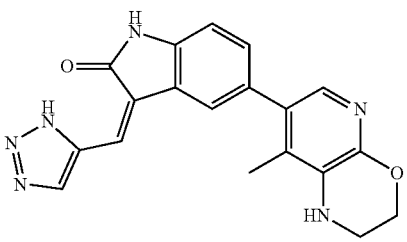 [SMILES: Cc1c(-c2ccc3c(c2)/C(=C/c2cnn[nH]2)C(=O)N3)cnc2c1NCCO2]

This compound was prepared as outlined above in procedures 1, 2, 3, and 5 using commercially available intermediate 1H-1,2,3-triazole-5-carbaldehyde.

$^1$H NMR (400 MHz, DMSO-d6) δ 10.68 (s, 1H), 9.26-8.22 (br m, 3H) 7.59 (s, 1H), 7.39 (s, 1H), 7.21 (d, J=7.9 Hz, 1H), 6.95 (d, J=8.0 Hz, 1H), 4.35 (s, 2H), 3.41 (s, 2H), 2.06 (s, 3H). LCMS-ESI$^+$ (m/z): [M+H]$^+$ calcd for $C_{19}H_{17}N_6O_2$: 361.1; found: 361.1.

Example 28: (Z)-3-((4-methyl-1H-pyrrol-2-yl)methylene)-5-(8-methyl-2,3-dihydro-1H-pyrido[2,3-b][1,4]oxazin-7-yl)indolin-2-one (C28)

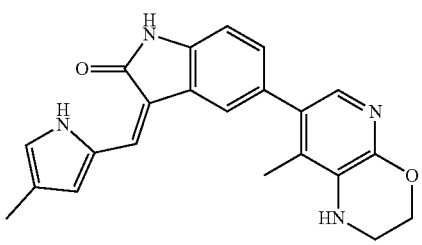 [SMILES: Cc1c[nH]c(/C=C2\C(=O)Nc3ccc(-c4cnc5c(c4C)NCCO5)cc32)c1]

This compound was prepared as outlined above in procedures 1, 2, 3, and 5 using commercially available intermediate 4-methyl-1H-pyrrole-2-carbaldehyde.

$^1$H NMR (400 MHz, Methanol-d4) δ 7.57 (s, 1H), 7.51 (d, J=1.6 Hz, 1H), 7.44 (s, 1H), 7.08 (td, J=7.5, 7.1, 2.2 Hz, 2H), 7.01 (d, J=7.9 Hz, 1H), 6.64 (s, 1H), 4.59 (t, J=4.5 Hz, 2H), 3.61 (t, J=4.5 Hz, 2H), 2.20 (s, 3H), 2.14 (s, 3H). LCMS-ESI$^+$ (m/z): [M+H]$^+$ calcd for $C_{22}H_{21}N_4O_2$: 373.2; found: 373.4.

Example 29: (Z)-3-((1H-pyrrol-2-yl)methylene)-5-(8-methyl-2,3-dihydro-1H-pyrido[2,3-b][1,4]oxazin-7-yl)indolin-2-one (C29)

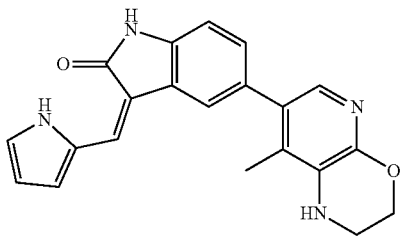 [SMILES: Cc1c(-c2ccc3c(c2)/C(=C/c2ccc[nH]2)C(=O)N3)cnc2c1NCCO2]

This compound was prepared as outlined above in procedures 1, 2, 3, and 5.

$^1$H NMR (400 MHz, Methanol-d4) δ 7.67 (s, 1H), 7.57-7.52 (m, 1H), 7.45 (s, 1H), 7.28-7.22 (m, 1H), 7.11 (dd, J=8.0, 1.7 Hz, 1H), 7.02 (dd, J=8.0, 0.5 Hz, 1H), 6.85-6.80 (m, 1H), 6.37 (dt, J=3.7, 2.3 Hz, 1H), 4.65-4.56 (m, 2H), 3.67-3.58 (m, 2H), 2.22 (s, 3H). LCMS-ESI$^+$ (m/z): [M+H]$^+$ calcd for $C_{21}H_{19}N_4O_2$: 359.1; found: 359.4.

Example 30: (Z)-3-((1H-pyrazol-5-yl)methylene)-5-(8-methyl-2,3-dihydro-1H-pyrido[2,3-b][1,4]oxazin-7-yl)indolin-2-one (C30)

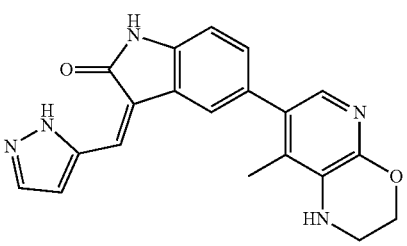 [SMILES: Cc1c(-c2ccc3c(c2)/C(=C/c2ccn[nH]2)C(=O)N3)cnc2c1NCCO2]

This compound was prepared as outlined above in procedures 1, 2, 3, and 5 using commercially available intermediate 1H-pyrazole-5-carbaldehyde.

$^1$H NMR (400 MHz, Methanol-d4) δ 7.75 (d, J=2.4 Hz, 1H), 7.63 (s, 1H), 7.42 (s, 1H), 7.21 (dd, J=7.9, 1.8 Hz, 1H), 7.00 (d, J=8.0 Hz, 1H), 6.73 (d, J=2.3 Hz, 1H), 4.52 (t, J=4.5 Hz, 2H), 3.57 (d, J=4.7 Hz, 2H), 2.18 (s, 3H). LCMS-ESI$^+$ (m/z): [M+H]$^+$ calcd for $C_{21}H_{18}N_5O_2$: 360.1; found: 360.4.

Example 31: (Z)-3-((1H-imidazol-2-yl)methylene)-5-(8-methyl-2,3-dihydro-1H-pyrido[2,3-b][1,4]oxazin-7-yl)indolin-2-one (C31)

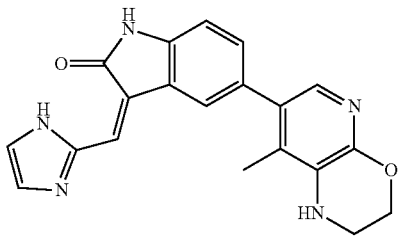 [SMILES: Cc1c(-c2ccc3c(c2)/C(=C/c2ncc[nH]2)C(=O)N3)cnc2c1NCCO2]

This compound was prepared as outlined above in procedures 1, 2, 3, and 5 using commercially available intermediate 1H-imidazole-2-carbaldehyde.

$^1$H NMR (400 MHz, Methanol-d4) δ 7.76 (s, 2H), 7.73 (d, J=1.6 Hz, 1H), 7.69 (s, 1H), 7.46 (s, 1H), 7.37 (dd, J=8.0, 1.7 Hz, 1H), 7.11 (d, J=8.1 Hz, 1H), 4.59 (dd, J=5.0, 3.9 Hz, 2H), 3.61 (t, J=4.5 Hz, 2H), 2.19 (s, 3H). LCMS-ESI$^+$ (m/z): [M+H]$^+$ calcd for $C_{20}H_{18}N_5O_2$: 360.1; found: 360.4.

Example 32: (Z)-3-((1H-imidazol-5-yl)methylene)-5-(8-methyl-2,3-dihydro-1H-pyrido[2,3-b][1,4]oxazin-7-yl)indolin-2-one (C32)

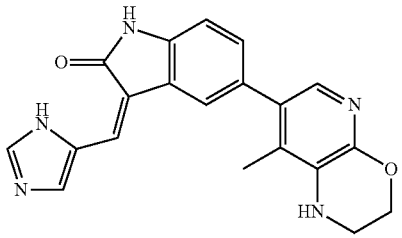 [SMILES: Cc1c(-c2ccc3c(c2)/C(=C/c2cnc[nH]2)C(=O)N3)cnc2c1NCCO2]

This compound was prepared as outlined above in procedures 1, 2, 3, and 5 using commercially available intermediate 1H-imidazole-5-carbaldehyde.

$^1$H NMR (400 MHz, Methanol-d4) δ 8.87 (s, 1H), 8.03 (d, J=1.3 Hz, 1H), 7.82 (s, 1H), 7.65 (d, J=1.8 Hz, 1H), 7.41 (s, 1H), 7.27 (dd, J=8.1, 1.7 Hz, 1H), 7.07 (d, J=8.0 Hz, 1H), 4.56-4.47 (m, 2H), 3.56 (t, J=4.5 Hz, 2H), 2.15 (s, 3H). LCMS-ESI$^+$ (m/z): [M+H]$^+$ calcd for $C_{21}H_{18}N_5O_2$: 360.1; found: 360.4.

Example 33: (Z)-7'-(3-((1H-imidazol-2-yl)methylene)-2-oxoindolin-5-yl)-8'-methylspiro[cyclopropane-1,3'-pyrido[2,3-b][1,4]oxazin]-2'(1'H)-one (C33)

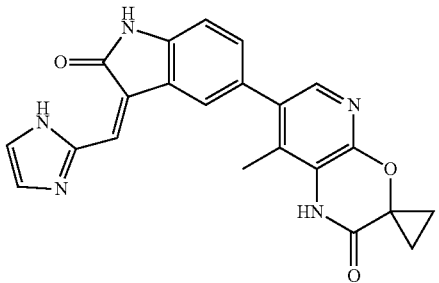 [SMILES: Cc1c(-c2ccc3c(c2)/C(=C/c2ncc[nH]2)C(=O)N3)cnc2c1NC(=O)C1(CC1)O2]

A. Preparation of ethyl 1-((5-bromo-4-methyl-3-nitropyridin-2-yl)oxy)cyclopropane-1-carboxylate (20)

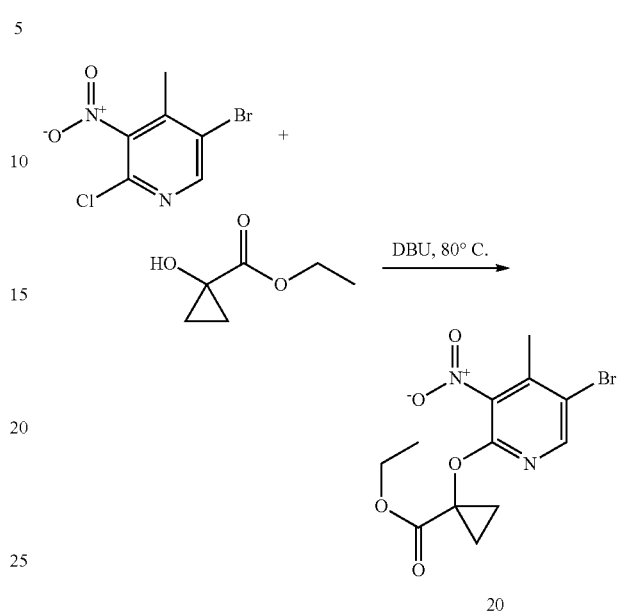

5-bromo-2-chloro-4-methyl-3-nitropyridine (0.5 g, 1.98 mmol) was weighed into a microwave vial and dissolved in ethyl 1-hydroxycyclopropane-1-carboxylate (6.0 eq). DBU (3.0 eq) was added, the vial was sealed, and the reaction was heated to 80° C. for 4 hours. The reaction was diluted with water (20 mL) and EtOAc (10 mL) and extracted multiple times with EtOAc (5×10 mL). Combined organic fractions were concentrated under reduced pressure and the crude material was purified by silica gel chromatography (MeOH/CH$_2$Cl$_2$) to give ethyl 1-((5-bromo-4-methyl-3-nitropyridin-2-yl)oxy)cyclopropane-1-carboxylate (20). LCMS-ESI$^+$ (m/z): [M+H]$^+$ calcd for $C_{12}H_{13}BrN_2O_5$: 345.0; found: 345.2.

B. Preparation of 7'-bromo-8'-methylspiro[cyclopropane-1,3'-pyrido[2,3-b][1,4]oxazin]-2'(1'H)-one (21)

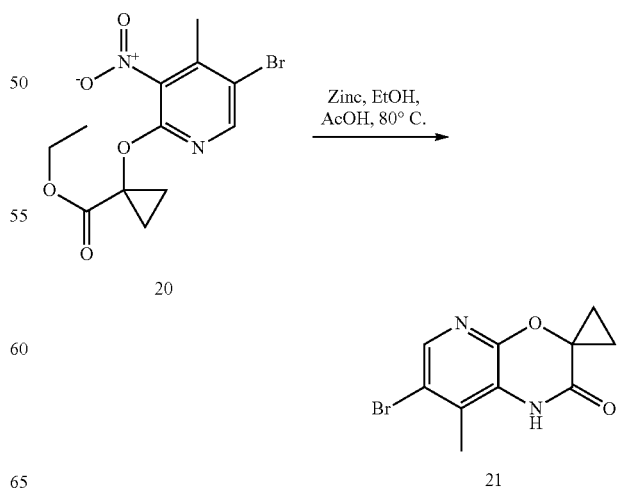

Ethyl 1-((5-bromo-4-methyl-3-nitropyridin-2-yl)oxy)cyclopropane-1-carboxylate (20) (0.182 g, 0.527 mmol) was dissolved in ethanol (1.0 mL) and acetic acid (4.0 mL) in a round bottom flask under argon. Zinc powder (5.5 eq) was added and the reaction was heated to 80° C. overnight. The reaction was concentrated to dryness under reduced pressure, dissolved in a minimal amount of MeOH, and filtered to remove solids. The filtrate was concentrated under reduce pressure and the crude material was purified by silica gel chromatography (Rf 0.6 in 10% MeOH/CH$_2$Cl$_2$) to give 7'-bromo-8'-methylspiro[cyclopropane-1,3'-pyrido[2,3-b][1,4]oxazin]-2'(1'H)-one (21). LCMS-ESI$^+$ (m/z): [M+H]$^+$ calcd for C$_{10}$H$_9$BrN$_2$O$_2$: 269.0; found: 269.1.

C. Preparation of (Z)-7'-(3-((1H-imidazol-2-yl)methylene)-2-oxoindolin-5-yl)-8'-methylspiro[cyclopropane-1,3'-pyrido[2,3-b][1,4]oxazin]-2'(1'H)-one (Example 33)

This compound was prepared as outlined in procedures 1, 2, 3, and 5 using 7'-bromo-8'-methylspiro[cyclopropane-1,3'-pyrido[2,3-b][1,4]oxazin]-2'(1'H)-one (21).

$^1$H NMR (400 MHz, DMSO-d6) δ 11.52 (s, 1H), 10.67 (s, 1H), 7.90-7.68 (m, 5H), 7.33 (dd, J=8.0, 1.7 Hz, 1H), 7.05 (d, J=8.0 Hz, 1H), 2.21 (s, 3H), 1.39-1.20 (m, 4H). LCMS-ESI$^+$ (m/z): [M+H]$^+$ calcd for C$_{22}$H$_{18}$N$_5$O$_3$: 400.1; found: 400.1.

Example 34: (Z)-3-((2-cyclopropyl-1H-imidazol-5-yl)methylene)-5-(8-methyl-2,3-dihydro-1H-pyrido[2,3-b][1,4]oxazin-7-yl)indolin-2-one (C34)

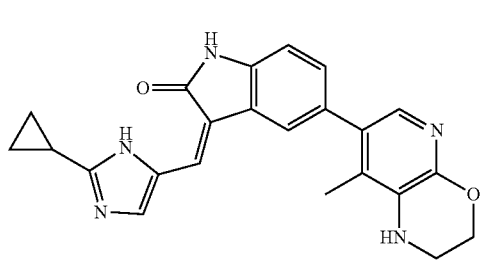 [SMILES: Cc1c(-c2ccc3c(c2)/C(=C/c2cnc(C4CC4)[nH]2)C(=O)N3)cnc2c1NCCO2]

This compound was prepared as outlined above in procedures 1, 2, 3, and 5 using commercially available intermediate 2-cyclopropyl-1H-imidazole-5-carbaldehyde.

$^1$H NMR (400 MHz, Methanol-d4) δ 7.94 (s, 1H), 7.71 (d, J=1.6 Hz, 1H), 7.49 (d, J=1.4 Hz, 1H), 7.38 (d, J=1.6 Hz, 1H), 7.14 (dd, J=10.6, 1.4 Hz, 1H), 4.58-4.49 (m, 2H), 3.63-3.52 (m, 2H), 2.47-2.37 (m, 1H), 2.17 (s, 3H), 1.49-1.39 (m, 2H), 1.30-1.21 (m, 2H). LCMS-ESI$^+$ (m/z): [M+H]$^+$ calcd for C$_{23}$H$_{22}$N$_5$O$_2$: 400.2; found: 400.5.

Example 35: (Z)-3-((2-cyclopropyl-1H-imidazol-5-yl)methylene)-7-fluoro-5-(8-methyl-2,3-dihydro-1H-pyrido[2,3-b][1,4]oxazin-7-yl)indolin-2-one (C35)

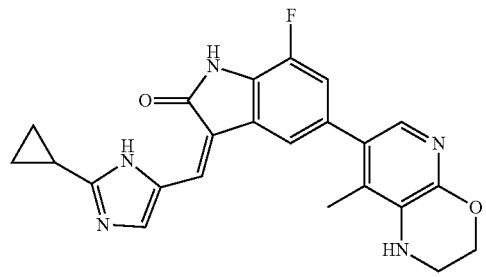 [SMILES: Cc1c(-c2cc(F)c3c(c2)/C(=C/c2cnc(C4CC4)[nH]2)C(=O)N3)cnc2c1NCCO2]

This compound was prepared as outlined above in procedures 1, 2, 3, and 5 using commercially available intermediates 2-cyclopropyl-1H-imidazole-5-carbaldehyde and 5-bromo-7-fluoroindolin-2-one.

$^1$H NMR (400 MHz, Methanol-d4) δ 7.96 (s, 1H), 7.81 (s, 1H), 7.49 (d, J=1.4 Hz, 1H), 7.44 (s, 1H), 7.14 (dd, J=10.6, 1.4 Hz, 1H), 4.58-4.50 (m, 2H), 3.62-3.53 (m, 2H), 2.47-2.38 (m, 1H), 2.17 (s, 3H), 1.49-1.39 (m, 2H), 1.30-1.21 (m, 2H). LCMS-ESI$^+$ (m/z): [M+H]$^+$ calcd for C$_{23}$H$_{21}$FN$_5$O$_2$: 418.2; found: 418.4.

Example 36: (Z)-3-(1-(1H-imidazol-5-yl)propylidene)-5-(8-methyl-2,3-dihydro-TH-pyrido[2,3-b][1,4]oxazin-7-yl)indolin-2-one (C36)

This compound was prepared as outline in procedures 4 and 5 using commercially available intermediate 1-(1H-imidazol-5-yl)propan-1-one.

$^1$H NMR (400 MHz, Methanol-d4) δ 8.98 (d, J=1.2 Hz, 1H), 8.20 (d, J=1.3 Hz, 1H), 7.62 (d, J=1.5 Hz, 1H), 7.50 (s, 1H), 7.33 (dd, J=8.0, 1.5 Hz, 1H), 7.12 (d, J=8.0 Hz, 1H), 4.62 (t, J=4.5 Hz, 2H), 3.63 (t, J=4.5 Hz, 2H), 3.17 (d, J=7.6 Hz, 2H), 2.22 (s, 3H), 1.36 (t, J=7.5 Hz, 3H). LCMS-ESI$^+$ (m/z): [M+H]$^+$ calcd for C$_{23}$H$_{22}$N$_5$O$_2$: 388.2; found: 388.2.

Example 37: (Z)-3-((1H-pyrrolo[2,3-c]pyridin-2-yl)methylene)-6-methyl-5-(8-methyl-2,3-dihydro-1H-pyrido[2,3-b][1,4]oxazin-7-yl)indolin-2-one (C37)

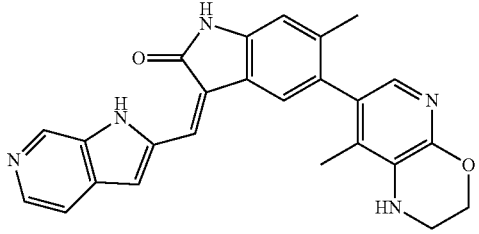

This compound was prepared as outlined above in procedures 1, 2, 3, and 5 using commercially available intermediates 5-bromo-6-methylindolin-2-one and 1H-pyrrolo[2,3-c]pyridine-2-carbaldehyde.

$^1$H NMR (400 MHz, Methanol-d4) δ 9.27 (q, J=0.8 Hz, 1H), 8.22 (dd, J=6.5, 0.8 Hz, 1H), 8.14 (dd, J=6.5, 0.8 Hz, 1H), 7.90 (s, 1H), 7.56 (s, 1H), 7.39 (s, 1H), 7.34 (d, J=0.7 Hz, 1H), 6.97 (s, 1H), 4.59 (t, J=4.5 Hz, 2H), 3.62 (td, J=4.2, 2.0 Hz, 2H), 2.13 (s, 3H), 2.03 (s, 3H). LCMS-ESI$^+$ (m/z): [M+H]$^+$ calcd for $C_{25}H_{22}N_5O_2$: 424.2; found: 424.1.

Example 38: (Z)-3-((1H-pyrrolo[3,2-b]pyridin-2-yl)methylene)-6-methyl-5-(8-methyl-2,3-dihydro-1H-pyrido[2,3-b][1,4]oxazin-7-yl)indolin-2-one (C38)

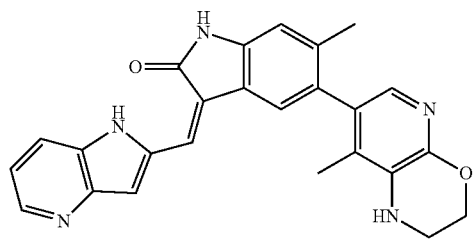 [SMILES: Cc1cc2c(cc1-c1cnc3c(c1C)NCCO3)/C(=C/c1cc3ncccc3[nH]1)C(=O)N2]

This compound was prepared as outlined above in procedures 1, 2, 3, and 5 using commercially available intermediates 5-bromo-6-methylindolin-2-one and 1H-pyrrolo[3,2-b]pyridine-2-carbaldehyde.

$^1$H NMR (400 MHz, Methanol-d4) δ 8.72 (dt, J=8.3, 1.0 Hz, 1H), 8.61 (dd, J=5.8, 1.1 Hz, 1H), 7.87 (s, 1H), 7.74 (dd, J=8.3, 5.8 Hz, 1H), 7.54 (s, 1H), 7.39 (s, 1H), 7.27 (d, J=0.8 Hz, 1H), 6.96 (s, 1H), 4.59 (t, J=4.5 Hz, 2H), 3.62 (td, J=4.3, 2.3 Hz, 2H), 2.13 (s, 3H), 2.03 (s, 3H). LCMS-ESI$^+$ (m/z): [M+H]$^+$ calcd for $C_{25}H_{22}N_5O_2$: 424.2; found: 424.1.

Example 39: (Z)-6-(3-((1H-pyrrolo[3,2-c]pyridin-2-yl)methylene)-2-oxoindolin-5-yl)-5-methyl-2H-benzo[b][1,4]oxazin-3(4H)-one (C39)

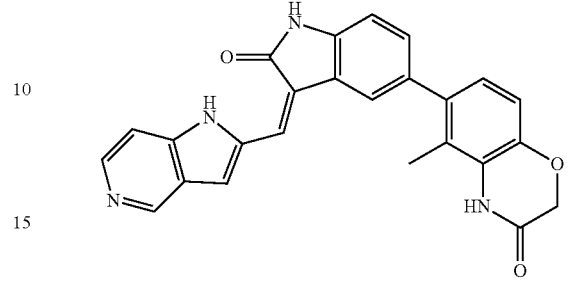

This compound was prepared as outlined above in procedures 2, 3, and 5 using commercially available intermediates 5-methyl-6-(4,4,5,5-tetramethyl-1,3,2-dioxaborolan-2-yl)-2H-benzo[b][1,4]oxazin-3(4H)-one and 1H-pyrrolo[3,2-c]pyridine-2-carbaldehyde.

$^1$H NMR (400 MHz, Methanol-d4) δ 8.68 (d, J=8.3 Hz, 1H), 8.59 (d, J=5.7 Hz, 1H), 7.96 (s, 1H), 7.72 (dd, J=8.3, 5.7 Hz, 1H), 7.67 (d, J=1.4 Hz, 1H), 7.29 (s, 1H), 7.26-7.19 (m, 1H), 7.02 (d, J=8.0 Hz, 1H), 6.90 (d, J=1.2 Hz, 2H), 4.56 (s, 2H), 2.65 (s, 1H), 2.19 (s, 3H). LCMS-ESI$^+$ (m/z): [M+H]$^+$ calcd for $C_{25}H_{19}N_4O_3$: 423.1; found: 423.4.

Example 40: (Z)-3-((1H-pyrrolo[3,2-c]pyridin-2-yl)methylene)-6-methyl-5-(8-methyl-2,3-dihydro-1H-pyrido[2,3-b][1,4]oxazin-7-yl)indolin-2-one (C40)

This compound was prepared as outlined above in procedures 1, 2, 3, and 5 using commercially available intermediates 5-bromo-6-methylindolin-2-one and 1H-pyrrolo[3,2-c]pyridine-2-carbaldehyde.

$^1$H NMR (400 MHz, Methanol-d4) δ 9.21 (d, J=0.9 Hz, 1H), 8.40 (dd, J=6.8, 0.9 Hz, 1H), 8.13 (dt, J=6.8, 0.9 Hz, 1H), 7.85 (s, 1H), 7.50 (d, J=3.1 Hz, 2H), 7.35 (s, 1H), 6.95 (s, 1H), 4.54 (t, J=4.5 Hz, 2H), 3.59 (q, J=4.2 Hz, 2H), 2.12 (s, 3H), 2.00 (s, 3H). LCMS-ESI$^+$ (m/z): [M+H]$^+$ calcd for $C_{25}H_{22}N_5O_2$: 424.2; found: 424.1.

Example 41: (Z)-3-((1H-pyrrolo[3,2-c]pyridin-2-yl)methylene)-5-(2,3-dihydro-1H-pyrido[2,3-b][1,4]oxazin-7-yl)-6-methylindolin-2-one (C41)

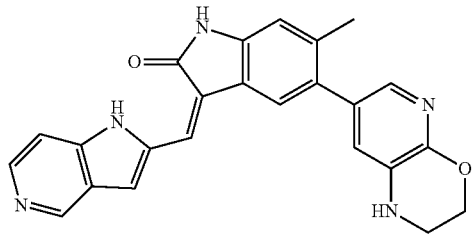 [SMILES: Cc1cc2c(cc1-c1cnc3c(c1)NCCO3)/C(=C/c1cc3cnccc3[nH]1)C(=O)N2]

This compound was prepared as outlined above in procedures 2, 3, and 5 using commercially available intermediates (2,3-dihydro-1H-pyrido[2,3-b][1,4]oxazin-7-yl)boronic acid and 1H-pyrrolo[3,2-c]pyridine-2-carbaldehyde.

$^1$H NMR (400 MHz, Methanol-d4) δ 9.20 (s, 1H), 8.39 (dd, J=6.8, 0.9 Hz, 1H), 8.12 (d, J=6.8 Hz, 1H), 7.87 (s, 1H), 7.57 (s, 1H), 7.51 (s, 1H), 7.37 (d, J=2.1 Hz, 1H), 7.03 (d, J=2.2 Hz, 1H), 6.90 (s, 1H), 4.49-4.43 (m, 2H), 3.47-3.42 (m, 3H), 2.30 (s, 4H). LCMS-ESI$^+$ (m/z): [M+H]$^+$ calcd for $C_{24}H_{20}N_5O_2$: 410.2; found: 410.1.

Example 42: (Z)-3-((1H-pyrrolo[3,2-c]pyridin-2-yl)methylene)-5-(2,3-dihydro-1H-pyrido[2,3-b][1,4]oxazin-7-yl)-7-fluoro-4-methylindolin-2-one (C42)

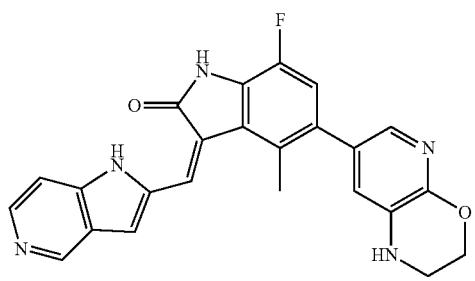 [SMILES: Cc1c(-c2cnc3c(c2)NCCO3)cc(F)c2c1/C(=C/c1cc3cnccc3[nH]1)C(=O)N2]

This compound was prepared as outlined above in procedures 2, 3, and 5 using 7-fluoro-4-methylindolin-2-one (19) and commercially available intermediates 1H-pyrrolo[3,2-c]pyridine-2-carbaldehyde and (2,3-dihydro-1H-pyrido[2,3-b][1,4]oxazin-7-yl)boronic acid.

$^1$H NMR (400 MHz, Methanol-d4) δ 9.25 (d, J=0.9 Hz, 1H), 8.41 (dd, J=6.7, 0.9 Hz, 1H), 8.15 (dt, J=6.8, 0.9 Hz, 1H), 8.07 (s, 1H), 7.74-7.62 (m, 1H), 7.37 (d, J=2.1 Hz, 1H), 7.07 (d, J=10.1 Hz, 1H), 7.05 (d, J=2.1 Hz, 1H), 4.54-4.45 (m, 2H), 3.47 (d, J=4.2 Hz, 3H), 2.56 (s, 3H). LCMS-ESI$^+$ (m/z): [M+H]$^+$ calcd for $C_{24}H_{19}FN_5O_2$: 428.1; found: 428.1.

Example 43: (Z)-3-((1H-pyrrolo[2,3-c]pyridin-2-yl)methylene)-6-fluoro-5-(8-methyl-2,3-dihydro-1H-pyrido[2,3-b][1,4]oxazin-7-yl)indolin-2-one (C43)

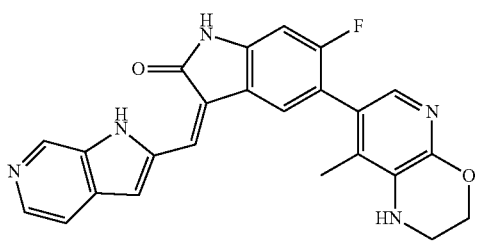

This compound was prepared as outlined above in procedures 1, 2, 3, and 5 using commercially available intermediates 5-bromo-6-fluoroindolin-2-one and 1H-pyrrolo[2,3-c]pyridine-2-carbaldehyde.

$^1$H NMR (400 MHz, Methanol-d4) δ 9.26 (s, 1H), 8.23-8.12 (m, 2H), 7.97 (s, 1H), 7.73 (d, J=7.0 Hz, 1H), 7.38 (d, J=11.9 Hz, 2H), 6.86 (d, J=9.4 Hz, 1H), 4.45 (t, J=4.4 Hz, 2H), 3.52 (s, 2H), 2.05 (d, J=1.6 Hz, 3H). LCMS-ESI$^+$ (m/z): [M+H]$^+$ calcd for $C_{24}H_{19}FN_5O_2$: 428.1; found: 428.4.

Example 44: (Z)-3-((1H-pyrrolo[3,2-b]pyridin-2-yl)methylene)-6-fluoro-5-(8-methyl-2,3-dihydro-1H-pyrido[2,3-b][1,4]oxazin-7-yl)indolin-2-one (C44)

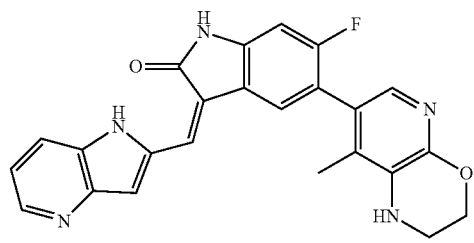

This compound was prepared as outlined above in procedures 1, 2, 3, and 5 using commercially available intermediates 5-bromo-6-fluoroindolin-2-one and 1H-pyrrolo[3,2-b]pyridine-2-carbaldehyde.

$^1$H NMR (400 MHz, Methanol-d4) δ 8.69 (d, J=8.3 Hz, 1H), 8.62-8.56 (m, 1H), 7.93 (s, 1H), 7.75-7.67 (m, 2H), 7.41 (s, 1H), 7.29 (s, 1H), 6.86 (d, J=9.5 Hz, 1H), 4.47 (t, J=4.4 Hz, 2H), 3.53 (s, 2H), 2.06 (d, J=1.6 Hz, 3H). LCMS-ESI$^+$ (m/z): [M+H]$^+$ calcd for $C_{24}H_{19}FN_5O_2$: 428.1; found: 428.4.

Example 45: (Z)-3-((1H-pyrrolo[2,3-c]pyridin-2-yl)methylene)-7-fluoro-5-(8-methyl-2,3-dihydro-1H-pyrido[2,3-b][1,4]oxazin-7-yl)indolin-2-one (C45)

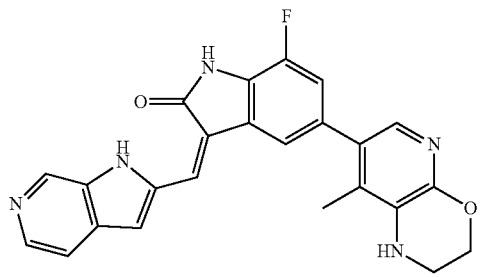 [SMILES: Cc1c(-c2cc(F)c3c(c2)/C(=C/c2cc4ccncc4[nH]2)C(=O)N3)cnc2c1NCCO2]

This compound was prepared as outlined above in procedures 1, 2, 3, and 5 using commercially available intermediates 5-bromo-7-fluoroindolin-2-one and 1H-pyrrolo[2,3-c]pyridine-2-carbaldehyde.

$^1$H NMR (400 MHz, Methanol-d4) δ 9.29 (s, 1H), 8.25-8.14 (m, 2H), 8.09 (s, 1H), 7.59 (s, 1H), 7.41 (d, J=2.7 Hz, 2H), 7.15 (d, J=10.5 Hz, 1H), 4.45 (t, J=4.5 Hz, 2H), 3.57-3.49 (m, 2H), 2.14 (s, 3H). LCMS-ESI$^+$ (m/z): [M+H]$^+$ calcd for $C_{24}H_{19}FN_5O_2$: 428.1; found: 428.4.

Example 46: (Z)-3-((1H-pyrrolo[3,2-b]pyridin-2-yl)methylene)-7-fluoro-5-(8-methyl-2,3-dihydro-1H-pyrido[2,3-b][1,4]oxazin-7-yl)indolin-2-one (C46)

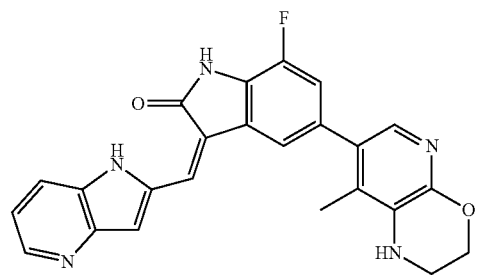 [SMILES: Cc1c(-c2cc(F)c3c(c2)/C(=C/c2cc4ncccc4[nH]2)C(=O)N3)cnc2c1NCCO2]

This compound was prepared as outlined above in procedures 1, 2, 3, and 5 using commercially available intermediates 5-bromo-7-fluoroindolin-2-one and 1H-pyrrolo[3,2-b]pyridine-2-carbaldehyde.

$^1$H NMR (400 MHz, Methanol-d4) δ 8.75-8.67 (m, 1H), 8.63 (dd, J=5.7, 1.1 Hz, 1H), 8.06 (s, 1H), 7.75 (dd, J=8.3, 5.7 Hz, 1H), 7.58 (d, J=1.4 Hz, 1H), 7.44 (s, 1H), 7.34 (d, J=0.9 Hz, 1H), 7.16 (dd, J=10.6, 1.4 Hz, 1H), 4.56-4.45 (m, 2H), 3.61-3.49 (m, 2H), 2.16 (s, 3H). LCMS-ESI$^+$ (m/z): [M+H]$^+$ calcd for $C_{24}H_{19}FN_5O_2$: 428.1; found: 428.4.

Example 47: (Z)-3-((1H-pyrrolo[3,2-c]pyridin-2-yl)methylene)-5-(8-methyl-2,3-dihydro-1H-pyrido[2,3-b][1,4]oxazin-7-yl)-1,3-dihydro-2H-pyrrolo[2,3-b]pyridin-2-one (C47)

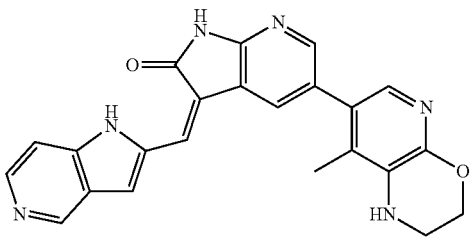 [SMILES: Cc1c(-c2cnc3c(c2)/C(=C/c2cc4cnccc4[nH]2)C(=O)N3)cnc2c1NCCO2]

This compound was prepared as outlined above in procedures 1, 2, 3, and 5 using commercially available intermediates 5-bromo-1,3-dihydro-2H-pyrrolo[2,3-b]pyridin-2-one and 1H-pyrrolo[3,2-c]pyridine-2-carbaldehyde.

$^1$H NMR (400 MHz, Methanol-d4) δ 9.24 (s, 1H), 8.41 (d, J=6.7 Hz, 1H), 8.16-8.01 (m, 4H), 7.59 (s, 1H), 7.37 (s, 1H), 4.38 (d, J=5.5 Hz, 2H), 3.51-3.46 (m, 2H), 2.11 (s, 3H). LCMS-ESI$^+$ (m/z): [M+H]$^+$ calcd for $C_{23}H_{19}N_6O_2$: 411.2; found: 411.4.

Example 48: (Z)-3-((1H-pyrrolo[3,2-c]pyridin-2-yl)methylene)-6-chloro-5-(8-methyl-2,3-dihydro-1H-pyrido[2,3-b][1,4]oxazin-7-yl)indolin-2-one (C48)

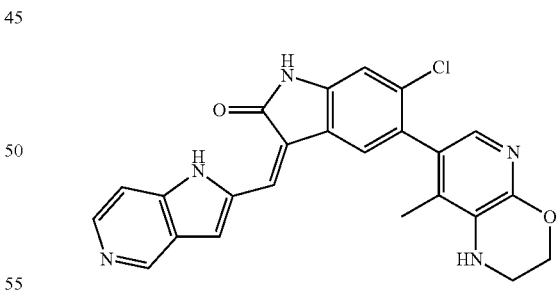

This compound was prepared as outlined above in procedures 1, 2, 3, and 5 using commercially available intermediates 5-bromo-6-chloroindolin-2-one and 1H-pyrrolo[3,2-c]pyridine-2-carbaldehyde.

$^1$H NMR (400 MHz, Methanol-d4) δ 9.23 (d, J=1.0 Hz, 1H), 8.40 (dd, J=6.8, 0.9 Hz, 1H), 8.14 (d, J=6.8 Hz, 1H), 7.96 (s, 1H), 7.69 (s, 1H), 7.55 (s, 1H), 7.37 (s, 1H), 7.15 (s, 1H), 4.51 (t, J=4.4 Hz, 2H), 3.55 (d, J=4.8 Hz, 2H), 2.02 (s, 3H). LCMS-ESI$^+$ (m/z): [M+H]$^+$ calcd for $C_{24}H_{19}ClN_5O_2$: 444.1; found: 444.9.

Example 49: (Z)-3-((1H-pyrrolo[3,2-c]pyridin-2-yl)methylene)-6-fluoro-5-(8-methyl-2,3-dihydro-1H-pyrido[2,3-b][1,4]oxazin-7-yl)indolin-2-one (C49)

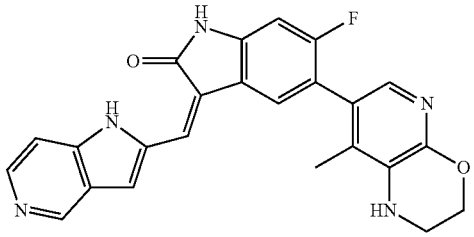 [SMILES: Cc1c(-c2cc3c(cc2F)NC(=O)/C3=C\c2cc3cnccc3[nH]2)cnc2c1NCCO2]

This compound was prepared as outlined above in procedures 1, 2, 3, and 5 using commercially available intermediates 5-bromo-6-fluoroindolin-2-one and 1H-pyrrolo[3,2-c]pyridine-2-carbaldehyde.

$^1$H NMR (400 MHz, Methanol-d4) δ 9.22 (d, J=0.9 Hz, 1H), 8.40 (dd, J=6.8, 0.9 Hz, 1H), 8.13 (dt, J=6.8, 0.9 Hz, 1H), 7.93 (s, 1H), 7.70 (d, J=7.0 Hz, 1H), 7.54 (s, 1H), 7.44 (s, 1H), 6.87 (d, J=9.5 Hz, 1H), 4.51 (t, J=4.5 Hz, 2H), 3.56 (s, 2H), 2.08 (d, J=1.7 Hz, 3H). LCMS-ESI$^+$ (m/z): [M+H]$^+$ calcd for $C_{24}H_{19}FN_5O_2$: 428.1; found: 428.4.

Example 50: (Z)-3-((1H-indol-2-yl)methylene)-6-chloro-5-(8-methyl-2,3-dihydro-1H-pyrido[2,3-b][1,4]oxazin-7-yl)indolin-2-one (C50)

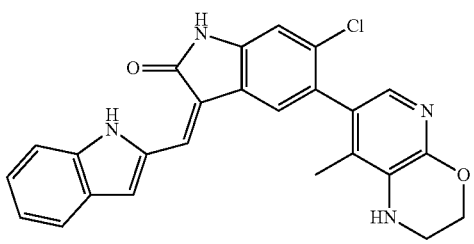 [SMILES: Cc1c(-c2cc3c(cc2Cl)NC(=O)/C3=C\c2cc3ccccc3[nH]2)cnc2c1NCCO2]

This compound was prepared as outlined above in procedures 1, 2, 3, and 5 using commercially available intermediates 5-bromo-6-chloroindolin-2-one and 1H-indole-2-carbaldehyde.

$^1$H NMR (400 MHz, Methanol-d4) δ 7.80 (d, J=1.6 Hz, 1H), 7.62 (d, J=8.9 Hz, 2H), 7.51-7.42 (m, 2H), 7.29 (ddd, J=8.3, 6.9, 1.1 Hz, 1H), 7.13-7.04 (m, 3H), 4.60 (t, J=4.5 Hz, 2H), 3.61 (q, J=4.2 Hz, 2H), 2.07 (s, 3H). LCMS-ESI$^+$ (m/z): [M+H]$^+$ calcd for $C_{25}H_{20}C_1N_4O_2$: 443.1; found: 443.9.

Example 51: (Z)-3-((1H-indol-2-yl)methylene)-6-fluoro-5-(8-methyl-2,3-dihydro-1H-pyrido[2,3-b][1,4]oxazin-7-yl)indolin-2-one (C51)

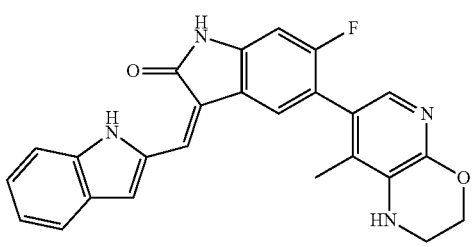 [SMILES: Cc1c(-c2cc3c(cc2F)NC(=O)/C3=C\c2cc3ccccc3[nH]2)cnc2c1NCCO2]

This compound was prepared as outlined above in procedures 1, 2, 3, and 5 using commercially available intermediates 5-bromo-6-fluoroindolin-2-one and 1H-indole-2-carbaldehyde.

$^1$H NMR (400 MHz, Methanol-d4) δ 7.78 (s, 1H), 7.61 (t, J=7.8 Hz, 2H), 7.50-7.43 (m, 2H), 7.28 (t, J=7.4 Hz, 1H), 7.10-7.03 (m, 2H), 6.83 (d, J=9.7 Hz, 1H), 4.55 (t, J=4.5 Hz, 2H), 3.62-3.53 (m, 2H), 2.11 (d, J=1.7 Hz, 3H). LCMS-ESI$^+$ (m/z): [M+H]$^+$ calcd for $C_{25}H_{20}FN_4O_2$: 427.2; found: 427.4.

Example 52: (Z)-3-((1H-pyrrolo[2,3-c]pyridin-2-yl)methylene)-5-(8-methyl-2,3-dihydro-1H-pyrido[2,3-b][1,4]oxazin-7-yl)indolin-2-one (C52)

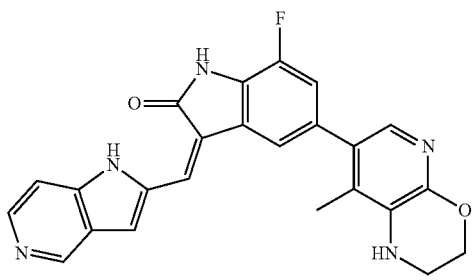 [SMILES: Cc1c(-c2cc(F)c3c(c2)/C(=C/c2cc4cnccc4[nH]2)C(=O)N3)cnc2c1NCCO2]

This compound was prepared as outlined above in procedures 1, 2, 3, and 5 using commercially available intermediates 5-bromo-7-fluoroindolin-2-one and 1H-pyrrolo[3,2-c]pyridine-2-carbaldehyde.

$^1$H NMR (400 MHz, Methanol-d4) δ 9.24 (s, 1H), 8.41 (d, J=6.9 Hz, 1H), 8.14 (d, J=6.8 Hz, 1H), 8.05 (s, 1H), 7.61-7.52 (m, 2H), 7.43 (s, 1H), 7.13 (d, J=10.6 Hz, 1H), 4.49 (t, J=4.5 Hz, 2H), 3.55 (t, J=4.5 Hz, 2H), 2.16 (s, 3H). LCMS-ESI$^+$ (m/z): [M+H]$^+$ calcd for $C_{24}H_{19}FN_5O_2$: 428.1; found: 428.4.

Example 53: (Z)-3-((1H-indol-2-yl)methylene)-7-fluoro-5-(8-methyl-2,3-dihydro-1H-pyrido[2,3-b][1,4]oxazin-7-yl)indolin-2-one (C53)

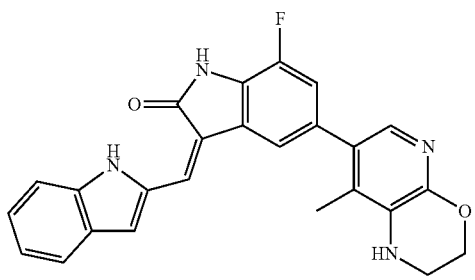 [SMILES: Cc1c(-c2cc(F)c3c(c2)/C(=C/c2cc4ccccc4[nH]2)C(=O)N3)cnc2c1NCCO2]

This compound was prepared as outlined above in procedures 1, 2, 3, and 5 using commercially available intermediates 5-bromo-7-fluoroindolin-2-one and 1H-indole-2-carbaldehyde.

$^1$H NMR (400 MHz, Methanol-d4) δ 7.88 (s, 1H), 7.63 (d, J=8.2 Hz, 1H), 7.47 (dd, J=12.0, 7.8 Hz, 3H), 7.33-7.27 (m, 1H), 7.12-6.99 (m, 3H), 4.52 (t, J=4.5 Hz, 2H), 3.57 (t, J=4.4 Hz, 2H), 2.18 (s, 3H). LCMS-ESI$^+$ (m/z): [M+H]$^+$ calcd for $C_{25}H_{20}FN_4O_2$: 427.2; found: 427.4.

Example 54: (Z)-3-((1H-pyrrolo[3,2-c]pyridin-2-yl)methylene)-7-fluoro-4-methyl-5-(8-methyl-2,3-dihydro-1H-pyrido[2,3-b][1,4]oxazin-7-yl)indolin-2-one (C54)

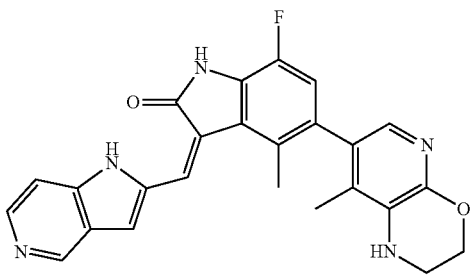 [SMILES: Cc1c(-c2cc(F)c3c(c2C)/C(=C/c2cc4cnccc4[nH]2)C(=O)N3)cnc2c1NCCO2]

This compound was prepared as outlined above in procedures 1, 2, 3, and 5 using 7-fluoro-4-methylindolin-2-one (19) and commercially available intermediate 1H-pyrrolo[3,2-c]pyridine-2-carbaldehyde.

$^1$H NMR (400 MHz, Methanol-d4) δ 9.25 (d, J=0.8 Hz, 1H), 8.42 (dd, J=6.8, 0.9 Hz, 1H), 8.15 (dt, J=6.8, 0.9 Hz, 1H), 8.07 (s, 1H), 7.70 (d, J=0.9 Hz, 1H), 7.42 (s, 1H), 7.04 (d, J=9.9 Hz, 1H), 4.63 (t, J=4.5 Hz, 2H), 3.64 (td, J=4.3, 2.4 Hz, 2H), 2.41 (s, 3H), 2.05 (s, 3H). LCMS-ESI$^+$ (m/z): [M+H]$^+$ calcd for $C_{25}H_{21}FN_5O_2$: 442.2; found: 442.1.

Example 55: (Z)-3-((1H-indol-2-yl)methylene)-5-(8-methyl-2,3-dihydro-1H-pyrido[2,3-b][1,4]oxazin-7-yl)-1,3-dihydro-2H-pyrrolo[2,3-b]pyridin-2-one (C55)

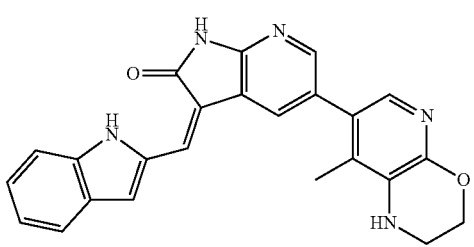 [SMILES: Cc1c(-c2cnc3c(c2)/C(=C/c2cc4ccccc4[nH]2)C(=O)N3)cnc2c1NCCO2]

This compound was prepared as outlined above in procedures 1, 2, 3, and 5 using commercially available intermediates 5-bromo-1,3-dihydro-2H-pyrrolo[2,3-b]pyridin-2-one and 1H-indole-2-carbaldehyde.

$^1$H NMR (400 MHz, Methanol-d4) δ 8.02 (d, J=14.7 Hz, 2H), 7.93 (s, 1H), 7.64 (d, J=7.9 Hz, 1H), 7.57-7.45 (m, 2H), 7.31 (t, J=7.4 Hz, 1H), 7.17-7.05 (m, 2H), 4.64 (d, J=5.4 Hz, 2H), 3.64 (s, 2H), 2.24 (s, 3H). LCMS-ESI$^+$ (m/z): [M+H]$^+$ calcd for $C_{24}H_{20}N_5O_2$: 410.2; found: 410.4.

Example 56: (Z)-3-((1H-indol-2-yl)methylene)-7-fluoro-4-methyl-5-(8-methyl-2,3-dihydro-1H-pyrido[2,3-b][1,4]oxazin-7-yl)indolin-2-one (C56)

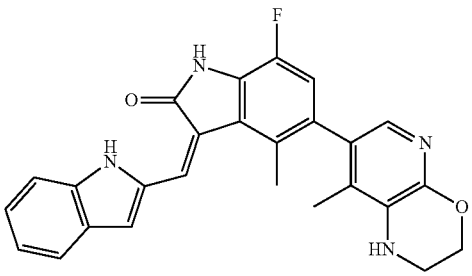 [SMILES: Cc1c(-c2cc(F)c3c(c2C)/C(=C/c2cc4ccccc4[nH]2)C(=O)N3)cnc2c1NCCO2]

This compound was prepared as outlined above in procedures 1, 2, 3, and 5 using 7-fluoro-4-methylindolin-2-one (19) and commercially available intermediate 1H-indole-2-carbaldehyde.

$^1$H NMR (400 MHz, Methanol-d4) δ 13.07 (s, 1H), 8.00 (d, J=1.6 Hz, 1H), 7.63 (d, J=8.1 Hz, 1H), 7.49 (dd, J=8.4, 1.0 Hz, 1H), 7.41 (s, 1H), 7.30 (ddd, J=8.2, 7.0, 1.1 Hz, 1H), 7.14 (d, J=1.1 Hz, 1H), 7.08 (ddd, J=8.1, 6.9, 1.0 Hz, 1H), 6.90 (d, J=10.0 Hz, 1H), 4.63 (t, J=4.6 Hz, 2H), 3.72-3.55 (m, 2H), 2.37 (s, 3H), 2.05 (s, 3H). LCMS-ESI$^+$ (m/z): [M+H]$^+$ calcd for $C_{26}H_{22}FN_4O_2$: 441.2; found: 441.1.

Example 57: (Z)-3-((1H-pyrrolo[3,2-b]pyridin-2-yl)methylene)-5-(8-methyl-2,3-dihydro-1H-pyrido[2,3-b][1,4]oxazin-7-yl)indolin-2-one (C57)

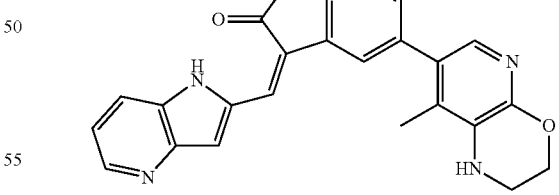

This compound was prepared as outlined above in procedures 1, 2, 3, and 5 using commercially available intermediate 1H-pyrrolo[3,2-b]pyridine-2-carbaldehyde.

$^1$H NMR (400 MHz, Methanol-d4) δ 8.69 (d, J=8.3 Hz, 1H), 8.60 (dd, J=5.7, 1.1 Hz, 1H), 8.00 (s, 1H), 7.76-7.69 (m, 2H), 7.41 (s, 1H), 7.29 (dd, J=8.1, 1.4 Hz, 2H), 7.06 (d, J=8.0 Hz, 1H), 4.49 (t, J=4.5 Hz, 2H), 3.60-3.50 (m, 2H), 2.15 (s, 3H). LCMS-ESI$^+$ (m/z): [M+H]$^+$ calcd for $C_{24}H_{20}N_5O_2$: 410.2; found: 410.4.

Example 58: (Z)-3-((1H-pyrrolo[2,3-c]pyridin-2-yl)methylene)-5-(8-methyl-2,3-dihydro-1H-pyrido[2,3-b][1,4]oxazin-7-yl)indolin-2-one (C58)

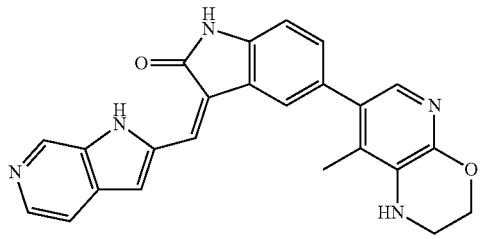 [SMILES: Cc1c(-c2ccc3c(c2)/C(=C/c2cc4ccncc4[nH]2)C(=O)N3)cnc2c1NCCO2]

This compound was prepared as outlined above in procedures 1, 2, 3, and 5 using commercially available intermediate 1H-pyrrolo[2,3-c]pyridine-2-carbaldehyde.

$^1$H NMR (400 MHz, Methanol-d4) δ 9.28 (q, J=0.9 Hz, 1H), 8.19 (ddd, J=29.8, 6.5, 0.8 Hz, 2H), 8.04 (s, 1H), 7.77 (d, J=1.6 Hz, 1H), 7.44 (s, 1H), 7.38 (d, J=0.8 Hz, 1H), 7.31 (dd, J=8.0, 1.7 Hz, 1H), 7.08 (d, J=7.9 Hz, 1H), 4.58-4.48 (m, 2H), 3.63-3.51 (m, 2H), 2.18 (s, 3H). LCMS-ESI$^+$ (m/z): [M+H]$^+$ calcd for $C_{24}N_{20}N_5O_2$: 410.2; found: 410.4.

Example 59: (Z)-3-((1H-benzo[d]imidazol-2-yl)methylene)-5-(8-methyl-2,3-dihydro-1H-pyrido[2,3-b][1,4]oxazin-7-yl)indolin-2-one (C59)

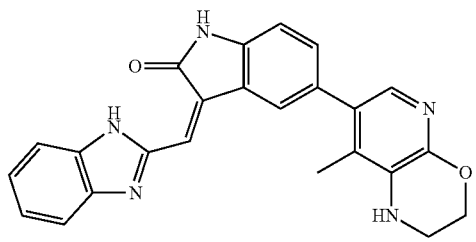 [SMILES: Cc1c(-c2ccc3c(c2)/C(=C/c2nc4ccccc4[nH]2)C(=O)N3)cnc2c1NCCO2]

This compound was prepared as outlined above in procedures 1, 2, 3, and 5 using commercially available intermediate 1H-benzo[d]imidazole-2-carbaldehyde.

$^1$H NMR (400 MHz, Methanol-d4) δ 7.86-7.72 (m, 4H), 7.51 (dd, J=6.3, 3.2 Hz, 2H), 7.46 (s, 1H), 7.34 (dd, J=8.0, 1.7 Hz, 1H), 7.09 (d, J=8.0 Hz, 1H), 4.56 (t, J=4.5 Hz, 2H), 3.60 (t, J=4.4 Hz, 2H), 2.19 (s, 3H). LCMS-ESI$^+$ (m/z): [M+H]$^+$ calcd for $C_{24}H_{20}N_5O_2$: 410.2; found: 410.4.

Example 60: (Z)-3-((1H-pyrrolo[3,2-c]pyridin-2-yl)methylene)-5-(8-methyl-2,3-dihydro-1H-pyrido[2,3-b][1,4]oxazin-7-yl)indolin-2-one (C60)

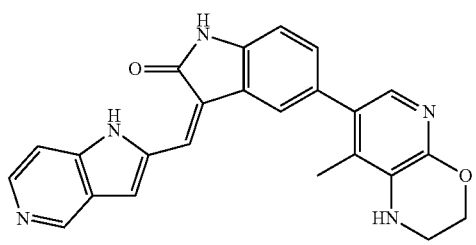 [SMILES: Cc1c(-c2ccc3c(c2)/C(=C/c2cc4cnccc4[nH]2)C(=O)N3)cnc2c1NCCO2]

This compound was prepared as outlined above in procedures 1, 2, 3, and 5 using commercially available intermediate 1H-pyrrolo[3,2-c]pyridine-2-carbaldehyde.

$^1$H NMR (400 MHz, Methanol-d4) δ 9.22 (d, J=0.9 Hz, 1H), 8.40 (dd, J=6.8, 0.9 Hz, 1H), 8.13 (d, J=6.8 Hz, 1H), 7.98 (s, 1H), 7.72 (s, 1H), 7.55 (s, 1H), 7.44 (d, J=3.1 Hz, 1H), 7.28 (d, J=8.1 Hz, 1H), 7.07 (d, J=8.0 Hz, 1H), 4.55 (t, J=4.7 Hz, 2H), 3.59 (t, J=4.4 Hz, 2H), 2.18 (d, J=2.7 Hz, 3H). LCMS-ESI$^+$ (m/z): [M+H]$^+$ calcd for $C_{24}H_{20}N_5O_2$: 410.2; found: 410.4.

Example 61: (Z)-3-((1H-pyrrolo[2,3-b]pyridin-2-yl)methylene)-5-(8-methyl-2,3-dihydro-1H-pyrido[2,3-b][1,4]oxazin-7-yl)indolin-2-one (C61)

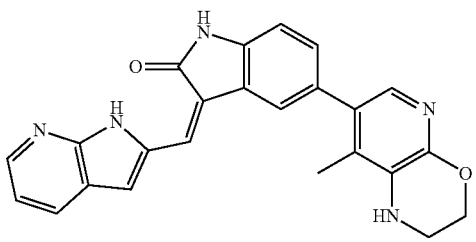 [SMILES: Cc1c(-c2ccc3c(c2)/C(=C/c2cc4cccnc4[nH]2)C(=O)N3)cnc2c1NCCO2]

This compound was prepared as outlined above in procedures 1, 2, 3, and 5 using commercially available intermediate 1H-pyrrolo[2,3-b]pyridine-2-carbaldehyde.

$^1$H NMR (400 MHz, Methanol-d4) δ 8.38 (dd, J=5.0, 1.6 Hz, 1H), 8.21 (dd, J=8.0, 1.5 Hz, 1H), 7.87 (s, 1H), 7.68 (d, J=1.7 Hz, 1H), 7.48 (s, 1H), 7.28-7.19 (m, 2H), 7.12 (s, 1H), 7.05 (d, J=8.0 Hz, 1H), 4.62 (t, J=4.5 Hz, 2H), 3.66-3.59 (m, 2H), 2.23 (s, 3H). LCMS-ESI$^+$ (m/z): [M+H]$^+$ calcd for $C_{25}H_{20}N_5O_2$: 410.2; found: 410.4.

Example 62: (Z)-3-((1H-indol-2-yl)methylene)-5-(8-methyl-2,3-dihydro-1H-pyrido[2,3-b][1,4]oxazin-7-yl)indolin-2-one (C62)

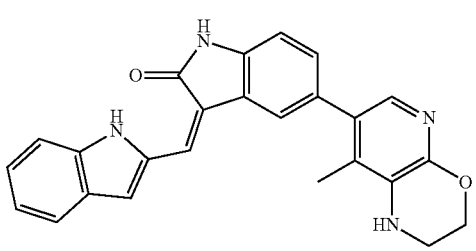 [SMILES: Cc1c(-c2ccc3c(c2)/C(=C/c2cc4ccccc4[nH]2)C(=O)N3)cnc2c1NCCO2]

This compound was prepared as outlined above in procedures 1, 2, 3, and 5 using commercially available intermediate 1H-indole-2-carbaldehyde.

$^1$H NMR (400 MHz, Methanol-d4) δ 7.82 (s, 1H), 7.65-7.58 (m, 2H), 7.47 (d, J=8.3 Hz, 1H), 7.41 (s, 1H), 7.27 (t, J=7.6 Hz, 1H), 7.15 (d, J=8.0 Hz, 1H), 7.10-6.99 (m, 3H), 4.49 (t, J=4.6 Hz, 2H), 3.59-3.51 (m, 2H), 2.16 (s, 3H). LCMS-ESI$^+$ (m/z): [M+H]$^+$ calcd for $C_{25}H_{21}N_4O_2$: 409.2; found: 409.5.

Example 63: (Z)-3-((1H-pyrrolo[2,3-c]pyridin-2-yl)methylene)-7-fluoro-4-methyl-5-(8-methyl-2,3-dihydro-1H-pyrido[2,3-b][1,4]oxazin-7-yl)indolin-2-one (C63)

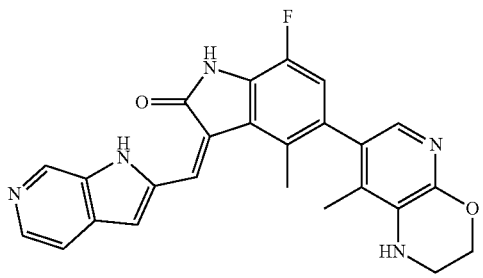 [SMILES: Cc1c(-c2cc(F)c3c(c2C)/C(=C/c2cc4ccncc4[nH]2)C(=O)N3)cnc2c1NCCO2]

This compound was prepared as outlined above in procedures 1, 2, 3, and 5 using 7-fluoro-4-methylindolin-2-one (19) and commercially available intermediate 1H-pyrrolo[2,3-c]pyridine-2-carbaldehyde.

$^1$H NMR (400 MHz, Methanol-d4) δ 9.31 (q, J=0.8 Hz, 1H), 8.24 (dd, J=6.5, 0.8 Hz, 1H), 8.17 (dd, J=6.5, 0.8 Hz, 1H), 8.09 (s, 1H), 7.51 (d, J=0.8 Hz, 1H), 7.37 (s, 1H), 7.06 (d, J=9.9 Hz, 1H), 4.56 (t, J=4.5 Hz, 2H), 3.60 (td, J=4.3, 2.2 Hz, 2H), 2.42 (s, 3H), 2.01 (s, 3H). LCMS-ESI$^+$ (m/z): [M+H]$^+$ calcd for $C_{25}H_{21}FN_5O_2$: 442.2; found: 442.1.

Example 64: (Z)-3-((1H-pyrrolo[3,2-b]pyridin-2-yl)methylene)-7-fluoro-4-methyl-5-(8-methyl-2,3-dihydro-1H-pyrido[2,3-b][1,4]oxazin-7-yl)indolin-2-one (C64)

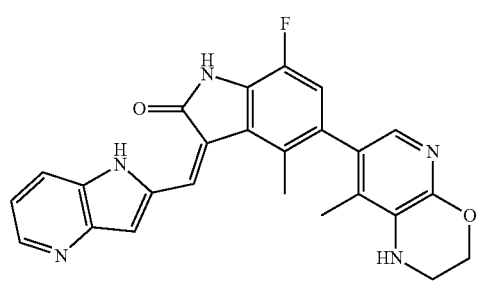 [SMILES: Cc1c(-c2cc(F)c3c(c2C)/C(=C/c2cc4ncccc4[nH]2)C(=O)N3)cnc2c1NCCO2]

This compound was prepared as outlined above in procedures 1, 2, 3, and 5 using 7-fluoro-4-methylindolin-2-one (19) and commercially available intermediate 1H-pyrrolo[3,2-b]pyridine-2-carbaldehyde.

$^1$H NMR (400 MHz, Methanol-d4) δ 8.76 (dt, J=8.5, 1.0 Hz, 1H), 8.64 (dd, J=5.7, 1.1 Hz, 1H), 8.08 (s, 1H), 7.77 (dd, J=8.4, 5.7 Hz, 1H), 7.48 (d, J=0.9 Hz, 1H), 7.39 (s, 1H), 7.06 (d, J=9.9 Hz, 1H), 4.66-4.51 (m, 2H), 3.62 (td, J=4.3, 2.0 Hz, 2H), 2.41 (s, 3H), 2.03 (s, 3H). LCMS-ESI$^+$ (m/z): [M+H]$^+$ calcd for $C_{25}H_{21}FN_5O_2$: 442.2; found: 442.1.

Example 65: (Z)-3-((1H-pyrazol-4-yl)methylene)-7-fluoro-4-methyl-5-(8-methyl-2,3-dihydro-1H-pyrido[2,3-b][1,4]oxazin-7-yl)indolin-2-one (C65)

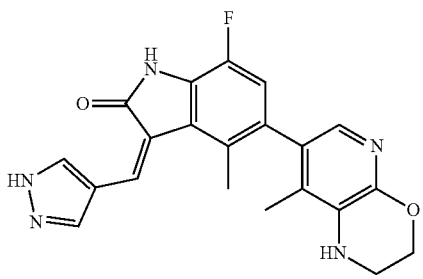 [SMILES: Cc1c(-c2cc(F)c3c(c2C)/C(=C/c2cn[nH]c2)C(=O)N3)cnc2c1NCCO2]

This compound was prepared as outlined above in procedures 1, 2, 3, and 5 using 7-fluoro-4-methylindolin-2-one (19) and commercially available intermediate 1H-pyrazole-4-carbaldehyde.

$^1$H NMR (400 MHz, Methanol-d4) δ 8.65 (s, 2H), 7.95 (s, 1H), 7.40 (s, 1H), 6.89 (d, J=10.0 Hz, 1H), 4.62 (q, J=6.2, 5.4 Hz, 2H), 3.63 (td, J=4.4, 2.6 Hz, 2H), 2.33 (s, 3H), 2.04 (s, 3H). LCMS-ESI$^+$ (m/z): [M+H]$^+$ calcd for $C_{21}H_{19}FN_5O_2$: 392.1; found: 392.1.

Example 66: (Z)-3-((1H-pyrazol-4-yl)methylene)-7-chloro-5-(8-methyl-2,3-dihydro-1H-pyrido[2,3-b][1,4]oxazin-7-yl)indolin-2-one (C66)

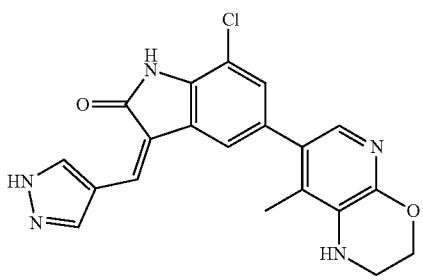 [SMILES: Cc1c(-c2cc(Cl)c3c(c2)/C(=C/c2cn[nH]c2)C(=O)N3)cnc2c1NCCO2]

This compound was prepared as outlined above in procedures 1, 2, 3, and 5 using commercially available intermediates 1H-pyrazole-4-carbaldehyde and 5-bromo-7-chloroindolin-2-one.

$^1$H NMR (400 MHz, Methanol-d4) δ 8.64 (s, 2H), 7.83 (s, 1H), 7.52 (d, J=1.5 Hz, 1H), 7.44 (s, 1H), 7.18 (d, J=1.5 Hz, 1H), 4.55 (t, J=4.4 Hz, 2H), 3.59 (t, J=4.5 Hz, 2H), 2.18 (s, 3H). LCMS-ESI$^+$ (m/z): [M+H]$^+$ calcd for $C_{20}H_{17}ClN_5O_2$: 394.1; found: 394.8.

Example 67: (Z)-3-((1H-pyrazol-4-yl)methylene)-7-methyl-5-(8-methyl-2,3-dihydro-1H-pyrido[2,3-b][1,4]oxazin-7-yl)indolin-2-one (C67)

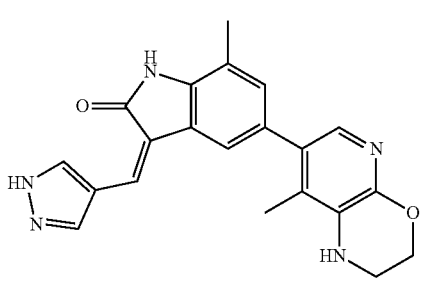 [SMILES: Cc1cc(-c2cnc3c(c2C)NCCO3)cc2c1NC(=O)/C2=C\c1cn[nH]c1]

This compound was prepared as outlined above in procedures 1, 2, 3, and 5 using commercially available intermediates 1H-pyrazole-4-carbaldehyde and 5-bromo-7-mrthylindolin-2-one.

$^1$H NMR (400 MHz, Methanol-d4) δ 8.62 (s, 2H), 7.74 (s, 1H), 7.42 (d, J=11.7 Hz, 2H), 6.98 (s, 1H), 4.60 (t, J=4.5 Hz, 2H), 3.62 (t, J=4.5 Hz, 2H), 2.33 (s, 3H), 2.21 (s, 3H). LCMS-ESI$^+$ (m/z): [M+H]$^+$ calcd for $C_{21}H_{20}N_5O_2$: 374.2; found: 374.4.

Example 68: (Z)-3-((3-methyl-1H-pyrazol-4-yl)methylene)-5-(8-methyl-2,3-dihydro-1H-pyrido[2,3-b][1,4]oxazin-7-yl)indolin-2-one (C68)

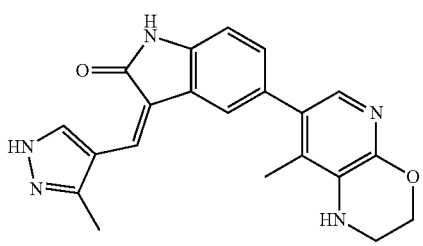 [SMILES: Cc1n[nH]cc1/C=C1\C(=O)Nc2ccc(-c3cnc4c(c3C)NCCO4)cc21]

This compound was prepared as outlined above in procedures 1, 2, 3, and 5 using commercially available intermediate 3-methyl-1H-pyrazole-4-carbaldehyde.

$^1$H NMR (400 MHz, Methanol-d4) δ 9.20 (s, 1H), 7.64 (dd, J=2.4, 0.8 Hz, 2H), 7.48 (s, 1H), 7.14 (dd, J=8.0, 1.7 Hz, 1H), 7.03-6.95 (m, 1H), 4.63 (dd, J=5.0, 3.9 Hz, 2H), 3.64 (dd, J=5.1, 4.0 Hz, 2H), 2.48 (s, 3H), 2.23 (s, 3H). LCMS-ESI$^+$ (m/z): [M+H]$^+$ calcd for $C_{21}H_{20}H_5O_2$: 374.2; found: 374.4.

Example 69: (Z)-3-((1H-pyrazol-4-yl)methylene)-5-(8-methyl-2,3-dihydro-1H-pyrido[2,3-b][1,4]oxazin-7-yl)indolin-2-one (C69)

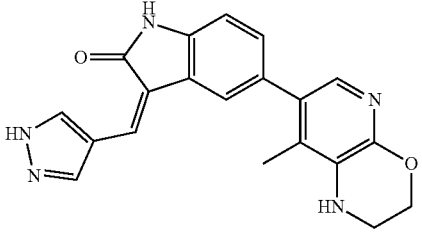 [SMILES: Cc1c(-c2ccc3c(c2)/C(=C/c2cn[nH]c2)C(=O)N3)cnc2c1NCCO2]

This compound was prepared as outlined above in procedures 1, 2, 3, and 5 using commercially available intermediate 1H-pyrazole-4-carbaldehyde.

$^1$H NMR (400 MHz, Methanol-d4) δ 8.61 (s, 2H), 7.77 (s, 1H), 7.57 (d, J=1.6 Hz, 1H), 7.43 (s, 1H), 7.14 (dd, J=8.0, 1.7 Hz, 1H), 6.99 (d, J=8.0 Hz, 1H), 4.62-4.50 (m, 2H), 3.60 (t, J=4.5 Hz, 2H), 2.19 (s, 3H). LCMS-ESI$^+$ (m/z): [M+H]$^+$ calcd for $C_{20}H_{18}N_5O_2$: 360.1; found: 360.4.

Example 70: (Z)-3-((1H-indol-3-yl)methylene)-5-(8-methyl-2,3-dihydro-1H-pyrido[2,3-b][1,4]oxazin-7-yl)indolin-2-one (C70)

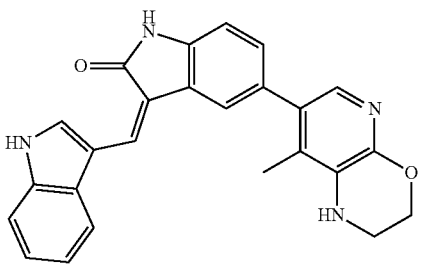

This compound was prepared as outlined above in procedures 1, 2, 3, and 5 using commercially available intermediate 1H-indole-3-carbaldehyde.

$^1$H NMR (400 MHz, Methanol-d4) δ 9.44 (s, 1H), 8.21 (s, 1H), 8.14 (s, 1H), 8.04-7.96 (m, 2H), 7.72 (d, J=1.6 Hz, 1H), 7.61 (d, J=7.8 Hz, 1H), 7.53-7.44 (m, 3H), 7.36 (s, 1H), 4.53 (t, J=4.5 Hz, 2H), 3.56 (t, J=4.4 Hz, 2H), 2.12 (s, 3H). LCMS-ESI$^+$ (m/z): [M+H]$^+$ calcd for $C_{25}H_{21}N_4O_2$: 409.2; found: 409.5.

Example 71: (Z)-3-((1H-imidazol-2-yl)methylene)-5-(2,3-dihydro-1H-pyrido[2,3-b][1,4]oxazin-7-yl)indolin-2-one (C71)

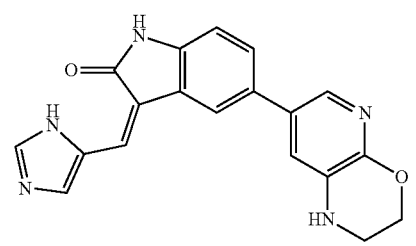 [SMILES: O=C1Nc2ccc(-c3cnc4c(c3)NCCO4)cc2/C1=C/c1cnc[nH]1]

This compound was prepared as outlined above in procedures 2, 3, and 5 using commercially available intermediate 1H-imidazole-2-carbaldehyde and 7-(4,4,5,5-tetramethyl-1,3,2-dioxaborolan-2-yl)-2,3-dihydro-1H-pyrido[2,3-b][1,4]oxazine.

$^1$H NMR (400 MHz, DMSO-d6) δ 11.44 (s, 1H), 8.06 (d, J=1.7 Hz, 1H), 7.89 (s, 1H), 7.77-7.68 (m, 3H), 7.52 (dd, J=8.1, 1.8 Hz, 1H), 7.19 (d, J=2.3 Hz, 1H), 7.02 (d, J=8.1 Hz, 1H), 4.32 (dd, J=5.2, 3.6 Hz, 2H), 3.33 (d, J=8.9 Hz, 2H). LCMS-ESI$^+$ (m/z): [M+H]$^+$ calcd for $C_{19}H_{15}N_5O_2$: 346.1; found: 346.1.

Example 72: ((Z)-3-((1H-imidazol-2-yl)methylene)-5-(8'-methyl-1',2'-dihydrospiro[cyclopropane-1,3'-pyrido[2,3-b][1,4]oxazin]-7'-yl)indolin-2-one (C72)

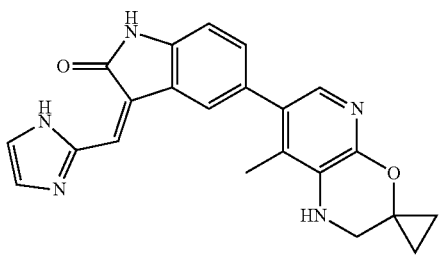 [SMILES: Cc1c(-c2ccc3c(c2)/C(=C/c2ncc[nH]2)C(=O)N3)cnc2c1NCC1(CC1)O2]

A. Preparation of 7'-bromo-8'-methyl-1',2'-dihydrospiro[cyclopropane-1,3'-pyrido[2,3-b][1,4]oxazine] ((22)

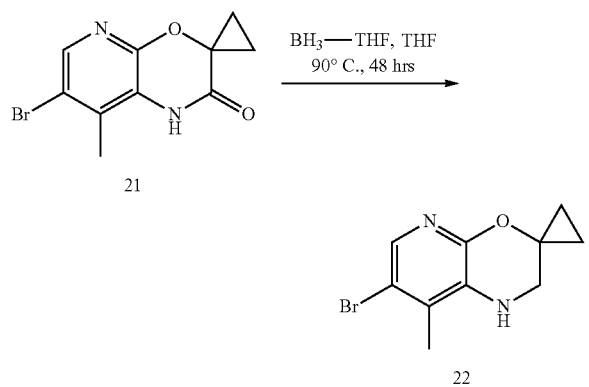

7'-bromo-8'-methylspiro[cyclopropane-1,3'-pyrido[2,3-b][1,4]oxazin]-2'(1'H)-one (260 mg, 0.966 mmol) (21) was dissolved in THF (2.0 mL) under argon and borane-THF (4 equiv.) was added. The reaction was heated to 90° C. for 24 hrs. Another 4 equiv. of borane-THF was added and the reaction was heated to 90° C. for another 24 hours. The reaction was cooled to room temperature, quenched with a 1:1 MeOH/water mixture (1 mL), concentrated under reduced pressure, dry loaded on to silica gel, and purified by silica gel chromatography (Rf 0.4 in 5% MeOH/CH$_2$Cl$_2$) to give 7'-bromo-8'-methyl-1',2'-dihydrospiro[cyclopropane-1,3'-pyrido[2,3-b][1,4]oxazine] (22). LCMS-ESI$^+$ (m/z): [M+H]$^+$ calcd for $C_{10}H_{11}BrN_2O$: 255.1; found: 255.1.

B. Preparation of (Z)-3-((1H-imidazol-2-yl)methylene)-5-(8'-methyl-1',2'-dihydrospiro[cyclopropane-1,3'-pyrido[2,3-b][1,4]oxazin]-7'-yl)indolin-2-one (C72)

This compound was prepared as outlined in procedures 1, 2, 3, and 5 using 7'-bromo-8'-methyl-1',2'-dihydrospiro[cyclopropane-1,3'-pyrido[2,3-b][1,4]oxazine] (22).

$^1$H NMR (400 MHz, DMSO-d6) δ 11.54 (s, 1H), 7.90-7.72 (m, 4H), 7.42-7.27 (m, 2H), 7.04 (d, J=8.0 Hz, 1H), 3.34 (s, 2H), 2.06 (s, 3H), 1.06-0.95 (m, 2H), 0.86-0.73 (m, 2H). LCMS-ESI$^+$ (m/z): [M+H]$^+$ calcd for $C_{22}H_{18}N_5O_3$: 386.1; found: 386.1.

HPK1 IC$_{50}$ Assay

The enzymatic activity of human HPK1 (MAP4K1) was monitored in a biochemical assay in the presence or absence of compounds and using a synthetic peptide substrate. An increase in phosphorylation of the peptide by HPK1 was indicative of its kinase activity.

Recombinant HPK1 kinase domain produced via baculovirus infection of insect cells was obtained from Proteros (Proteros Biostructures #PR-0322) and was pre-activated in the presence of 2 mM ATP (Sigma-Aldrich, cat #GE27-2056-01) and 2 mM magnesium chloride for 16 hours at 4° C. The protein reaction mixture was then loaded to a desalting column (Thermo Fisher Scientific, Cat #89889) to remove excess ATP. HPK1 was eluted with buffer containing 20 mM Tris (2-Amino-2-(hydroxymethyl)propane-1,3-diol) pH 8.0, 150 mM NaCl, 2 mM dithiothreitol and 5% glycerol, and was frozen at −80° C. for later use. HPK1 dual phosphorylation was confirmed by mass spectrometry.

Ten nanoliters of test compounds dissolved in DMSO at various concentrations were dispensed into a 384-well ProxiPlate (PerkinElmer #6008289). Five microliters of a solution of recombinant HPK1 diluted in HPK1 kinase assay buffer (50 mM BES [N,N-Bis(2-hydroxyethyl)-2-aminoethanesulfonic acid], pH 7.0; 10 mM magnesium chloride; 0.01% Triton X-100; 1 mM dithiothreitol; 0.01% bovine serum albumin; 0.1 mM sodium orthovanadate) was added to the compound-containing plate and was incubated for 15 minutes at 25° C. Five microliters of a mixture of ATP (Sigma-Aldrich #A6559) and peptide substrate STK S1 (Cisbio #61ST1BLC) diluted in HPK1 kinase assay buffer was then added to start the reaction. Final concentrations were 0.15 nM for HPK1, 10 μM for ATP, and 1 μM for the STK S1 peptide substrate. The reaction mixture was incubated at 25° C. for 3 hours and was stopped with the addition of 10 μl of an EDTA (Ethylenediaminetetraacetic acid)-containing detection buffer (Cisbio #62SDBRDF) supplemented with Europium cryptate-labeled anti-phospho-serine/threonine antibodies (Cisbio #62ST1PEJ) and XL665-labeled streptavidin (Cisbio #610SAXLG). The mixture was incubated for 16 hours at room temperature and peptide phosphorylation was measured by time-resolved fluorescence energy transfer (665 nm/620 nm) on an Envision plate reader (PerkinElmer).

Data in Table 1 were normalized based on positive (staurosporine) and negative (DMSO) controls. Least squares curve fittings were performed using a four-parameter variable slope nonlinear regression model. IC$_{50}$ is defined as the concentration of compound required to inhibit 50% of maximum phosphorylation. IC$_{50}$ values from multiple experiments were averaged by geometric mean and the standard deviation was calculated.

TABLE 1

| Compound No. | HPK1 IC$_{50}$ (nM) |
|---|---|
| C1 | 0.05 |
| C2 | 1.95 |
| C3 | 0.19 |
| C4 | 0.15 |
| C5 | 7.43 |
| C6 | 0.12 |
| C7 | 0.29 |
| C8 | 0.18 |
| C9 | 0.09 |
| C10 | 0.22 |
| C11 | 0.44 |
| C12 | 0.67 |
| C13 | 0.51 |
| C14 | 0.29 |
| C15 | 0.07 |
| C16 | 0.05 |
| C17 | 0.05 |
| C18 | 3.02 |
| C19 | 1.88 |
| C20 | 0.16 |
| C21 | 0.07 |
| C22 | 2.61 |
| C23 | 1.98 |
| C24 | 2.93 |
| C25 | 0.05 |
| C26 | 0.05 |
| C27 | 1.64 |
| C28 | 0.05 |
| C29 | 0.05 |
| C30 | 0.97 |
| C31 | 0.77 |
| C32 | 0.26 |
| C33 | 5.66 |
| C34 | 0.13 |
| C35 | 0.05 |
| C36 | 1.00 |
| C37 | 0.69 |
| C38 | 0.11 |
| C39 | 7.03 |
| C40 | 0.07 |
| C41 | 5.73 |
| C42 | 9.30 |
| C43 | 0.13 |
| C44 | 0.05 |
| C45 | 0.17 |
| C46 | 0.05 |
| C47 | 1.13 |
| C48 | 0.16 |
| C49 | 0.16 |
| C50 | 0.19 |
| C51 | 0.16 |
| C52 | 0.10 |
| C53 | 0.16 |
| C54 | 0.27 |
| C55 | 1.24 |
| C56 | 0.51 |
| C57 | 0.05 |
| C58 | 0.11 |
| C59 | 0.28 |
| C60 | 0.06 |
| C61 | 1.10 |
| C62 | 0.05 |
| C63 | 0.41 |
| C64 | 0.31 |
| C65 | 1.03 |
| C66 | 6.90 |
| C67 | 4.33 |
| C68 | 0.32 |
| C69 | 0.26 |
| C70 | 0.42 |
| C71 | 66.7 |
| C72 | 2.13 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter and is not intended to limit the appended claims to the specific embodiments illustrated.

What is claimed:

1. A method of treating a disease or disorder associated with increased hematopoietic progenitor kinase 1 (HPK1) activity in a subject in need thereof, comprising administering to the subject a therapeutically effective amount of a (i)-compound of Formula I:

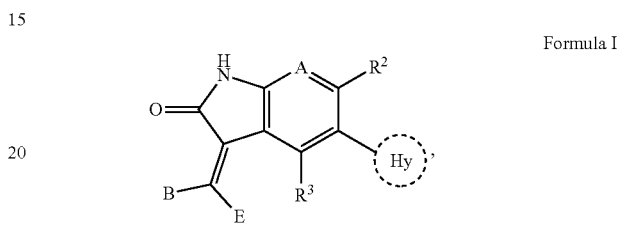

Formula I or a pharmaceutically acceptable salt thereof, wherein:
A is N or CR$^1$;
each R$^1$, R$^2$, and R$^3$ is independently H, halogen, -CN, -N(R$^{13}$)$_2$, C$_1$-C$_3$ alkyl, C$_1$-C$_3$ haloalkyl, C$_2$-C$_3$ alkynyl, C$_1$-C$_3$ alkoxy, or —SO$_2$R$^{13}$, wherein the C$_2$-C$_3$ alkynyl is unsubstituted or substituted with 1, 2, or 3 R$^9$ groups;

one of B and E is (G) and the other is J;
J is H, —CN, C$_1$-C$_3$ alkyl, or C$_3$-C$_6$ cycloalkyl; wherein the C$_1$-C$_3$ alkyl or C$_3$-C$_6$ cycloalkyl is unsubstituted or substituted with 1, 2, or 3 R$^{10}$ groups;

(G) is a group of formula

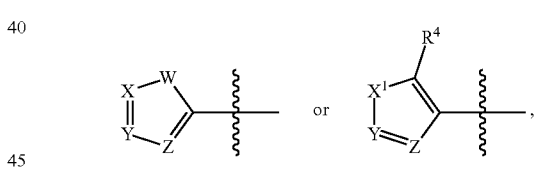

wherein
W is NR$^4$ or S;
X is N or CR$^5$;
Y is N or CR$^6$;
Z is N or CR$^7$;
X$^1$ is NH;
R$^4$ is H;
each R$^5$, R$^6$, and R$^7$ is independently H, halogen, —CN, -CON(R$^8$)$_2$, -NR$^{13}$C(O)R$^{13}$, —SO$_2$N(R$^{13}$)$_2$, C$_1$-C$_3$ alkyl, C$_1$-C$_3$ alkoxy, -N(R$^{13}$)$_2$, C$_3$-C$_6$ cycloalkyl, C$_6$-C$_{10}$ aryl, 5-10 membered heteroaryl having 1, 2, or 3 heteroatoms independently selected from N, O, and S, and 4-6 membered heterocyclyl having 1, 2, or 3 heteroatoms independently selected from N, O, and S; wherein the C$_1$-C$_3$ alkyl, C$_1$-C$_3$ alkoxy, C$_3$-C$_6$ cycloalkyl, C$_6$-C$_{10}$ aryl, 5-10 membered heteroaryl, or 4-6 membered heterocyclyl is unsubstituted or substituted with 1, 2, or 3 R$^{11}$ groups;
or wherein R$^5$ and R$^6$, or R$^6$ and R$^7$ together with atoms to which they are attached form a phenyl or a 5-6 membered heteroaryl having 1 or 2 heteroatoms independently selected from N, O, and S; wherein the phenyl or the 5-6 membered heteroaryl is unsubstituted or substituted with 1, 2, or 3 $R^{11}$ groups;

each $R^8$ is independently H or $C_1$-$C_3$ alkyl, wherein the $C_1$-$C_3$ alkyl is unsubstituted or substituted with 1, 2, or 3 $R^{12}$ groups; or wherein two $R^8$ groups together with the nitrogen they are attached to form a 4-6 membered heterocyclic ring having 1 or 2 heteroatoms selected from the group consisting of N, O, or S, wherein the 4-6 membered heterocyclic ring is unsubstituted or substituted with 1, 2, or 3 $R^{12}$ groups;

each $R^9$ is independently —$OR^{13}$, $C_1$-$C_3$ alkyl, or $C_3$-$C_6$ cycloalkyl;

each $R^{10}$ and $R^{11}$ is independently selected from the group consisting of —$OR^{13}$, halogen, CN, —$N(R^8)_2$, —CON$(R^8)_2$, —$N(R^{13})COR^{13}$, —$S(O)_2R^{13}$, $C_1$-$C_3$alkyl, $C_3$-$C_6$ cycloalkyl, 4-6 membered heterocyclyl having 1, 2, or 3 heteroatoms independently selected from N, O, and S, $C_6$-$C_{10}$ aryl, and 5-10 membered heteroaryl having 1, 2, or 3 heteroatoms independently selected from N, O, and S;

each $R^{12}$ is independently —$OR^{13}$, $C_1$-$C_3$ alkyl, or —$N(R^{13})_2$; wherein the $C_1$-$C_3$ alkyl is unsubstituted or substituted with 1, 2, or 3 groups independently selected from —$OR^{13}$ and —$N(R^{13})_2$, each $R^{13}$ is independently H or $C_1$-$C_3$ alkyl, wherein the $C_1$-$C_3$ alkyl is unsubstituted or substituted with 1, 2, or 3 $R^{22}$ groups;

each $R^{22}$ is independently selected from the group consisting of halogen, —OH, $C_1$-$C_3$ alkyl, $C_1$-$C_3$ alkoxy, —$NH_2$, —$NH(C_1$-$C_3$ alkyl), —$N(C_1$-$C_3$ alkyl)$_2$ wherein each $C_1$-$C_3$ alkyl is same or different, $C_3$-$C_6$ cycloalkyl, 4-6 membered heterocyclyl with 1, 2, or 3 heteroatoms selected from N, O, and S, $C_6$-$C_{10}$ aryl, and 5-10 membered heteroaryl having 1, 2, or 3 heteroatoms independently selected from N, O, and S; and Hy is a group of formula:

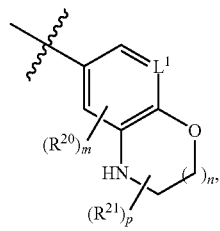

wherein $L^1$ is N or $CR^{19}$;
n is 0, 1 or 2;
m is 0, 1, or 2;
p is 0, 1, 2, 3, 4, 5, or 6;
$R^{19}$ is H, —$OR^{13}$, halogen, CN, —$N(R^{13})_2$, or $C_1$-$C_3$ alkyl;
each $R^{20}$ is independently —$OR^{13}$, halogen, CN, —$N(R^{13})_2$, or $C_1$-$C_3$ alkyl; and
each $R^{21}$ is independently —$OR^{13}$, oxo, halogen, CN, —$N(R^{13})_2$, or $C_1$-$C_3$ alkyl;
or two $R^{21}$ groups on same or adjoining atoms are joined together to form a 3-6 membered carbocyclic ring or a 3-6 membered heterocyclic ring having 1 or 2 heteroatoms selected from N, O, and S;

and (ii) a therapeutically effective amount of one or more additional therapeutic agents.

2. The method of claim 1, wherein the compound is of a Formula I-Z:

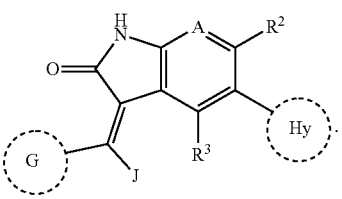

Formula I-Z

3. The method of claim 1, wherein the compound is of a Formula I-E:

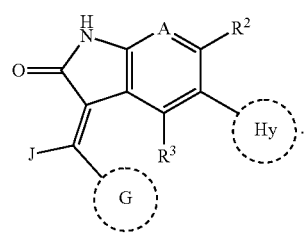

Formula I-E

4. The method of claim 1, wherein G is

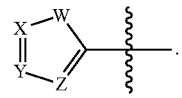

5. The method of claim 1, wherein G is

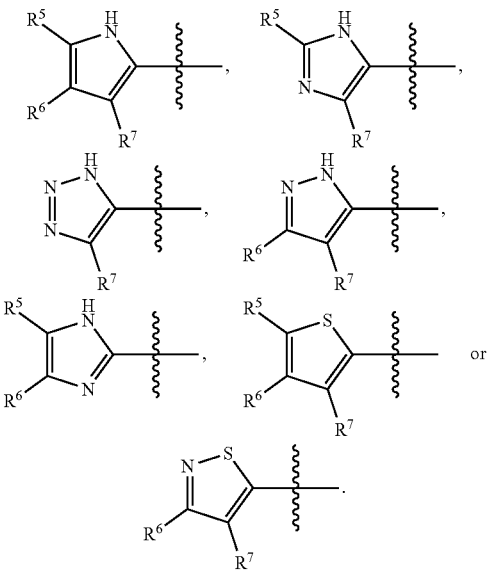

6. The method of claim 1, wherein  is

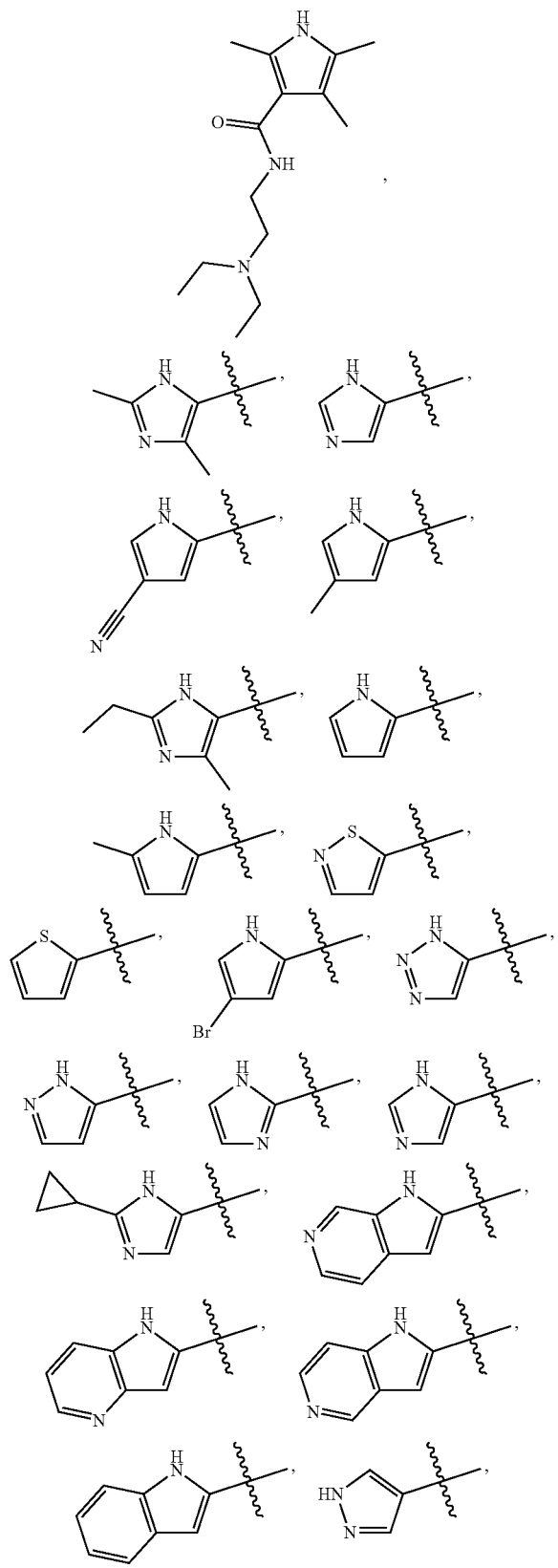

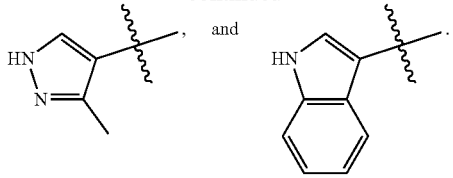

7. The method of claim 1, wherein the compound is of a Formula II-Z:

Formula II-Z

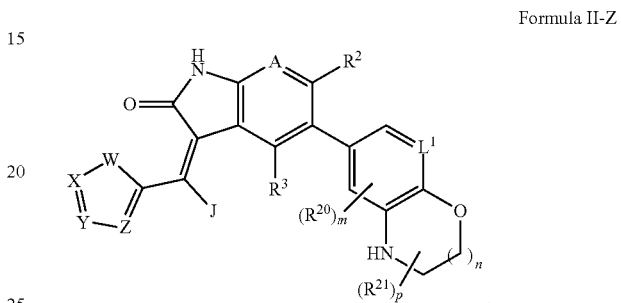

8. The method of claim 1, wherein the compound is of a Formula IIa-Z:

Formula IIa-Z

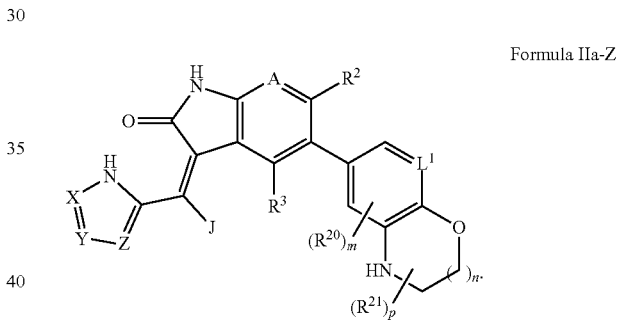

9. The method of claim 1, wherein each $R^5$, $R^6$, and $R^7$ is independently H, halogen, —CN, —CON($R^8$)$_2$, —NR$^{13}$C(O)R$^{13}$, —SO$_2$N($R^{13}$)$_2$, $C_1$-$C_3$ alkyl, 5-6 membered heteroaryl having 1 or 2 heteroatoms independently selected from N, O and S, or $C_3$-$C_6$ cycloalkyl; wherein the $C_1$-$C_3$ alkyl or the $C_3$-$C_6$ cycloalkyl is unsubstituted or substituted with 1, 2, or 3 $R^{11}$ groups.

10. The method of claim 1, wherein $R^5$ is H, $C_1$-$C_3$ alkyl, or $C_3$-$C_6$ cycloalkyl.

11. The method of claim 1, wherein $R^6$ is H, halogen, CN, $C_1$-$C_3$ alkyl, or CON($R^8$)$_2$.

12. The method of claim 1, wherein $R^7$ is H or $C_1$-$C_3$ alkyl.

13. The method of claim 1, wherein each $R^5$, $R^6$, and $R^7$ is H.

14. The method of claim 1, wherein:
X is CR$^5$;
Y is CR$^6$, and
wherein $R^5$ and $R^6$ together with atoms to which they are attached form a phenyl or 5-6 membered heteroaryl having 1 or 2 heteroatoms independently selected from N, O, and S; wherein the phenyl or the 5-6 membered heteroaryl is unsubstituted or substituted with 1, 2, or 3 $R^{11}$ groups.

15. The method of claim 1, wherein
Y is $CR^6$;
Z is $CR^7$, and
wherein $R^6$ and $R^7$ together with atoms to which they are attached form a phenyl or 5-6 membered heteroaryl having 1 or 2 heteroatoms independently selected from N, O, and S; wherein the phenyl or the 5-6 membered heteroaryl is unsubstituted or substituted with 1, 2, or 3 $R^{11}$ groups.

16. The method of claim 1, wherein $R^{11}$ is selected from the group consisting of (i) CN, (ii) —$N(R^8)_2$, (iii) —$N(R^{13})COR^{13}$, and (iv) 4-6 membered heterocyclyl having 1, 2, or 3, heteroatoms independently selected from N, O, and S;
wherein each $R^{13}$ is independently H or $C_1$-$C_3$ alkyl, wherein the $C_1$-$C_3$ alkyl is unsubstituted or substituted with 1, 2, or 3 $R^{22}$ groups; and
each $R^{22}$ is independently selected from the group consisting of halogen, —OH, $C_1$-$C_3$ alkyl, $C_1$-$C_3$ alkoxy, —$NH_2$, —$NH(C_1$-$C_3$ alkyl), —$N(C_1$-$C_3$ alkyl)$_2$ wherein each $C_1$-$C_3$ alkyl is same or different, $C_3$-$C_6$ cycloalkyl, 4-6 membered heterocyclyl with 1, 2, or 3 heteroatoms selected from N, O, and S, $C_6$-$C_{10}$ aryl, and 5-10 membered heteroaryl having 1, 2, or 3 heteroatoms independently selected from N, O, and S.

17. The method of claim 1, wherein $R^{11}$ is selected from the group consisting of (i) -CN, (ii) —$NH_2$, (iii) —NH-$COR^{13}$, and (iv) 6 membered heterocyclyl having 1 or 2 heteroatoms independently selected from N and O; wherein $R^{13}$ is $C_1$-$C_3$ alkyl.

18. The method of claim 1, wherein the compound has a Formula IIb-Z:

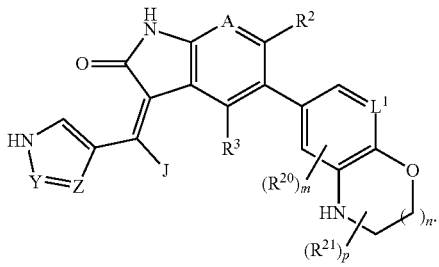

Formula IIb-Z wherein
L is N or $CR^{15}$;
M is N or $CR^{16}$;
Q is N or $CR^{17}$; and
R is N or $CR^{18}$; wherein each $R^{15}$, $R^{16}$, $R^{17}$, and $R^{18}$ is independently selected from the group consisting of H, halogen, CN, —$N(R^8)_2$, —$CON(R^8)_2$, —$N(R^{13})COR^{13}$, —$S(O)_2R^{13}$, $C_1$-$C_3$ alkyl, $C_1$-$C_3$ alkoxy, $C_6$-$C_{10}$ aryl, 5-10 membered heteroaryl having 1, 2, or 3 heteroatoms independently selected from N, O, and S, and 4-6 membered heterocyclyl having 1, 2, or 3 heteroatoms independently selected from N, O, and S.

19. The method of claim 18, wherein each $R^{15}$, $R^{16}$, $R^{17}$, and $R^{18}$ is independently selected from the group consisting of H, CN, —$N(R^8)_2$, and —$N(R^{13})COR^{13}$.

20. The method of claim 19, wherein Z is $CR^7$.

21. The method of claim 1, wherein  is

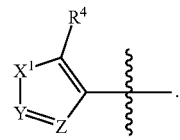

22. The method of claim 1, wherein the compound is of Formula III-Z:

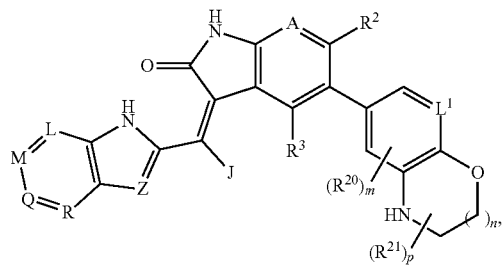

Formula III-Z

23. The method of claim 1, wherein Y is N.
24. The method of claim 1, wherein Z is $CR^7$.
25. The method of claim 1, wherein  is

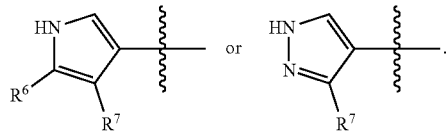

26. The method of claim 1, wherein $R^7$ is H or $CH_3$.
27. The method of claim 1, wherein the compound has a Formula IIIa-Z:

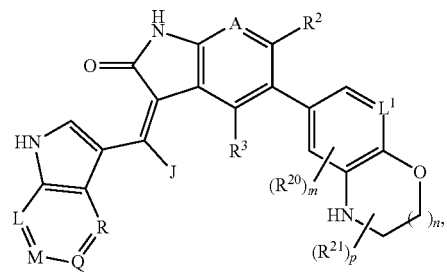

Formula IIIa-Z wherein
L is N or $CR^{15}$;
M is N or $CR^{16}$;
Q is N or $CR^{17}$; and
R is N or $CR^{18}$;
wherein each $R^{15}$, $R^{16}$, $R^{17}$, and $R^{18}$ is independently selected from the group consisting of H, halogen, CN, —$N(R^8)_2$, —$CON(R^8)_2$, —$N(R^{13})COR^{13}$, —$S(O)_2R^{13}$, $C_1$-$C_3$alkyl, $C_1$-$C_3$ alkoxy, $C_6$-$C_{10}$ aryl, 5-10 membered heteroaryl having 1, 2, or 3 heteroatoms independently selected from N, O, and S, and 4-6 membered heterocyclyl having 1, 2, or 3 heteroatoms independently selected from N, O, and S.

28. The method of claim 27, wherein each $R^{15}$, $R^{16}$, $R^{17}$, and $R^{18}$ is independently selected from the group consisting of H, CN, —N($R^8$)$_2$, and —N($R^{13}$)COR$^{13}$.

29. The method, wherein:
L is N; M is CR$^{16}$; Q is CR$^{17}$; and R is CR$^{18}$;
M is N; L is CR$^{15}$, Q is CR$^{17}$; and R is CR$^{18}$;
Q is N; L is CR$^{15}$; M is CR$^{16}$; and R is CR$^{18}$; or
R is N; L is CR$^{15}$; M is CR$^{16}$; and Q is CR$^{17}$.

30. The method of claim 27, wherein $R^{15}$, $R^{16}$, $R^{17}$, and $R^{18}$ are each H.

31. The method of claim 1, wherein A in CR$^1$.

32. The method of claim 1, wherein each $R^1$, $R^2$, and $R^3$ is independently H, halogen, C$_1$-C$_3$ alkyl, or C$_2$-C$_3$ alkynyl, wherein the C$_2$-C$_3$ alkynyl is unsubstituted or substituted with 1, 2, or 3 $R^9$ groups.

33. The method of claim 1, wherein both $R^1$ and $R^3$ are H.

34. The method of claim 1, wherein $R^2$ is H, halogen, CN, —N($R^{13}$)$_2$, C$_1$-C$_3$ alkoxy, C$_1$-C$_3$ alkyl, or C$_2$-C$_3$ alkynyl, wherein the C$_2$-C$_3$ alkynyl is unsubstituted or substituted with 1, 2, or 3 $R^9$ groups.

35. The method of claim 1, wherein $R^9$ is —OH, CH$_3$, or cyclopropyl.

36. The method of claim 1, wherein $R^2$ is H, C$_1$, F, —CH$_3$, —CN, —NH$_2$, —SO$_2$CH$_3$, OCH$_3$

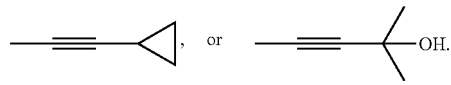

37. The method of claim 1, wherein $R^1$ is H, halogen or C$_1$-C$_3$ alkyl.

38. The method of claim 1, wherein $R^1$ is F or C$_1$ and $R^2$ is H.

39. The method of claim 1, wherein $R^1$ is F or C$_1$; $R^2$ is H; and $R^3$ is H or C$_1$-C$_3$ alkyl.

40. The method of claim 1, wherein each $R^1$, $R^2$, and $R^3$ is H.

41. The method of claim 1, wherein J is H or C$_1$-C$_3$ alkyl.

42. The method of claim 1, wherein m is 0 or 1; and p is 0, 1, 2, or 3.

43. The method of claim 1, wherein
m is 0 or 1;
p is 0, 1, 2, or 3;
$R^{20}$ is
C$_3$ alkyl; and
each $R^{21}$ is independently a halogen or oxo;
or two $R^{21}$ groups on same atoms are joined together to form a 3-6 membered carbocyclic ring or a 3-6 membered heterocyclic ring.

44. The method of claim 1, $R^{20}$ is C$_1$-C$_3$ alkyl.

45. The method of claim 1, and p is 0, 1, or 2.

46. The method of claim 1, wherein in p is 2 and the two $R^{21}$ groups are on same atom and are joined together to form a 3-6 membered carbocyclic ring or a 3-6 membered heterocyclic ring.

47. The method of claim 1, wherein p is 1 and $R^{21}$ is oxo.

48. The method of claim 1, wherein n is 0, 1, or 2.

49. The method of claim 1, wherein  is

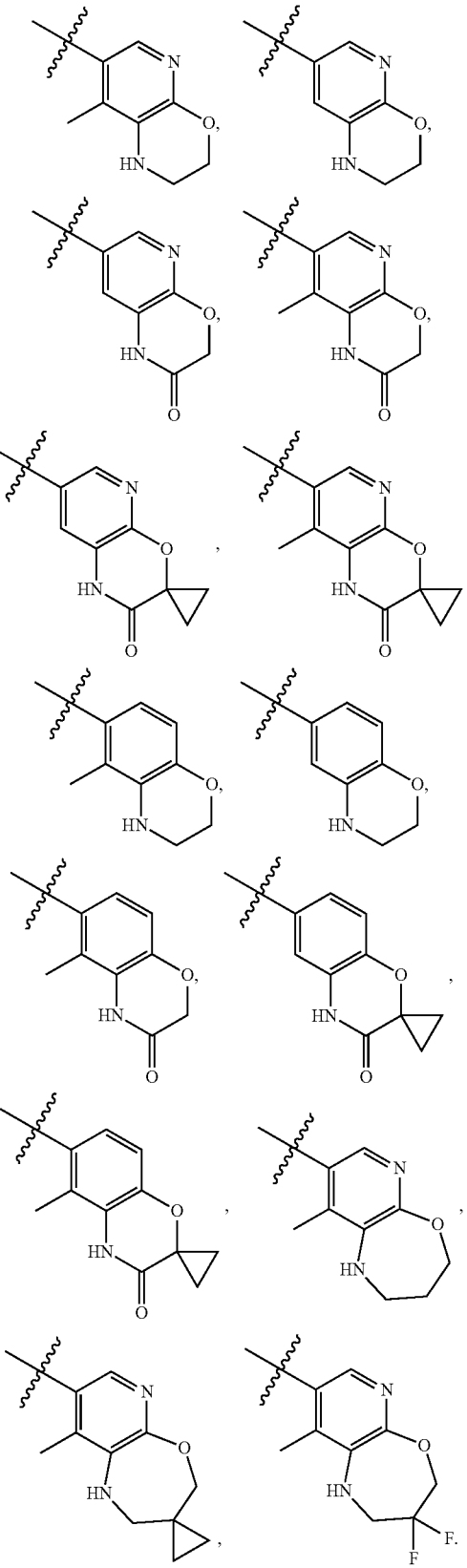

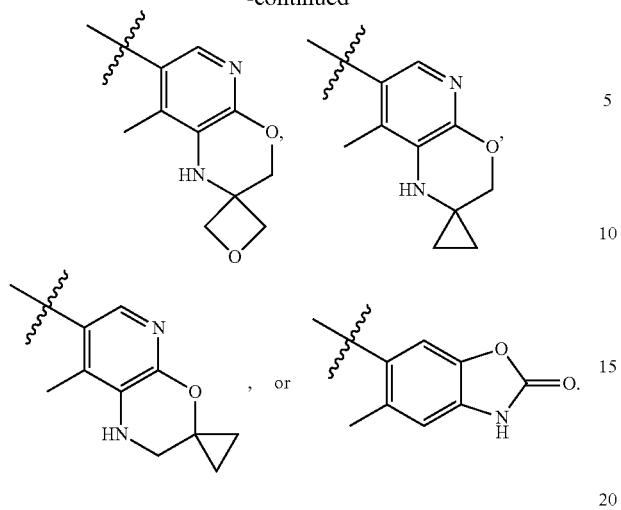
50. The method of claim 1, wherein the compound is selected from the group consisting of:
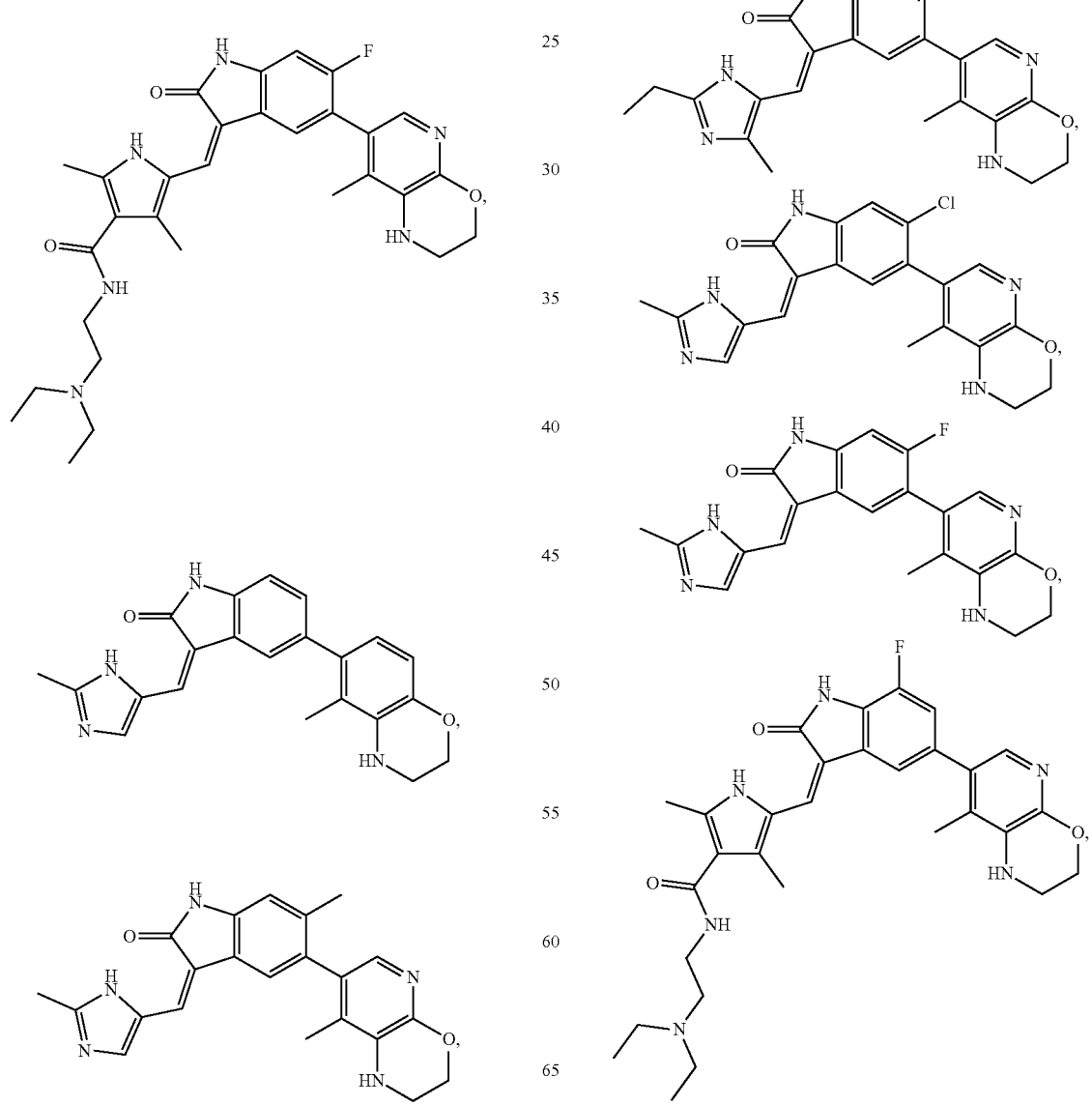

193
-continued
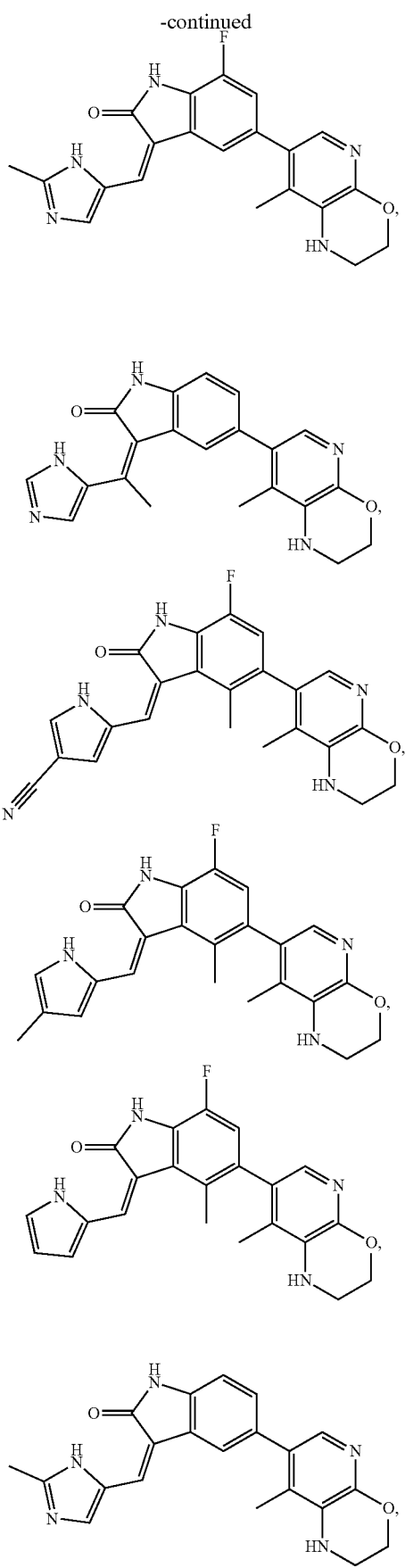
194
-continued
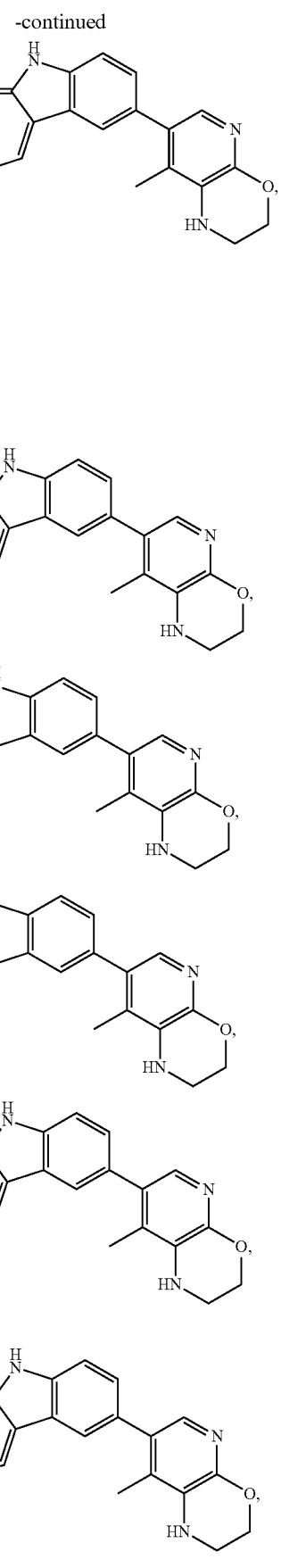

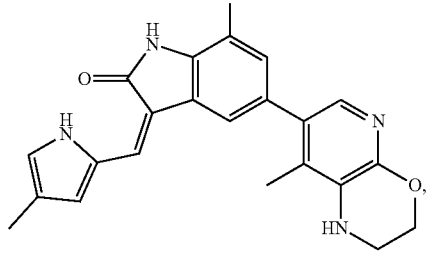
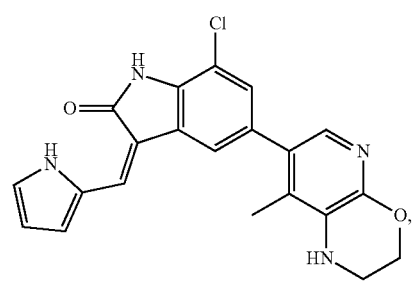
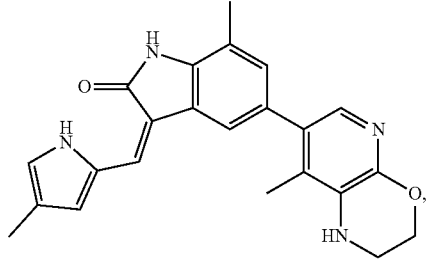
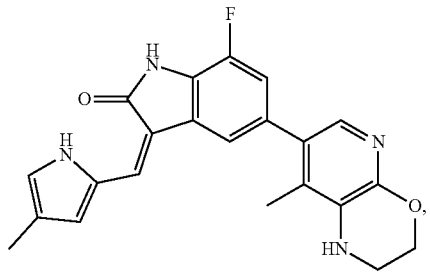
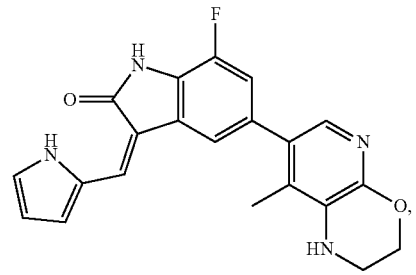
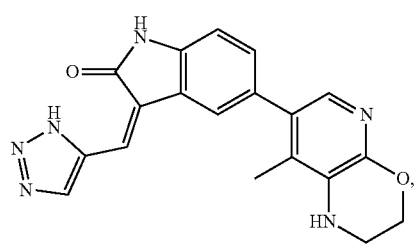
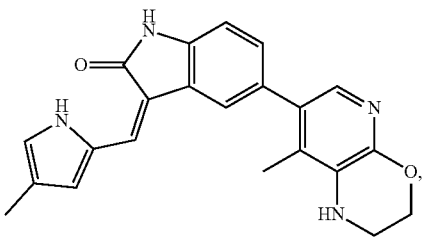
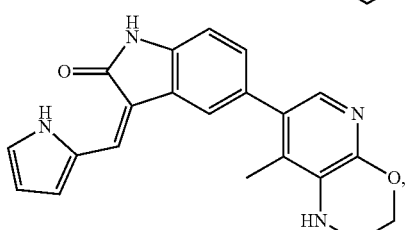
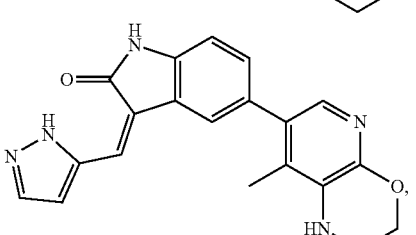
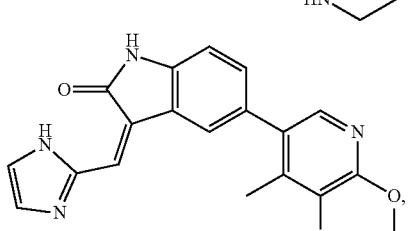
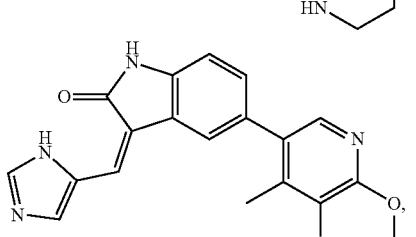
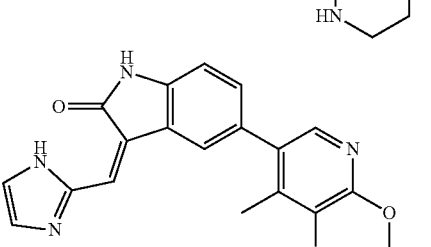
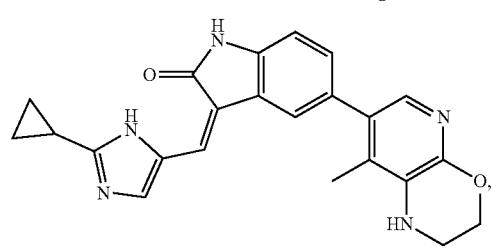

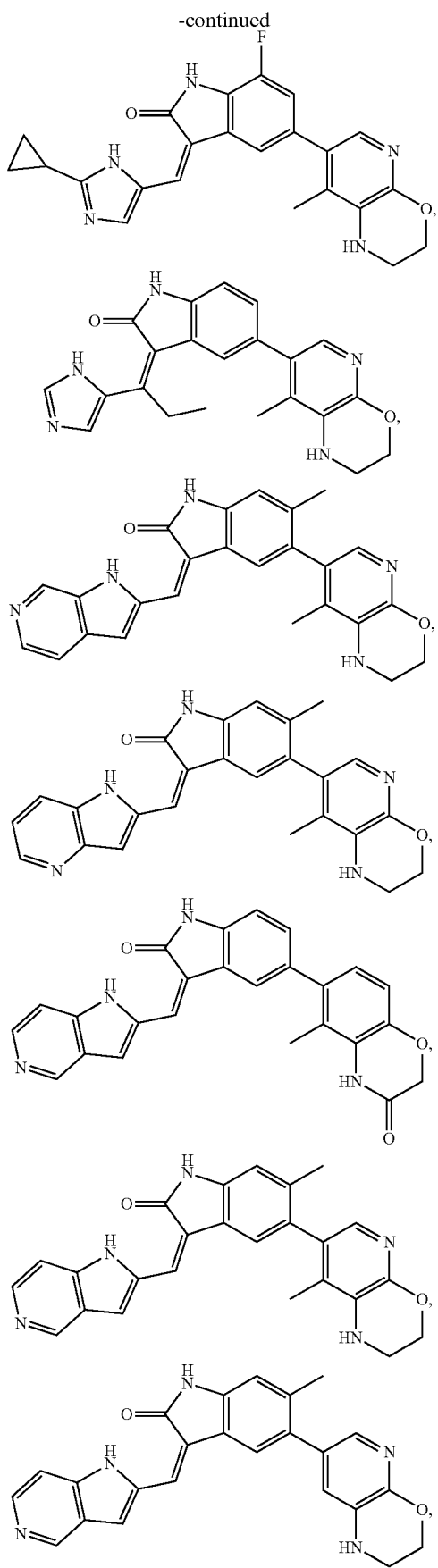
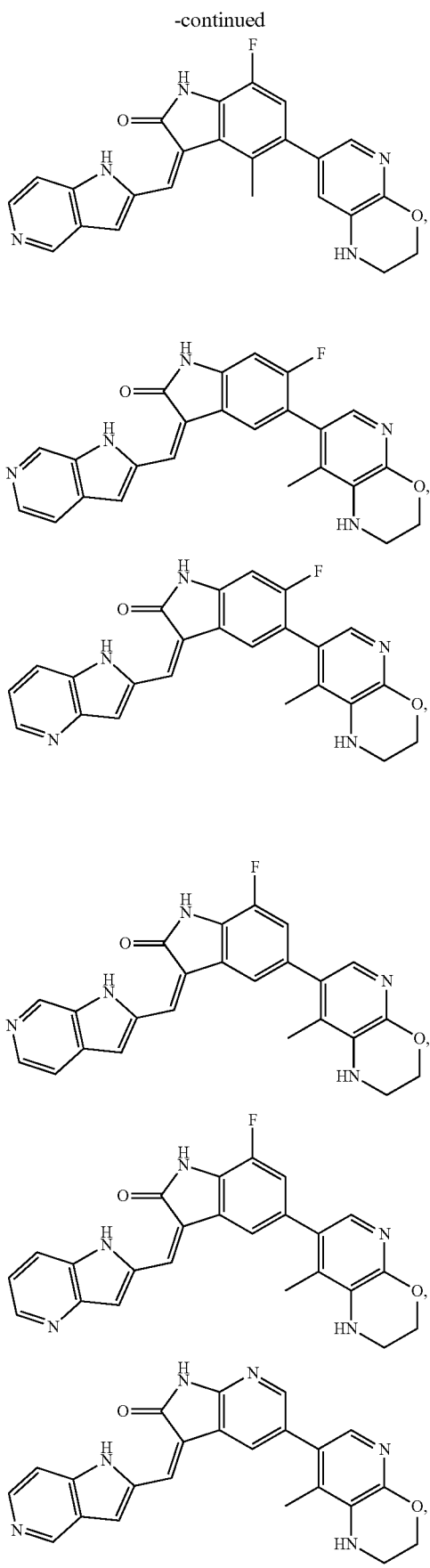

199
-continued
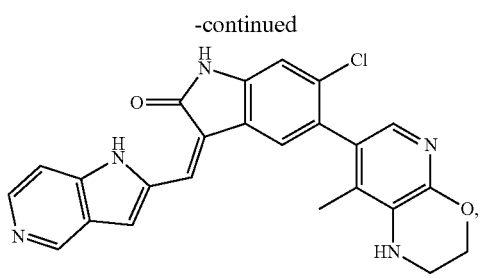
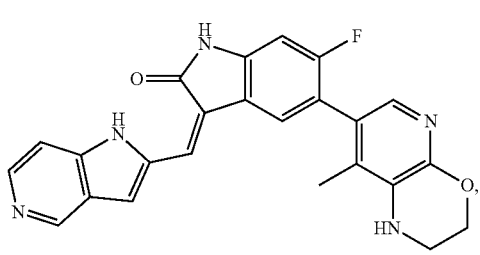
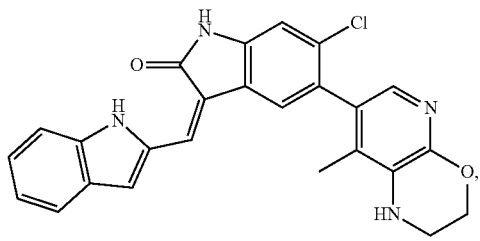
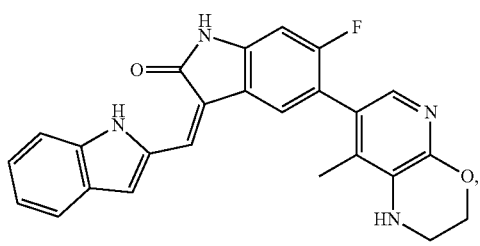
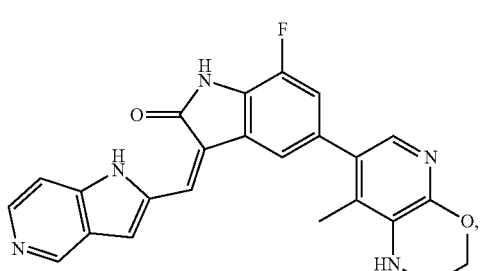
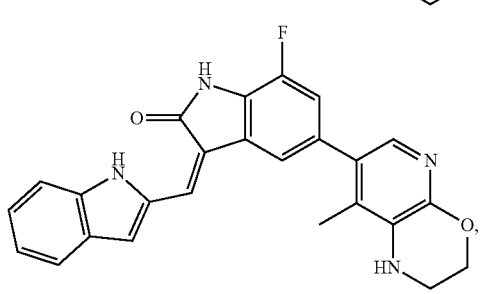
200
-continued
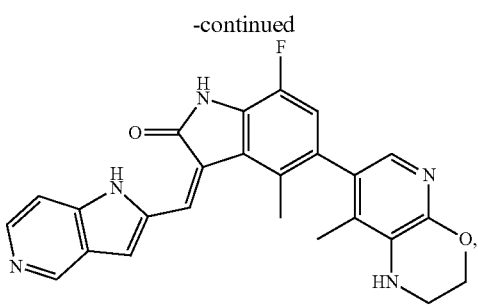
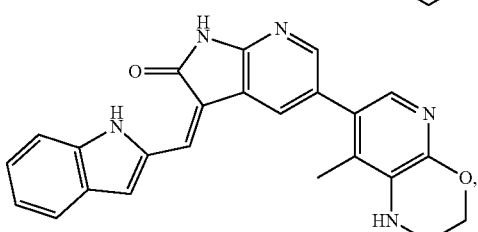
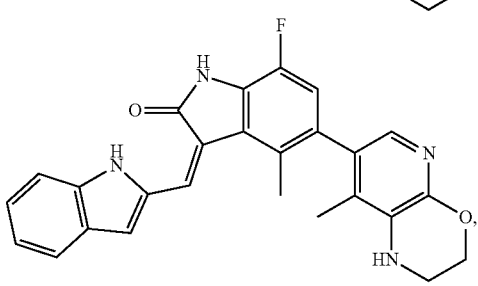
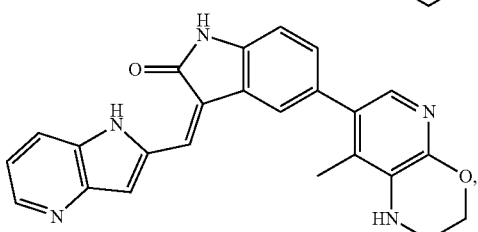
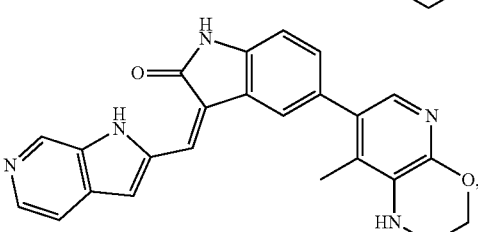
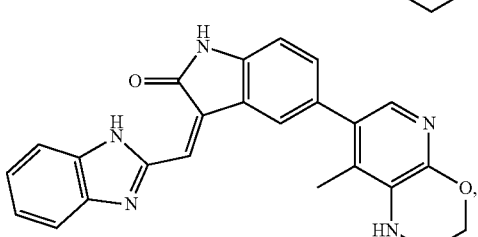
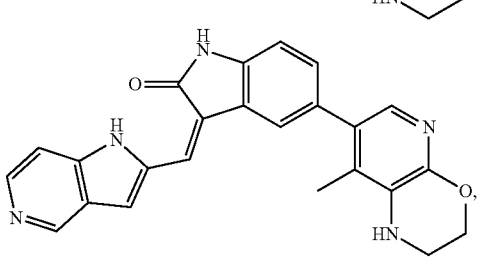

-continued

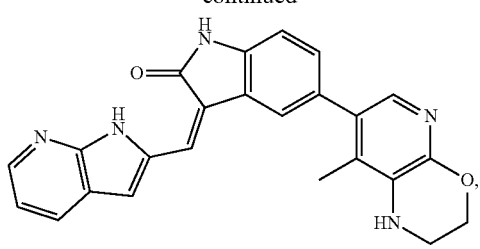

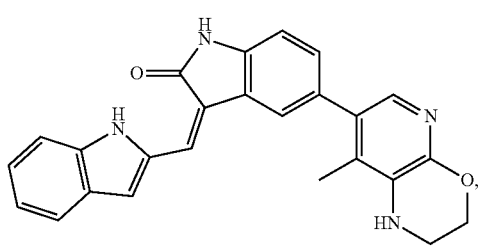

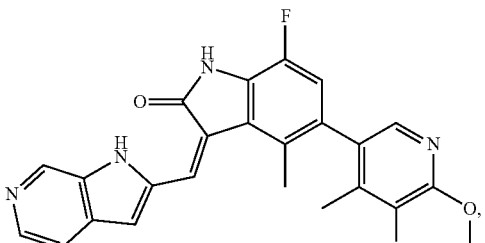

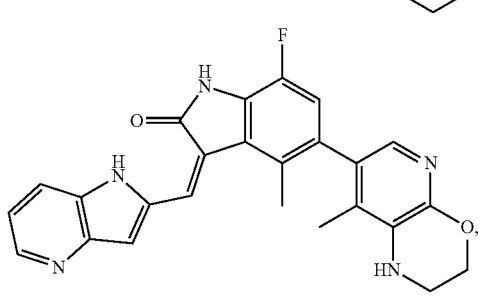

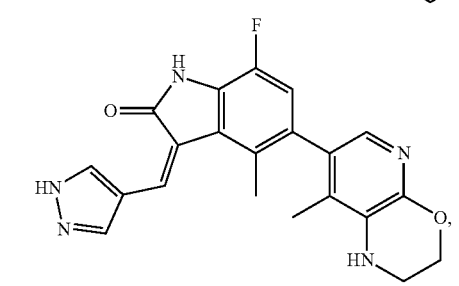

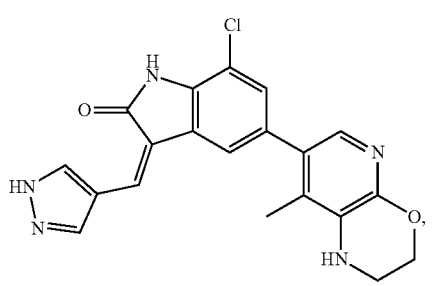

-continued

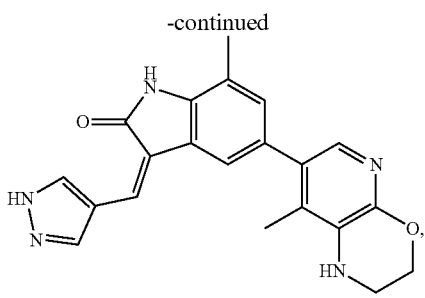

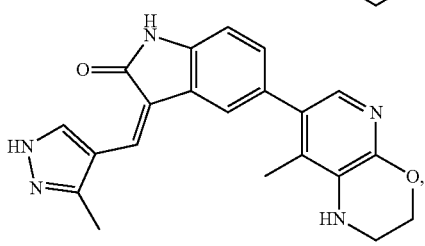

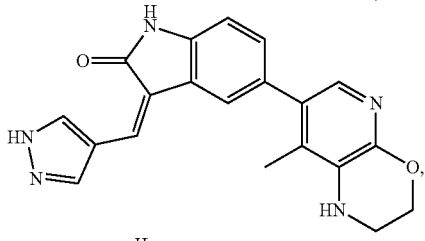

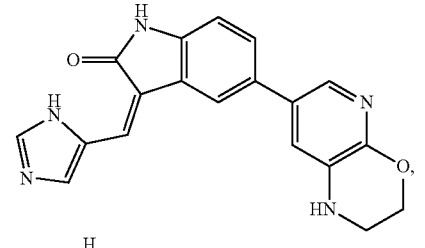

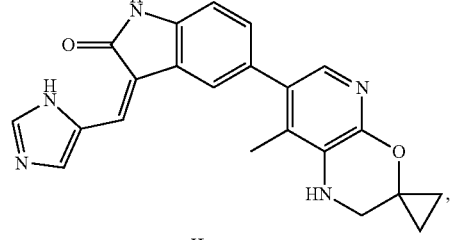

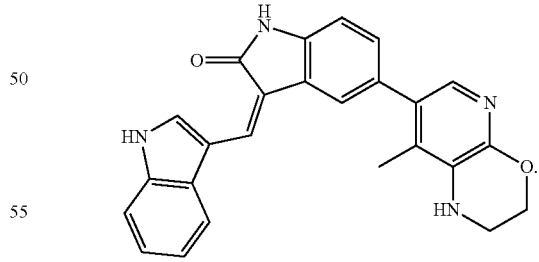, and

51. The method of claim 1, wherein the one or more additional therapeutic agents is selected from the group consisting of: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, OX40 agonists, GITR agonists, CD27 agonists, CD28 agonists, CD40 agonists, CD137 agonists, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C—X—C chemokine receptor type 4 (CXCR-4) inhibitors, B7-H3 inhibitors, CD73 inhibitors, inhibitory RNA, IL2/15/17 fusion proteins, MKNK½ inhibitors, JAK inhibitors, and PI3K inhibitors, or a pharmaceutically acceptable salt of any of the foregoing, or any combinations thereof.

52. The method of claim 1, wherein the one or more additional therapeutic agents is selected from the group consisting of: rituxan, doxorubicin, gemcitabine, nivolumab, pembrolizumab, pidilizumab, PDR001, TSR-001, atezolizumab, durvalumab, avelumab, pidilizumab, TSR-042, BMS-986016, ruxolitinib, N-(cyanomethyl)-4-[2-(4-morpholinoanilino)pyrimidin-4-yl]benzamide, XL147, BKM120, GDC-0941, BAY80-6946, PX-866, CH5132799, XL756, BEZ235, and GDC-0980, wortmannin, LY294002, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5-carbonitrile, and ipilimumab, or a pharmaceutically acceptable salt of any of the foregoing, or any combinations thereof.

53. The method of claim 1, wherein the one or more additional therapeutic agents is selected from the group consisting of idelalisib, tirabrutinib, momelotinib, and entospletinib, or a pharmaceutically acceptable salt of any of the foregoing, or any combinations thereof.

54. The method of claim 1, wherein the one or more additional therapeutic agents is a PD1 inhibitor or PDL1 inhibitor.

* * * * *